(12) United States Patent
Tavazoie et al.

(10) Patent No.: US 11,648,220 B2
(45) Date of Patent: May 16, 2023

(54) METHODS FOR THE TREATMENT OF MYELOID DERIVED SUPPRESSOR CELLS RELATED DISORDERS

(71) Applicant: The Rockefeller University, New York, NY (US)

(72) Inventors: Sohail Tavazoie, New York, NY (US); Masoud Tavazoie, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 16/069,436

(22) PCT Filed: Jan. 11, 2017

(86) PCT No.: PCT/US2017/012906
§ 371 (c)(1),
(2) Date: Jul. 11, 2018

(87) PCT Pub. No.: WO2017/123568
PCT Pub. Date: Jul. 20, 2017

(65) Prior Publication Data
US 2019/0029984 A1   Jan. 31, 2019

Related U.S. Application Data

(60) Provisional application No. 62/332,963, filed on May 6, 2016, provisional application No. 62/277,260, filed on Jan. 11, 2016.

(51) Int. Cl.
*A61K 31/195* (2006.01)
*A61K 38/14* (2006.01)
(Continued)

(52) U.S. Cl.
CPC ........ *A61K 31/195* (2013.01); *A61K 31/4174* (2013.01); *A61K 31/675* (2013.01);
(Continued)

(58) Field of Classification Search
CPC .............. A61K 2300/00; A61K 31/195; A61K 31/4174; A61K 31/675; A61K 38/14;
(Continued)

(56) References Cited

U.S. PATENT DOCUMENTS 9,399,028 B2 * 7/2016 Tavazoie ............ A61K 31/4174
10,669,296 B2 * 6/2020 Martinez ............... C07C 259/06
(Continued)

FOREIGN PATENT DOCUMENTS

CN   103054844 B   4/2014
CN   104780976 A   7/2015
(Continued)

OTHER PUBLICATIONS

Jedd D. Wolchok, et al. . (N Engl J Med 2013; 369:122-133 DOI: 10.1056/NEJMoa1302369, Jul. 11, 2013, 8).*
(Continued)

*Primary Examiner* — San Ming R Hui
(74) *Attorney, Agent, or Firm* — Fox Rothschild LLP

(57) ABSTRACT

The invention features methods of treating disorders related to increased levels of myeloid derived suppressor cells such as cancer or infections. The disclosure also provides methods of treating cancer including combinations of LXRβ agonists and immunotherapies such as PD1 inhibitors, PDL1 inhibitors, and adoptive T-cell transfer therapy.

16 Claims, 12 Drawing Sheets
Specification includes a Sequence Listing.

(51) Int. Cl.
| | |
|---|---|
| *A61P 31/12* | (2006.01) |
| *A61P 31/04* | (2006.01) |
| *A61P 35/00* | (2006.01) |
| *A61K 31/4174* | (2006.01) |
| *A61K 31/675* | (2006.01) |
| *A61K 45/06* | (2006.01) |

(52) U.S. Cl.
CPC .............. *A61K 38/14* (2013.01); *A61K 45/06* (2013.01); *A61P 31/04* (2018.01); *A61P 31/12* (2018.01); *A61P 35/00* (2018.01)

(58) Field of Classification Search
CPC .......... A61K 45/06; A61P 31/04; A61P 31/12; A61P 35/00
USPC .............................................................. 514/9
See application file for complete search history.

(56) References Cited

U.S. PATENT DOCUMENTS

| | | | | |
|---|---|---|---|---|
| 10,869,926 | B2* | 12/2020 | Zhou ................... | C07K 16/2818 |
| 2008/0085879 | A1* | 4/2008 | Xie ........................ | A61K 31/18 |
| | | | | 514/182 |
| 2014/0186295 | A1 | 7/2014 | Kupper et al. | |
| 2015/0073053 | A1 | 3/2015 | Tavazoie et al. | |
| 2016/0271149 | A1* | 9/2016 | Einhorn ............... | A61K 31/195 |
| 2017/0066791 | A1* | 3/2017 | Martinez ............. | A61K 31/165 |
| 2017/0119807 | A1 | 5/2017 | Lee et al. | |

FOREIGN PATENT DOCUMENTS

| | | |
|---|---|---|
| JP | 2015-532642 A | 11/2015 |
| WO | 2011115892 A1 | 9/2011 |
| WO | 16100619 A2 | 6/2016 |

OTHER PUBLICATIONS

Srivastava MK, (Immunotargets Ther. 2012; 1: 7-12. Published online Oct. 11, 2012. doi: 10.2147/ITT.S32617, Targeting myeloid-derived suppressor cells augments antitumor activity against lung cancer. Immunotargets Ther.*

Duarte Domingues et al. (Abstract, Published Online:Dec. 12, 2014https://doi.org/10.2217/imt.14.82, Immunotherapy, vol. 6, No. 11; Immunotherapy and lung cancer: current developments and novel targeted therapies).*

Scott J. Antonia et al. DOI: 10.1200/jco.2014.32.15_suppl.8023 Journal of Clinical Oncology 32, No. 15_suppl (May 20, 2014) 8023-8023. Published online May 20, 2014.).*

Ostrand-Rosenberg et al., "Myeloid-Derived Suppressor Cells: Linking Inflammation and Cancer," The Journal of Immunology (Apr. 15, 2009); 182(8):4499-4506.

Draghiciu et al., "Myeloid derived suppressor cells—An overview of combat strategies to increase immunotherapy efficacy,"—10Oncoimmunology (Jan. 2015); 4(1):e954829—pp. 1-10.

Zeng et al., "Liver X receptors agonists impede hepatitis C virus infection in an idol-dependent manner," Antiviral Research (Sep. 2012); 95(3):245-256.

Pencheva et al., "Broad-Spectrum Therapeutic Suppression of Metastatic Melanoma through Nuclear Hormone Receptor Activation," Cell (Feb. 2014); 156(5):986-1001.

* cited by examiner

Tumor-infiltrating MDSC
B16F10 +/- GW3965
FIG. 1A
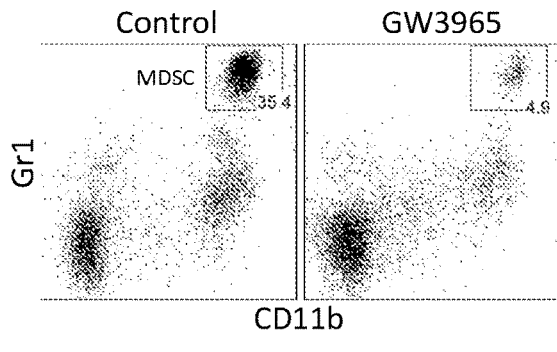
FIG. 1B
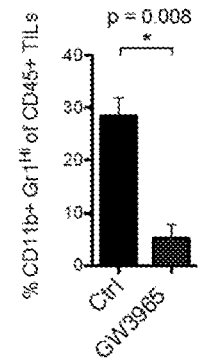
Tumor-infiltrating MDSC (Gr1+ cells)
Immunohistochemistry
B16F10 +/- GW3965
FIG. 1C
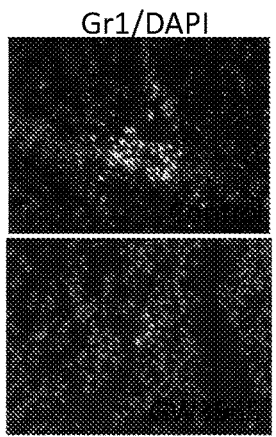
FIG. 1D
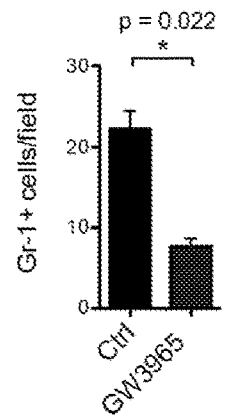
Correlation between anti-tumor activity and MDSC reduction
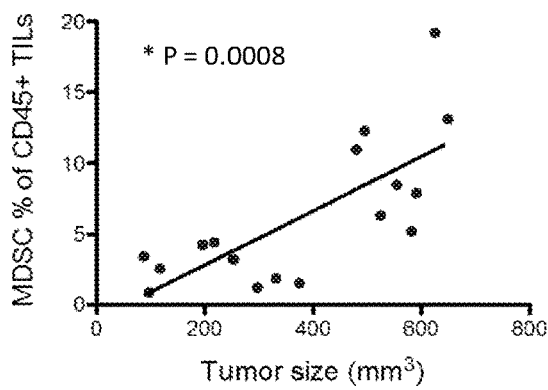
FIG. 1E Activated tumor-infiltrating CD8+ T-cells
B16F10 +/- GW3965
FIG. 2A    FIG. 2B
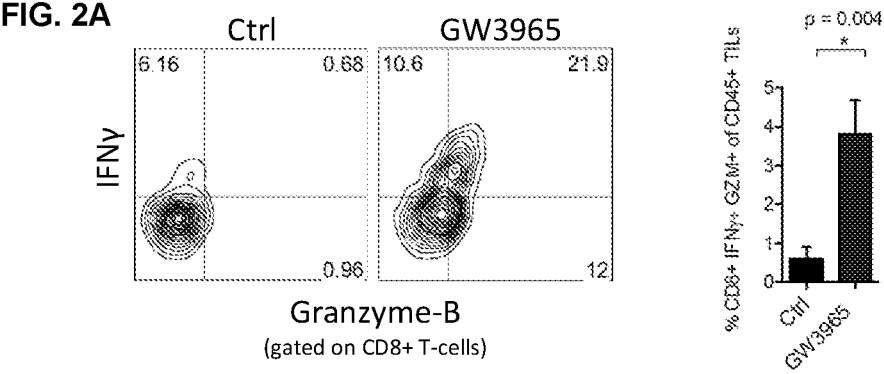
Granzyme-B
(gated on CD8+ T-cells)
T-cell activation correlates
with MDSC reduction
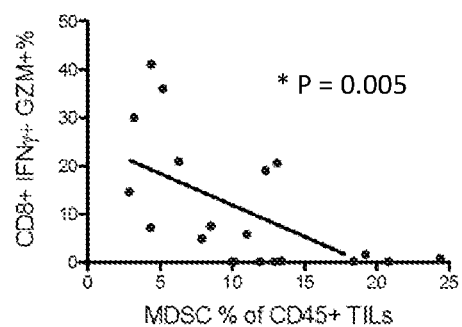
FIG. 2C Tumor-infiltrating G-MDSCs (Ly6G+) and M-MDSCs (Ly6C+)
B16F10 +/- RGX-104

Circulating MDSC
B16F10 +/- RGX-104

MDSC-mediated suppression of T-cells in co-culture *in vitro*

MDSC survival *in vitro*

RGX-104 enhances the T-cell response induced with anti-PD-1

RGX-104 boosts the efficacy of adoptive T-cell transfer of melanoma-targeting CD8+ T-cells (pmel CD8+ cells) in B16F10

B16F10 tumor growth in
Wild-type mice +/- GW3965

ApoE-depleted B16F10 in ApoE$^{-/-}$ mice +/- GW3965

FIG. 7B   FIG. 7C

ApoE deficient mice have higher levels of systemic MDSCs

LRP8 deficient mice have higher levels of systemic MDSCs

LXRα/β deficient mice have higher levels of systemic MDSCs

ApoE deficient MDSCs functionally suppress T-cell activation *in vitro*

ApoE deficient MDSCs exhibit enhanced survival *in vitro* and are resistant to LXR agonists Tumor growth of B16F10 in
wild-type (ApoE WT) vs. ApoE deficient (Apoe -/-) mice
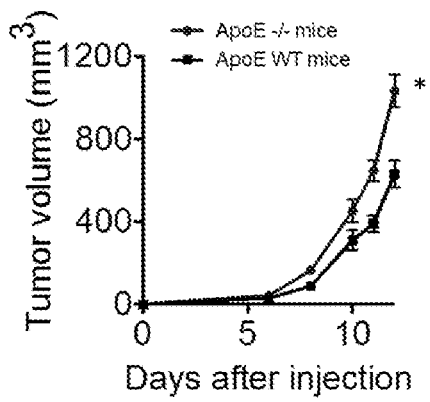
FIG. 11A
Circulating MDSC in B16F10 tumor-bearing mice
(Wild-type vs. ApoE deficient mice)
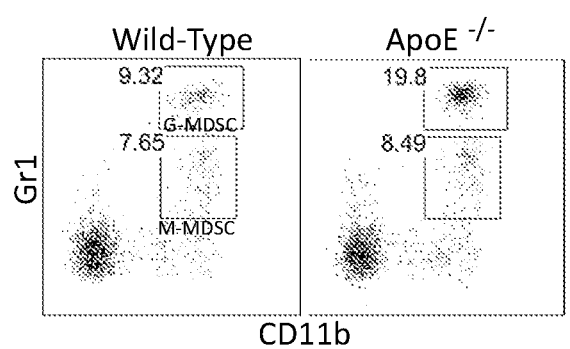
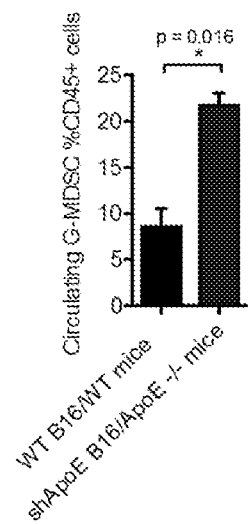
FIG. 11B          FIG. 11C

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: LRP1 forward primer

<400> SEQUENCE: 1
tttaacagca ccgagtacca g                                              21

<210> SEQ ID NO 2
<211> LENGTH: 19

```
<212> TYPE: DNA
<213> ORGANISM: Artificial
<220> FEATURE:
<223> OTHER INFORMATION: LRP1 reverse primer

<400> SEQUENCE: 2
caggcagatg tcagagcag                                              19
```

METHODS FOR THE TREATMENT OF MYELOID DERIVED SUPPRESSOR CELLS RELATED DISORDERS

CROSS-REFERENCE TO RELATED APPLICATIONS

The present application is a National Stage Application under 35 U.S.C. §371 of International Application No. PCT/US2017/012906 filed Jan. 11, 2017, which claims the benefit under 35 U.S.C. 119(e) of U.S. Provisional Application No. 62/277,260, filed Jan. 11, 2016 and U.S. Provisional Application No. 62/332,963, filed May 6, 2016, the contents of which are incorporated herein by reference.

BACKGROUND

Myeloid derived suppressor cells (MDSCs) are a heterogeneous population of cells of myeloid origin that consist of myeloid progenitors and immature macrophages, immature granulocytes, and immature dendritic cells. MDSCs are present in an activated state that is characterized by the increased production of reactive oxygen species, reactive nitrogen species, and arginase. MDSCs have been found to be suppressors of various T-cell functions, including T-cell proliferation and T-cell activation. Phenotypes of MDSCs in mice include $CD11b^+Gr1^+$, $CD11b^+Ly6G^+Ly6C^-$, and $CD11b^+Ly6C^+Ly6G^-$. In humans, the phenotypes of MDSCs include $Lin^-HLA^-DR^-CD33^+$ and $CD11b^+CD14^-CD33^+$. It has been shown that MDSC levels are increased in several cancer and infection types. It has been further shown that increased levels of MDSCs may lead to a decrease in responsiveness to immunotherapies such as PD1 inhibitors, PDL1 inhibitors, and adoptive T-cell transfer therapy. For example, as described in Weber et al. Cancer Immunol. Res. 2016 4(4):345-353, high levels of myeloid-derived suppressor cells (MDSC) were associated with poor survival in patients treated with nivolumab who had progressed after ipilimumab. Thus, there is a need to develop therapies that are capable decreasing the level of MDSCs in a patient for the treatment of cancer and/or to increase response of the cancer to immunotherapies.

SUMMARY OF THE INVENTION

The invention features methods of treating disorders related to MDSCs (e.g., cancer or infection) by administering an LXRβ agonist. In some embodiments, the LXRβ agonist is administered in combination with a second agent to treat the disease (e.g., an anticancer agent or an anti-infective agent). The inventors have discovered that LXRβ agonists are capable of lowering MDSC levels in subjects, e.g., subjects with elevated levels such as subjects with cancer or bacterial, viral, or fungal infections. The lowering of MDSC levels may allow the subjects immune system to more effectively work against the cancer or infection and/or increase efficacy of treatments administered to the subjects, e.g., immunotherapy treatments for cancer.

Accordingly, in an aspect, the invention features a method of treating cancer in a subject, the method including: (a) determining the level of myeloid derived suppressor cells (e.g., monocytic and/or granulocytic myeloid derived suppressor cells) and/or the level of activated T-cells in the subject; and (b) administering an effective amount of an LXRβ agonist to the subject if the level of myeloid derived suppressor cells are greater than a predetermined level (e.g., the level in a sample from a subject that does not have cancer) and/or the level of activated T-cells is lower than a predetermined level (e.g., the level in a sample from a subject that does not have cancer).

In certain embodiments, step (b) further includes administering an immunotherapy (e.g., an antibody such as an anti-PD1 or anti-PDL1 antibody or adoptive T-cell transfer therapy) to the subject. In some embodiments, the immunotherapy is administered concurrently with the LXRβ agonist. In some embodiments, the immunotherapy is administered prior (e.g., at least one day, at least two days, at least three days, at least one week, at least two weeks prior) to the LXRβ agonist. In some embodiments, the immunotherapy is administered subsequently (e.g., at least one day, at least two days, at least three days, at least one week, at least two weeks later) to initiating the LXRβ agonist therapy.

In particular embodiments of any of the methods of the invention, the activated T-cells are CD8+ T-cells.

In some embodiments of any of the methods of the invention, the level of myeloid derived suppressor cells and/or the level of activated T-cells is determined in the tumor microenviroment (e.g., by determining the level in a tumor sample such as a tumor sample from a biopsy). In some embodiments of any of the methods of the invention, the level of myeloid derived suppressor cells and/or the level of activated T-cells is determined systemically (e.g., by determining the level in a plasma sample). In some embodiments of any of the methods of the invention, the myeloid derived suppressor cells are monocytic myeloid derived suppressor cells (e.g., circulating monocytic myeloid derived suppressor cells). In some embodiments of any of the methods of the invention, the myeloid derived suppressor cells are granulocytic myeloid derived suppressor cells. In some embodiments of any of the methods of the invention, the myeloid derived suppressor cells express CD11b (+), Lin(-), HLA-DR(low/-), and/or CD14(+) on their surface. In some embodiments of any of the methods of the invention, the myeloid derived suppressor cells express CD11b(+), Lin(-), HLA-DR(low/-), and CD14(+) on their surface. In some embodiments of any of the methods of the invention, the myeloid derived suppressor cells express CD11b(+), Lin(-), HLA-DR(low/-), and/or CD15(+) on their surface. In some embodiments of any of the methods of the invention, the myeloid derived suppressor cells express CD11b(+), Lin(-), HLA-DR(low/-), and CD15(+) on their surface. In some embodiments of any of the methods of the invention, the myeloid derived suppressor cells are any known in the art, for example, those described in Talmadge et al. Nat. Rev. Cancer 2013 13(10):739-752.

In certain embodiments of any of the methods of the invention, the subject has not been previously administered an immunotherapy prior to step (a).

In some embodiments of any of the methods of the invention, administration of an LXRβ agonist to a subject prior to subsequent treatment with an immunotherapy may increase the response of the cancer to the immunotherapy by lowering the MDSC (e.g., monocytic and/or granulocytic MDSC) levels in the subject which may limit the effectiveness of the immunotherapy.

In another aspect, the invention features a method of treating cancer in a subject, the method including: (a) administering an effective amount of an LXRβ agonist to the subject, without concurrently administering an immunotherapy; and (b) administering an effective amount of an immunotherapy to the subject within 2 to 10 days (e.g., within 2 days, within 3 days, within 4 days, within 5 days, within 6 days, within 7 days, within 8 days, within 9 days, within 10 days) of initiating step (a).

In another aspect, the invention features a method of treating cancer in a subject, wherein the subject has a compromised immune system (e.g., the subject has been determined to have decreased levels of activated T-cells or increased levels of MDSCs (e.g., monocytic and/or granulocytic MDSCs), or the subject is likely to have a decreased immune response based on the subject's medical history such as prior treatment history), the method including administering an effective amount of an LXRβ agonist to the subject. In some embodiments, the subject has decreased levels of ApoE, LRP1, LRP8, and/or LXRβ (e.g., in the tumor microenvironment or systemically, including immune cells) compared to a predetermined reference value (e.g., a value in a sample from a healthy subject).

In another aspect, the invention features a method of treating cancer in a subject, wherein the subject has an elevated level (e.g., the subject has a level about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, greater as compared to a reference such as the level in a sample from a healthy subject or a level that indicates an increased likelihood of response to an immunotherapy) of myeloid derived suppressor cells such as monocytic and/or granulocytic myeloid derived suppressor cells (e.g., in the tumor microenvironment or systemically), the method including administering an effective amount of an LXRβ agonist.

MDSCs have been implicated in the lack of response of cancer in subjects to immunotherapies. Since immunotherapies rely on the subjects immunosystem to treat the cancer, e.g., by increasing T-cell activation, high level of MDSCs, which decrease T-cell activation, may be responsible for the lack of response. Thus, treatment of a subject with an LXRβ agonist may increase response to immunotherapies in certain subjects.

In one embodiment of any of the foregoing methods, the subject has a cancer that has failed to respond to a previously administered an immunotherapy (e.g., the cancer of the subject has progressed despite treatment with the immunotherapy).

In some embodiments of any of the foregoing methods, the cancer is resistant to an immunotherapy (e.g., the cancer has been determined to be resistant to immunotherapies such as by genetic markers or the level of MDSCs (e.g., monocytic and/or granulocytic MDSCs) in a sample, or is likely to be resistant, to immunotherapies such as a cancer that has failed to respond to an immunotherapy).

In another aspect, the invention features a method of treating cancer that has failed to respond to an immunotherapy in a subject, the method including administering an effective amount of an LXRβ agonist to the subject in combination with an immunotherapy.

In another aspect, the invention features a method of treating cancer that is resistant to immunotherapy in a subject, the method including administering an effective amount of an LXRβ agonist to the subject in combination with an immunotherapy.

In another aspect, the invention features a method of suppressing the growth of myeloid derived suppressor cells such as monocytic and/or granulocytic myeloid derived suppressor cells (e.g., inhibiting proliferation and/or killing the MDSCs) in a tumor microenvironment, the method including increasing the level of ApoE in the microenvironment by contacting a non-myeloid derived suppressor cell with an LXR agonist.

In some embodiments of any of the foregoing methods, the subject has an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, of MDSCs as compared to a reference such as the level in a sample from a healthy subject or a sample from a subject that responds to immunotherapy; or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more of MDSCs (e.g., monocytic and/or granulocytic MDSCs) as compared to a reference such as the level in a sample from a healthy subject or a sample from a subject that responds to immunotherapy.

In some embodiments of any of the foregoing methods, the subject has a decrease by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, of activated T-cells as compared to a reference such as the level in a sample from a healthy subject or a sample from a subject that responds to immunotherapy; or a decrease by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more of activated T-cells as compared to a reference such as the level in a sample from a healthy subject or a sample from a subject that responds to immunotherapy.

In one embodiment of any of the foregoing methods, the immunotherapy, when present, is a CTLA-4 inhibitor, a PD1 inhibitor, a PDL1 inhibitor, or adoptive T-cell transfer therapy. In some embodiments, the immunotherapy is a PD-1 inhibitor such as a PD-1 antibody, a PD-L1 inhibitor such as a PD-L1 antibody, a CTLA-4 inhibitor such as a CTLA-4 antibody, a CSF-1R inhibitor, an IDO inhibitor, an A1 adenosine inhibitor, an A2A adenosine inhibitor, an A2B adenosine inhibitor, an A3A adenosine inhibitor, an arginase inhibitor, or an HDAC inhibitor. In some embodiments, the immunotherapy is a PD-1 inhibitor (e.g., nivolumab, pembrolizumab, pidilizumab, BMS 936559, and MPDL3280A). In some embodiments, the immunotherapy is a PD-L1 inhibitor (e.g., atezolizumab and MEDI4736). In some embodiments, the immunotherapy is a CTLA-4 inhibitor (e.g., ipilimumab). In some embodiments, the immunotherapy is a CSF-1R inhibitor (e.g., pexidartinib and AZD6495). In some embodiments, the immunotherapy is an IDO inhibitor (e.g., norharmane, rosmarinic acid, and alpha-methyl-tryptophan). In some embodiments, the immunotherapy is an A1 adenosine inhibitor (e.g., 8-cyclopentyl-1,3-dimethylxanthine, 8-cyclopentyl-1,3-dipropylxanthine, 8-phenyl-1,3-dipropylxanthine, bamifylline, BG-9719, BG-9928, FK-453, FK-838, rolofylline, or N-0861). In some embodiments, the immunotherapy is an A2A adenosine inhibitor (e.g., ATL-4444, istradefylline, MSX-3, preladenant, SCH-58261, SCH-412,348, SCH-442,416, ST-1535, VER-6623, VER-6947, VER-7835, viadenant, or ZM-241,385). In some embodiments, the immunotherapy is an A2B adenosine inhibitor (e.g., ATL-801, CVT-6883, MRS-1706, MRS-1754, OSIP-339,391, PSB-603, PSB-0788, or PSB-1115). In some embodiments, the immunotherapy is an A3A adenosine inhibitor (e.g., KF-26777, MRS-545, MRS-1191, MRS-1220, MRS-1334, MRS-1523, MRS-3777, MRE-3005-F20, MRE-3008-F20, PSB-11, OT-7999, VUF-5574, and SSR161421). In some embodiments, the immunotherapy is an arginase inhibitor (e.g., an arginase antibody, (2s)-(+)-amino-5-iodoacetamidopentanoic acid, NG-hydroxy-L-arginine, (2S)-(+)-amino-6-iodoacetamidohexanoic acid, or (R)-2-amino-6-borono-2-(2-(piperidin-1-yl)ethyl)hexanoic acid. In some embodiments, the immunotherapy is an HDAC inhibitor (e.g., valproic acid, SAHA, or romidepsin).

In another embodiment of any of the foregoing methods, the method further includes administering to the subject an additional anticancer therapy (e.g., an antiproliferative). In some embodiments, the additional anticancer therapy is any one of the antiproliferatives listed in Table 4.

In particular embodiments, the antiproliferative is: a chemotherapeutic or cytotoxic agent, a differentiation-inducing agent (e.g. retinoic acid, vitamin D, cytokines), a hormonal agent, an immunological agent, or an anti-angiogenic agent. Chemotherapeutic and cytotoxic agents include, but are not limited to, alkylating agents, cytotoxic antibiotics, antimetabolites, vinca alkaloids, etoposides, and others (e.g., paclitaxel, taxol, docetaxel, taxotere, cis-platinum). A list of additional compounds having antiproliferative activity can be found in L. Brunton, B. Chabner and B. Knollman (eds). Goodman and Gilman's The Pharmacological Basis of Therapeutics, Twelfth Edition, 2011, McGraw Hill Companies, New York, N.Y.

In certain embodiments, the antiproliferative is a PD1 inhibitor, a VEGF inhibitor, a VEGFR2 inhibitor, a PDL1 inhibitor, a BRAF inhibitor, a CTLA-4 inhibitor, a MEK inhibitor, an ERK inhibitor, vemurafenib, dacarbazine, trametinib, dabrafenib, MEDI-4736, an mTOR inhibitor, a CAR-T therapy, abiraterone, enzalutamine, ARN-509, 5-FU, FOLFOX, FOLFIRI, herceptin, xeloda, a PD1 antibody (e.g., pembrolizumab or nivolumab), a PDL-1 antibody, a CTLA-4 antibody (e.g, ipilimumab), ramucirumab, rindopepimut, glembatumumab, vedotin, ANG1005, and/or ANG4043.

In some embodiments, the cancer is a renal cell carcinoma and the antiproliferative is a PD1 inhibitor, a PDL-1 inhibitor, or an mTOR inhibitor. In other embodiments, the cancer is diffuse large B-cell lymphoma and the antiproliferative is a CAR-T therapy. In certain embodiments, the cancer is prostate cancer and the antiproliferative is abiraterone, enzalutamide, or ARN-509. In some embodiments, the cancer is hepatocellular carcinoma, gastric cancer, or esophageal cancer and the antiproliferative is 5-FU, FOLFOX, FOLFIRI, herceptin, or xeloda. In some embodiments, the cancer is sarcoma and the antiproliferative is gemcitabine. In other embodiments, the cancer is pancreatic cancer and the antiproliferative is irinotecan, cisplatin, abraxane, a taxane (e.g., paclitaxel or docetaxel), or capecitabine.

The method may further include administering an antiproliferative selected from the group consisting of alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelin A receptor antagonist, retinoic acid receptor agonists, immuno-modulators, hormonal and antihormonal agents, photodynamic agents, tyrosine kinase inhibitors, antisense compounds, corticosteroids, HSP90 inhibitors, proteosome inhibitors (for example, NPI-0052), CD40 inhibitors, anti-CSI antibodies, FGFR3 inhibitors, VEGF inhibitors, MEK inhibitors, cyclin D1 inhibitors, NF-kB inhibitors, anthracyclines, histone deacetylases, kinesin inhibitors, phosphatase inhibitors, COX2 inhibitors, mTOR inhibitors, calcineurin antagonists, IMiDs, or other agents used to treat proliferative diseases. Examples of such compounds are provided in Table 4.

In particular embodiments, the antiproliferative and/or immunotherapy and LXR agonist are administered within 28 days of each other (e.g., within 21, 14, 10, 7, 5, 4, 3, 2, or 1 days) or within 24 hours (e.g., 12, 6, 3, 2, or 1 hours; or concomitantly) each in an amount that together are effective to treat the subject.

In another aspect, the invention features a method of treating an infection (e.g., a bacterial infection, a viral infection, or a parasitic infection) in a subject, wherein the subject has an elevated level of myeloid derived suppressor cells such as monocytic and/or granulocytic myeloid derived suppressor cells (e.g., compared to a sample from a healthy subject), the method including administering an effective amount of an LXRβ agonist. In some embodiments, the method further includes administering the subject an anti-infective agent.

In some embodiments, the anti-infective agent and LXR agonist are administered within 28 days of each other (e.g., within 21, 14, 10, 7, 5, 4, 3, 2, or 1 days) or within 24 hours (e.g., 12, 6, 3, 2, or 1 hours; or concomitantly) each in an amount that together are effective to treat the subject.

In certain embodiments of any of the foregoing methods, administering comprises contacting a cell with an effective amount of an LXRβ agonist.

In some embodiments of any of the foregoing methods, the LXRβ agonist is selective for LXRβ over LXRα.

In some embodiments of any of the foregoing methods, the LXRβ agonist is any compound described herein (e.g., any compound having the structure of any one of Formula I-XXXVI or any one of compounds 1-826).

In some embodiments of any of the foregoing methods, the LXR agonist has the structure of Formula IV:

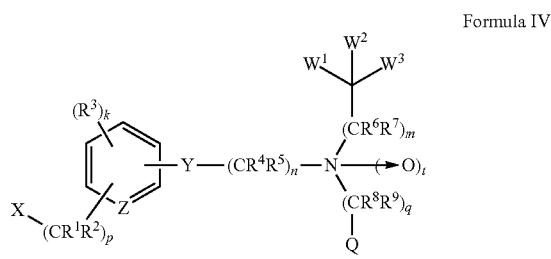

Formula IV wherein:

X is selected from hydrogen, $C_1$-$C_8$ alkyl, halo, —$OR^{10}$, —$NR^{10}R^{11}$, nitro, cyano, —$COOR^{10}$, or —$COR^{10}$.

Z is CH, $CR^3$ or N, wherein when Z is CH or $CR^3$, k is 0-4 and t is 0 or 1, and when Z is N, k is 0-3 and t is 0;

Y is selected from —O—, —S—, —N($R^{12}$)—, and —C($R^4$)($R^5$)—;

$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$alkyl-C(O)$SR^{12}$, —$C_0$-$C_6$alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$alkyl-$OR^{12}$, —$C_0$-$C_6$alkyl-$SO_3H$, —$C_0$-$C_6$alkyl-$SO_2NR^{13}R^{14}$, —$C_0$-$C_6$alkyl-$SO_2R^{12}$, —$C_0$-$C_6$alkyl-$SOR^{15}$, —$C_0$-$C_6$alkylOCOR^{15}$, —$C_0$-$C_6$alkyl-OC(O)$NR^{13}R^{14}$, —$C_0$-$C_6$alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^2$ is selected from H, halo, $C_1$-$C_6$alkyl, $C_2$-$C_6$alkenyl, $C_2$-$C_6$ alkynyl, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl$CO_2R^{12}$, —$C_0$-$C_6$ alkyl-C(O)$SR^{12}$, —$C_0$-$C_6$ alkyl$CONR^{13}R^{14}$, —$C_0$-$C_6$alkyl-$COR^{15}$, —$C_0$-$C_6$ alkylOCOR$^{15}$, —$C_0$-$C_6$alkyl-OCONR$^{13}R^{14}$, —$C_0$-$C_6$alkyl-$NR^{13}CONR^{13}R^{14}$, —$C_0$-$C_6$ alkyl-$NR^{13}COR^{15}$, —$C_0$-$C_6$alkyl-Het, —$C_0$-$C_6$alkyl-Ar, and —$C_0$-$C_6$alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$alkyl-$SOR^{15}$, —$C_0$-$C_6$alkyl-$OCOR^{15}$, —$C_0$-$C_6$ alkyl-OC(O)$NR^{13}R^{14}$, —$C_0$-$C_6$ alkyl-OC(O)$OR^5$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{13}R^{14}$, —$C_0$-$C_6$ alkyl$SR^{12}$, —$C_0$-$C_6$ alkyl-$OR^{12}$, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$OCOR^{15}$, —$C_0$-$C_6$ alkyl-$OCONR^{13}R^{14}$, —$C_0$-$C_6$ alkyl$NR^{13}CONR^{13}R^{14}$, —$C_0$-$C_6$ alkyl-$NR^{13}COR^{15}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar, and Het; wherein said $C_3$-$C_8$ cycloalkyl, Ar, and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl$CO_2R^{12}$, —$C_0$-$C_6$ alkyl-C(O)$SR^{12}$, —$C_0$-$C_6$ alkyl$CONR^{13}R^{14}$, —$C_0$-$C_6$ alkyl-$COR^5$, —$C_0$-$C_6$ alkyl$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkylNR$^{13}$C(O)$OR^5$, —$C_0$-$C_6$ alkyl-$NR^{13}$C(O)$NR^{13}R^{14}$, and —$C_0$-$C_6$alkyl-$NR^{13}COR^{15}$, where said $C_1$-$C_6$alkyl is optionally unsubstituted or substituted by one or more halo substituents;

p is 0-8;

n is 2-8;

m is 0 or 1;

q is 0 or 1;

t is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{13}R^{14}$, —$C_0$-$C_6$ alkyl-$OR^{12}$, —$C_0$-$C_6$ alkyl-$SR^{12}$, —$C_1$-$C_6$ alkyl-Het, —$C_1$-$C_6$ alkyl-Ar, and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkylSO$_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar, and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ and $R^{11}$ are each independently selected from H, $C_1$-$C_{12}$ alkyl, $C_3$-$C_{12}$ alkenyl, $C_3$-$C_{12}$ alkynyl, —$C_0$-$C_8$ alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$ alkyl-O-Het, —$C_0$-$C_8$ alkyl-O—$C_3$-$C_7$ cycloalkyl, —$C_0$-$C_8$ alkyl-S(O)$_x$—$C_0$-$C_6$ alkyl, —$C_0$-$C_8$ alkyl-S(O)$_x$—Ar, —$C_0$-$C_8$ alkyl-S(O)$_x$—Het, —$C_0$-$C_8$ alkyl-S(O)$_x$—$C_3$-$C_7$ cycloalkyl, —$C_0$-$C_8$ alkyl-NH—Ar, —$C_0$-$C_8$ alkyl-NH-Het, —$C_0$-$C_8$ alkyl-NH—$C_3$-$C_7$ cycloalkyl, —$C_0$-$C_8$ alkyl-N($C_1$-$C_4$ alkyl)-Ar, —$C_0$-$C_8$ alkyl-N($C_1$-$C_4$ alkyl)-Het, —$C_0$-$C_8$ alkyl-N($C_1$-$C_4$ alkyl-$C_3$-$C_7$ cycloalkyl, —$C_0$-$C_8$ alkyl-Ar, —$C_0$-$C_8$ alkyl-Het, and —$C_0$-$C_8$ alkyl-$C_3$-$C_7$ cycloalkyl, where x is 0, 1, or 2, or $R^{10}$ and $R^{11}$, together with the nitrogen to which they are attached, form a 4-7 membered heterocyclic ring which optionally contains one or more additional heteroatoms selected from N, O, and S, wherein said $C_1$-$C_{12}$ alkyl, $C_3$-$C_{12}$ alkenyl, or $C_3$-$C_{12}$ alkynyl is optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$alkyl), unsubstituted —$OC_1$-$C_6$ alkyl, —$CO_2H$, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —SO₃H, —SO₂NH₂, —SO₂NH(unsubstituted $C_1$-$C_6$alkyl) and —SO₂N(unsubstituted $C_1$-$C_6$alkyl)(unsubstituted $C_1$-$C_6$ alkyl);

$R^{12}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{13}$ and each $R^{14}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl, or $R^{13}$ and $R^{14}$ together with the nitrogen to which they are attached form a 4-7 membered heterocyclic ring which optionally contains one or more additional heteroatoms selected from N, O, and S;

and $R^{15}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl;

or a pharmaceutically acceptable salt thereof.

In some embodiments of any of the foregoing methods, the LXRβ agonist has the structure of Formula V:

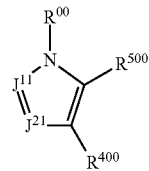

Formula V or a pharmaceutically acceptable salt thereof, wherein:

$J^{11}$ is —N═ and $J^{21}$ is —$CR^{300}$—, or $J^{11}$ is —$CR^{200}$— and $J^{21}$ is ═N—;

$R^{00}$ is $G^1$, $G^{21}$, or $R^N$;

$R^{200}$ is $G^1$, $G^{21}$, or $R^C$;

$R^{300}$ and $R^{400}$ are independently $R^C$ or Q, provided one and only one of $R^{300}$, $R^{400}$, and $R^{500}$ is Q;

Q is $C_{3-6}$ cycloalkyl, heteroaryl or heterocyclyl, each optionally substituted with 1 to 4 $R^Q$, or Q is —X—Y—Z; wherein each $R^Q$ is independently aryloxy, aralkyloxy, aryloxyalkyl, aryl-$C_0$-$C_6$ alkylcarboxy, $C(R^{110})$═$C(R^{110})$— COOH, oxo, ═S, —Z, —Y'—Z, or —X—Y—Z, wherein each $R^Q$ is optionally substituted with 1 to 4 $R^{80}$;

$R^{500}$ is $G^1$ $G^{21}$, Q, or $R^C$; provided that only one of $R^{00}$, $R^{200}$, and $R^{500}$ is $G^1$ and only one of $R^{00}$, N═, and $R^{500}$ is $G^{21}$;

$G^{21}$ is -$J^0$-$K^0$, wherein $J^0$ and $K^0$ are independently aryl or heteroaryl, each optionally substituted with one to four $R^K$ groups; each $R^K$ is independently hydrogen, halogen, $CR^{110}$═$CR^{110}COOR^{110}$, nitro, —Z, —Y—Z, or —X—Y—Z;

$G^1$ is -$L^{10}$-R, wherein $L^{10}$ is a bond, $L^{50}$, $L^{60}$, -$L^{50}$-$L^{60}$-$L^{50}$-, or -$L^{60}$-$L^{50}$-$L^{50}$-, wherein each $L^{50}$ is independently —$[C(R^{150})_2]_m$—;

each $L^{60}$ is independently —CS—, —CO—, —SO₂—, —O—, —$CON(R^{110})$—, —$CONR^{11}N(R^{110})$—, —$C(═NR^{110})$—, —$C(NOR^{11})$—, —$C(═N—N(R^{110})_2)$—, —$C_3$-$C_8$ cycloalkyl-, or -heterocyclyl-, wherein the cycloalkyl or heterocyclyl is optionally substituted with one to 4 $R^{140}$ groups; or each $L^{60}$ is independently $C_2$-$C_6$ alidiyl, wherein the alidiyl chain is optionally interrupted by —$C(R^{100})_2$—, —$C(R^{110})_2C(R^{110})_2$—, —$C(R^{11})C(R^{110})$—, —$C(R^{110})_2O$—, —$C(R^{110})_zNR^{110}$—, —C C—, —O—, —S—, —$N(RO)CO$—, —$N(R^{100})CO_2$—, —$CON(R^{110})$—, —CO—, —$CO_2$—, —$OC(═O)$—, —$OC(═O)N(R^{100})$, —SO₂—, —$N(R^{100})SO_2$—, or —$SO_2N(R^{100})$;

R is aryl, heterocyclyl, heteroaryl or —$(C_3$-$C_6)$ cycloalkyl, wherein R is optionally substituted with 1 to 4 $R^A$, wherein each $R^A$ is independently halogen, nitro, heterocyclyl, $C_1$-$C_6$ alkyl, $C_2$-$C_6$ alkenyl, $C_2$-$C_6$ alkynyl, $C_3$-$C_8$ cycloalkyl, $(C_3$-$C_8$ cycloalkyl)-$C_1$-$C_6$ alkyl-, $(C_3$-$C_8$ cycloalkenyl)-$C_1$-$C_6$ alkyl-, $(C_3$-$C_8$ cycloalkyl)-$C_1$-$C_6$ alkenyl-, arylalkyl, aryloxy, aryl-$C_{1-6}$ alkoxy, $C_1$-$C_6$ haloalkyl, $SO_2R^{110}$, $OR^{110}$, $SR^{110}$, $N_3$, $SOR^{110}$, $COR^{110}$, $SO_2N(R^{110})_2$, $SO_2NR^{110}COR^{110}$, C≡N, $C(O)OR^{110}$, $CON(R^{110})_2$, —CON$(R^{110})OR^{110}$, $OCON(R^{110})_2$, —$NR^{110}COR^{110}$, $NR^{110}CON(R^{110})_2$, $NR^{110}COOR^{110}$, —$C(═N—OH)R^{110}$, —$C(═S)N(R^{110})_2$, —$S(═O)N(R^{110})_2$, —$S(═O)OR^{110}$, —$N(R^{110})S(═O)_2R^{110}$, —$C(═O)N(R^{110})N(R^{110})_2$, —$OC(═O)$—$R^{110}$, —$OC(═O)$—$OR^{110}$ or $N(R^{11})_2$, wherein each $R^A$ is optionally substituted with 1 to 4 groups which independently are -halogen, —$C_1$-$C_6$ alkyl, aryloxy, $C_{0-6}$ alkylSO₂$R^{110}$, $C_{0-6}$ alkylCOOR$^{110}$, $C_{1-6}$ alkoxyaryl, $C_1$-$C_6$ haloalkyl, —$SO_2R^{110}$, —$OR^{110}$, —$SR^{110}$, —$N_3$, —$SO_2R^{110}$, —$COR^{110}$, —$SO_2N(R^{110})_2$, —$SO_2NR^{110}COR^{110}$, —C≡N, —$C(O)OR^{110}$, —$CON(R^{110})_2$, —$CON(R^{110})OR^{110}$, —$OCON(R^{110})_2$, —$NR^{110}COR^{110}$, —$NR^{110}CON(R^{110})_2$, —$NR^{110}COOR^{110}$, or —$N(R^{110})_2$;

$R^N$ is -$L^{31}$-$R^{60}$, wherein $L^{31}$ is a bond, —$X^3(CH_2)_n$—$X^3$—, —$(CH_2)_m$—X3-$(CH_2)_n$— or —$(CH_2)_{1+w}$—, —$Y^3$—$(CH_2)_w$—, wherein each w is independently 0-5: and each $X^3$ is independently a bond, —$C(R^{110})_2$—, —$C(R^{110})_2C(R^{110})_2$—, —$C(R^{110})$═$C(R^{110})$—, —C≡C—, —CO—, —CS—, —$CONR^{100}$—, —$C(═N)(R^{100})$—, —$C(═N—OR^{110})$—, —$C[═N—N(R^{110})_2]$, —$CO_2$—, —$SO_2$—, or —$SO_2N(R^{110})$—; and $Y^3$ is —O—, —S—, —$NR^{70}$—, —$N(R^{100})CO$—, —$N(R^{110})CO_2$—, —OCO—, —$OC(═O)N(R^{100})$—, —$NR^{100}CONR^{100}$—, —$N(R^{110})SO_2$—, or —$NR^{100}CSNR^{100}$—;

or $L^{31}$ is $C_{2-6}$ alidiyl chain wherein the alidiyl chain is optionally interrupted by —$C(R^{110})_2$—, —$C(R^{110})_2C(R^{110})_2$—, —$C(R^{110})$═$C(R^{110})$—, —$C(R^{110})_2O$—, —$C(R^{110})_2NR^{110}$—, —C≡C—, —O—, —S—, —$N(R^{100})CO$—, —$N(R^{100})CO_2$—, —$CON(R^{100})$—, —CO—, —$CO_2$—, —$OC(═O)$—, —$OC(═O)N(R^{110})$—, —$SO_2$—, —$N(R^{100})SO_2$—, or —$SO_2N(R^{100})$; and $R^{60}$ is $C_1$-$C_6$ alkyl, $C_1$-$C_6$ halo alkyl, aryl, $C_3$-$C_8$ cycloalkyl, heteroaryl, heterocyclyl, —CN, —$C(═O)R^{110}$, —$C(═O)OR^{110}$, —$C(═O)N(R^{110})_2$, —$N(R^{110})_2$, —$SO_2R^{110}$, —$S(═O)_2N(R^{110})_2$, —$C(═O)N(R^{110})N(R^{110})_2$ or —$C(═O)N(R^{11})(OR^{110})$, wherein the aryl, heteroaryl, cycloalkyl, or heterocyclyl is optionally substituted with 1 to 4 $R^{60a}$, wherein each $R^{60a}$ is independently —Z, —Y'—Z, or —X—Y—Z;

each $R^C$ is independently -$L^{30}$-$R^{70}$, wherein each $L^{30}$ is independently a bond or —$(CH_2)_m$—$V^{10}$—$(CH_2)_n$—, wherein $V^{10}$ is —$C(R^{110})_2$—, —$C(R^{110})_2C(R^{110})_2$—, —$C(R^{110})$═$C(R^{110})$—, —$C(R^{110})_2O$—, —$C(R^{110})_2NR^{110}$—, —C≡C—, —O—, —S—, —$NR^{10}$—, —$N(R^{100})CO$—, —$N(R^{100})CO2$-, —OCO—, —CO—, —CS—, —$CONR^{100}$—, —$C(═N—R^{110})$—, —$C(═N—OR^{110})$—, —C[=N—N(R$^{110}$)$_2$], —CO$_2$—, —OC(=O)—, —OC(=O)N(R$^{100}$)—, —SO$_2$—, —N(R$^{100}$)SO$_2$—, —SO$_2$N(R$^{100}$)—, —NR$^{100}$CONR—, —NR$^{100}$CSNR$^{100}$—, C$_3$-C$_6$ cycloalkyl, or C$_3$-C$_6$ cyclohaloalkyl; or each L$^{30}$ is independently C$_2$-C$_6$ alidiyl, wherein the alidiyl chain is optionally interrupted by —C(R$^{110}$)$_2$—, —C(R$^{110}$)$_2$C(R$^{110}$)$_2$—, —C(R$^{110}$)C(R$^{110}$)—, —C(R$^{110}$)$_2$O—, —C(R$^{110}$)$_2$NR$^{110}$—, —C≡C—, —O—, —S—, —N(R$^{100}$)CO—, —N(R$^{100}$)CO$_2$—, —NR$^{110}$—, —CON(R$^{100}$)—, —CO—, —CO$_2$—, —O(C=O)—, —O(C=O)N(R$^{100}$)—, —SO$_2$—, —N(R$^{100}$)SO$_2$—, or —SO$_2$N(R$^{100}$)—;

each R$^{70}$ is independently hydrogen, halogen, nitro, aryl, heteroaryl, heterocyclyl, —Z, —Y—Z, or —X—Y—Z, wherein the aryl, heteroaryl, and heterocyclyl, are each optionally substituted with 1 to 4 R$^{7a}$, wherein each R$^{70a}$ is independently aryloxy, aralkyloxy, aryloxyalkyl, aryl-C$_0$-C$_6$ alkylcarboxy, C(R$^{110}$)=C(R$^{11}$)—COOH, oxo, —Z, —Y'—Z, or —X—Y—Z, wherein each R$^{70a}$ is optionally substituted with 1 to 4 R$^{80}$, and wherein each R$^{80}$ is independently halogen, C$_1$-C$_6$ alkyl, C$_1$-C$_6$ alkoxy, C$_1$-C$_8$S haloalkyl, C$_1$-C$_8$ haloalkyl(OR$^{110}$), C$_0$-C$_6$ alkylOR$^{110}$, C$_0$-C$_6$ alkylCON(R$^{110}$)$_2$, C$_0$-C$_6$ alkylCOR$^{110}$, C$_0$-C$_6$ alkylCOOR$^{110}$, or C$_0$-C$_6$ alkylSO$_2$R$^{110}$;

each R$^{100}$ is independently —R$^{110}$, —C(=O)R$^{110}$, —CO$_2$R$^{110}$, or —SO$_2$R$^{110}$;

each R$^{110}$ is independently -hydrogen, —C$_1$-C$_6$ alkyl, C$_2$-C$_6$ alkenyl, —C$_1$-C$_6$ alkynyl, —C$_1$-C$_6$ haloalkyl, or —N(R$^{12}$)$_2$, wherein any of R$^{110}$ is optionally substituted with 1 to 4 radicals of R$^{120}$;

each R$^{120}$ is independently halogen, cyano, nitro, oxo, —B(OR$^{130}$), C$_0$-C$_6$ alkylN(R$^{13}$)$_2$, C$_1$-C$_6$ haloalkyl, C$_1$-C$_6$ alkyl, C$_1$-C$_6$ alkoxy, (C$_0$-C$_6$ alkyl)C=O(OR$^{130}$), C$_0$-C$_6$ alkylOR$^{130}$, C$_0$-C$_6$ alkylCOR$^{130}$, C$_0$-C$_6$alkylSO$_2$R$^{130}$, C$_0$-C$_6$alkylCON(R$^{13}$)$_2$, C$_0$-C$_6$alkylCONR$^{130}$OR$^{130}$, C$_0$-C$_6$alkylSO$_2$N(R$^{130}$)$_2$, C$_0$-C$_6$ alkylSR$^{130}$, C$_0$-C$_6$ haloalkylOR$^{130}$, C$_0$-C$_6$ alkylCN, —C$_0$-C$_6$ alkyN(R$^{13}$)$_2$, —NR$^{13}$SO$_2$R$^{13}$, or —OC$_{0-6}$ alkyl-COOR$^{130}$;

each R$^{130}$ is independently hydrogen, C$_1$-C$_6$ alkyl, C$_2$-C$_6$ alkenyl, or C$_2$-C$_6$ alkynyl;

each R$^{140}$ is independently C$_1$-C$_6$ alkyl, C$_1$-C$_6$ alkoxy, halogen, C$_1$-C$_6$ haloalkyl, C$_0$-C$_6$ alkylCON(R$^{110}$)$_2$, C$_0$-C$_6$ alkylCONR$^{110}$R$^{10}$, C$_0$-C$_6$ alkylOR$^{110}$, or C$_0$-C$_6$ alkyl-COOR$^{110}$; and each R$^{150}$ is independently hydrogen, halogen, OR$^{130}$, (C$_1$-C$_6$) alkyl or (C$_1$-C$_6$) haloalkyl, wherein
each alkyl is optionally substituted with at least one group which are each independently halogen, cyano, nitro, azido, OR$^{130}$, C(O)R$^{130}$, C(O)OR$^{13}$C(O)N(R$^{130}$)$_2$, N(R$^{130}$)$_2$, N(R$^{130}$)C(O)R$^{13}$, N(R$^{130}$)S(O)$_2$R$^{13}$, —OC(O)OR$^{130}$, OC(O)N(R$^{130}$)$_2$, N(R$^{130}$)C(O)OR$^{130}$, N(R$^{130}$)C(O)N(R$^{130}$), SR$^{130}$, S(O)R$^{130}$, S(O)$_2$R', or S(O)$_2$N(R$^{130}$)$_2$; or two R$^{150}$ (bonded to same or different atoms) can be taken together to form a C$_3$-C$_6$ cycloalkyl;

each X is independently —O—, —S—, or —N(R$^{100}$)—;

each Y is independently —[C(R$^{150}$)$_2$]$_p$—, or —C$_2$-C$_6$ alkenyl, wherein p is 1, 2, 3, 4, 5, or 6;

each Y' is independently —[C(R$^{150}$)$_2$]$_p$—, —C$_2$-C$_6$ alkenyl C$_3$-C$_8$ cycloalkyl, or heterocyclyl, wherein the cycloalkyl or heterocyclyl is optionally substituted with 1 to 3 Z groups;

each Z is independently —H, halogen, —OR$^{110}$, —SR$^{110}$, —C(=O)R$^{110}$, —C(=O)OR$^{110}$, —C(=O)N(R$^{110}$)$_2$, —N(R$^{100}$)$_2$, —N$_3$, —NO$_2$, —C(=N—OH)R$^{110}$, —C(=S)N(R$^{110}$)$_2$, —CN, —S(=O)R$^{110}$, —S(=O)N(R$^{110}$)$_2$, —S(=O)OR$^{110}$, —S(=O)$_2$R$^{110}$, S(=O)$_2$N(R$^{110}$)$_2$, —NR$^{110}$COR$^{110}$, —N(R$^{110}$)C(=O)N(R$^{110}$)$_2$, —N(R$^{110}$)COOR$^{110}$, —N(R$^{110}$)S(=O)$_2$R$^{110}$, —C(=O)N(R$^{110}$)N(R$^{110}$)$_2$, —C(=O)N(R$^{110}$)(OR$^{110}$), —OC(=O)—R$^{110}$, —OC(=O)—OR$^{110}$, or —OC(=O)—N(R$^{110}$)$_2$; and each m and n is independently 0, 1, 2, 3, 4, 5, or 6.

In some embodiments of any of the foregoing methods, LXRβ agonist is any compound described herein or a pharmaceutically acceptable salt thereof. In some embodiments of any of the foregoing methods, the LXRβ agonist is a compound of any one of Formula I-XXXVI or a pharmaceutically acceptable salt thereof. In some embodiments of any of the foregoing methods, LXRβ agonist is any one of compounds 1-826 or a pharmaceutically acceptable salt thereof. In some embodiments of any of the foregoing methods, the LXR agonist is compound 682, compound 692, compound 705, compound 718, or compound 719, or a pharmaceutically acceptable salt thereof.

In certain embodiments of any of the foregoing methods, the cancer is a drug resistant cancer or has failed to respond to a prior therapy (e.g., a cancer resistant to, or a cancer that has failed to respond to prior treatment with, vemurafenib, dacarbazine, a CTLA4 inhibitor, a PD1 inhibitor, interferon therapy, a BRAF inhibitor, a MEK inhibitor, radiotherapy, temozolimide, irinotecan, a CAR-T therapy, herceptin, perjeta, tamoxifen, xeloda, docetaxol, platinum agents such as carboplatin, taxanes such as paclitaxel and docetaxel, ALK inhibitors, MET inhibitors, alimta, abraxane, adriamycin, gemcitabine, avastin, halaven, neratinib, a PARP inhibitor, ARN810, an mTOR inhibitor, topotecan, gemzar, a VEGFR2 inhibitor, a folate receptor antagonist, demcizumab, fosbretabulin, or a PDL1 inhibitor).

In some embodiments of any of the foregoing methods, the cancer is metastatic. The cancer can include cells exhibiting migration and/or invasion of migrating cells and/or include cells exhibiting endothelial recruitment and/or angiogenesis. In some embodiments, the cancer is a cell migration cancer. In some embodiments, the cell migration cancer is a non-metastatic cell migration cancer.

The cancer can be a cancer spread via seeding the surface of the peritoneal, pleural, pericardial, or subarachnoid spaces. Alternatively, the cancer can be a cancer spread via the lymphatic system, or a cancer spread hematogenously.

In some embodiments, the cancer is a cell migration cancer that is a non-metastatic cell migration cancer, such as ovarian cancer, mesothelioma, or primary lung cancer.

In certain embodiments, the LXR agonist increases the expression level of ApoE at least 2.5-fold in vitro. In some embodiments, the LXRβ agonist is selective for LXRβ over LXRα. In other embodiments, the LXRβ agonist has activity for LXRβ that is at least 2.5-fold greater than the activity of the agonist for LXRα. In some embodiments, the LXRβ agonist has activity for LXRβ that is at least 10-fold greater than the activity of the agonist for LXRα. In some embodiments, the LXRβ agonist has activity for LXRβ that is at least 100-fold greater than the activity of the agonist for LXRα. In some embodiments, the LXR agonist has activity for LXRβ that is at least within 2.5-fold of the activity of the agonist for LXRα.

In some embodiments of any of the foregoing methods, the cancer is breast cancer such as triple negative breast cancer, colon cancer, renal cell cancer, non-small cell lung cancer, hepatocellular carcinoma, gastric cancer, ovarian cancer, pancreatic cancer, esophageal cancer, prostate cancer, sarcoma, glioblastoma, diffuse large B-cell lymphoma, leukemia (e.g., acute myeloid leukemia), or melanoma. In some embodiments of any of the foregoing methods, the cancer is melanoma. In some embodiments of any of the foregoing methods, the cancer is breast cancer. In some embodiments of any of the foregoing methods, the cancer is renal cell cancer. In some embodiments of any of the foregoing methods, the cancer is pancreatic cancer. In some embodiments of any of the foregoing methods, the cancer is non-small cell lung cancer. In some embodiments of any of the foregoing methods, the cancer is colon cancer. In some embodiments of any of the foregoing methods, the cancer is ovarian cancer. In some embodiments of any of the foregoing methods, the cancer is glioblastoma. In some embodiments, the cancer is breast cancer. In some embodiments, the cancer is prostate cancer. In some embodiments, the cancer is diffuse large B-cell lymphoma. In some embodiments, the cancer is leukemia (e.g., acute myeloid leukemia).

In particular embodiments, the cancer is melanoma (e.g., metastatic melanoma) that is resistant to, or has failed to respond to prior treatment with, vemurafenib, dacarbazine, interferon therapy, a CTLA-4 inhibitor, a BRAF inhibitor, a MEK inhibitor, a PD1 inhibitor, a PDL-1 inhibitor, and/or a CAR-T therapy. In some embodiments, the cancer is glioblastoma that is resistant to, or has failed to respond to prior treatment with, temozolimide, radiotherapy, avastin, irinotecan, a VEGFR2 inhibitor, a CAR-T therapy, and/or an mTOR inhibitor. In some embodiments, the cancer is non-small cell lung cancer such as metastatic non-small cell lung cancer (e.g., EGFR-wild type non-small cell lung cancer and/or squamous non-small cell lung cancer) that is resistant to, or has failed to respond to prior treatment with, an EGFR inhibitor, platinum agents (e.g., carboplatin), avastin, an ALK inhibitor, a MET inhibitor, a taxane (e.g., paclitaxel and/or doceltaxel), gemzar, alimta, radiotherapy, a PD1 inhibitor, a PDL1 inhibitor, and/or a CAR-T therapy. In some embodiments, the cancer is a breast cancer (e.g., triple negative breast cancer) that is resistant to, or has failed to respond to prior treatment with, herceptin, perjeta, tamoxifen, xeloda, docetaxel, carboplatin, paclitaxel, abraxane, adriamycin, gemcitabine, avastin, halaven, neratinib, a PARP inhibitor, a PD1 inhibitor, a PDL1 inhibitor, a CAR-T therapy, ARN810, and/or an mTOR inhibitor. In some embodiments, the cancer is ovarian cancer (e.g., metastatic ovarian cancer) that is resistant to, or has failed to respond to prior treatment with, a PARP inhibitor, avastin, platinum agents such as carboplatin, paclitaxel, docetaxel, topotecan, gemzar, a VEGR2 inhibitor, a folate receptor antagonist, a PD1 inhibitor, a PDL1 inhibitor, a CAR-T therapy, demcizumab, and/or fosbretabulin.

As described herein, there is a correlation between responsiveness to an LXRβ agonist and expression of LRP1 in a tumor sample. Accordingly, in some embodiments of any of the foregoing methods, the cancer has increased expression of LRP1 compared to a predetermined level (e.g., a level determined to correlate with efficacy and/or the level in sample from a subject that does not respond to LXRβ agonist treatment.

Chemical Terms

As used herein, the term "compound," is meant to include all stereoisomers, geometric isomers, tautomers, and isotopically enriched forms of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins and C=N double bonds can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure may also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. Herein a phrase of the form "optionally substituted X" (e.g., optionally substituted alkyl) is intended to be equivalent to "X, wherein X is optionally substituted" (e.g., "alkyl, wherein the alkyl is optionally substituted"). It is not intended to mean that the feature "X" (e.g., alkyl) per se is optional.

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 7, from 1 to 11, or from 1 to 21 carbons. In some embodiments, the alkyl group is further substituted with 1, 2, 3, or 4 substituents as described herein.

Non-limiting examples of optionally substituted acyl groups include, alkoxycarbonyl, alkoxycarbonylacyl, arylalkoxycarbonyl, aryloyl, carbamoyl, carboxyaldehyde, (heterocyclyl) imino, and (heterocyclyl)oyl: The "alkoxycarbonyl" group, which as used herein, represents an alkoxy, as defined herein, attached to the parent molecular group through a carbonyl atom (e.g., —C(O)—OR, where R is H or an optionally substituted $C_{1-6}$, $C_{1-10}$, or $C_{1-20}$ alkyl group). Exemplary unsubstituted alkoxycarbonyl include from 1 to 21 carbons (e.g., from 1 to 11 or from 1 to 7 carbons). In some embodiments, the alkoxy group is further substituted with 1, 2, 3, or 4 substituents as described herein.

The "alkoxycarbonylacyl" group, which as used herein, represents an acyl group, as defined herein, that is substituted with an alkoxycarbonyl group, as defined herein (e.g., —C(O)-alkyl-C(O)—OR, where R is an optionally substituted $C_{1-6}$, $C_{1-10}$, or $C_{1-20}$ alkyl group). Exemplary unsubstituted alkoxycarbonylacyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ acyl, $C_{1-10}$ alkoxycarbonyl-$C_{1-10}$ acyl, or $C_{1-20}$ alkoxycarbonyl-$C_{1-20}$ acyl). In some embodiments, each alkoxy and alkyl group is further independently substituted with 1, 2, 3, or 4 substituents, as described herein (e.g., a hydroxy group) for each group.

The "arylalkoxycarbonyl" group, which as used herein, represents an arylalkoxy group, as defined herein, attached to the parent molecular group through a carbonyl (e.g., —C(O)—O-alkyl-aryl). Exemplary unsubstituted arylalkoxy groups include from 8 to 31 carbons (e.g., from 8 to 17 or from 8 to 21 carbons, such as $C_{6-10}$ aryl-$C_{1-6}$ alkoxy-carbonyl, $C_{6-10}$ aryl-$C_{1-10}$ alkoxy-carbonyl, or $C_{6-10}$ aryl-$C_{1-20}$ alkoxy-carbonyl). In some embodiments, the arylalkoxycarbonyl group can be substituted with 1, 2, 3, or 4 substituents as defined herein.

The "aryloyl" group, which as used herein, represents an aryl group, as defined herein, that is attached to the parent molecular group through a carbonyl group. Exemplary unsubstituted aryloyl groups are of 7 to 11 carbons. In some embodiments, the aryl group can be substituted with 1, 2, 3, or 4 substituents as defined herein.

The "carbamoyl" group, which as used herein, represents —C(O)—N($R^{N1}$)$_2$, where the meaning of each $R^{N1}$ is found in the definition of "amino" provided herein.

The "carboxyaldehyde" group, which as used herein, represents an acyl group having the structure —CHO.

The "(heterocyclyl) imino" group, which as used herein, represents a heterocyclyl group, as defined herein, attached to the parent molecular group through an imino group.

In some embodiments, the heterocyclyl group can be substituted with 1, 2, 3, or 4 substituent groups as defined herein.

The "(heterocyclyl)oyl" group, which as used herein, represents a heterocyclyl group, as defined herein, attached to the parent molecular group through a carbonyl group. In some embodiments, the heterocyclyl group can be substituted with 1, 2, 3, or 4 substituent groups as defined herein.

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, and neopentyl, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N($R^{N1}$)$_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —CO$_2$$R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —C(O)NR$^{B'}$R$^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2$R$^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —SO$_2$NR$^{E'}$R$^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)R$^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N0}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —NR$^{H'}$C(O)R$^{I'}$, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —NR$^{J'}$C(O)OR$^{K'}$, wherein $R^{J'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, and isopropylene. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the alkylene can be further substituted with 1, 2, 3, or 4 substituent groups as defined herein for an alkyl group.

Non-limiting examples of optionally substituted alkyl and alkylene groups include acylaminoalkyl, acyloxyalkyl, alkoxyalkyl, alkoxycarbonylalkyl, alkylsulfinyl, alkylsulfinylalkyl, aminoalkyl, carbamoylalkyl, carboxyalkyl, carboxyaminoalkyl, haloalkyl, hydroxyalkyl, perfluoroalkyl, and sulfoalkyl:

The "acylaminoalkyl" group, which as used herein, represents an acyl group, as defined herein, attached to an amino group that is in turn attached to the parent molecular group through an alkylene group, as defined herein (i.e., -alkyl-N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylaminoalkyl groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkylene group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}{}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The "acyloxyalkyl" group, which as used herein, represents an acyl group, as defined herein, attached to an oxygen atom that in turn is attached to the parent molecular group though an alkylene group (i.e., -alkyl-O—C(O)—R, where R is H or an optionally substituted $C_{1-6}$, $C_{1-10}$, or $C_{1-20}$ alkyl group). Exemplary unsubstituted acyloxyalkyl groups include from 1 to 21 carbons (e.g., from 1 to 7 or from 1 to 11 carbons). In some embodiments, the alkylene group is, independently, further substituted with 1, 2, 3, or 4 substituents as described herein.

The "alkoxyalkyl" group, which as used herein, represents an alkyl group that is substituted with an alkoxy group. Exemplary unsubstituted alkoxyalkyl groups include between 2 to 40 carbons (e.g., from 2 to 12 or from 2 to 20 carbons, such as $C_{1-6}$ alkoxy-$C_{1-6}$ alkyl, $C_{1-10}$ alkoxy-$C_{1-10}$ alkyl, or $C_{1-20}$ alkoxy-$C_{1-20}$ alkyl). In some embodiments, the alkyl and the alkoxy each can be further substituted with 1, 2, 3, or 4 substituent groups as defined herein for the respective group.

The "alkoxycarbonylalkyl" group, which as used herein, represents an alkyl group, as defined herein, that is substituted with an alkoxycarbonyl group, as defined herein (e.g., -alkyl-C(O)—OR, where R is an optionally substituted $C_{1-20}$, $C_{1-10}$, or $C_{1-6}$ alkyl group). Exemplary unsubstituted alkoxycarbonylalkyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkyl, $C_{1-10}$ alkoxycarbonyl-$C_{1-10}$ alkyl, or $C_{1-20}$ alkoxycarbonyl-$C_{1-20}$ alkyl). In some embodiments, each alkyl and alkoxy group is further independently substituted with 1, 2, 3, or 4 substituents as described herein (e.g., a hydroxy group).

The "alkylsulfinylalkyl" group, which as used herein, represents an alkyl group, as defined herein, substituted with an alkylsulfinyl group. Exemplary unsubstituted alkylsulfinylalkyl groups are from 2 to 12, from 2 to 20, or from 2 to 40 carbons. In some embodiments, each alkyl group can be further substituted with 1, 2, 3, or 4 substituent groups as defined herein.

The "aminoalkyl" group, which as used herein, represents an alkyl group, as defined herein, substituted with an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "carbamoylalkyl" group, which as used herein, represents an alkyl group, as defined herein, substituted with a carbamoyl group, as defined herein. The alkyl group can be further substituted with 1, 2, 3, or 4 substituent groups as described herein.

The "carboxyalkyl" group, which as used herein, represents an alkyl group, as defined herein, substituted with a carboxy group, as defined herein. The alkyl group can be further substituted with 1, 2, 3, or 4 substituent groups as described herein, and the carboxy group can be optionally substituted with one or more O-protecting groups.

The "carboxyaminoalkyl" group, which as used herein, represents an aminoalkyl group, as defined herein, substituted with a carboxy, as defined herein. The carboxy, alkyl, and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group, and/or an O-protecting group).

The "haloalkyl" group, which as used herein, represents an alkyl group, as defined herein, substituted with a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —$CF_3$), —$CHF_2$, —$CH_2F$, —$CCl_3$, —$CH_2CH_2Br$, —$CH_2CH(CH_2CH_2Br)CH_3$, and —$CHICH_3$. In some embodiments, the haloalkyl group can be further substituted with 1, 2, 3, or 4 substituent groups as described herein for alkyl groups.

The "hydroxyalkyl" group, which as used herein, represents an alkyl group, as defined herein, substituted with one to three hydroxy groups, with the proviso that no more than one hydroxy group may be attached to a single carbon atom of the alkyl group, and is exemplified by hydroxymethyl and dihydroxypropyl. In some embodiments, the hydroxyalkyl group can be substituted with 1, 2, 3, or 4 substituent groups (e.g., O-protecting groups) as defined herein for an alkyl.

The "perfluoroalkyl" group, which as used herein, represents an alkyl group, as defined herein, where each hydrogen radical bound to the alkyl group has been replaced by a fluoride radical. Perfluoroalkyl groups are exemplified by trifluoromethyl.

The "sulfoalkyl" group, which as used herein, represents an alkyl group, as defined herein, substituted with a sulfo group of —$SO_3H$. In some embodiments, the alkyl group can be further substituted with 1, 2, 3, or 4 substituent groups as described herein, and the sulfo group can be further substituted with one or more O-protecting groups (e.g., as described herein).

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

Non-limiting examples of optionally substituted alkenyl groups include, alkoxycarbonylalkenyl, aminoalkenyl, and hydroxyalkenyl:

The "alkoxycarbonylalkenyl" group, which as used herein, represents an alkenyl group, as defined herein, that is substituted with an alkoxycarbonyl group, as defined herein (e.g., -alkenyl-C(O)—OR, where R is an optionally substituted $C_{1-20}$, $C_{1-10}$, or $C_{1-6}$ alkyl group). Exemplary unsubstituted alkoxycarbonylalkenyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkenyl, $C_{1-10}$ alkoxycarbonyl-$C_{2-10}$ alkenyl, or $C_{1-20}$ alkoxycarbonyl-$C_{2-20}$ alkenyl). In some embodiments, each alkyl, alkenyl, and alkoxy group is further independently substituted with 1, 2, 3, or 4 substituents as described herein (e.g., a hydroxy group).

The "aminoalkenyl" group, which as used herein, represents an alkenyl group, as defined herein, substituted with an amino group, as defined herein. The alkenyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "hydroxyalkenyl" group, which as used herein, represents an alkenyl group, as defined herein, substituted with one to three hydroxy groups, with the proviso that no more than one hydroxy group may be attached to a single carbon atom of the alkyl group, and is exemplified by dihydroxypropenyl, and hydroxyisopentenyl. In some embodiments, the hydroxyalkenyl group can be substituted with 1, 2, 3, or 4 substituent groups (e.g., O-protecting groups) as defined herein for an alkyl.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, and 1-propynyl. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

Non-limiting examples of optionally substituted alkynyl groups include alkoxycarbonylalkynyl, aminoalkynyl, and hydroxyalkynyl:

The "alkoxycarbonylalkynyl" group, which as used herein, represents an alkynyl group, as defined herein, that is substituted with an alkoxycarbonyl group, as defined herein (e.g., -alkynyl-C(O)—OR, where R is an optionally substituted $C_{1-20}$, $C_{1-10}$, or $C_{1-6}$ alkyl group). Exemplary unsubstituted alkoxycarbonylalkynyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkynyl, $C_{1-10}$ alkoxycarbonyl-$C_{2-10}$ alkynyl, or $C_{1-20}$ alkoxycarbonyl-$C_{2-20}$ alkynyl). In some embodiments, each alkyl, alkynyl, and alkoxy group is further independently substituted with 1, 2, 3, or 4 substituents as described herein (e.g., a hydroxy group).

The "aminoalkynyl" group, which as used herein, represents an alkynyl group, as defined herein, substituted with an amino group, as defined herein. The alkynyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "hydroxyalkynyl" group, which as used herein, represents an alkynyl group, as defined herein, substituted with one to three hydroxy groups, with the proviso that no more than one hydroxy group may be attached to a single carbon atom of the alkyl group. In some embodiments, the hydroxyalkynyl group can be substituted with 1, 2, 3, or 4 substituent groups (e.g., O-protecting groups) as defined herein for an alkyl.

The term "amidine," as used herein, represents a —C(=NH)$NH_2$ group.

The term "amino," as used herein, represents —N($R^{N1}$)$_2$, wherein each $R^{N1}$ is, independently, H, OH, $NO_2$, N($R^{N2}$)$_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the invention can be an unsubstituted amino (i.e., —$NH_2$) or a substituted amino (i.e., —N($R^{N1}$)$_2$). In a preferred embodiment, amino is —$NH_2$ or —$NHR^{N1}$, wherein $R^{N1}$ is, independently, OH, $NO_2$, $NH_2$, $NR^{N2}{}_2$, $SO_2OR^{N2}$, $SO_2R^{N2}$, $SOR^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N2}$ can be H, $C_{1-20}$ alkyl (e.g., $C_{1-6}$ alkyl), or $C_{6-10}$ aryl.

Non-limiting examples of optionally substituted amino groups include acylamino and carbamyl:

The "acylamino" group, which as used herein, represents an acyl group, as defined herein, attached to the parent molecular group though an amino group, as defined herein (i.e., —N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}{}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The "carbamyl" group, which as used herein, refers to a carbamate group having the structure —NR$^{N1}$C(=O)OR or —OC(=O)N(R$^{N1}$)$_2$, where the meaning of each R$^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "amino acid," as described herein, refers to a molecule having a side chain, an amino group, and an acid group (e.g., a carboxy group of —CO$_2$H or a sulfo group of —SO$_3$H), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N(R$^{N1}$)$_2$, where R$^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —CO$_2$R$^{A'}$, where R$^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2$R$^{D'}$, where R$^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (19) —NR$^{H'}$C(O)R$^{I'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (20) —NR$^{J'}$C(O)OR$^{K'}$, wherein R$^{J'}$ is selected from the group consisting of (a1) hydrogen and (b1) $C_{1-6}$ alkyl, and R$^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N0}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; and (21) amidine. In some embodiments, each of these groups can be further substituted as described herein.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, and indenyl, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) alkyl, (b) $C_{6-10}$ aryl, and (c) alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "arylalkyl" group, which as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as $C_{1-6}$ alk-$C_{6-10}$ aryl, C-10 alk-$C_{6-10}$ aryl, or $C_{1-20}$ alk-$C_6$ to aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "azido" represents an —$N_3$ group, which can also be represented as —N=N=N.

The term "bicyclic," as used herein, refer to a structure having two rings, which may be aromatic or non-aromatic. Bicyclic structures include spirocyclyl groups, as defined herein, and two rings that share one or more bridges, where such bridges can include one atom or a chain including two, three, or more atoms. Exemplary bicyclic groups include a bicyclic carbocyclyl group, where the first and second rings are carbocyclyl groups, as defined herein; a bicyclic aryl groups, where the first and second rings are aryl groups, as defined herein; bicyclic heterocyclyl groups, where the first ring is a heterocyclyl group and the second ring is a carbocyclyl (e.g., aryl) or heterocyclyl (e.g., heteroaryl) group; and bicyclic heteroaryl groups, where the first ring is a heteroaryl group and the second ring is a carbocyclyl (e.g., aryl) or heterocyclyl (e.g., heteroaryl) group. In some embodiments, the bicyclic group can be substituted with 1, 2, 3, or 4 substituents as defined herein for cycloalkyl, heterocyclyl, and aryl groups.

The term "boranyl," as used herein, represents —$B(R^{B1})_3$, where each $R^{B1}$ is, independently, selected from the group consisting of H and optionally substituted alkyl. In some embodiments, the boranyl group can be substituted with 1, 2, 3, or 4 substituents as defined herein for alkyl.

The terms "carbocyclic" and "carbocyclyl," as used herein, refer to an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbonyl," as used herein, represents a C(O) group, which can also be represented as C=O.

The term "carboxy," as used herein, means —$CO_2H$.

The term "cyano," as used herein, represents an —CN group.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, and bicycle heptyl.

When the cycloalkyl group includes one carbon-carbon double bond, the cycloalkyl group can be referred to as a "cycloalkenyl" group. Exemplary cycloalkenyl groups include cyclopentenyl, and cyclohexenyl. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "cycloalkylalkyl" group, which as used herein, represents a cycloalkyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "diastereomer," as used herein means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "heteroalkyl," as used herein, refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups. The terms "heteroalkenyl" and heteroalkynyl," as used herein refer to alkenyl and alkynyl groups, as defined herein, respectively, in which one or two of the constituent carbon atoms have each been replaced by nitrogen, oxygen, or sulfur. In some embodiments, the heteroalkenyl and heteroalkynyl groups can be further substituted with 1, 2, 3, or 4 substituent groups as described herein for alkyl groups.

Non-limiting examples of optionally substituted heteroalkyl, heteroalkenyl, and heteroalkynyl groups include acyloxy, alkenyloxy, alkoxy, alkoxyalkoxy, alkoxycarbonylalkoxy, alkynyloxy, aminoalkoxy, arylalkoxy, carboxyalkoxy, cycloalkoxy, haloalkoxy, (heterocyclyl)oxy, perfluoroalkoxy, thioalkoxy, and thioheterocyclylalkyl:

The "acyloxy" group, which as used herein, represents an acyl group, as defined herein, attached to the parent molecular group though an oxygen atom (i.e., —O—C(O)—R, where R is H or an optionally substituted $C_{1-6}$, $C_{1-10}$, or $C_{1-20}$ alkyl group). Exemplary unsubstituted acyloxy groups include from 1 to 21 carbons (e.g., from 1 to 7 or from 1 to 11 carbons). In some embodiments, the alkyl group is further substituted with 1, 2, 3, or 4 substituents as described herein.

The "alkenyloxy" group, which as used here, represents a chemical substituent of formula —OR, where R is a $C_{2-20}$ alkenyl group (e.g., $C_{2-6}$ or $C_{2-10}$ alkenyl), unless otherwise specified. Exemplary alkenyloxy groups include ethenyloxy, and propenyloxy. In some embodiments, the alkenyl group can be further substituted with 1, 2, 3, or 4 substituent groups as defined herein (e.g., a hydroxy group).

The "alkoxy" group, which as used herein, represents a chemical substituent of formula —OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), and t-butoxy. In some embodiments, the alkyl group can be further substituted with 1, 2, 3, or 4 substituent groups as defined herein (e.g., hydroxy or alkoxy).

The "alkoxyalkoxy" group, which as used herein, represents an alkoxy group that is substituted with an alkoxy group. Exemplary unsubstituted alkoxyalkoxy groups include between 2 to 40 carbons (e.g., from 2 to 12 or from 2 to 20 carbons, such as $C_{1-6}$ alkoxy-$C_{1-6}$ alkoxy, $C_{1-10}$ alkoxy-$C_{1-10}$ alkoxy, or $C_{1-20}$ alkoxy-$C_{1-20}$ alkoxy). In some embodiments, the each alkoxy group can be further substituted with 1, 2, 3, or 4 substituent groups as defined herein.

The "alkoxycarbonylalkoxy" group, which as used herein, represents an alkoxy group, as defined herein, that is substituted with an alkoxycarbonyl group, as defined herein (e.g., —O-alkyl-C(O)—OR, where R is an optionally substituted $C_{1-6}$, $C_{1-10}$, or $C_{1-20}$ alkyl group). Exemplary unsubstituted alkoxycarbonylalkoxy include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkoxy, $C_{1-10}$ alkoxycarbonyl-$C_{1-10}$ alkoxy, or $C_{1-20}$ alkoxycarbonyl-$C_{1-20}$ alkoxy). In some embodiments, each alkoxy group is further independently substituted with 1, 2, 3, or 4 substituents, as described herein (e.g., a hydroxy group).

The "alkynyloxy" group, which as used herein, represents a chemical substituent of formula —OR, where R is a $C_{2-20}$ alkynyl group (e.g., $C_{2-6}$ or $C_{2-10}$ alkynyl), unless otherwise specified. Exemplary alkynyloxy groups include ethynyloxy, and propynyloxy. In some embodiments, the alkynyl group can be further substituted with 1, 2, 3, or 4 substituent groups as defined herein (e.g., a hydroxy group).

The "aminoalkoxy" group, which as used herein, represents an alkoxy group, as defined herein, substituted with an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy).

The "arylalkoxy" group, which as used herein, represents an alkaryl group, as defined herein, attached to the parent molecular group through an oxygen atom. Exemplary unsubstituted arylalkoxy groups include from 7 to 30 carbons (e.g., from 7 to 16 or from 7 to 20 carbons, such as $C_{6-10}$ aryl-$C_{1-6}$ alkoxy, $C_{6-10}$ aryl-$C_{1-10}$ alkoxy, or $C_{6-10}$ aryl-$C_{1-20}$ alkoxy). In some embodiments, the arylalkoxy group can be substituted with 1, 2, 3, or 4 substituents as defined herein.

The "aryloxy" group, which as used herein, represents a chemical substituent of formula —OR', where R' is an aryl group of 6 to 18 carbons, unless otherwise specified. In some embodiments, the aryl group can be substituted with 1, 2, 3, or 4 substituents as defined herein.

The "carboxyalkoxy" group, which as used herein, represents an alkoxy group, as defined herein, substituted with a carboxy group, as defined herein. The alkoxy group can be further substituted with 1, 2, 3, or 4 substituent groups as described herein for the alkyl group, and the carboxy group can be optionally substituted with one or more O-protecting groups.

The "cycloalkoxy" group, which as used herein, represents a chemical substituent of formula —OR, where R is a $C_{3-8}$ cycloalkyl group, as defined herein, unless otherwise specified. The cycloalkyl group can be further substituted with 1, 2, 3, or 4 substituent groups as described herein. Exemplary unsubstituted cycloalkoxy groups are from 3 to 8 carbons. In some embodiment, the cycloalkyl group can be further substituted with 1, 2, 3, or 4 substituent groups as described herein.

The "haloalkoxy" group, which as used herein, represents an alkoxy group, as defined herein, substituted with a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —$OCF_3$), —$OCHF_2$, —$OCH_2F$, —$OCCl_3$, —$OCH_2CH_2Br$, —$OCH_2CH(CH_2CH_2Br)CH_3$, and —$OCHICH_3$. In some embodiments, the haloalkoxy group can be further substituted with 1, 2, 3, or 4 substituent groups as described herein for alkyl groups.

The "(heterocyclyl)oxy" group, which as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The "perfluoroalkoxy" group, which as used herein, represents an alkoxy group, as defined herein, where each hydrogen radical bound to the alkoxy group has been replaced by a fluoride radical. Perfluoroalkoxy groups are exemplified by trifluoromethoxy.

The "alkylsulfinyl" group, which as used herein, represents an alkyl group attached to the parent molecular group through an —S(O)— group. Exemplary unsubstituted alkylsulfinyl groups are from 1 to 6, from 1 to 10, or from 1 to 20 carbons. In some embodiments, the alkyl group can be further substituted with 1, 2, 3, or 4 substituent groups as defined herein.

The "thioarylalkyl" group, which as used herein, represents a chemical substituent of formula —SR, where R is an arylalkyl group. In some embodiments, the arylalkyl group can be further substituted with 1, 2, 3, or 4 substituent groups as described herein.

The "thioalkoxy" group as used herein, represents a chemical substituent of formula —SR, where R is an alkyl group, as defined herein. In some embodiments, the alkyl group can be further substituted with 1, 2, 3, or 4 substituent groups as described herein.

The "thioheterocyclylalkyl" group, which as used herein, represents a chemical substituent of formula —SR, where R is an heterocyclylalkyl group. In some embodiments, the heterocyclylalkyl group can be further substituted with 1, 2, 3, or 4 substituent groups as described herein.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heteroarylalkyl" refers to a heteroaryl group, as defined herein, attached to the parent molecular group through an alkylene group, as defined herein. Exemplary unsubstituted heteroarylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Heteroarylalkyl groups are a subset of heterocyclylalkyl groups.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, and benzothienyl. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, and benzothienyl, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

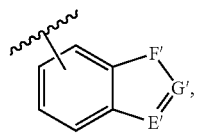

where
E' is selected from the group consisting of —N— and —CH—; F' is selected from the group consisting of —N=CH—, —NH—CH$_2$—, —NH—C(O)—, —NH—, —CH=N—, —CH$_2$—NH—, —C(O)—NH—, —CH=CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{1-6}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl)imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "heterocyclylalkyl" group, which as used herein, represents a heterocyclyl group, as defined herein, attached to the parent molecular group through an alkylene group, as defined herein. Exemplary unsubstituted heterocyclylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heterocyclyl, $C_{1-10}$ alk-$C_{1-12}$ heterocyclyl, or $C_{1-20}$ alk-$C_{1-12}$ heterocyclyl). In some embodiments, the alkylene and the heterocyclyl each can be further substituted with 1, 2, 3, or 4 substituent groups as defined herein for the respective group.

The term "hydrocarbon," as used herein, represents a group consisting only of carbon and hydrogen atoms.

The term "hydroxy," as used herein, represents an —OH group. In some embodiments, the hydroxy group can be substituted with 1, 2, 3, or 4 substituent groups (e.g., O-protecting groups) as defined herein for an alkyl.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, alkaryl groups such as benzyl, triphenylmethyl, and benzyloxymethyl, and silyl groups, such as trimethylsilyl. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," 3$^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, and pivaloyl; optionally substituted arylcarbonyl groups, such as benzoyl; silyl groups, such as trimethylsilyl (TMS), tert-butyldimethylsilyl (TBDMS), tri-iso-propylsilyloxymethyl (TOM), and triisopropylsilyl (TIPS); ether-forming groups with the hydroxyl, such methyl, methoxymethyl, tetrahydropyranyl, benzyl, p-methoxybenzyl, and trityl; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, and methyloxycarbonyl; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, and 3-methyl-2-butenoxycarbonyl; haloalkoxycarbonyls, such as 2-chloroethoxycarbonyl, 2-chloroethoxycarbonyl, and 2,2,2-trichloroethoxycarbonyl; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, and fluorenylmethyloxycarbonyl; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, and 2-chloro-4-nitrophenoxycarbonyl); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethyl silyl)ethoxy]ethyl; 2-trimethyl silylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenylmethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, and 1,3-dioxolane; acylal groups; and dithiane groups, such as 1,3-dithianes, and 1,3-dithiolane); carboxylic acid-protecting groups (e.g., ester groups, such as methyl ester, benzyl ester, t-butyl ester, and orthoesters; and oxazoline groups.

The term "oxo" as used herein, represents =O.

The prefix "perfluoro," as used herein, represents anyl group, as defined herein, where each hydrogen radical bound to the alkyl group has been replaced by a fluoride radical. For example, perfluoroalkyl groups are exemplified by trifluoromethyl.

The term "protected hydroxyl," as used herein, refers to an oxygen atom bound to an O-protecting group.

The term "spirocyclyl," as used herein, represents a $C_{2-7}$ alkylene diradical, both ends of which are bonded to the same carbon atom of the parent group to form a spirocyclic group, and also a $C_{1-6}$ heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfonyl," as used herein, represents an —S(O)$_2$— group.

The term "thiol," as used herein represents an —SH group.

Definitions

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

By "biological sample" or "sample" is meant a fluid or solid sample from a subject. Biological samples may include cells; nucleic acid, protein, or membrane extracts of cells; or blood or biological fluids including (e.g., plasma, serum, saliva, urine, bile). Solid biological samples include samples taken from feces, the rectum, central nervous system, bone, breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, and the thymus. Fluid biological samples include samples taken from the blood, serum, plasma, pancreatic fluid, CSF, semen, prostate fluid, seminal fluid, urine, saliva, sputum, mucus, bone marrow, lymph, and tears. Samples may be obtained by standard methods including, e.g., venous puncture and surgical biopsy. In certain embodiments, the biological sample is a blood, plasma, or serum sample. In some embodiments, the biological sample is a tumor sample from a biopsy.

The term "cancer" refers to any cancer caused by the proliferation of malignant neoplastic cells, such as tumors, neoplasms, carcinomas, sarcomas, leukemias, and lymphomas.

"Cell migration" as used in this application involves the invasion by the cancer cells into the surrounding tissue and the crossing of the vessel wall to exit the vasculature in distal organs of the cancer cell.

By "cell migration cancers" is meant cancers that migrate by invasion by the cancer cells into the surrounding tissue and the crossing of the vessel wall to exit the vasculature in distal organs of the cancer cell.

By "determining the level of a cell type" is meant the detection of a cell type by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure cell levels generally include, but are not limited to, flow cytometry and immunohistochemistry. Exemplary methods are provided herein. In some embodiments of any of the foregoing methods, the level of MDSCs and/or activated T-cells may be determined as described in Iclozan et al. Cancer Immunol. Immunother. 2013, 62(5): 909-918. In some embodiments of any of the foregoing methods, the level of MDSCs and/or activated T-cells may be determined as described in Kitano et al. Cancer Immunol. Res. 2014, 2(8); 812-821.

A cancer "determined to be drug resistant," as used herein, refers to a cancer that is drug resistant, based on unresponsiveness or decreased responsiveness to a chemotherapeutic agent, or is predicted to be drug resistant based on a prognostic assay (e.g., a gene expression assay).

By a "drug resistant" cancer is meant a cancer that does not respond, or exhibits a decreased response to, one or more chemotherapeutic agents (e.g., any agent described herein such as any compound of Table 3).

The term "effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "effective amount" does not in fact require successful treatment be achieved in a particular individual. Rather, an effective amount may be that amount that provides a particular desired pharmacological response in a significant number of subjects when administered to patients in need of such treatment. It is specifically understood that particular subjects may, in fact, be "refractory" to an "effective amount." To give but one example, a refractory subject may have a low bioavailability such that clinical efficacy is not obtainable. In some embodiments, reference to an effective amount may be a reference to an amount as measured in one or more specific tissues (e.g., a tissue affected by the disease, disorder or condition) or fluids (e.g., blood, saliva, serum, sweat, tears, urine, etc). Those of ordinary skill in the art will appreciate that, in some embodiments, an effective amount may be formulated and/or administered in a single dose. In some embodiments, an effective amount may be formulated and/or administered in a plurality of doses, for example, as part of a dosing regimen.

As used herein, the term "failed to respond to a prior therapy" or "refractory to a prior therapy," refers to a cancer that progressed despite treatment with the therapy.

By "level" is meant a level of a cell type, as compared to a reference. The reference can be any useful reference, as defined herein. By a "decreased level" or an "increased level" of a cell type is meant a decrease or increase in cell level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a cell type may be expressed in mass/vol (e.g., g/dL, mg/mL, g/mL, ng/mL) or percentage relative to total cells in a sample. In some embodiments of any of the foregoing methods, the reference is a sample from a healthy subject such as a subject that does not have cancer. In some embodiments of any of the foregoing methods, the reference is an artificial sample with a level (e.g., a level of MDSCs such as monocytic and/or granulocytic MDSCs or activated T-cells) shown beneficial in the treatment of a disorder.

As used herein, "metastatic nodule" refers to an aggregation of tumor cells in the body at a site other than the site of the original tumor.

As used herein, "metastatic tumor" refers to a tumor or cancer in which the cancer cells forming the tumor have a high potential to or have begun to, metastasize, or spread from one location to another location or locations within a subject, via the lymphatic system or via haematogenous spread, for example, creating secondary tumors within the subject. Such metastatic behavior may be indicative of malignant tumors. In some cases, metastatic behavior may be associated with an increase in cell migration and/or invasion behavior of the tumor cells.

Examples of cancers that can be defined as metastatic include but are not limited to non-small cell lung cancer, breast cancer, ovarian cancer, colorectal cancer, biliary tract cancer, bladder cancer, brain cancer including glioblastomas and medullablastomas, cervical cancer, choriocarcinoma, endometrial cancer, esophageal cancer, gastric cancer, hematological neoplasms, multiple myeloma, leukemia, intraepithelial neoplasms, liver cancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

As used herein, "migrating cancer" refers to a cancer in which the cancer cells forming the tumor migrate and subsequently grow as malignant implants at a site other than the site of the original tumor. The cancer cells migrate via seeding the surface of the peritoneal, pleural, pericardial, or subarachnoid spaces to spread into the body cavities; via invasion of the lymphatic system through invasion of lymphatic cells and transport to regional and distant lymph nodes and then to other parts of the body; via haematogenous spread through invasion of blood cells; or via invasion of the surrounding tissue. Migrating cancers include metastatic tumors and cell migration cancers, such as ovarian cancer, mesothelioma, and primary lung cancer, each of which is characterized by cellular migration.

"Non-metastatic cell migration cancer" as used herein refers to cancers that do not migrate via the lymphatic system or via haematogenous spread.

As used herein, the term "pharmaceutical composition" refers to an active compound, formulated together with one or more pharmaceutically acceptable carriers. In some embodiments, active compound is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Those of ordinary skill in the art are familiar with a variety of agents and materials useful as excipients.

The term "pharmaceutically acceptable salt," as use herein, refers to those salts of the compounds described here that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

"Predetermined level" as used herein, refers to a pre-specified particular level of one or more particular cell type, e.g., MDSCs such as monocytic and/or granulocytic MDSCs or activated T-cells. In some embodiments, a predetermined level is an absolute value or range. In some embodiments, a predetermined level is a relative value. In some embodiments, a predetermined level is the same as or different (e.g., higher or lower than) a level of one or more particular cell type in a reference, e.g., a reference tumor sample, or a level specified in a reference document such as a pharmaceutical specification.

In some embodiments, a predetermined level is an absolute level or range of one or more cell type in a sample. In some embodiments, a predetermined level is a level or range of one or more cell types in a sample relative to total level of cells in the sample. In some embodiments, a predetermined level is a level or range of one or more cell types in a sample relative to total level of cells in the sample. In some embodiments, a predetermined level is expressed as a percent.

"Progression-free survival" as used herein, refers to the length of time during and after medication or treatment during which the disease being treated (e.g., cancer) does not get worse.

"Proliferation" as used in this application involves reproduction or multiplication of similar forms (cells) due to constituting (cellular) elements.

As used herein, "slowing the spread of metastasis" refers to reducing or stopping the formation of new loci; or reducing, stopping, or reversing the tumor load.

As used herein, "slowing the spread of migrating cancer" refers to reducing or stopping the formation of new loci; or reducing, stopping, or reversing the tumor load.

The term "subject," as used herein, refers to a human or non-human animal (e.g., a mammal such as a non-human primate, horse, cow, or dog).

The term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used herein, "tumor seeding" refers to the spillage of tumor cell clusters and their subsequent growth as malignant implants at a site other than the site of the original tumor.

The term "PD-1 inhibitor," as used herein, refers to a compound such as an antibody capable of inhibiting the activity of the protein that in humans is encoded by the PDCD1 gene. Known PD-1 inhibitors include nivolumab, pembrolizumab, pidilizumab, BMS 936559, and MPDL328OA.

The term "PD-L1 inhibitor," as used herein, refers to a compound such as an antibody capable of inhibiting the activity of the protein that in humans is encoded by the CD274 gene. Known PD-L1 inhibitors include atezolizumab and MEDI4736.

The term "CTLA-4 inhibitor," as used herein, refers to a compound such as an antibody capable of inhibiting the activity of the protein that in humans is encoded by the CTLA4 gene. Known CTLA-4 inhibitors include ipilimumab.

The term "CSF-1R inhibitors," as used herein refers to a compound such as an antibody capable of inhibiting the activity of the protein that in humans is encoded by the CSF1R gene. Known CSF-1R inhibitors include pexidartinib and AZD6495.

The term "IDO inhibitor," as used herein, refers to a compound such as an antibody capable of inhibiting the activity of the protein that in humans is encoded by the IDO1 gene. Known IDO inhibitors include norharmane, rosmarinic acid, and alpha-methyl-tryptophan.

The term "A1 adenosine inhibitor," as used herein, refers to a compound such as an antibody capable of inhibiting the activity of the protein that in humans is encoded by the ADORA1 gene. Known A1 adenosine inhibitors include 8-cyclopentyl-1,3-dimethylxanthine, 8-cyclopentyl-1,3-dipropylxanthine, 8-phenyl-1,3-dipropylxanthine, bamifylline, BG-9719, BG-9928, FK-453, FK-838, rolofylline, and N-0861.

The term "A2A adenosine inhibitor," as used herein, refers to a compound such as an antibody capable of inhibiting the activity of the protein that in humans is encoded by the ADORA2A gene. Known A2A adenosine inhibitors include ATL-4444, istradefylline, MSX-3, preladenant, SCH-58261, SCH-412,348, SCH-442,416, ST-1535, VER-6623, VER-6947, VER-7835, viadenant, and ZM-241,385.

The term "A2B adenosine inhibitor," as used herein, refers to a compound such as an antibody capable of inhibiting the activity of the protein that in humans is encoded by the ADORA2B gene. Known A2B adenosine inhibitors include ATL-801, CVT-6883, MRS-1706, MRS-1754, OSIP-339,391, PSB-603, PSB-0788, and PSB-1115.

The term "A3A adenosine inhibitor," as used herein, refers to a compound such as an antibody capable of inhibiting the activity of the protein that in humans is encoded by the ADORA3 gene. Known A3A adenosine inhibitors include KF-26777, MRS-545, MRS-1191, MRS-1220, MRS-1334, MRS-1523, MRS-3777, MRE-3005-F20, MRE-3008-F20, PSB-11, OT-7999, VUF-5574, and SSR161421.

The term "arginase inhibitor," as used herein, refers to a compound capable of inhibiting the activity of a protein that in humans is encoded by the ARG1 or ARG2 genes. Known arginase inhibitors include (2s)-(+)-amino-5-iodoacetamidopentanoic acid, NG-hydroxy-L-arginine, (2S)-(+)-amino-6-iodoacetamidohexanoic acid, and (R)-2-amino-6-borono-2-(2-(piperidin-1-yl)ethyl)hexanoic acid.

The term "HDAC inhibitor," as used herein, refers to a compound such as an antibody that is capable of inhibiting the activity of the protein that is a member of the histone deacetylase class of enzymes, e.g., HDAC1, HDAC2, HDAC3, HDAC4, HDAC5, HDAC6, HDAC7, HDAC8, HDAC9, HDAC10, HDAC11, SIRT1, SIRT2, SIRT3, SIRT4, SIRT5, SIRT6, and SIRT7. Known HDAC inhibitors include valproic acid, SAHA, and romidepsin.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

BRIEF DESCRIPTION OF THE DRAWINGS

FIG. 1A is an image of a flow cytometry plot illustrating the population of MDSCs (Gr1+CD11b+ cells) in a control treated sample compared to a sample treated with compound 682.

FIG. 1B is a graph illustrating the quantification of MDSCs (Gr1+CD11b+ cells) in a control treated sample compared to a sample treated with compound 682.

FIG. 1C is an image from a confocal microscope of tumors immunohistochemically stained for the MDSC marker Gr1.

FIG. 1D is a graph illustrating quantification of the number of Gr1+ cells in a control treated sample compared to a sample treated with compound 682 per microscopic low-power field.

FIG. 1E is a graph illustrating the correlation between tumor size and the number of MDSCs (Gr1+CD11b+ cells) in B16F10 tumor bearing mice treated with compound 682.

FIG. 2A is an image of a flow cytometry plot illustrating the population of activated CD8+ cells in control treated B16F10 tumor-bearing mice compared to B16F10 tumor-bearing mice treated with compound 682.

FIG. 2B is a graph illustrating quantification of activated CD8+ cells in control treated B 16F10 tumor-bearing mice compared to B 16F10 tumor-bearing mice treated with compound 682.

FIG. 2C is a graph illustrating the correlation between tumor size and the number of activated CD8+ cells in B16F10 tumor bearing mice treated with compound 682.

FIG. 7B is graph illustrating tumor growth by B16F10 cells depleted of ApoE by shRNA subcutaneously injected into ApoE deficient mice. Following tumor growth to 5-10 mm$^3$ in volume, mice were fed a control chow or a chow supplemented with compound 682 (100 mg/kg).

FIG. 7C is a graph illustrating quantification of MDSCs isolated from ApoE depleted B 16F10 treated tumors grown in ApoE deficient mice treated with control or compound 682.

FIG. 11A is a graph illustrating tumor growth by B16F10 cells subcutaneously injected into C57BL/6 mice or B16F10 cells depleted of ApoE with shRNA injected in ApoE deficient mice.

FIG. 11B is an image of flow-cytometry plots showing the populations of circulating G-MDSCs (Gr1 high) and M-MDSCs (Gr1 int) in wild-type mice bearing B16F10 tumors or from ApoE deficient mice bearing ApoE depleted B16F10 tumors.

FIG. 11C is a graph illustrating quantification of circulating MDSCs from wild-type mice bearing B16F10 tumors and from ApoE deficient mice bearing ApoE depleted B16F10 tumors.

DETAILED DESCRIPTION OF THE INVENTION

Figure 3A:
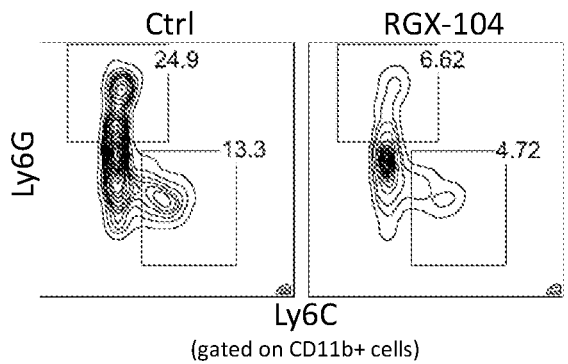
FIG. 3A is an image of a flow cytometry plot illustrating the population of G-MDSCs (Ly6-G+) and M-MDSCs (Ly6-C+) in control treated B16F10 tumor-bearing mice compared to B16F10 tumor-bearing mice treated with compound 705. (gated on total CD11b+ cells)

The present invention features methods for the treatment of disorders MDSC related disorders such as cancer and infections. For example, LXRβ agonists described herein may be used to reduce the levels of MDSCs (e.g., monocytic and/or granulocytic MDSCs) in a subject to treat these disorders. In some embodiments, the LXRβ agonists may be used in combination with immunotherapies to treat cancer, e.g., cancer that is resistant to, or failed to respond to, an immunotherapy.

Compounds

In some embodiments, the LXRβ agonist is a compound of Formula I:

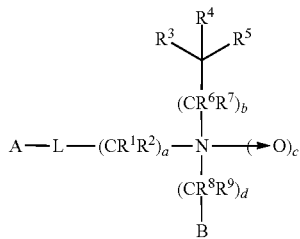

Formula I wherein A is:

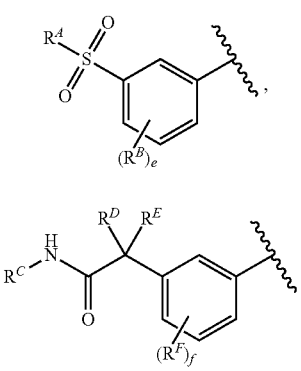

Formula Ia

Formula Ib

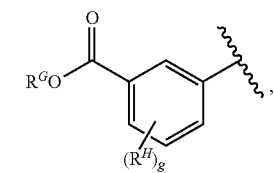

Formula Ic

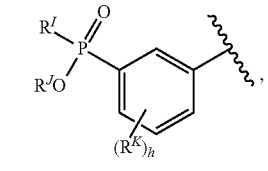

Formula Id

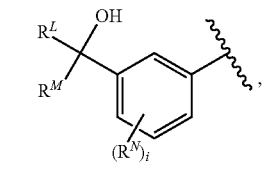

Formula Ie

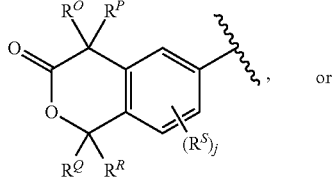

Formula If or

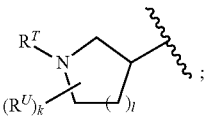

Formula Ig wherein e, f, g, h, and i are independently 0, 1, 2, 3, or 4;
j is 0, 1, 2, or 3;
k is 0, 1, 2, 3, 4, 5, 6, 7, or 8;
l is 0 1, or 2;
$R^A$, $R^C$, $R^I$, $R^L$, $R^M$, and $R^T$ are independently hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^D$, $R^E$, $R^G$, $R^O$, $R^P$, $R^Q$, and $R^R$ are independently hydrogen, hydroxy, optionally substituted amino, azido, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

each $R^B$, $R^F$, $R^H$, $R^K$, $R^N$, and $R^S$ are independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^J$ is hydrogen, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; or $R^J$ and $R^J$ combine to form an optionally substituted $C_2$-$C_9$ heterocyclyl or $R^J$ and $R^K$ combine to form an optionally substituted $C_2$-$C_9$ heterocyclyl;

$R^U$ is hydroxyl, oxo, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and L is absent, —O—, —S—, —N($R^{12}$)—, or —C($R^4$)($R^5$)—;

a is 2, 3, 4, 5, 6, 7, or 8;

b, c, and d are independently 0 or 1;

each $R^1$, $R^2$, $R^6$, $R^7$, $R^8$, and $R^9$ are independently hydrogen, hydroxyl, halo, optionally substituted amino, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; or $R^1$ and $R^2$ combine to form an optionally substituted $C_3$-$C_{10}$ cycloalkyl, optionally substituted $C_2$-$C_9$ heteroaryl, or optionally substituted $C_2$-$C_9$ heterocyclyl; or $R^6$ and $R^7$ combine to form an optionally substituted $C_3$-$C_{10}$ cycloalkyl, optionally substituted $C_2$-$C_9$ heteroaryl, or optionally substituted $C_2$-$C_9$ heterocyclyl; or $R^8$ and $R^9$ combine to form an optionally substituted $C_3$-$C_{10}$ cycloalkyl, optionally substituted $C_2$-$C_9$ heteroaryl, or optionally substituted $C_2$-$C_9$ heterocyclyl;

$R^3$ is hydrogen, hydroxyl, optionally substituted amino, optionally substituted $C_1$-$C_6$ alkyl, optionally substituted $C_3$-$C_{10}$ cycloalkyl, optionally substituted $C_6$-$C_{10}$ aryl, optionally substituted $C_2$-$C_9$ heteroaryl, or optionally substituted $C_2$-$C_9$ heterocyclyl;

$R^4$ and $R^5$ are independently hydrogen, hydroxyl, halo, optionally substituted amino, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and B is optionally substituted $C_3$-$C_{10}$ cycloalkyl, optionally substituted $C_6$-$C_{10}$ aryl, optionally substituted $C_2$-$C_9$ heteroaryl, or optionally substituted $C_2$-$C_9$ heterocyclyl;

or a pharmaceutically acceptable salt thereof and/or a prodrug thereof.

In some embodiments, c is 0. In other embodiments, $R^4$ is hydrogen. In certain embodiments, $R^4$ is fluorine. In some embodiments, $R^5$ is hydrogen. In some embodiments, $R^5$ is fluorine. In certain embodiments, b is 1. In some embodiments, b is 0. In some embodiments, each $R^6$ is hydrogen. In other embodiments, each $R^7$ is hydrogen. In certain embodiments, d is 1. In some embodiments, each $R^8$ is hydrogen. In other embodiments, each $R^9$ is hydrogen. In certain embodiments, $R^3$ is optionally substituted $C_6$-$C_{10}$ aryl (e.g., phenyl or 4-fluoro-phenyl). In some embodiments, $R^5$ is optionally substituted $C_6$-$C_{10}$ aryl (e.g., phenyl). In some embodiments, $R^5$ is optionally substituted $C_3$-$C_{10}$ cycloalkyl (e.g., cyclohexyl). In some embodiments, $R^4$ is optionally substituted $C_1$-$C_6$ alkyl (e.g., methyl). In certain embodiments, $R^5$ is optionally substituted $C_1$-$C_6$ alkyl (e.g., methyl). In some embodiments, $R^4$ and $R^5$ are both optionally substituted $C_1$-$C_6$ alkyl (e.g., methyl). In some embodiments, $R^5$ is hydrogen, methyl, or phenyl. In other embodiments, a is 3. In certain embodiments, each $R^1$ is hydrogen. In some embodiments, each $R^2$ is hydrogen. In other embodiments, at least one $R^2$ is optionally substituted $C_1$-$C_6$ alkyl (e.g., methyl). In certain embodiments, —$(CR^1R^2)_3$— has the structure:

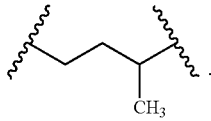

In some embodiments, —$(CR^1R^2)_3$— has the structure:

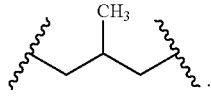 [SMILES: *CC(C)C*]

In some embodiments, —$(CR^1R^2)_3$— has the structure:

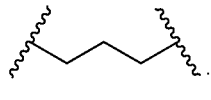

In some embodiments, —$(CR^1R^2)_3$— has the structure:

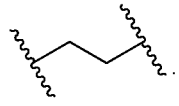

In certain embodiments, L is —O—. In certain embodiments, L is absent. In some embodiments, B is optionally substituted $C_6$-$C_{10}$ aryl (e.g., 2-chloro-3-trifluoromethyl-phenyl, 2-fluoro-3-trifluoromethyl-phenyl, 3-(1,1,2,2-tetrafluoroethoxy)-phenyl, 3-trifluoromethyl-phenyl, 3-trifluoromethyl-4-fluoro-phenyl, 3-trifluoromethoxy-phenyl, or 2,2-difluoro-1,3-benzodioxole).

In some embodiments, A is:

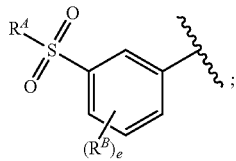

Formula Ia wherein e is 0, 1, 2, 3, or 4;

$R^A$ is hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and each $R^B$ is independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

or a prodrug thereof.

In other embodiments, $R^A$ is optionally substituted $C_1$-$C_6$ alkyl (e.g., methyl). In certain embodiments, e is 0. In some embodiments, e is 1 or 2. In other embodiments, each $R^B$ is halo (e.g., fluoro), optionally substituted $C_1$-$C_6$ alkyl (e.g., —$CH_2OH$, —$CD_2OH$, —$CH_2CH_2OH$, —$C(CH_3)_2OH$, —$CH(CH_3)OH$, —$C(CF_3)_2OH$, —$CH(CF_3)OH$, —$CH_2OP(O)(OH)_2$, —$CH_2NH_2$, or —$CH_2NHC(O)CH_3$), or optionally substituted $C_1$-$C_6$ acyl (e.g., —C(O)OH, —C(O)OCH_3, —C(O)CH_3, —C(O)NHCH_3, —C(O)NH_2, —C(O)N(CH_3)_2, —C(O)CF_3, or —C(O)H).

In some embodiments, A is:

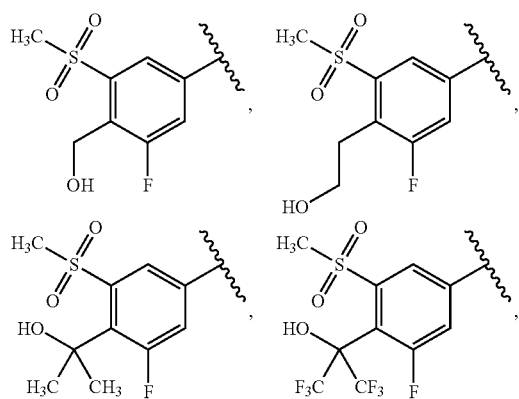

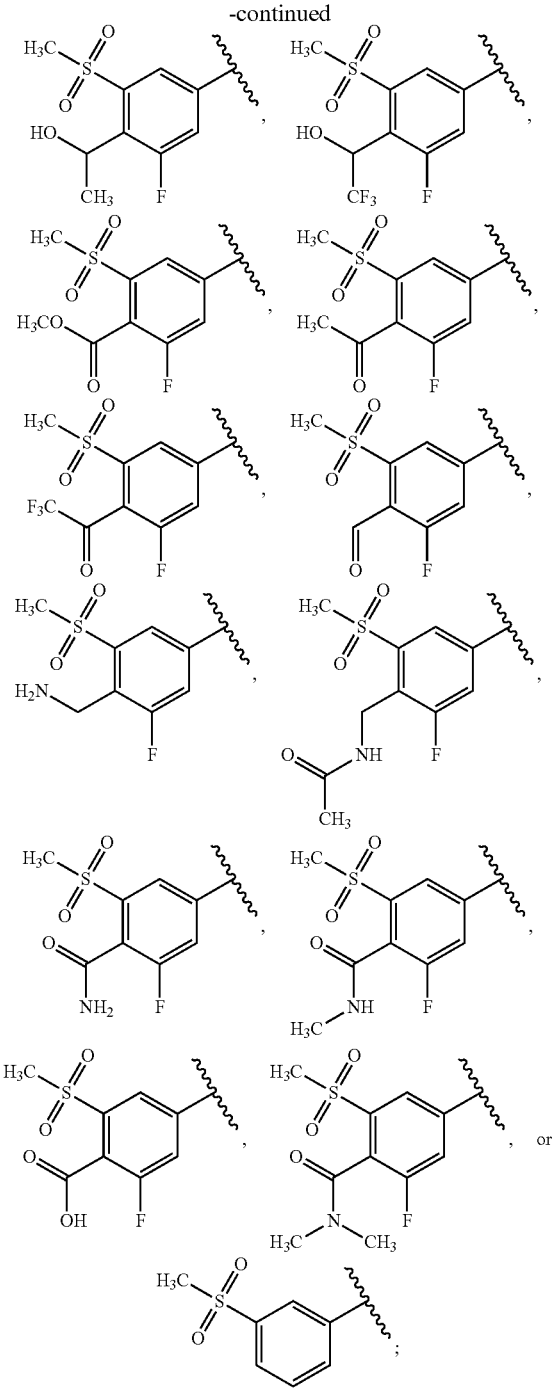

or a prodrug thereof.
In some embodiments, A is:

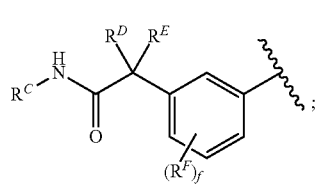

Formula Ib wherein f is 0, 1, 2, 3, or 4;

$R^C$ is hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^D$ and $R^E$ are independently hydrogen, hydroxy, optionally substituted amino, azido, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and each $R^F$ is independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

or a prodrug thereof.

In other embodiments, f is 0. In certain embodiments, $R^D$ is hydroxyl or optionally substituted $C_1$-$C_6$ heteroalkyl (e.g., —SO$_2$—CH$_3$). In some embodiments, $R^E$ is hydrogen, halo, or optionally substituted $C_1$-$C_6$ alkyl (e.g., methyl). In other embodiments, $R^F$ is hydrogen, halo, or optionally substituted $C_1$-$C_6$ alkyl (e.g., methyl).

In some embodiments, A is:

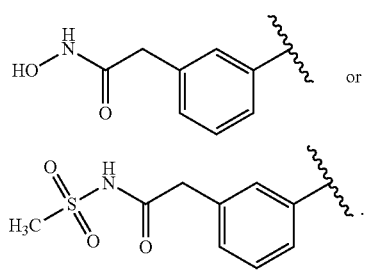

In some embodiments, A is:

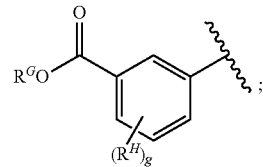

Formula Ic wherein g is 0, 1, 2, 3, or 4;

$R^G$ is hydrogen, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and each $R^H$ is independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

or a prodrug thereof.

In other embodiments, g is 0. In certain embodiments, $R^H$ is hydrogen.

In some embodiments, A is:

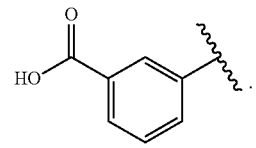

In some embodiments, A is:

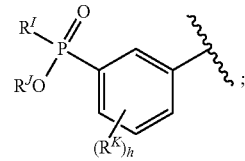

Formula Id wherein h is 0, 1, 2, 3, or 4;

$R^I$ is hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^J$ is independently hydrogen, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; or $R^I$ and $R^J$ combine to form an optionally substituted $C_2$-$C_9$ heterocyclyl; or $R^J$ and $R^K$ combine to form an optionally substituted $C_2$-$C_9$ heterocyclyl; and each $R^K$ is independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

or a prodrug thereof.

In other embodiments, $R^J$ is hydrogen or $R^J$ and $R^K$ combine to form an optionally substituted $C_2$-$C_9$ heterocyclyl. In certain embodiments, $R^I$ is optionally substituted $C_1$-$C_6$ alkyl (e.g., methyl). In some embodiments, h is 0. In other embodiments, h is 1. In certain embodiments, $R^K$ is optionally substituted $C_1$-$C_6$ alkyl (e.g., —$CH_2OH$) or $R^J$ and $R^K$ combine to form an optionally substituted $C_2$-$C_9$ heterocyclyl (e.g., A is

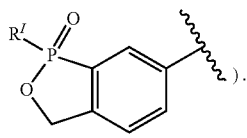).

In some embodiments, A is:

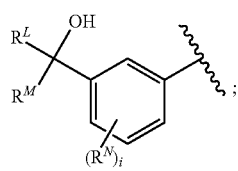

Formula Ie wherein i is 0, 1, 2, 3, or 4;

$R^L$ and $R^M$ are independently hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$—$C_6$ alkyl, optionally substituted $C_2$-$C_9$ heterocyclyl, or optionally substituted $C_2$-$C_9$ heterocyclyl $C_1$-$C_6$ alkyl; and each $R^N$ is independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

or a prodrug thereof.

In other embodiments, i is 0. In certain embodiments, $R^L$ is hydrogen or optionally substituted $C_1$-$C_6$ alkyl (e.g., methyl or trifluoromethyl). In some embodiments, $R^M$ is hydrogen or optionally substituted $C_1$-$C_6$ alkyl (e.g., methyl or trifluoromethyl).

In some embodiments, A is:

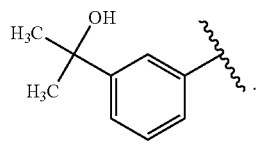

In some embodiments, A is:

Formula If

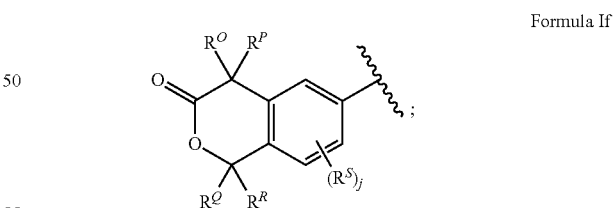

wherein j is 0, 1, 2, or 3;

$R^O$, $R^P$, $R^Q$, and $R^R$ are independently hydrogen, hydroxyl, optionally substituted amino, azido, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$—$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and each $R^S$ is independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

or a prodrug thereof.

In other embodiments, j is 0. In certain embodiments, $R^O$ is hydrogen, halo, or optionally substituted $C_1$-$C_6$ alkyl. In some embodiments, $R^P$ is hydrogen, halo, or optionally substituted $C_1$-$C_6$ alkyl. In other embodiments, $R^Q$ is hydrogen. In certain embodiments, $R^R$ is hydrogen.

In certain embodiments, A is:

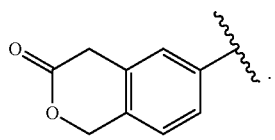 [SMILES: *c1ccc2c(c1)CC(=O)OC2]

In some embodiments, A is:

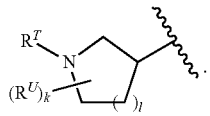

Formula Ig wherein k is 0, 1, 2, 3, 4, 5, 6, 7, or 8;
l is 0, 1, or 2;
$R^T$ is hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

each $R^U$ is independently hydroxyl, oxo, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and or a prodrug thereof.

In certain embodiments, k is 0. In certain embodiments, l is 0. In some embodiments, l is 1. In certain embodiments, l is 2. In other embodiments, $R^T$ is optionally substituted $C_1$-$C_6$ alkyl
(e.g., —CH$_2$CO$_2$H or

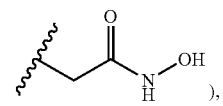

), or, optionally substituted $C_1$-$C_6$ heteroalkyl (e.g., —SO$_2$—CH$_3$).

In other embodiments, k is 0. In certain embodiments, k is 1. In some embodiments, $R^u$ is optionally substituted $C_1$-$C_6$ acyl (e.g., —CO$_2$H) or optionally substituted $C_1$-$C_6$ alkyl (e.g., —CH$_2$OH). In some embodiments, l is 0. In other embodiments, l is 1. In certain embodiments, l is 2.

In some embodiments, A is:

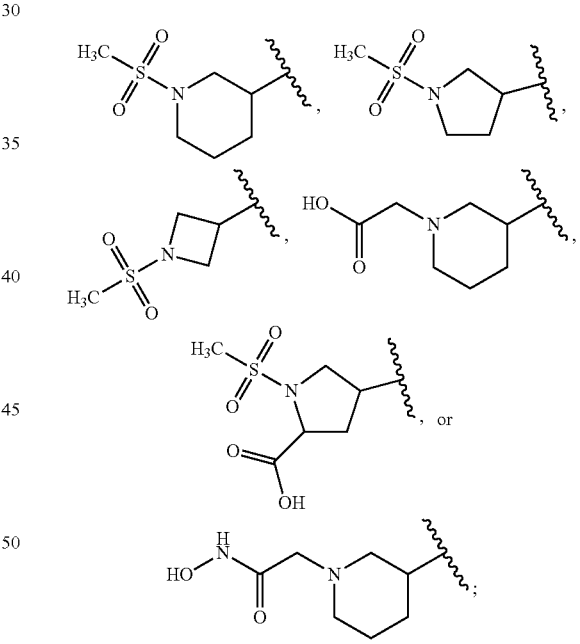

or a prodrug thereof.

In some embodiments, the compound is a prodrug, or a pharmaceutically acceptable salt of a prodrug (e.g., A includes an —OR$^V$ group, wherein R$^V$ is:

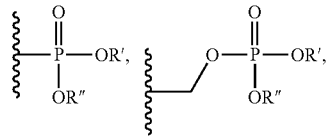

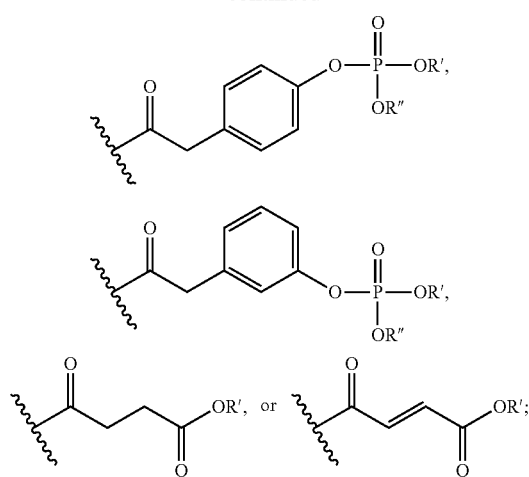
wherein each R' and R" is independently hydrogen, optionally substituted $C_1$-$C_6$ alkyl, such as methyl or t-butyl, or optionally substituted $C_6$-$C_{10}$ aryl $C_1$-$C_6$ alkyl, such as benzyl).
In some embodiments A is:
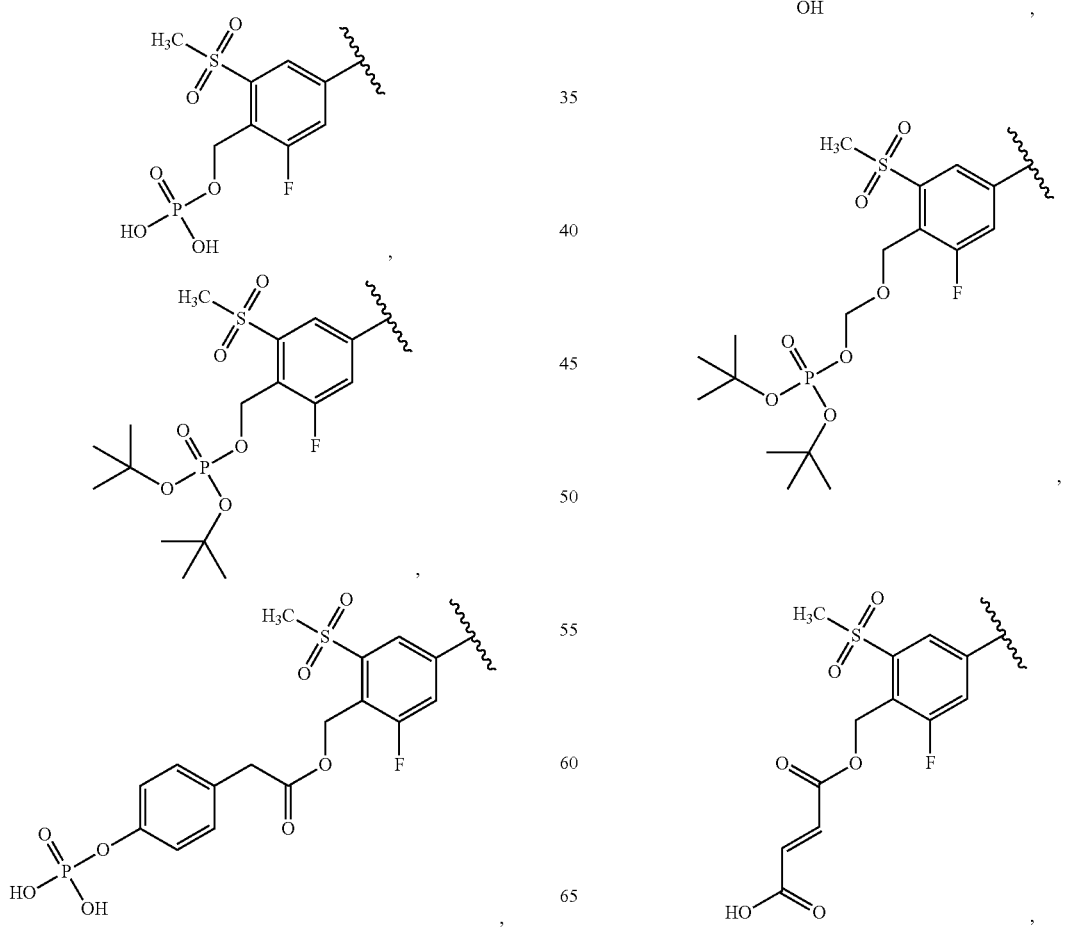
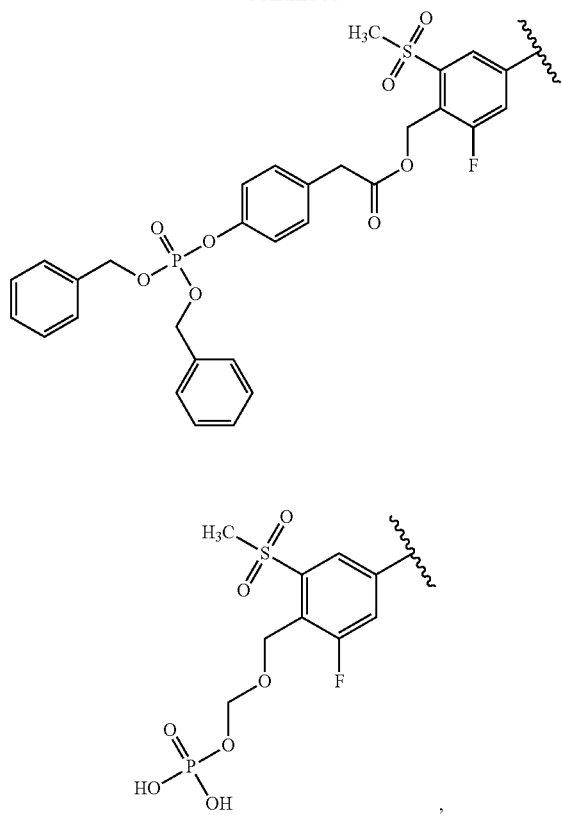

-continued
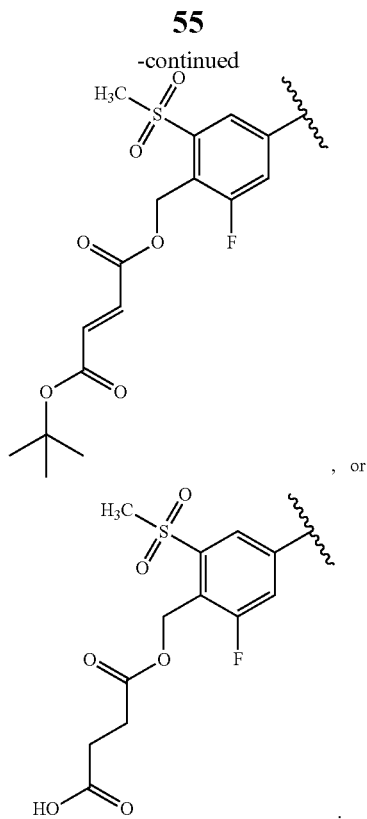
, or
In some embodiments, the compound has the structure:
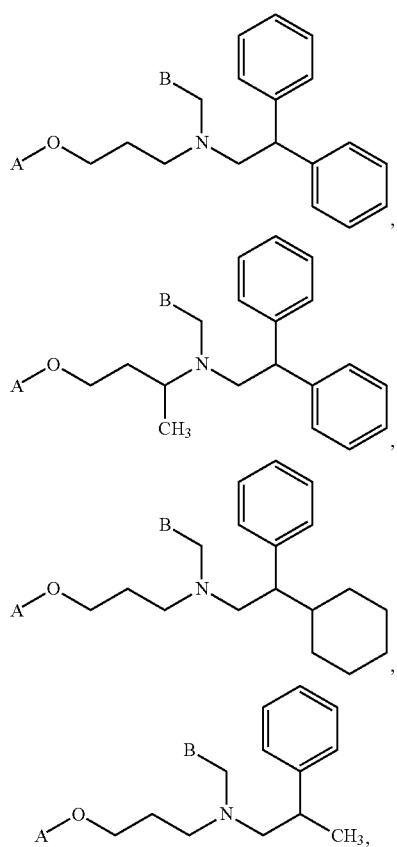
-continued
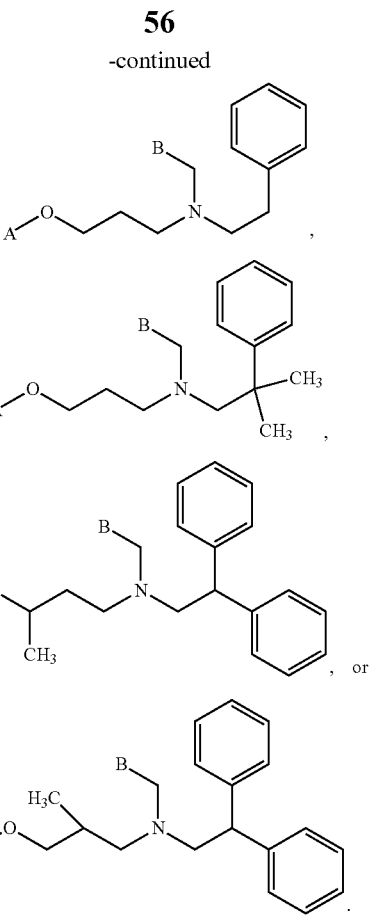
In some embodiments, the compound has the structure:
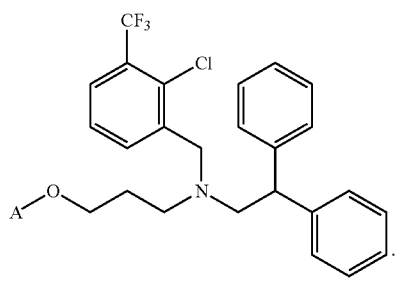
In certain embodiments, the compound has the structure:
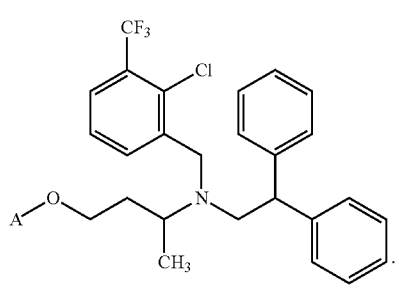

In certain embodiments, the compound has the structure:

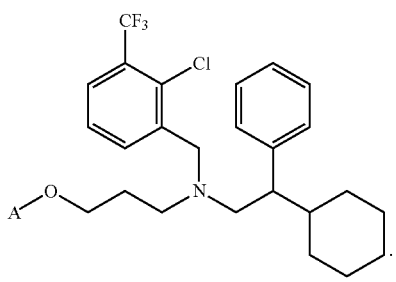

In some embodiments, the compound has the structure:

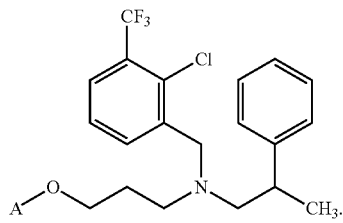

In certain embodiments, the compound has the structure:

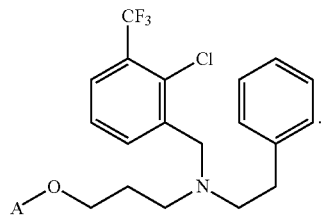

In some embodiments, the compound has the structure:

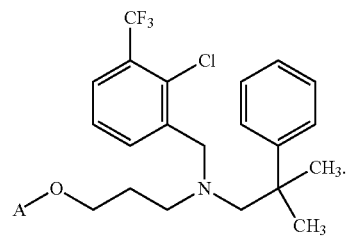

In some embodiments, the compound has the structure:

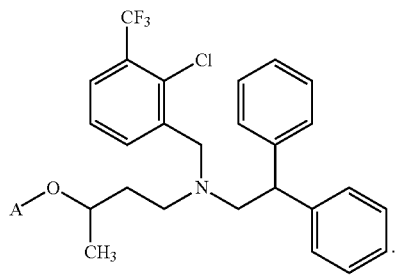

In certain embodiments, the compound has the structure:

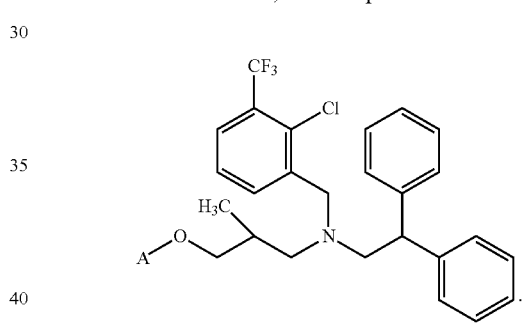

In some embodiments, the LXRβ agonist is any one of compounds 1 to 97 of Table 1:

TABLE 1

| Exemplary Compounds of the Invention | |
|---|---|
| # | Structure |
| 1 | ![compound 1] |

TABLE 1-continued
Exemplary Compounds of the Invention
| # | Structure |
|---|---|
| 2 | 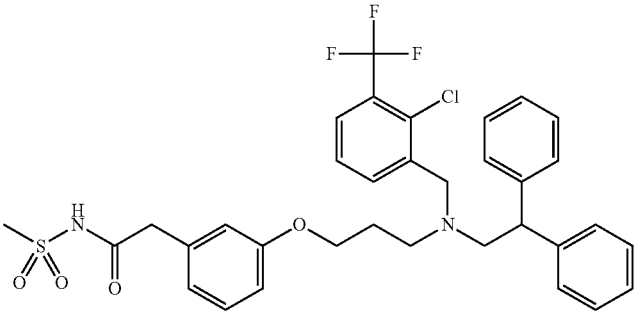 [SMILES: CS(=O)(=O)NC(=O)Cc1cccc(OCCCN(Cc2cccc(C(F)(F)F)c2Cl)CC(c2ccccc2)c2ccccc2)c1] |
| 3 | 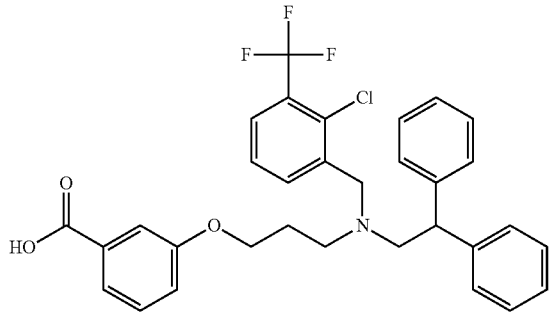 [SMILES: O=C(O)c1cccc(OCCCN(Cc2cccc(C(F)(F)F)c2Cl)CC(c2ccccc2)c2ccccc2)c1] |
| 4 | 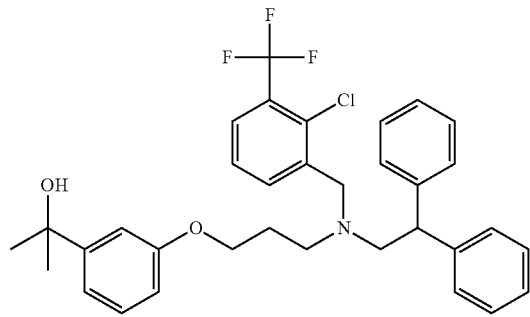 [SMILES: CC(C)(O)c1cccc(OCCCN(Cc2cccc(C(F)(F)F)c2Cl)CC(c2ccccc2)c2ccccc2)c1] |
| 5 | 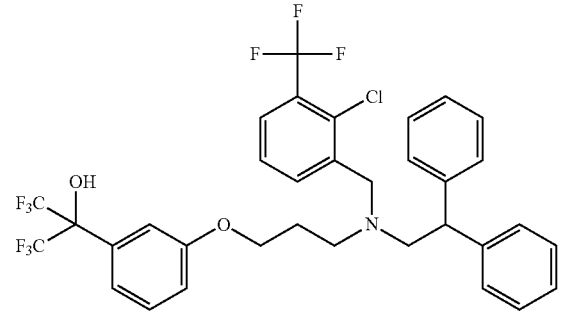 [SMILES: OC(c1cccc(OCCCN(Cc2cccc(C(F)(F)F)c2Cl)CC(c2ccccc2)c2ccccc2)c1)(C(F)(F)F)C(F)(F)F] |

TABLE 1-continued

Exemplary Compounds of the Invention

| # | Structure |
|---|---|
| 6 | (isochroman-3-one with O-propyl-N(CH2-2-chloro-3-trifluoromethylphenyl)(2,2-diphenylethyl) substituent) |
| 7 | (3-methylsulfonylphenyl-O-propyl-N(CH2-2-chloro-3-trifluoromethylphenyl)(2,2-diphenylethyl)) |
| 8 | (2-methylsulfonyl-4-(O-propyl-N(CH2-2-chloro-3-trifluoromethylphenyl)(2,2-diphenylethyl))-6-fluoro-3-(hydroxymethyl)phenyl) |
| 9 | (2-methylsulfonyl-4-(O-propyl-N(CH2-2-chloro-3-trifluoromethylphenyl)(2,2-diphenylethyl))-6-fluoro-3-(hydroxymethyl)phenyl, with (R)-methyl stereocenter on propyl chain) |

TABLE 1-continued
Exemplary Compounds of the Invention
| # | Structure |
|---|---|
| 10 | 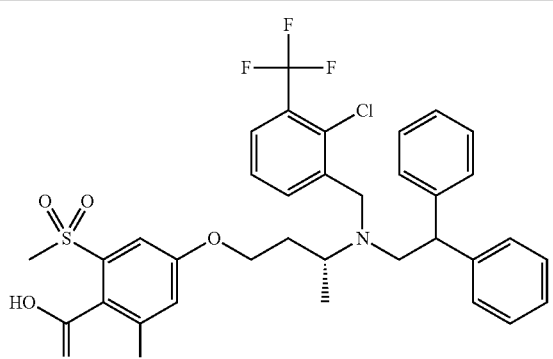 |
| 11 | 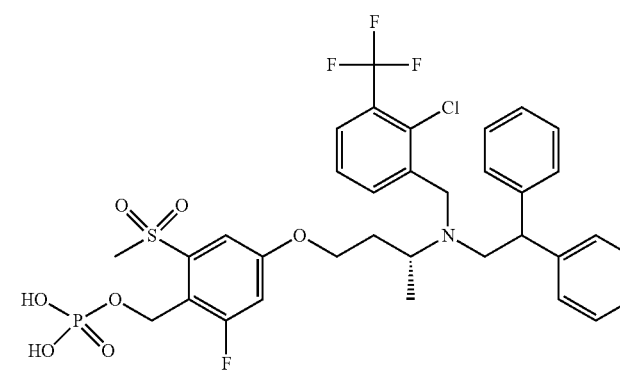 |
| 12 | 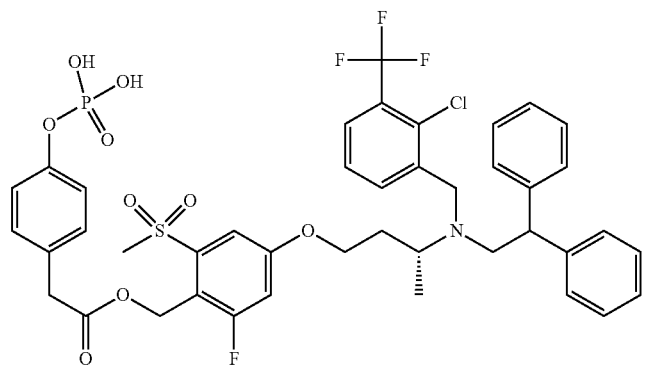 [SMILES: C[C@H](CCOc1cc(F)c(COC(=O)Cc2ccc(OP(=O)(O)O)cc2)c(S(C)(=O)=O)c1)N(Cc1cccc(C(F)(F)F)c1Cl)CC(c1ccccc1)c1ccccc1] |
| 13 | 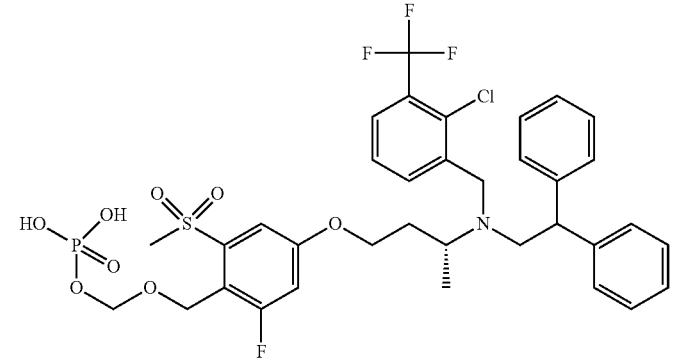 [SMILES: C[C@H](CCOc1cc(F)c(COCOP(=O)(O)O)c(S(C)(=O)=O)c1)N(Cc1cccc(C(F)(F)F)c1Cl)CC(c1ccccc1)c1ccccc1] |

TABLE 1-continued
Exemplary Compounds of the Invention
| # | Structure |
|---|---|
| 14 | 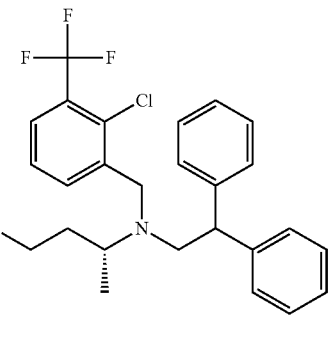 |
| 15 | 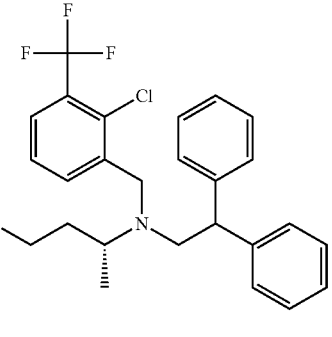 |
| 16 | 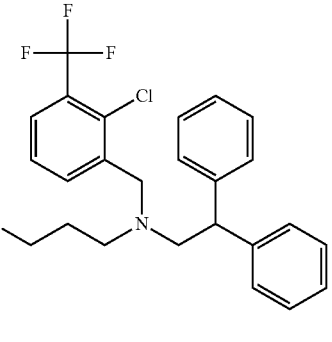 |
| 17 | 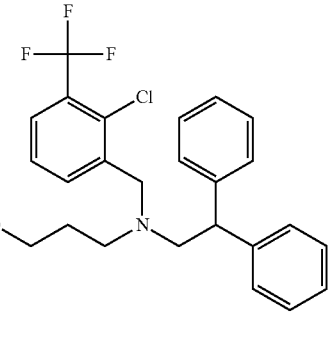 |

TABLE 1-continued
Exemplary Compounds of the Invention
| # | Structure |
|---|---|
| 18 | 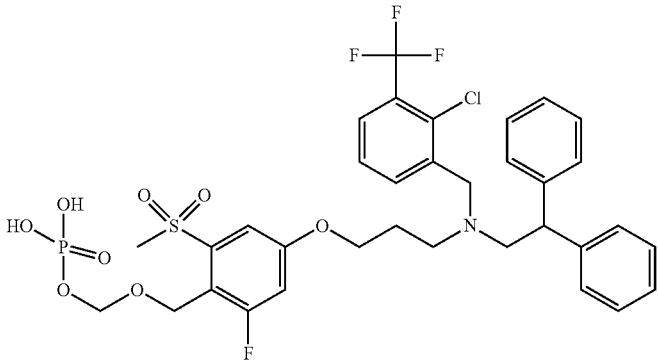 [SMILES: CS(=O)(=O)c1cc(OCCCN(Cc2cccc(C(F)(F)F)c2Cl)CC(c2ccccc2)c2ccccc2)cc(F)c1COCOP(=O)(O)O] |
| 19 | 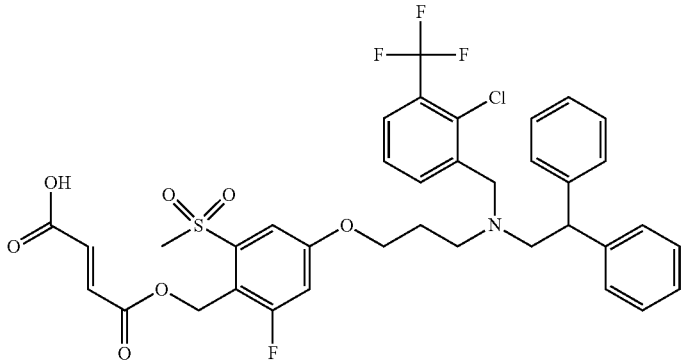 [SMILES: CS(=O)(=O)c1cc(OCCCN(Cc2cccc(C(F)(F)F)c2Cl)CC(c2ccccc2)c2ccccc2)cc(F)c1COC(=O)/C=C/C(=O)O] |
| 20 | 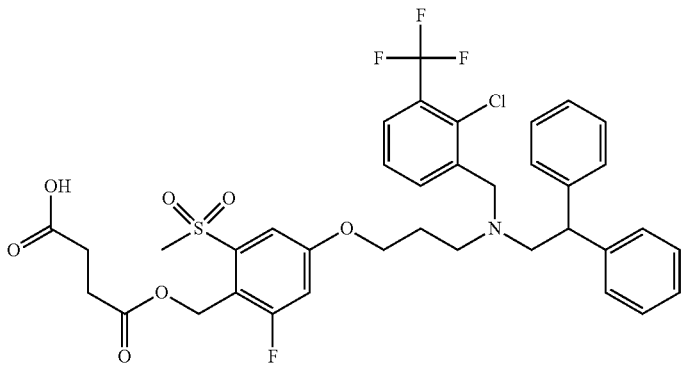 [SMILES: CS(=O)(=O)c1cc(OCCCN(Cc2cccc(C(F)(F)F)c2Cl)CC(c2ccccc2)c2ccccc2)cc(F)c1COC(=O)CCC(=O)O] |
| 21 | 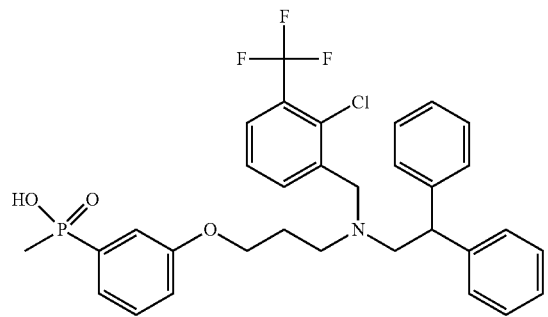 [SMILES: CP(=O)(O)c1cccc(OCCCN(Cc2cccc(C(F)(F)F)c2Cl)CC(c2ccccc2)c2ccccc2)c1] |

TABLE 1-continued
Exemplary Compounds of the Invention
| # | Structure |
|---|---|
| 22 | 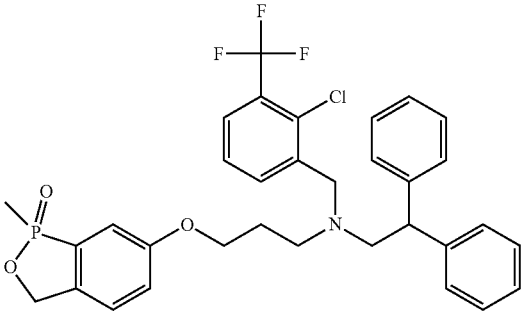 [SMILES: CP1(=O)OCc2ccc(OCCCN(Cc3cccc(C(F)(F)F)c3Cl)CC(c3ccccc3)c3ccccc3)cc21] |
| 23 | 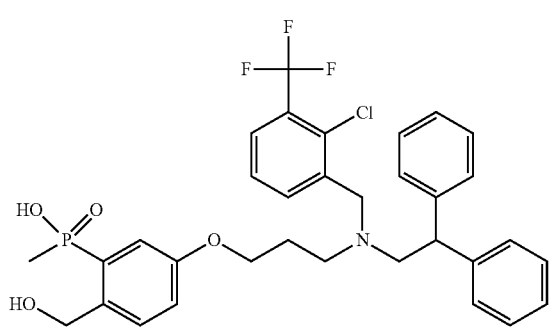 [SMILES: CP(=O)(O)c1cc(OCCCN(Cc2cccc(C(F)(F)F)c2Cl)CC(c2ccccc2)c2ccccc2)ccc1CO] |
| 24 | 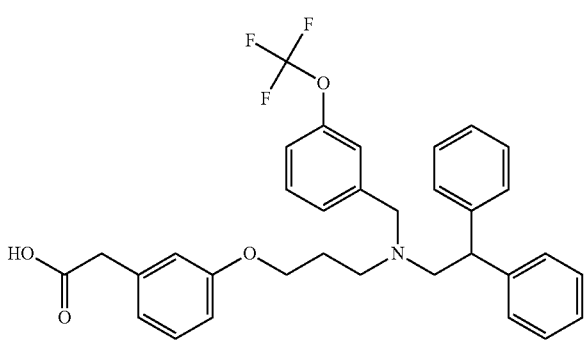 [SMILES: O=C(O)Cc1cccc(OCCCN(Cc2cccc(OC(F)(F)F)c2)CC(c2ccccc2)c2ccccc2)c1] |
| 25 | 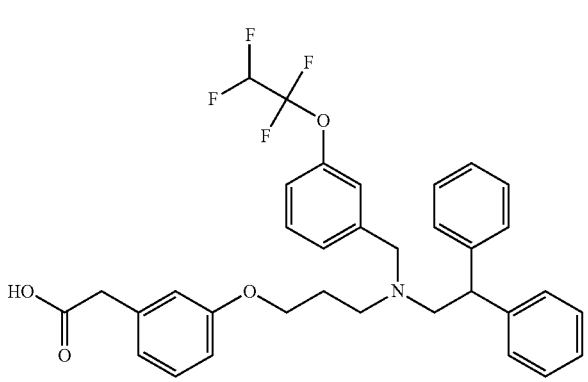 [SMILES: O=C(O)Cc1cccc(OCCCN(Cc2cccc(OC(F)(F)C(F)F)c2)CC(c2ccccc2)c2ccccc2)c1] |

TABLE 1-continued
Exemplary Compounds of the Invention
| # | Structure |
|---|---|
| 26 | 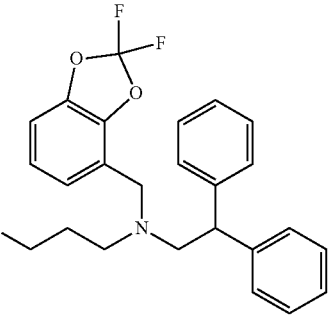 |
| 27 | 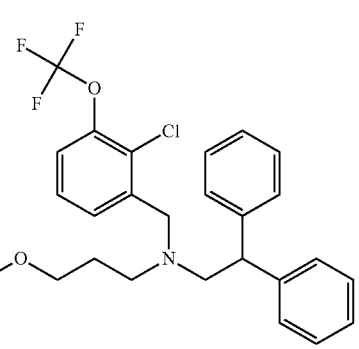 |
| 28 | 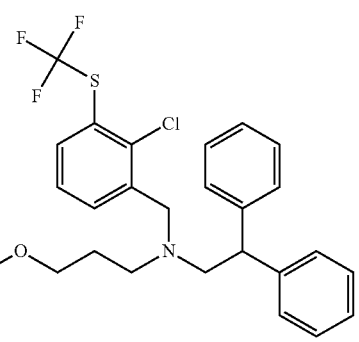 |
| 29 | 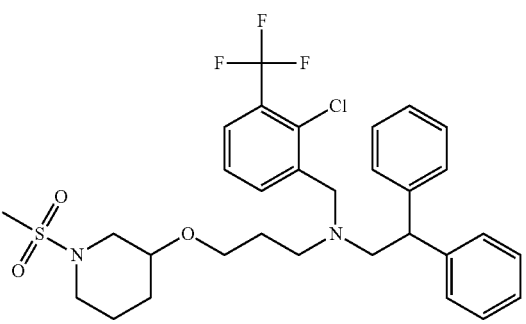 [SMILES: CS(=O)(=O)N1CCCC(OCCCN(Cc2cccc(C(F)(F)F)c2Cl)CC(c2ccccc2)c2ccccc2)C1] |

TABLE 1-continued
Exemplary Compounds of the Invention
| # | Structure |
|---|---|
| 30 | 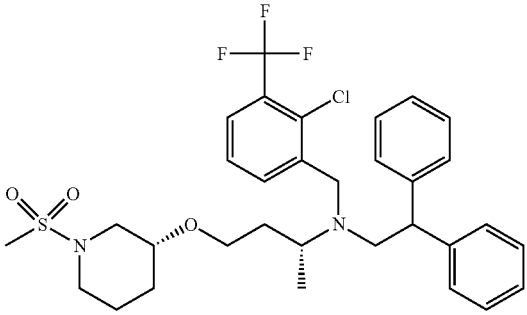 [SMILES: C[C@H](CCO[C@@H]1CCCN(S(C)(=O)=O)C1)N(Cc1cccc(C(F)(F)F)c1Cl)CC(c1ccccc1)c1ccccc1] |
| 31 | 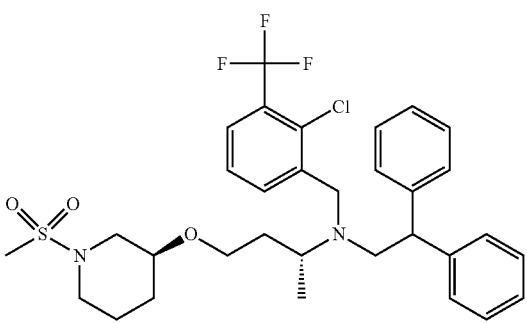 [SMILES: C[C@H](CCO[C@H]1CCCN(S(C)(=O)=O)C1)N(Cc1cccc(C(F)(F)F)c1Cl)CC(c1ccccc1)c1ccccc1] |
| 32 | 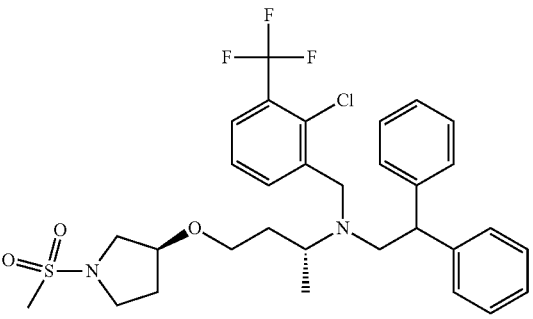 [SMILES: C[C@H](CCO[C@H]1CCN(S(C)(=O)=O)C1)N(Cc1cccc(C(F)(F)F)c1Cl)CC(c1ccccc1)c1ccccc1] |
| 33 | 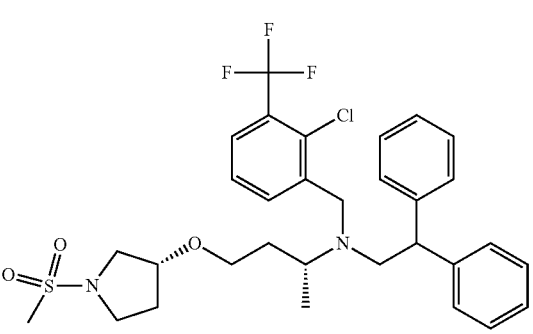 [SMILES: C[C@H](CCO[C@@H]1CCN(S(C)(=O)=O)C1)N(Cc1cccc(C(F)(F)F)c1Cl)CC(c1ccccc1)c1ccccc1] |

TABLE 1-continued
Exemplary Compounds of the Invention
| # | Structure |
|---|---|
| 34 | 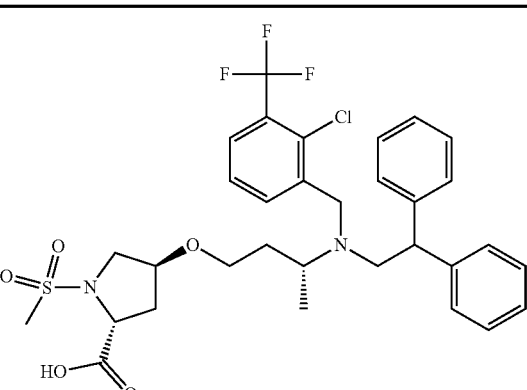 |
| 35 | 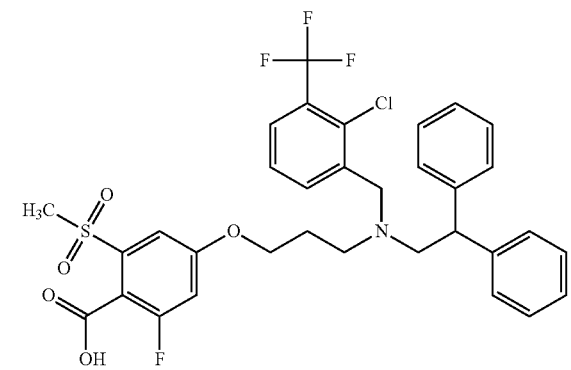 [SMILES: CS(=O)(=O)c1cc(OCCCN(Cc2cccc(C(F)(F)F)c2Cl)CC(c2ccccc2)c2ccccc2)cc(F)c1C(=O)O] |
| 36 | 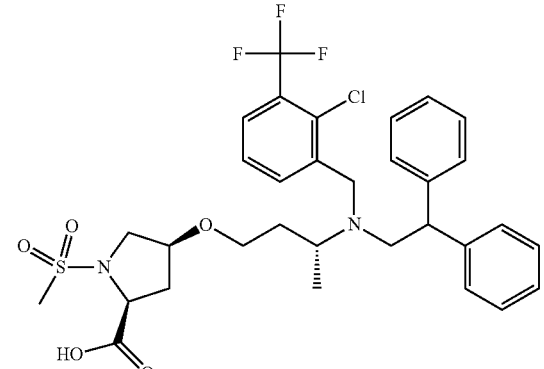 |
| 37 | 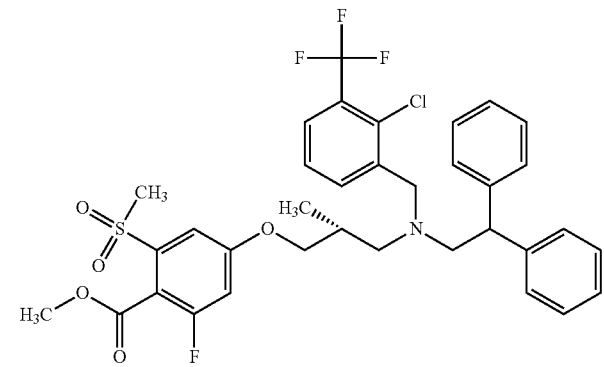 [SMILES: COC(=O)c1c(F)cc(OC[C@H](C)CN(Cc2cccc(C(F)(F)F)c2Cl)CC(c2ccccc2)c2ccccc2)cc1S(C)(=O)=O] |

TABLE 1-continued

Exemplary Compounds of the Invention

| # | Structure |
|---|-----------|
| 38 | 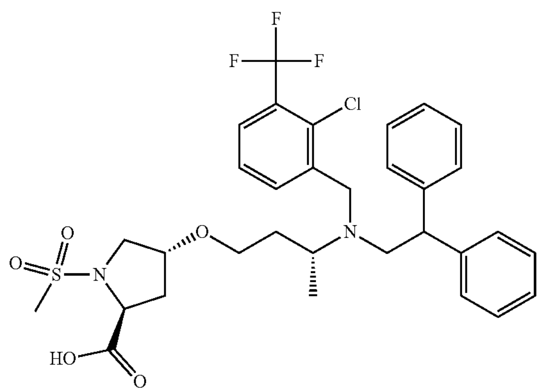 [SMILES: C[C@H](CCO[C@@H]1C[C@@H](C(=O)O)N(S(C)(=O)=O)C1)N(Cc1cccc(C(F)(F)F)c1Cl)CC(c1ccccc1)c1ccccc1] |
| 39 | 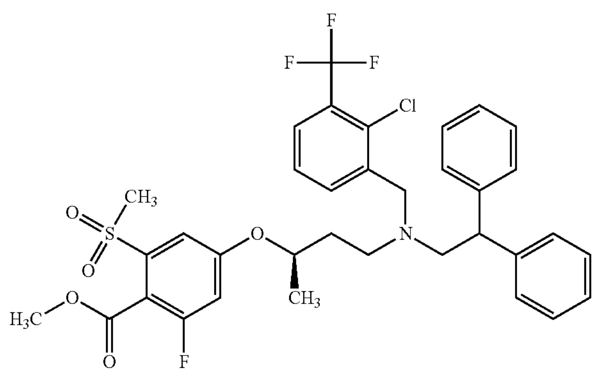 [SMILES: COC(=O)c1c(F)cc(O[C@H](C)CCN(Cc2cccc(C(F)(F)F)c2Cl)CC(c2ccccc2)c2ccccc2)cc1S(C)(=O)=O] |
| 40 | 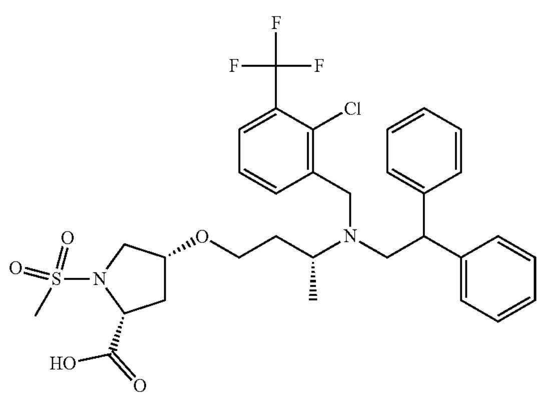 [SMILES: C[C@H](CCO[C@@H]1C[C@H](C(=O)O)N(S(C)(=O)=O)C1)N(Cc1cccc(C(F)(F)F)c1Cl)CC(c1ccccc1)c1ccccc1] |
| 42 | 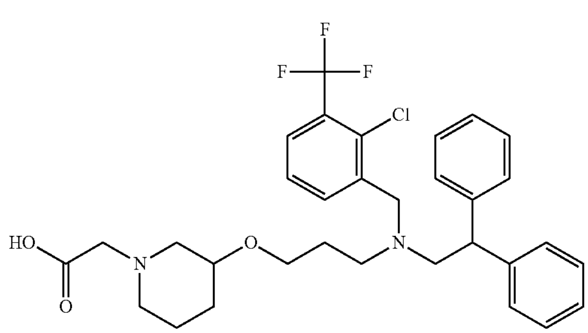 [SMILES: O=C(O)CN1CCCC(OCCCN(Cc2cccc(C(F)(F)F)c2Cl)CC(c2ccccc2)c2ccccc2)C1] |

TABLE 1-continued
Exemplary Compounds of the Invention
| # | Structure |
|---|---|
| 43 | 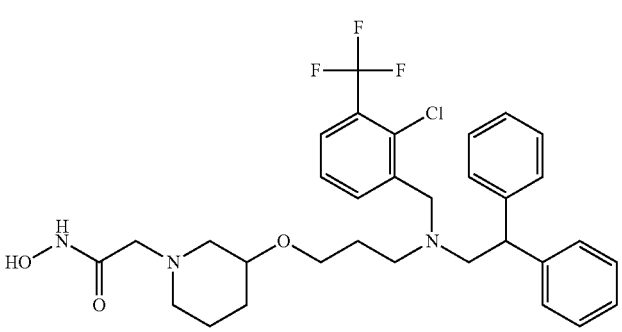 [SMILES: O=C(CN1CCCC(OCCCN(Cc2cccc(C(F)(F)F)c2Cl)CC(c2ccccc2)c2ccccc2)C1)NO] |
| 44 | 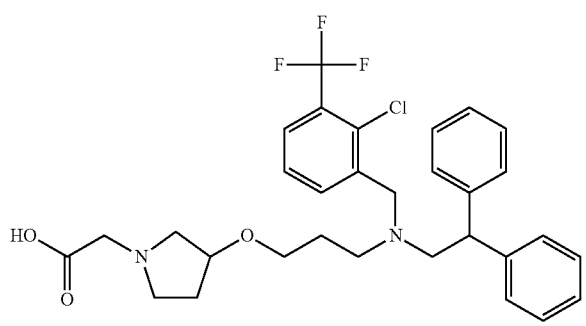 [SMILES: O=C(O)CN1CCC(OCCCN(Cc2cccc(C(F)(F)F)c2Cl)CC(c2ccccc2)c2ccccc2)C1] |
| 45 | 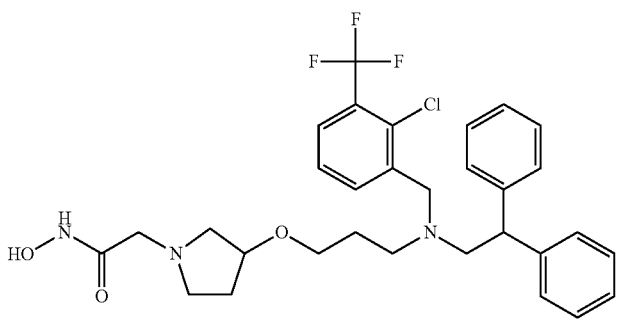 [SMILES: O=C(CN1CCC(OCCCN(Cc2cccc(C(F)(F)F)c2Cl)CC(c2ccccc2)c2ccccc2)C1)NO] |
| 59 | 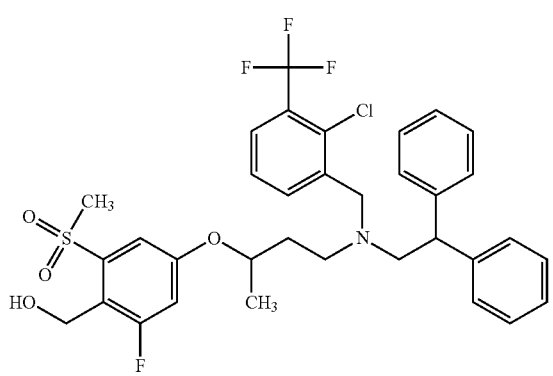 [SMILES: CC(CCN(Cc1cccc(C(F)(F)F)c1Cl)CC(c1ccccc1)c1ccccc1)Oc1cc(F)c(CO)c(S(C)(=O)=O)c1] |

TABLE 1-continued
Exemplary Compounds of the Invention
| # | Structure |
|---|---|
| 60 | 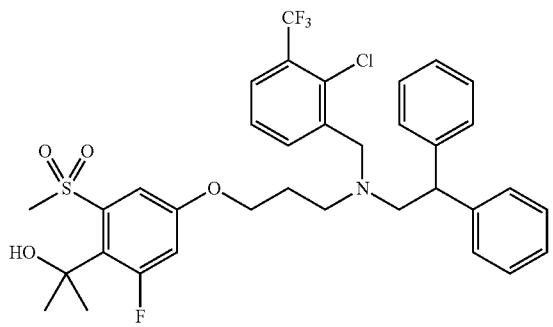 [SMILES: CC(C)(O)c1c(F)cc(OCCCN(Cc2cccc(C(F)(F)F)c2Cl)CC(c2ccccc2)c2ccccc2)cc1S(C)(=O)=O] |
| 61 | 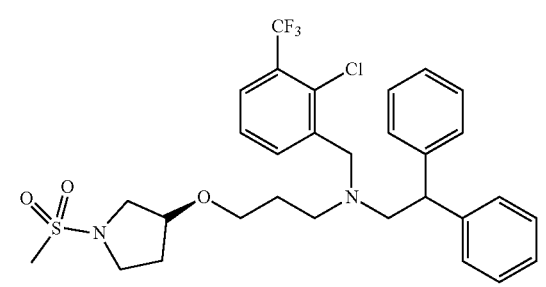 |
| 62 | 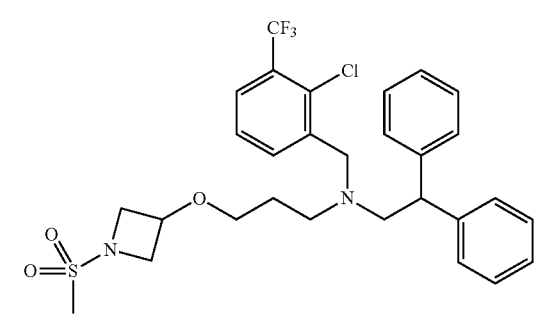 [SMILES: CS(=O)(=O)N1CC(OCCCN(Cc2cccc(C(F)(F)F)c2Cl)CC(c2ccccc2)c2ccccc2)C1] |
| 63 | 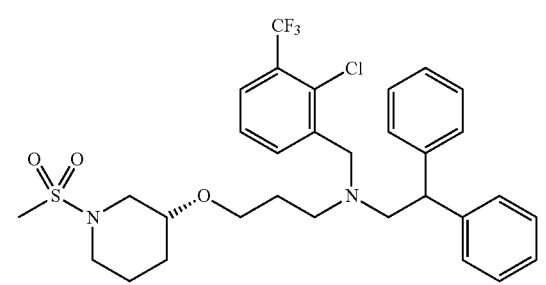 |
| 64 | 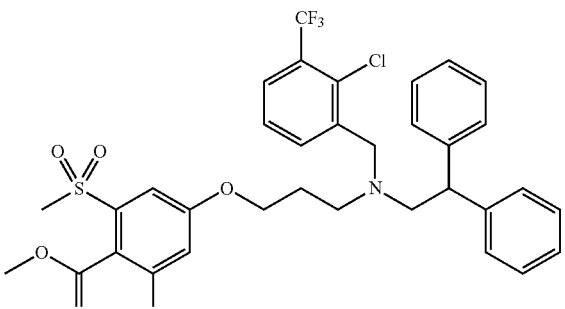 |

TABLE 1-continued

Exemplary Compounds of the Invention

| # | Structure |
|---|---|
| 65 | 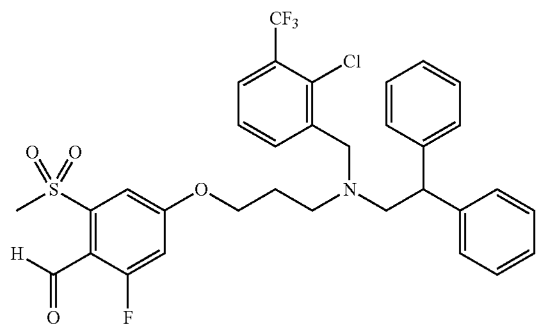 [SMILES: CS(=O)(=O)c1cc(OCCCN(Cc2cccc(C(F)(F)F)c2Cl)CC(c2ccccc2)c2ccccc2)cc(F)c1C=O] |
| 66 | 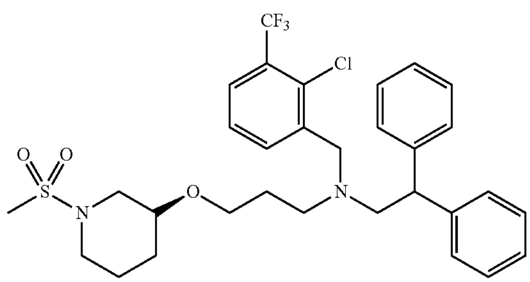 |
| 67 | 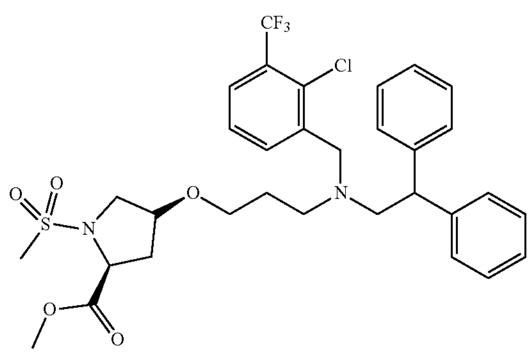 |
| 68 | 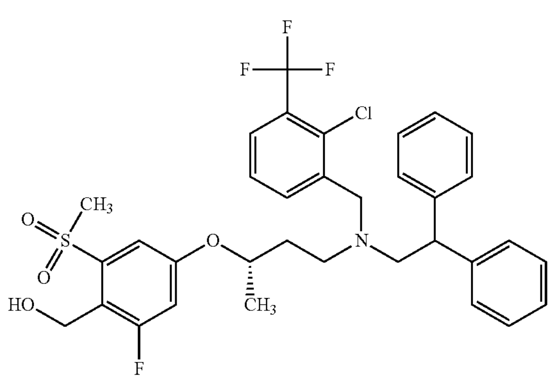 [SMILES: C[C@@H](CCN(Cc1cccc(C(F)(F)F)c1Cl)CC(c1ccccc1)c1ccccc1)Oc1cc(F)c(CO)c(S(C)(=O)=O)c1] |

TABLE 1-continued

Exemplary Compounds of the Invention

| # | Structure |
|---|---|
| 69 | 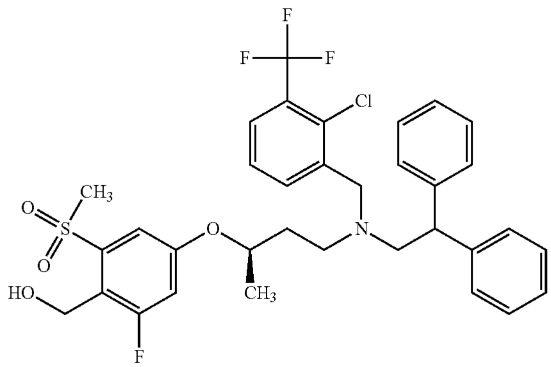 [SMILES: C[C@H](CCN(Cc1cccc(C(F)(F)F)c1Cl)CC(c1ccccc1)c1ccccc1)Oc1cc(F)c(CO)c(S(C)(=O)=O)c1] |
| 70 | 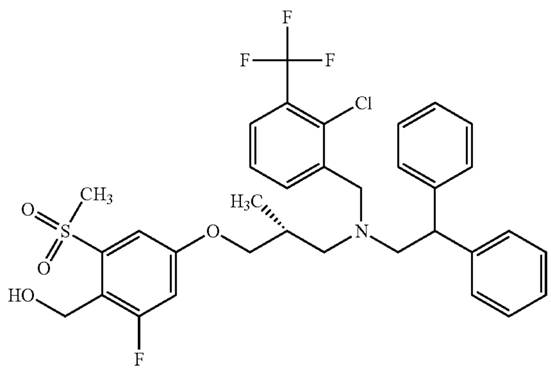 [SMILES: C[C@@H](COc1cc(F)c(CO)c(S(C)(=O)=O)c1)CN(Cc1cccc(C(F)(F)F)c1Cl)CC(c1ccccc1)c1ccccc1] |
| 71 | 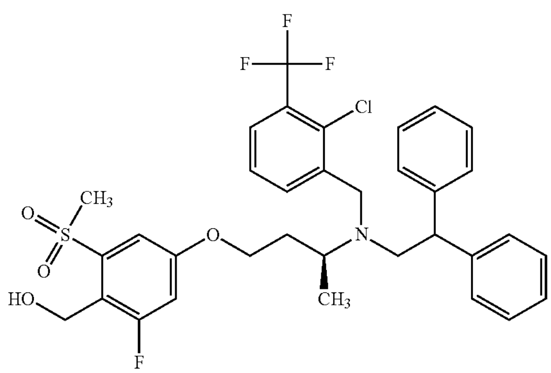 [SMILES: C[C@@H](CCOc1cc(F)c(CO)c(S(C)(=O)=O)c1)N(Cc1cccc(C(F)(F)F)c1Cl)CC(c1ccccc1)c1ccccc1] |
| 72 | 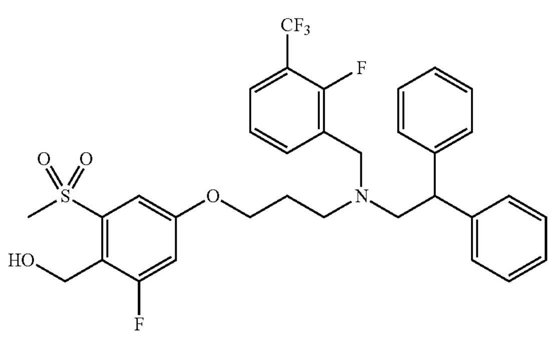 [SMILES: CS(=O)(=O)c1cc(OCCCN(Cc2cccc(C(F)(F)F)c2F)CC(c2ccccc2)c2ccccc2)cc(F)c1CO] |

TABLE 1-continued
Exemplary Compounds of the Invention
| # | Structure |
|---|---|
| 73 | 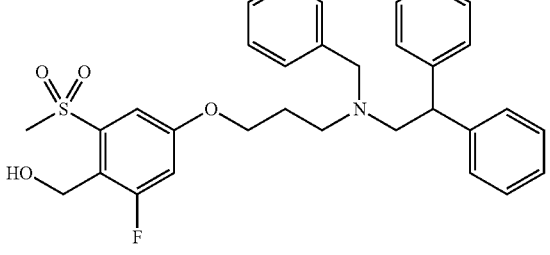 |
| 74 | 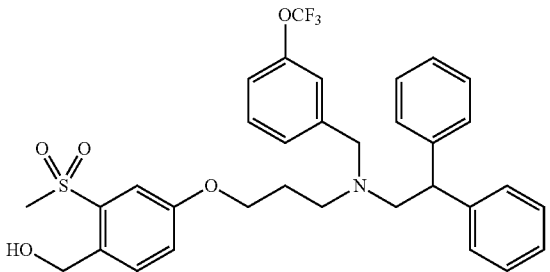 |
| 75 | 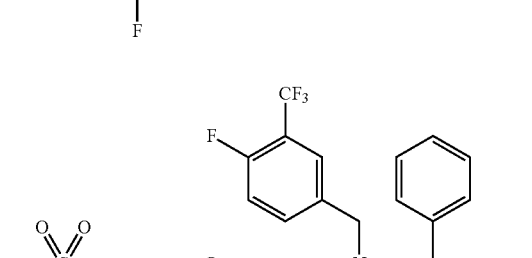 |
| 77 | 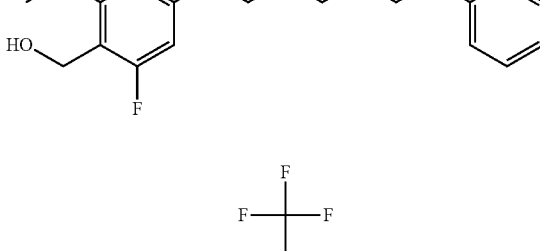 |

TABLE 1-continued
Exemplary Compounds of the Invention
| # | Structure |
|---|---|
| 78 | 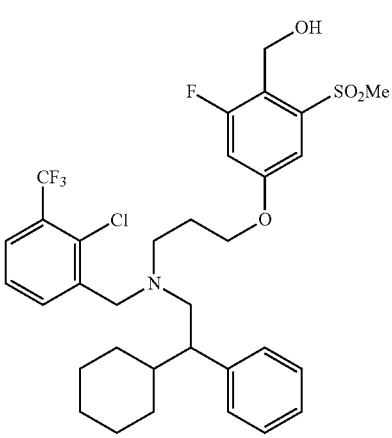 [SMILES: CS(=O)(=O)c1cc(OCCCN(Cc2cccc(C(F)(F)F)c2Cl)CC(c2ccccc2)C2CCCCC2)cc(F)c1CO] |
| 79 | 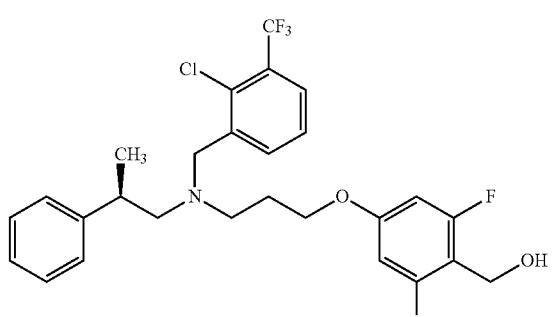 |
| 80 | 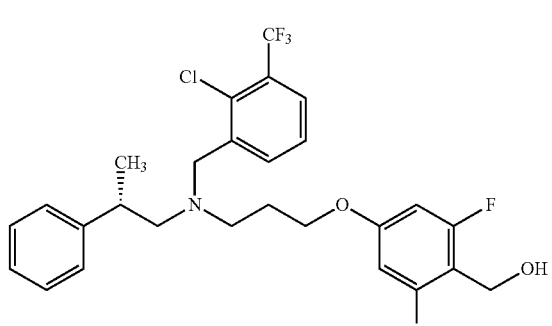 |
| 81 | 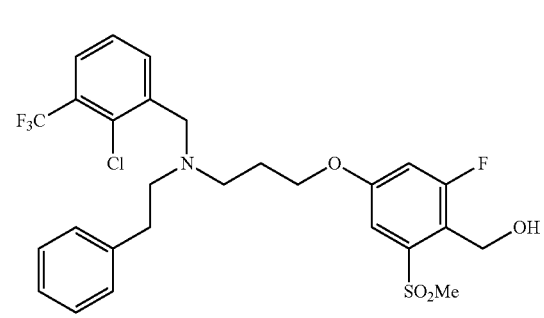 [SMILES: CS(=O)(=O)c1cc(OCCCN(CCc2ccccc2)Cc2cccc(C(F)(F)F)c2Cl)cc(F)c1CO] |

TABLE 1-continued
Exemplary Compounds of the Invention
| # | Structure |
|---|---|
| 82 | 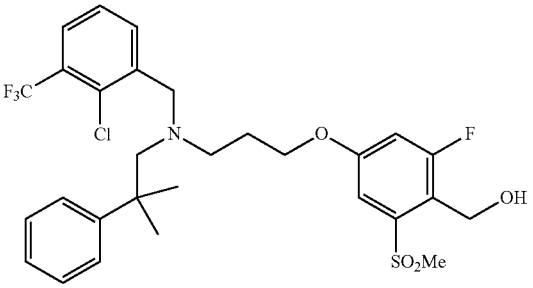 [SMILES: CC(C)(CN(CCCOc1cc(F)c(CO)c(S(C)(=O)=O)c1)Cc1cccc(C(F)(F)F)c1Cl)c1ccccc1] |
| 83 | 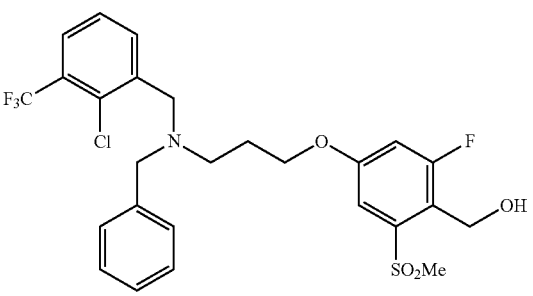 [SMILES: CS(=O)(=O)c1cc(OCCCN(Cc2ccccc2)Cc2cccc(C(F)(F)F)c2Cl)cc(F)c1CO] |
| 84 | 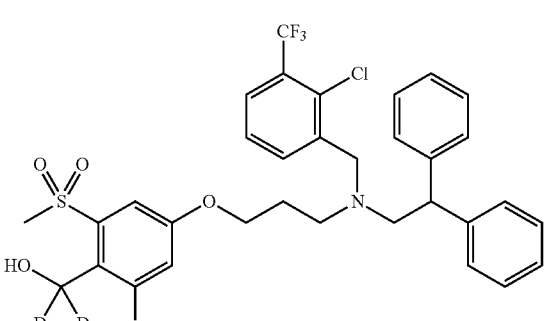 |
| 85 | 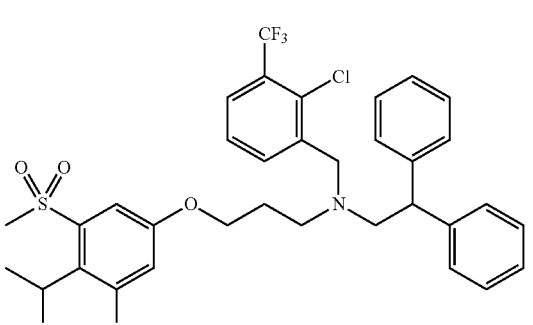 |
| 87 | 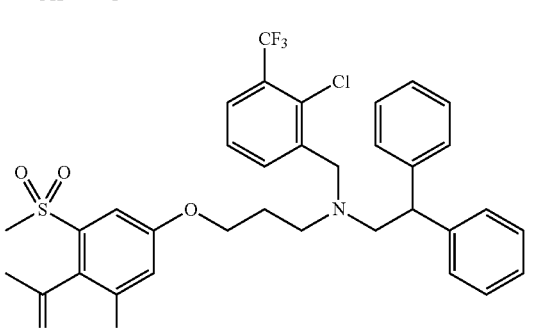 |

TABLE 1-continued

Exemplary Compounds of the Invention

| # | Structure |
|---|-----------|
| 88 | 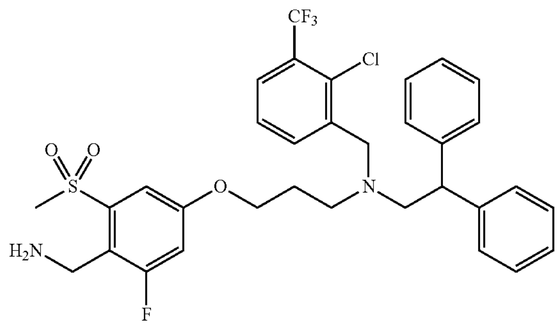 [SMILES: CS(=O)(=O)c1cc(OCCCN(Cc2cccc(C(F)(F)F)c2Cl)CC(c2ccccc2)c2ccccc2)cc(F)c1CN] |
| 89 | 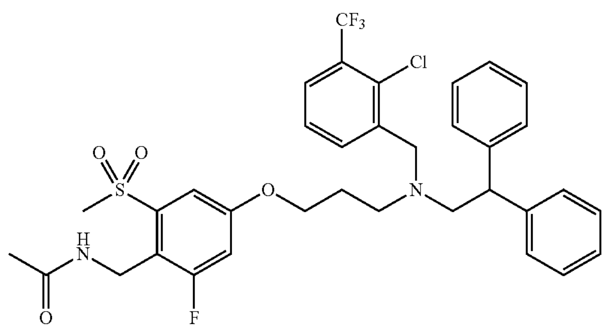 [SMILES: CC(=O)NCc1c(F)cc(OCCCN(Cc2cccc(C(F)(F)F)c2Cl)CC(c2ccccc2)c2ccccc2)cc1S(C)(=O)=O] |
| 90 | 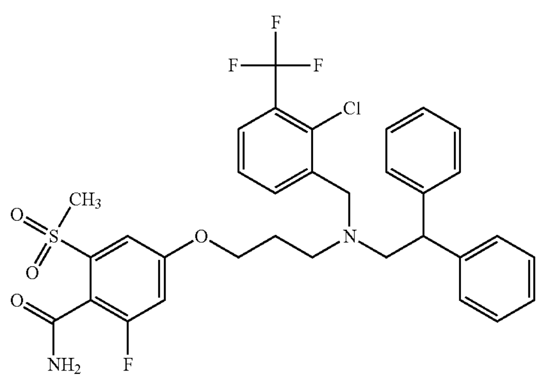 |
| 91 | 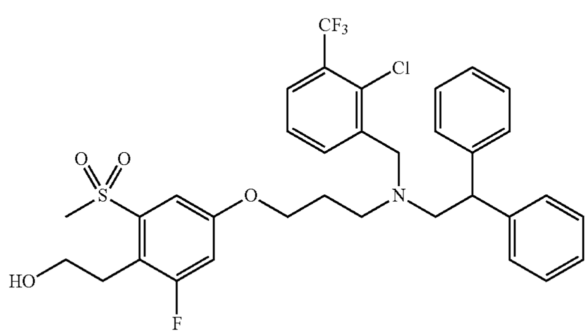 [SMILES: CS(=O)(=O)c1cc(OCCCN(Cc2cccc(C(F)(F)F)c2Cl)CC(c2ccccc2)c2ccccc2)cc(F)c1CCO] |

TABLE 1-continued
Exemplary Compounds of the Invention
| # | Structure |
|---|-----------|
| 92 | 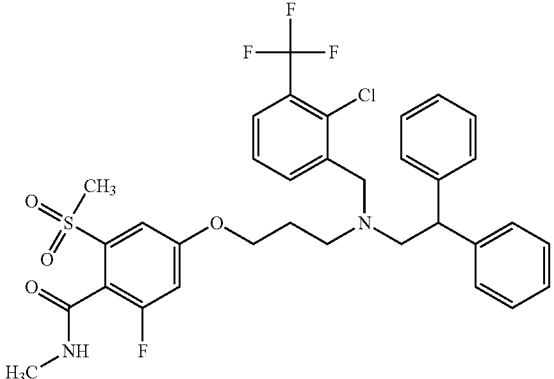 |
| 93 | 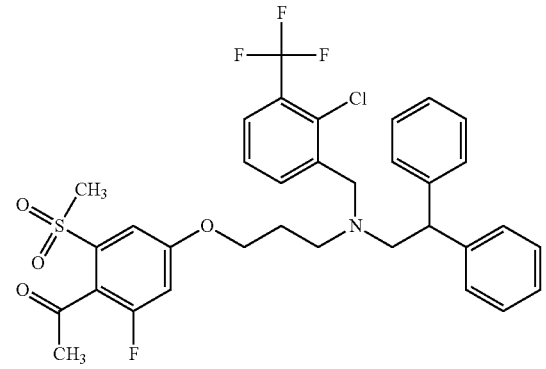 [SMILES: CC(=O)c1c(F)cc(OCCCN(Cc2cccc(C(F)(F)F)c2Cl)CC(c2ccccc2)c2ccccc2)cc1S(C)(=O)=O] |
| 94 | 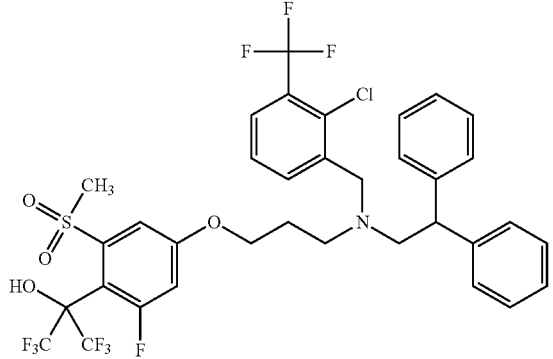 [SMILES: CS(=O)(=O)c1cc(OCCCN(Cc2cccc(C(F)(F)F)c2Cl)CC(c2ccccc2)c2ccccc2)cc(F)c1C(O)(C(F)(F)F)C(F)(F)F] |
| 95 | 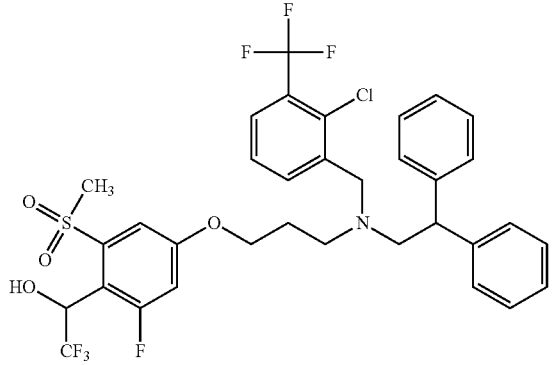 [SMILES: CS(=O)(=O)c1cc(OCCCN(Cc2cccc(C(F)(F)F)c2Cl)CC(c2ccccc2)c2ccccc2)cc(F)c1C(O)C(F)(F)F] |

TABLE 1-continued

Exemplary Compounds of the Invention

| # | Structure |
|---|---|
| 96 | 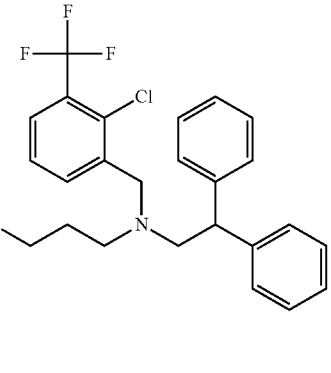 |
| 97 | 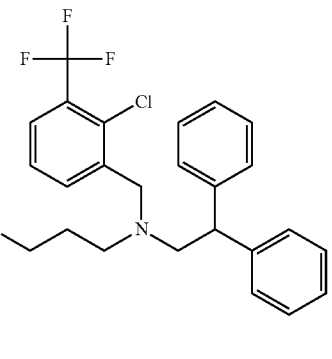 |

In some embodiments, the LXRβ agonist is any one of compounds 98-680 in Table 2.

TABLE 2

LXRβ agonists

| # | Name |
|---|---|
| 98 | (2-fluoro-6-methanesulfonyl-4-{3-[(2-methyl-2-phenylpropyl)({[3-(trifluoromethyl)phenyl]methyl})amino]propoxy}phenyl)methanol |
| 99 | (2-fluoro-6-methanesulfonyl-4-{3-[(2-phenylethyl)({[3-(trifluoromethyl)phenyl]methyl})amino]propoxy}phenyl)methanol |
| 100 | (2-fluoro-6-methanesulfonyl-4-{3-[(2-phenylpropyl)({[3-(trifluoromethyl)phenyl]methyl})amino]propoxy}phenyl)methanol |
| 101 | (4-{3-[benzyl({[2-fluoro-3-(trifluoromethyl)phenyl]methyl})amino]propoxy}-2-fluoro-6-methanesulfonylphenyl)methanol |
| 102 | (4-{3-[benzyl({[3-(trifluoromethyl)phenyl]methyl})amino]propoxy}-2-fluoro-6-methanesulfonylphenyl)methanol |
| 103 | [2-fluoro-4-(3-{[(4-fluorophenyl)methyl]({[3-(trifluoromethyl)phenyl]methyl})amino}propoxy)-6-methanesulfonylphenyl]methanol |
| 104 | [2-fluoro-4-(3-{[2-(4-fluorophenyl)-2-methylpropyl]({[3-(trifluoromethyl)phenyl]methyl})amino}propoxy)-6-methanesulfonylphenyl]methanol |
| 105 | [2-fluoro-4-(3-{[2-(4-fluorophenyl)ethyl]({[3-(trifluoromethyl)phenyl]methyl})amino}propoxy)-6-methanesulfonylphenyl]methanol |
| 106 | [2-fluoro-4-(3-{[2-(4-fluorophenyl)propyl]({[3-(trifluoromethyl)phenyl]methyl})amino}propoxy)-6-methanesulfonylphenyl]methanol |
| 107 | {4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}methanol |

TABLE 2-continued

| LXRβ agonists | |
|---|---|
| # | Name |

| | |
|---|---|
| 108 | [4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]methanol |
| 109 | [4-(3-{[2,2-difluoro-2-(4-fluorophenyl)ethyl]({[3-(trifluoromethyl)phenyl]methyl})amino}propoxy)-2-fluoro-6-methanesulfonylphenyl]methanol |
| 110 | {4-[3-({[2-chloro-3-(trifluoromethyl)phenyl]methyl}[(4-fluorophenyl)methyl]amino)propoxy]-2-fluoro-6-methanesulfonylphenyl}methanol |
| 111 | {4-[3-({[2-chloro-3-(trifluoromethyl)phenyl]methyl}[2-(4-fluorophenyl)-2-methylpropyl]amino)propoxy]-2-fluoro-6-methanesulfonylphenyl}methanol |
| 112 | {4-[3-({[2-chloro-3-(trifluoromethyl)phenyl]methyl}[2-(4-fluorophenyl)ethyl]amino)propoxy]-2-fluoro-6-methanesulfonylphenyl}methanol |
| 113 | {4-[3-({[2-chloro-3-(trifluoromethyl)phenyl]methyl}[2-(4-fluorophenyl)propyl]amino)propoxy]-2-fluoro-6-methanesulfonylphenyl}methanol |
| 114 | {2-fluoro-4-[3-({[2-fluoro-3-(trifluoromethyl)phenyl]methyl}(2-methyl-2-phenylpropyl)amino)propoxy]-6-methanesulfonylphenyl}methanol |
| 115 | {2-fluoro-4-[3-({[2-fluoro-3-(trifluoromethyl)phenyl]methyl}(2-phenylethyl)amino)propoxy]-6-methanesulfonylphenyl}methanol |
| 116 | {2-fluoro-4-[3-({[2-fluoro-3-(trifluoromethyl)phenyl]methyl}(2-phenylpropyl)amino)propoxy]-6-methanesulfonylphenyl}methanol |
| 117 | {2-fluoro-4-[3-({[2-fluoro-3-(trifluoromethyl)phenyl]methyl}[(4-fluorophenyl)methyl]amino)propoxy]-6-methanesulfonylphenyl}methanol |
| 118 | {2-fluoro-4-[3-({[2-fluoro-3-(trifluoromethyl)phenyl]methyl}[2-(4-fluorophenyl)-2-methylpropyl]amino)propoxy]-6-methanesulfonylphenyl}methanol |
| 119 | {2-fluoro-4-[3-({[2-fluoro-3-(trifluoromethyl)phenyl]methyl}[2-(4-fluorophenyl)ethyl]amino)propoxy]-6-methanesulfonylphenyl}methanol |
| 120 | {2-fluoro-4-[3-({[2-fluoro-3-(trifluoromethyl)phenyl]methyl}[2-(4-fluorophenyl)propyl]amino)propoxy]-6-methanesulfonylphenyl}methanol |
| 121 | (2-methanesulfonyl-4-{3-[(2-methyl-2-phenylpropyl)({[3-(trifluoromethyl)phenyl]methyl})amino]propoxy}phenyl)methanol |
| 122 | (2-methanesulfonyl-4-{3-[(2-phenylethyl)({[3-(trifluoromethyl)phenyl]methyl})amino]propoxy}phenyl)methanol |
| 123 | (2-methanesulfonyl-4-{3-[(2-phenylpropyl)({[3-(trifluoromethyl)phenyl]methyl})amino]propoxy}phenyl)methanol |
| 124 | {4-[3-({[2-chloro-3-(trifluoromethyl)phenyl]methyl}(2,2-diphenylethyl)amino)propoxy]-2-methanesulfonylphenyl}methanol |
| 125 | (4-{3-[(2,2-diphenylethyl)({[2-fluoro-3-(trifluoromethyl)phenyl]methyl})amino]propoxy}-2-methanesulfonylphenyl)methanol |
| 126 | (4-{3-[(2,2-diphenylethyl)({[3-(trifluoromethyl)phenyl]methyl})amino]propoxy}-2-methanesulfonylphenyl)methanol |
| 127 | (4-{3-[benzyl({[2-chloro-3-(trifluoromethyl)phenyl]methyl})amino]propoxy}-2-methanesulfonylphenyl)methanol |
| 128 | (4-{3-[benzyl({[2-fluoro-3-(trifluoromethyl)phenyl]methyl})amino]propoxy}-2-methanesulfonylphenyl)methanol |
| 129 | (4-{3-[benzyl({[3-(trifluoromethyl)phenyl]methyl})amino]propoxy}-2-methanesulfonylphenyl)methanol |
| 130 | [4-(3-{[(4-fluorophenyl)methyl]({[3-(trifluoromethyl)phenyl]methyl})amino}propoxy)-2-methanesulfonylphenyl]methanol |
| 131 | [4-(3-{[2-(4-fluorophenyl)-2-methylpropyl]({[3-(trifluoromethyl)phenyl]methyl})amino}propoxy)-2-methanesulfonylphenyl]methanol |
| 132 | [4-(3-{[2-(4-fluorophenyl)ethyl]({[3-(trifluoromethyl)phenyl]methyl})amino}propoxy)-2-methanesulfonylphenyl]methanol |
| 133 | [4-(3-{[2-(4-fluorophenyl)propyl]({[3-(trifluoromethyl)phenyl]methyl})amino}propoxy)-2-methanesulfonylphenyl]methanol |
| 134 | {4-[3-({[2-chloro-3-(trifluoromethyl)phenyl]methyl}[2,2-difluoro-2-(4-fluorophenyl)ethyl]amino)propoxy]-2-methanesulfonylphenyl}methanol |
| 135 | [4-(3-{[2,2-difluoro-2-(4-fluorophenyl)ethyl]({[2-fluoro-3-(trifluoromethyl)phenyl]methyl})amino}propoxy)-2-methanesulfonylphenyl]methanol |
| 136 | [4-(3-{[2,2-difluoro-2-(4-fluorophenyl)ethyl]({[3-(trifluoromethyl)phenyl]methyl})amino}propoxy)-2-methanesulfonylphenyl]methanol |
| 137 | {4-[3-({[2-chloro-3-(trifluoromethyl)phenyl]methyl}(2-methyl-2-phenylpropyl)amino)propoxy]-2-methanesulfonylphenyl}methanol |
| 138 | {4-[3-({[2-chloro-3-(trifluoromethyl)phenyl]methyl}(2-phenylethyl)amino)propoxy]-2-methanesulfonylphenyl}methanol |

TABLE 2-continued

LXRβ agonists

| # | Name |
|---|---|
| 139 | {4-[3-({[2-chloro-3-(trifluoromethyl)phenyl]methyl}(2-phenylpropyl)amino)propoxy]-2-methanesulfonylphenyl}methanol |
| 140 | {4-[3-({[2-chloro-3-(trifluoromethyl)phenyl]methyl}[(4-fluorophenyl)methyl]amino)propoxy]-2-methanesulfonylphenyl}methanol |
| 141 | {4-[3-({[2-chloro-3-(trifluoromethyl)phenyl]methyl}[2-(4-fluorophenyl)-2-methylpropyl]amino)propoxy]-2-methanesulfonylphenyl}methanol |
| 142 | {4-[3-({[2-chloro-3-(trifluoromethyl)phenyl]methyl}[2-(4-fluorophenyl)ethyl]amino)propoxy]-2-methanesulfonylphenyl}methanol |
| 143 | {4-[3-({[2-chloro-3-(trifluoromethyl)phenyl]methyl}[2-(4-fluorophenyl)propyl]amino)propoxy]-2-methanesulfonylphenyl}methanol |
| 144 | {4-[3-({[2-fluoro-3-(trifluoromethyl)phenyl]methyl}(2-methyl-2-phenylpropyl)amino)propoxy]-2-methanesulfonylphenyl}methanol |
| 145 | {4-[3-({[2-fluoro-3-(trifluoromethyl)phenyl]methyl}(2-phenylethyl)amino)propoxy]-2-methanesulfonylphenyl}methanol |
| 146 | {4-[3-({[2-fluoro-3-(trifluoromethyl)phenyl]methyl}(2-phenylpropyl)amino)propoxy]-2-methanesulfonylphenyl}methanol |
| 147 | {4-[3-({[2-fluoro-3-(trifluoromethyl)phenyl]methyl}[(4-fluorophenyl)methyl]amino)propoxy]-2-methanesulfonylphenyl}methanol |
| 148 | {4-[3-({[2-fluoro-3-(trifluoromethyl)phenyl]methyl}[2-(4-fluorophenyl)-2-methylpropyl]amino)propoxy]-2-methanesulfonylphenyl}methanol |
| 149 | {4-[3-({[2-fluoro-3-(trifluoromethyl)phenyl]methyl}[2-(4-fluorophenyl)ethyl]amino)propoxy]-2-methanesulfonylphenyl}methanol |
| 150 | {4-[3-({[2-fluoro-3-(trifluoromethyl)phenyl]methyl}[2-(4-fluorophenyl)propyl]amino)propoxy]-2-methanesulfonylphenyl}methanol |
| 151 | [3-(3-methanesulfonylphenoxy)propyl](2-methyl-2-phenylpropyl){[3-(trifluoromethyl)phenyl]methyl}amine |
| 152 | [3-(3-methanesulfonylphenoxy)propyl](2-phenylethyl){[3-(trifluoromethyl)phenyl]methyl}amine |
| 153 | [3-(3-methanesulfonylphenoxy)propyl](2-phenylpropyl){[3-(trifluoromethyl)phenyl]methyl}amine |
| 154 | (2,2-diphenylethyl)({[2-fluoro-3-(trifluoromethyl)phenyl]methyl})[3-(3-methanesulfonylphenoxy)propyl]amine |
| 155 | (2,2-diphenylethyl)[3-(3-methanesulfonylphenoxy)propyl]{[3-(trifluoromethyl)phenyl]methyl}amine |
| 156 | benzyl({[2-chloro-3-(trifluoromethyl)phenyl]methyl})[3-(3-methanesulfonylphenoxy)propyl]amine |
| 157 | benzyl({[2-fluoro-3-(trifluoromethyl)phenyl]methyl})[3-(3-methanesulfonylphenoxy)propyl]amine |
| 158 | benzyl[3-(3-methanesulfonylphenoxy)propyl]{[3-(trifluoromethyl)phenyl]methyl}amine |
| 159 | [(4-fluorophenyl)methyl][3-(3-methanesulfonylphenoxy)propyl]{[3-(trifluoromethyl)phenyl]methyl}amine |
| 160 | [2-(4-fluorophenyl)-2-methylpropyl][3-(3-methanesulfonylphenoxy)propyl]{[3-(trifluoromethyl)phenyl]methyl}amine |
| 161 | [2-(4-fluorophenyl)ethyl][3-(3-methanesulfonylphenoxy)propyl]{[3-(trifluoromethyl)phenyl]methyl}amine |
| 162 | [2-(4-fluorophenyl)propyl][3-(3-methanesulfonylphenoxy)propyl]{[3-(trifluoromethyl)phenyl]methyl}amine |
| 163 | {[2-chloro-3-(trifluoromethyl)phenyl]methyl}[2,2-difluoro-2-(4-fluorophenyl)ethyl][3-(3-methanesulfonylphenoxy)propyl]amine |
| 164 | [2,2-difluoro-2-(4-fluorophenyl)ethyl]({[2-fluoro-3-(trifluoromethyl)phenyl]methyl})[3-(3-methanesulfonylphenoxy)propyl]amine |
| 165 | [2,2-difluoro-2-(4-fluorophenyl)ethyl][3-(3-methanesulfonylphenoxy)propyl]{[3-(trifluoromethyl)phenyl]methyl}amine |
| 166 | {[2-chloro-3-(trifluoromethyl)phenyl]methyl}[3-(3-methanesulfonylphenoxy)propyl](2-methyl-2-phenylpropyl)amine |
| 167 | {[2-chloro-3-(trifluoromethyl)phenyl]methyl}[3-(3-methanesulfonylphenoxy)propyl](2-phenylethyl)amine |
| 168 | {[2-chloro-3-(trifluoromethyl)phenyl]methyl}[3-(3-methanesulfonylphenoxy)propyl](2-phenylpropyl)amine |
| 169 | {[2-chloro-3-(trifluoromethyl)phenyl]methyl}[(4-fluorophenyl)methyl][3-(3-methanesulfonylphenoxy)propyl]amine |
| 170 | {[2-chloro-3-(trifluoromethyl)phenyl]methyl}[2-(4-fluorophenyl)-2-methylpropyl][3-(3-methanesulfonylphenoxy)propyl]amine |
| 171 | {[2-chloro-3-(trifluoromethyl)phenyl]methyl}[2-(4-fluorophenyl)ethyl][3-(3-methanesulfonylphenoxy)propyl]amine |
| 172 | {[2-chloro-3-(trifluoromethyl)phenyl]methyl}[2-(4-fluorophenyl)propyl][3-(3-methanesulfonylphenoxy)propyl]amine |
| 173 | {[2-fluoro-3-(trifluoromethyl)phenyl]methyl}[3-(3-methanesulfonylphenoxy)propyl](2-methyl-2-phenylpropyl)amine |
| 174 | {[2-fluoro-3-(trifluoromethyl)phenyl]methyl}[3-(3-methanesulfonylphenoxy)propyl](2-phenylethyl)amine |
| 175 | {[2-fluoro-3-(trifluoromethyl)phenyl]methyl}[3-(3-methanesulfonylphenoxy)propyl](2-phenylpropyl)amine |
| 176 | {[2-fluoro-3-(trifluoromethyl)phenyl]methyl}[(4-fluorophenyl)methyl][3-(3-methanesulfonylphenoxy)propyl]amine |

TABLE 2-continued

| | LXRβ agonists |
|---|---|
| # | Name |
| 177 | {[2-fluoro-3-(trifluoromethyl)phenyl]methyl}[2-(4-fluorophenyl)-2-methylpropyl][3-(3-methanesulfonylphenoxy)propyl]amine |
| 178 | {[2-fluoro-3-(trifluoromethyl)phenyl]methyl}[2-(4-fluorophenyl)ethyl][3-(3-methanesulfonylphenoxy)propyl]amine |
| 179 | {[2-fluoro-3-(trifluoromethyl)phenyl]methyl}[2-(4-fluorophenyl)propyl][3-(3-methanesulfonylphenoxy)propyl]amine |
| 180 | 1-(2-fluoro-6-methanesulfonyl-4-{3-[(2-phenylethyl)({[3-(trifluoromethyl)phenyl]methyl})amino]propoxy}phenyl)ethan-1-ol |
| 181 | 1-(2-fluoro-6-methanesulfonyl-4-{3-[(2-methyl-2-phenylpropyl)({[3-(trifluoromethyl)phenyl]methyl})amino]propoxy}phenyl)ethan-1-ol |
| 182 | 1-(2-fluoro-6-methanesulfonyl-4-{3-[(2-phenylpropyl)({[3-(trifluoromethyl)phenyl]methyl})amino]propoxy}phenyl)ethan-1-ol |
| 183 | 1-(4-{3-[(2,2-diphenylethyl)({[2-fluoro-3-(trifluoromethyl)phenyl]methyl})amino]propoxy}-2-fluoro-6-methanesulfonylphenyl)ethan-1-ol |
| 184 | 1-(4-{3-[(2,2-diphenylethyl)({[3-(trifluoromethyl)phenyl]methyl})amino]propoxy}-2-fluoro-6-methanesulfonylphenyl)ethan-1-ol |
| 185 | 1-(4-{3-[benzyl({[2-chloro-3-(trifluoromethyl)phenyl]methyl})amino]propoxy}-2-fluoro-6-methanesulfonylphenyl)ethan-1-ol |
| 186 | 1-(4-{3-[benzyl({[2-fluoro-3-(trifluoromethyl)phenyl]methyl})amino]propoxy}-2-fluoro-6-methanesulfonylphenyl)ethan-1-ol |
| 187 | 1-(4-{3-[benzyl({[3-(trifluoromethyl)phenyl]methyl})amino]propoxy}-2-fluoro-6-methanesulfonylphenyl)ethan-1-ol |
| 188 | 1-[2-fluoro-4-(3-{[(4-fluorophenyl)methyl]({[3-(trifluoromethyl)phenyl]methyl})amino}propoxy)-6-methanesulfonylphenyl]ethan-1-ol |
| 189 | 1-[2-fluoro-4-(3-{[2-(4-fluorophenyl)-2-methylpropyl]({[3-(trifluoromethyl)phenyl]methyl})amino}propoxy)-6-methanesulfonylphenyl]ethan-1-ol |
| 190 | 1-[2-fluoro-4-(3-{[2-(4-fluorophenyl)ethyl]({[3-(trifluoromethyl)phenyl]methyl})amino}propoxy)-6-methanesulfonylphenyl]ethan-1-ol |
| 191 | 1-[2-fluoro-4-(3-{[2-(4-fluorophenyl)propyl]({[3-(trifluoromethyl)phenyl]methyl})amino}propoxy)-6-methanesulfonylphenyl]ethan-1-ol |
| 192 | 1-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}ethan-1-ol |
| 193 | 1-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]ethan-1-ol |
| 194 | 1-[4-(3-{[2,2-difluoro-2-(4-fluorophenyl)ethyl]({[3-(trifluoromethyl)phenyl]methyl})amino}propoxy)-2-fluoro-6-methanesulfonylphenyl]ethan-1-ol |
| 195 | 1-{4-[3-({[2-chloro-3-(trifluoromethyl)phenyl]methyl}(2-methyl-2-phenylpropyl)amino)propoxy]-2-fluoro-6-methanesulfonylphenyl}ethan-1-ol |
| 196 | 1-{4-[3-({[2-chloro-3-(trifluoromethyl)phenyl]methyl}(2-phenylpropyl)amino)propoxy]-2-fluoro-6-methanesulfonylphenyl}ethan-1-ol |
| 197 | 1-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}ethan-1-ol |
| 198 | 1-{4-[3-({[2-chloro-3-(trifluoromethyl)phenyl]methyl}[(4-fluorophenyl)methyl]amino)propoxy]-2-fluoro-6-methanesulfonylphenyl}ethan-1-ol |
| 199 | 1-{4-[3-({[2-chloro-3-(trifluoromethyl)phenyl]methyl}[2-(4-fluorophenyl)ethyl]amino)propoxy]-2-fluoro-6-methanesulfonylphenyl}ethan-1-ol |
| 200 | 1-{2-fluoro-4-[3-({[2-fluoro-3-(trifluoromethyl)phenyl]methyl}(2-methyl-2-phenylpropyl)amino)propoxy]-6-methanesulfonylphenyl}ethan-1-ol |
| 201 | 1-{4-[3-({[2-chloro-3-(trifluoromethyl)phenyl]methyl}[2-(4-fluorophenyl)propyl]amino)propoxy]-2-fluoro-6-methanesulfonylphenyl}ethan-1-ol |
| 202 | 1-{2-fluoro-4-[3-({[2-fluoro-3-(trifluoromethyl)phenyl]methyl}(2-phenylethyl)amino)propoxy]-6-methanesulfonylphenyl}ethan-1-ol |
| 203 | 1-{2-fluoro-4-[3-({[2-fluoro-3-(trifluoromethyl)phenyl]methyl}(2-phenylpropyl)amino)propoxy]-6-methanesulfonylphenyl}ethan-1-ol |
| 204 | 1-{2-fluoro-4-[3-({[2-fluoro-3-(trifluoromethyl)phenyl]methyl}[(4-fluorophenyl)methyl]amino)propoxy]-6-methanesulfonylphenyl}ethan-1-ol |
| 205 | 1-{4-[3-({[2-chloro-3-(trifluoromethyl)phenyl]methyl}(2-phenylethyl)amino)propoxy]-2-fluoro-6-methanesulfonylphenyl}ethan-1-ol |
| 206 | 1-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}ethan-1-ol |
| 207 | 1-{2-fluoro-4-[3-({[2-fluoro-3-(trifluoromethyl)phenyl]methyl}[2-(4-fluorophenyl)ethyl]amino)propoxy]-6-methanesulfonylphenyl}ethan-1-ol |

TABLE 2-continued

LXRβ agonists

| # | Name |
|---|------|
| 208 | 1-{2-fluoro-4-[3-({[2-fluoro-3-(trifluoromethyl)phenyl]methyl}[2-(4-fluorophenyl)propyl]amino)propoxy]-6-methanesulfonylphenyl}ethan-1-ol |
| 209 | 1-(2-methanesulfonyl-4-{3-[(2-methyl-2-phenylpropyl)({[3-(trifluoromethyl)phenyl]methyl})amino]propoxy}phenyl)ethan-1-ol |
| 210 | 1-(2-methanesulfonyl-4-{3-[(2-phenylethyl)({[3-(trifluoromethyl)phenyl]methyl})amino]propoxy}phenyl)ethan-1-ol |
| 211 | 1-(2-methanesulfonyl-4-{3-[(2-phenylpropyl)({[3-(trifluoromethyl)phenyl]methyl})amino]propoxy}phenyl)ethan-1-ol |
| 212 | 1-(4-[3-[(2,2-diphenylethyl)({[2-fluoro-3-(trifluoromethyl)phenyl]methyl})amino]propoxy}-2-methanesulfonylphenyl)ethan-1-ol |
| 213 | 1-(4-{3-[(2,2-diphenylethyl)({[3-(trifluoromethyl)phenyl]methyl})amino]propoxy}-2-methanesulfonylphenyl)ethan-1-ol |
| 214 | 1-(4-{3-[benzyl({[2-chloro-3-(trifluoromethyl)phenyl]methyl})amino]propoxy}-2-methanesulfonylphenyl)ethan-1-ol |
| 215 | 1-(4-{3-[benzyl({[2-fluoro-3-(trifluoromethyl)phenyl]methyl})amino]propoxy}-2-methanesulfonylphenyl)ethan-1-ol |
| 216 | 1-(4-{3-[benzyl({[3-(trifluoromethyl)phenyl]methyl})amino]propoxy}-2-methanesulfonylphenyl)ethan-1-ol |
| 217 | 1-[4-(3-{[(4-fluorophenyl)methyl]({[3-(trifluoromethyl)phenyl]methyl})amino}propoxy)-2-methanesulfonylphenyl]ethan-1-ol |
| 218 | 1-[4-(3-{[2-(4-fluorophenyl)-2-methylpropyl]({[3-(trifluoromethyl)phenyl]methyl})amino}propoxy)-2-methanesulfonylphenyl]ethan-1-ol |
| 219 | 1-[4-(3-{[2-(4-fluorophenyl)ethyl]({[3-(trifluoromethyl)phenyl]methyl})amino}propoxy)-2-methanesulfonylphenyl]ethan-1-ol |
| 220 | 1-[4-(3-{[2-(4-fluorophenyl)propyl]({[3-(trifluoromethyl)phenyl]methyl})amino}propoxy)-2-methanesulfonylphenyl]ethan-1-ol |
| 221 | 1-{4-[3-({[2-chloro-3-(trifluoromethyl)phenyl]methyl}[2,2-difluoro-2-(4-fluorophenyl)ethyl]amino)propoxy]-2-methanesulfonylphenyl}ethan-1-ol |
| 222 | 1-[4-(3-{[2,2-difluoro-2-(4-fluorophenyl)ethyl]({[2-fluoro-3-(trifluoromethyl)phenyl]methyl})amino}propoxy)-2-methanesulfonylphenyl]ethan-1-ol |
| 223 | 1-[4-(3-{[2,2-difluoro-2-(4-fluorophenyl)ethyl]({[3-(trifluoromethyl)phenyl]methyl})amino}propoxy)-2-methanesulfonylphenyl]ethan-1-ol |
| 224 | 1-{4-[3-({[2-chloro-3-(trifluoromethyl)phenyl]methyl}(2-methyl-2-phenylpropyl)amino)propoxy]-2-methanesulfonylphenyl}ethan-1-ol |
| 225 | 1-{4-[3-({[2-chloro-3-(trifluoromethyl)phenyl]methyl}(2-phenylethyl)amino)propoxy]-2-methanesulfonylphenyl}ethan-1-ol |
| 226 | 1-{4-[3-({[2-chloro-3-(trifluoromethyl)phenyl]methyl}(2-phenylpropyl)amino)propoxy]-2-methanesulfonylphenyl}ethan-1-ol |
| 227 | 1-{4-[3-({[2-chloro-3-(trifluoromethyl)phenyl]methyl}[(4-fluorophenyl)methyl]amino)propoxy]-2-methanesulfonylphenyl}ethan-1-ol |
| 228 | 1-{4-[3-({[2-chloro-3-(trifluoromethyl)phenyl]methyl}[2-(4-fluorophenyl)-2-methylpropyl]amino)propoxy]-2-methanesulfonylphenyl}ethan-1-ol |
| 229 | 1-{4-[3-({[2-chloro-3-(trifluoromethyl)phenyl]methyl}[2-(4-fluorophenyl)ethyl]amino)propoxy]-2-methanesulfonylphenyl}ethan-1-ol |
| 230 | 1-{4-[3-({[2-chloro-3-(trifluoromethyl)phenyl]methyl}[2-(4-fluorophenyl)propyl]amino)propoxy]-2-methanesulfonylphenyl}ethan-1-ol |
| 231 | 1-{4-[3-({[2-fluoro-3-(trifluoromethyl)phenyl]methyl}(2-methyl-2-phenylpropyl)amino)propoxy]-2-methanesulfonylphenyl}ethan-1-ol |
| 232 | 1-{4-[3-({[2-fluoro-3-(trifluoromethyl)phenyl]methyl}(2-phenylethyl)amino)propoxy]-2-methanesulfonylphenyl}ethan-1-ol |
| 233 | 1-{4-[3-({[2-fluoro-3-(trifluoromethyl)phenyl]methyl}(2-phenylpropyl)amino)propoxy]-2-methanesulfonylphenyl}ethan-1-ol |
| 234 | 1-{4-[3-({[2-fluoro-3-(trifluoromethyl)phenyl]methyl}[(4-fluorophenyl)methyl]amino)propoxy]-2-methanesulfonylphenyl}ethan-1-ol |
| 235 | 1-{4-[3-({[2-fluoro-3-(trifluoromethyl)phenyl]methyl}[2-(4-fluorophenyl)-2-methylpropyl]amino)propoxy]-2-methanesulfonylphenyl}ethan-1-ol |
| 236 | 1-{4-[3-({[2-fluoro-3-(trifluoromethyl)phenyl]methyl}[2-(4-fluorophenyl)ethyl]amino)propoxy]-2-methanesulfonylphenyl}ethan-1-ol |
| 237 | 1-{4-[3-({[2-fluoro-3-(trifluoromethyl)phenyl]methyl}[2-(4-fluorophenyl)propyl]amino)propoxy]-2-methanesulfonylphenyl}ethan-1-ol |
| 238 | 1-{4-[3-({[2-chloro-3-(trifluoromethyl)phenyl]methyl}(2,2-diphenylethyl)amino)propoxy]-2-methanesulfonylphenyl}ethan-1-ol |
| 239 | 2-fluoro-6-methanesulfonyl-4-{3-[(2-phenylethyl)({[3-(trifluoromethyl)phenyl]methyl})amino]propoxy}benzaldehyde |
| 240 | 4-{3-[(2,2-diphenylethyl)({[2-fluoro-3-(trifluoromethyl)phenyl]methyl})amino]propoxy}-2-fluoro-6-methanesulfonylbenzaldehyde |

TABLE 2-continued

LXRβ agonists

| # | Name |
|---|------|
| 241 | 2-fluoro-6-methanesulfonyl-4-{3-[(2-methyl-2-phenylpropyl)({[3-(trifluoromethyl)phenyl]methyl})amino]propoxy}benzaldehyde |
| 242 | 4-{3-[(2,2-diphenylethyl)({[3-(trifluoromethyl)phenyl]methyl})amino]propoxy}-2-fluoro-6-methanesulfonylbenzaldehyde |
| 243 | 4-{3-[benzyl({[2-chloro-3-(trifluoromethyl)phenyl]methyl})amino]propoxy}-2-fluoro-6-methanesulfonylbenzaldehyde |
| 244 | 4-{3-[benzyl({[2-fluoro-3-(trifluoromethyl)phenyl]methyl})amino]propoxy}-2-fluoro-6-methanesulfonylbenzaldehyde |
| 245 | 4-{3-[benzyl({[3-(trifluoromethyl)phenyl]methyl})amino]propoxy}-2-fluoro-6-methanesulfonylbenzaldehyde |
| 246 | 2-fluoro-4-(3-{[(4-fluorophenyl)methyl]({[3-(trifluoromethyl)phenyl]methyl})amino}propoxy)-6-methanesulfonylbenzaldehyde |
| 247 | 2-fluoro-4-(3-{[2-(4-fluorophenyl)-2-methylpropyl]({[3-(trifluoromethyl)phenyl]methyl})amino}propoxy)-6-methanesulfonylbenzaldehyde |
| 248 | 2-fluoro-4-(3-{[2-(4-fluorophenyl)ethyl]({[3-(trifluoromethyl)phenyl]methyl})amino}propoxy)-6-methanesulfonylbenzaldehyde |
| 249 | 2-fluoro-4-(3-{[2-(4-fluorophenyl)propyl]({[3-(trifluoromethyl)phenyl]methyl})amino}propoxy)-6-methanesulfonylbenzaldehyde |
| 250 | 4-(3-{[2,2-difluoro-2-(4-fluorophenyl)ethyl]({[2-fluoro-3-(trifluoromethyl)phenyl]methyl})amino}propoxy)-2-fluoro-6-methanesulfonylbenzaldehyde |
| 251 | 4-[3-({[2-chloro-3-(trifluoromethyl)phenyl]methyl}[2,2-difluoro-2-(4-fluorophenyl)ethyl]amino)propoxy]-2-fluoro-6-methanesulfonylbenzaldehyde |
| 252 | 4-(3-{[2,2-difluoro-2-(4-fluorophenyl)ethyl]({[3-(trifluoromethyl)phenyl]methyl})amino}propoxy)-2-fluoro-6-methanesulfonylbenzaldehyde |
| 253 | 4-[3-({[2-chloro-3-(trifluoromethyl)phenyl]methyl}(2-methyl-2-phenylpropyl)amino)propoxy]-2-fluoro-6-methanesulfonylbenzaldehyde |
| 254 | 4-[3-({[2-chloro-3-(trifluoromethyl)phenyl]methyl}(2-phenylethyl)amino)propoxy]-2-fluoro-6-methanesulfonylbenzaldehyde |
| 255 | 4-[3-({[2-chloro-3-(trifluoromethyl)phenyl]methyl}(2-phenylpropyl)amino)propoxy]-2-fluoro-6-methanesulfonylbenzaldehyde |
| 256 | 4-[3-({[2-chloro-3-(trifluoromethyl)phenyl]methyl}[(4-fluorophenyl)methyl]amino)propoxy]-2-fluoro-6-methanesulfonylbenzaldehyde |
| 257 | 4-[3-({[2-chloro-3-(trifluoromethyl)phenyl]methyl}[2-(4-fluorophenyl)-2-methylpropyl]amino)propoxy]-2-fluoro-6-methanesulfonylbenzaldehyde |
| 258 | 2-fluoro-4-[3-({[2-fluoro-3-(trifluoromethyl)phenyl]methyl}(2-methyl-2-phenylpropyl)amino)propoxy]-6-methanesulfonylbenzaldehyde |
| 259 | 4-[3-({[2-chloro-3-(trifluoromethyl)phenyl]methyl}[2-(4-fluorophenyl)propyl]amino)propoxy]-2-fluoro-6-methanesulfonylbenzaldehyde |
| 260 | 2-fluoro-4-[3-({[2-fluoro-3-(trifluoromethyl)phenyl]methyl}(2-phenylethyl)amino)propoxy]-6-methanesulfonylbenzaldehyde |
| 261 | 2-fluoro-4-[3-({[2-fluoro-3-(trifluoromethyl)phenyl]methyl}(2-phenylpropyl)amino)propoxy]-6-methanesulfonylbenzaldehyde |
| 262 | 2-fluoro-4-[3-({[2-fluoro-3-(trifluoromethyl)phenyl]methyl}[(4-fluorophenyl)methyl]amino)propoxy]-6-methanesulfonylbenzaldehyde |
| 263 | 2-fluoro-4-[3-({[2-fluoro-3-(trifluoromethyl)phenyl]methyl}[2-(4-fluorophenyl)-2-methylpropyl]amino)propoxy]-6-methanesulfonylbenzaldehyde |
| 264 | 2-fluoro-6-methanesulfonyl-4-{3-[(2-phenylpropyl)({[3-(trifluoromethyl)phenyl]methyl})amino]propoxy}benzaldehyde |
| 265 | 2-fluoro-4-[3-({[2-fluoro-3-(trifluoromethyl)phenyl]methyl}[2-(4-fluorophenyl)ethyl]amino)propoxy]-6-methanesulfonylbenzaldehyde |
| 266 | 2-fluoro-4-[3-({[2-fluoro-3-(trifluoromethyl)phenyl]methyl}[2-(4-fluorophenyl)propyl]amino)propoxy]-6-methanesulfonylbenzaldehyde |
| 267 | 4-[3-({[2-chloro-3-(trifluoromethyl)phenyl]methyl}[2-(4-fluorophenyl)ethyl]amino)propoxy]-2-fluoro-6-methanesulfonylbenzaldehyde |
| 268 | 2-methanesulfonyl-4-{3-[(2-methyl-2-phenylpropyl)({[3-(trifluoromethyl)phenyl]methyl})amino]propoxy}benzaldehyde |
| 269 | 2-methanesulfonyl-4-{3-[(2-phenylethyl)({[3-(trifluoromethyl)phenyl]methyl})amino]propoxy}benzaldehyde |
| 270 | 2-methanesulfonyl-4-{3-[(2-phenylpropyl)({[3-(trifluoromethyl)phenyl]methyl})amino]propoxy}benzaldehyde |
| 271 | 4-{3-[(2,2-diphenylethyl)({[2-fluoro-3-(trifluoromethyl)phenyl]methyl})amino]propoxy}-2-methanesulfonylbenzaldehyde |
| 272 | 4-{3-[(2,2-diphenylethyl)({[3-(trifluoromethyl)phenyl]methyl})amino]propoxy}-2-methanesulfonylbenzaldehyde |
| 273 | 4-{3-[benzyl({[2-chloro-3-(trifluoromethyl)phenyl]methyl})amino]propoxy}-2-methanesulfonylbenzaldehyde |

TABLE 2-continued

LXRβ agonists

| # | Name |
|---|---|
| 274 | 4-{3-[benzyl({[2-fluoro-3-(trifluoromethyl)phenyl]methyl})amino]propoxy}-2-methanesulfonylbenzaldehyde |
| 275 | 4-{3-[benzyl({[3-(trifluoromethyl)phenyl]methyl})amino]propoxy}-2-methanesulfonylbenzaldehyde |
| 276 | 4-(3-{[(4-fluorophenyl)methyl]({[3-(trifluoromethyl)phenyl]methyl})amino}propoxy)-2-methanesulfonylbenzaldehyde |
| 277 | 4-(3-{[2-(4-fluorophenyl)-2-methylpropyl]({[3-(trifluoromethyl)phenyl]methyl})amino}propoxy)-2-methanesulfonylbenzaldehyde |
| 278 | 4-(3-{[2-(4-fluorophenyl)ethyl]({[3-(trifluoromethyl)phenyl]methyl})amino}propoxy)-2-methanesulfonylbenzaldehyde |
| 279 | 4-(3-{[2-(4-fluorophenyl)propyl]({[3-(trifluoromethyl)phenyl]methyl})amino}propoxy)-2-methanesulfonylbenzaldehyde |
| 280 | 4-[3-({[2-chloro-3-(trifluoromethyl)phenyl]methyl}[2,2-difluoro-2-(4-fluorophenyl)ethyl]amino)propoxy]-2-methanesulfonylbenzaldehyde |
| 281 | 4-(3-{[2,2-difluoro-2-(4-fluorophenyl)ethyl]({[2-fluoro-3-(trifluoromethyl)phenyl]methyl})amino}propoxy)-2-methanesulfonylbenzaldehyde |
| 282 | 4-(3-{[2,2-difluoro-2-(4-fluorophenyl)ethyl]({[3-(trifluoromethyl)phenyl]methyl})amino}propoxy)-2-methanesulfonylbenzaldehyde |
| 283 | 4-[3-({[2-chloro-3-(trifluoromethyl)phenyl]methyl}(2-methyl-2-phenylpropyl)amino)propoxy]-2-methanesulfonylbenzaldehyde |
| 284 | 4-[3-({[2-chloro-3-(trifluoromethyl)phenyl]methyl}(2-phenylethyl)amino)propoxy]-2-methanesulfonylbenzaldehyde |
| 285 | 4-[3-({[2-chloro-3-(trifluoromethyl)phenyl]methyl}(2-phenylpropyl)amino)propoxy]-2-methanesulfonylbenzaldehyde |
| 286 | 4-[3-({[2-chloro-3-(trifluoromethyl)phenyl]methyl}(2,2-diphenylethyl)amino)propoxy]-2-methanesulfonylbenzaldehyde |
| 287 | 4-[3-({[2-chloro-3-(trifluoromethyl)phenyl]methyl}[(4-fluorophenyl)methyl]amino)propoxy]-2-methanesulfonylbenzaldehyde |
| 288 | 4-[3-({[2-chloro-3-(trifluoromethyl)phenyl]methyl}[2-(4-fluorophenyl)-2-methylpropyl]amino)propoxy]-2-methanesulfonylbenzaldehyde |
| 289 | 4-[3-({[2-chloro-3-(trifluoromethyl)phenyl]methyl}[2-(4-fluorophenyl)ethyl]amino)propoxy]-2-methanesulfonylbenzaldehyde |
| 290 | 4-[3-({[2-chloro-3-(trifluoromethyl)phenyl]methyl}[2-(4-fluorophenyl)propyl]amino)propoxy]-2-methanesulfonylbenzaldehyde |
| 291 | 4-[3-({[2-fluoro-3-(trifluoromethyl)phenyl]methyl}(2-methyl-2-phenylpropyl)amino)propoxy]-2-methanesulfonylbenzaldehyde |
| 292 | 4-[3-({[2-fluoro-3-(trifluoromethyl)phenyl]methyl}(2-phenylethyl)amino)propoxy]-2-methanesulfonylbenzaldehyde |
| 293 | 4-[3-({[2-fluoro-3-(trifluoromethyl)phenyl]methyl}(2-phenylpropyl)amino)propoxy]-2-methanesulfonylbenzaldehyde |
| 294 | 4-[3-({[2-fluoro-3-(trifluoromethyl)phenyl]methyl}[(4-fluorophenyl)methyl]amino)propoxy]-2-methanesulfonylbenzaldehyde |
| 295 | 4-[3-({[2-fluoro-3-(trifluoromethyl)phenyl]methyl}[2-(4-fluorophenyl)-2-methylpropyl]amino)propoxy]-2-methanesulfonylbenzaldehyde |
| 296 | 4-[3-({[2-fluoro-3-(trifluoromethyl)phenyl]methyl}[2-(4-fluorophenyl)ethyl]amino)propoxy]-2-methanesulfonylbenzaldehyde |
| 297 | 4-[3-({[2-fluoro-3-(trifluoromethyl)phenyl]methyl}[2-(4-fluorophenyl)propyl]amino)propoxy]-2-methanesulfonylbenzaldehyde |
| 298 | methyl 2-fluoro-6-methanesulfonyl-4-{3-[(2-methyl-2-phenylpropyl)({[3-(trifluoromethyl)phenyl]methyl})amino]propoxy}benzoate |
| 299 | methyl 2-fluoro-6-methanesulfonyl-4-{3-[(2-phenylpropyl)({[3-(trifluoromethyl)phenyl]methyl})amino]propoxy(benzoate |
| 300 | methyl 4-{3-[(2,2-diphenylethyl)({[3-(trifluoromethyl)phenyl]methyl})amino]propoxy}-2-fluoro-6-methanesulfonylbenzoate |
| 301 | methyl 2-fluoro-6-methanesulfonyl-4-{3-[(2-phenylethyl)({[3-(trifluoromethyl)phenyl]methyl})amino]propoxy}benzoate |
| 302 | methyl 4-{3-[(2,2-diphenylethyl)({[2-fluoro-3-(trifluoromethyl)phenyl]methyl})amino]propoxy}-2-fluoro-6-methanesulfonylbenzoate |
| 303 | methyl 4-{3-[benzyl({[2-chloro-3-(trifluoromethyl)phenyl]methyl})amino]propoxy}-2-fluoro-6-methanesulfonylbenzoate |
| 304 | methyl 4-{3-[benzyl({[2-fluoro-3-(trifluoromethyl)phenyl]methyl})amino]propoxy}-2-fluoro-6-methanesulfonylbenzoate |
| 305 | methyl 4-{3-[benzyl({[3-(trifluoromethyl)phenyl]methyl})amino]propoxy}-2-fluoro-6-methanesulfonylbenzoate |
| 306 | methyl 2-fluoro-4-(3-{[(4-fluorophenyl)methyl]({[3-(trifluoromethyl)phenyl]methyl})amino}propoxy)-6-methanesulfonylbenzoate |

TABLE 2-continued

LXRβ agonists

| # | Name |
|---|---|
| 307 | methyl 2-fluoro-4-(3-{[2-(4-fluorophenyl)-2-methylpropyl]({[3-(trifluoromethyl)phenyl]methyl})amino}propoxy)-6-methanesulfonylbenzoate |
| 308 | methyl 2-fluoro-4-(3-{[2-(4-fluorophenyl)ethyl]({[3-(trifluoromethyl)phenyl]methyl})amino}propoxy)-6-methanesulfonylbenzoate |
| 309 | methyl 2-fluoro-4-(3-{[2-(4-fluorophenyl)propyl]({[3-(trifluoromethyl)phenyl]methyl})amino}propoxy)-6-methanesulfonylbenzoate |
| 310 | methyl 4-[3-({[2-chloro-3-(trifluoromethyl)phenyl]methyl}[2,2-difluoro-2-(4-fluorophenyl)ethyl]amino)propoxy]-2-fluoro-6-methanesulfonylbenzoate |
| 311 | methyl 4-(3-{[2,2-difluoro-2-(4-fluorophenyl)ethyl]({[2-fluoro-3-(trifluoromethyl)phenyl]methyl})amino}propoxy)-2-fluoro-6-methanesulfonylbenzoate |
| 312 | methyl 4-(3-{[2,2-difluoro-2-(4-fluorophenyl)ethyl]({[3-(trifluoromethyl)phenyl]methyl})amino}propoxy)-2-fluoro-6-methanesulfonylbenzoate |
| 313 | methyl 4-[3-({[2-chloro-3-(trifluoromethyl)phenyl]methyl}(2-methyl-2-phenylpropyl)amino)propoxy]-2-fluoro-6-methanesulfonylbenzoate |
| 314 | methyl 4-[3-({[2-chloro-3-(trifluoromethyl)phenyl]methyl}(2-phenylethyl)amino)propoxy]-2-fluoro-6-methanesulfonylbenzoate |
| 315 | methyl 4-[3-({[2-chloro-3-(trifluoromethyl)phenyl]methyl}[2-(4-fluorophenyl)-2-methylpropyl]amino)propoxy]-2-fluoro-6-methanesulfonylbenzoate |
| 316 | methyl 4-[3-({[2-chloro-3-(trifluoromethyl)phenyl]methyl}[(4-fluorophenyl)methyl]amino)propoxy]-2-fluoro-6-methanesulfonylbenzoate |
| 317 | methyl 4-[3-({[2-chloro-3-(trifluoromethyl)phenyl]methyl}(2-phenylpropyl)amino)propoxy]-2-fluoro-6-methanesulfonylbenzoate |
| 318 | methyl 4-[3-({[2-chloro-3-(trifluoromethyl)phenyl]methyl}[2-(4-fluorophenyl)propyl]amino)propoxy]-2-fluoro-6-methanesulfonylbenzoate |
| 319 | methyl 4-[3-({[2-chloro-3-(trifluoromethyl)phenyl]methyl}[2-(4-fluorophenyl)ethyl]amino)propoxy]-2-fluoro-6-methanesulfonylbenzoate |
| 320 | methyl 2-fluoro-4-[3-({[2-fluoro-3-(trifluoromethyl)phenyl]methyl}(2-methyl-2-phenylpropyl)amino)propoxy]-6-methanesulfonylbenzoate |
| 321 | methyl 2-fluoro-4-[3-({[2-fluoro-3-(trifluoromethyl)phenyl]methyl}(2-phenylethyl)amino)propoxy]-6-methanesulfonylbenzoate |
| 322 | methyl 2-fluoro-4-[3-({[2-fluoro-3-(trifluoromethyl)phenyl]methyl}(2-phenylpropyl)amino)propoxy]-6-methanesulfonylbenzoate |
| 323 | methyl 2-fluoro-4-[3-({[2-fluoro-3-(trifluoromethyl)phenyl]methyl}[(4-fluorophenyl)methyl]amino)propoxy]-6-methanesulfonylbenzoate |
| 324 | methyl 2-fluoro-4-[3-({[2-fluoro-3-(trifluoromethyl)phenyl]methyl}[2-(4-fluorophenyl)-2-methylpropyl]amino)propoxy]-6-methanesulfonylbenzoate |
| 325 | methyl 2-fluoro-4-[3-({[2-fluoro-3-(trifluoromethyl)phenyl]methyl}[2-(4-fluorophenyl)ethyl]amino)propoxy]-6-methanesulfonylbenzoate |
| 326 | methyl 2-fluoro-4-[3-({[2-fluoro-3-(trifluoromethyl)phenyl]methyl}[2-(4-fluorophenyl)propyl]amino)propoxy]-6-methanesulfonylbenzoate |
| 327 | methyl 2-methanesulfonyl-4-{3-[(2-methyl-2-phenylpropyl)({[3-(trifluoromethyl)phenyl]methyl})amino]propoxy}benzoate |
| 328 | methyl 2-methanesulfonyl-4-{3-[(2-phenylethyl)({[3-(trifluoromethyl)phenyl]methyl})amino]propoxy}benzoate |
| 329 | methyl 2-methanesulfonyl-4-{3-[(2-phenylpropyl)({[3-(trifluoromethyl)phenyl]methyl})amino]propoxy}benzoate |
| 330 | methyl 4-{3-[(2,2-diphenylethyl)({[2-fluoro-3-(trifluoromethyl)phenyl]methyl})amino]propoxy}-2-methanesulfonylbenzoate |
| 331 | methyl 4-{3-[(2,2-diphenylethyl)({[3-(trifluoromethyl)phenyl]methyl})amino]propoxy}-2-methanesulfonylbenzoate |
| 332 | methyl 4-{3-[benzyl({[2-chloro-3-(trifluoromethyl)phenyl]methyl})amino]propoxy}-2-methanesulfonylbenzoate |
| 333 | methyl 4-{3-[benzyl({[2-fluoro-3-(trifluoromethyl)phenyl]methyl})amino]propoxy}-2-methanesulfonylbenzoate |
| 334 | methyl 4-{3-[benzyl({[3-(trifluoromethyl)phenyl]methyl})amino]propoxy}-2-methanesulfonylbenzoate |
| 335 | methyl 4-(3-{[(4-fluorophenyl)methyl]({[3-(trifluoromethyl)phenyl]methyl})amino}propoxy)-2-methanesulfonylbenzoate |
| 336 | methyl 4-(3-{[2-(4-fluorophenyl)-2-methylpropyl]({[3-(trifluoromethyl)phenyl]methyl})amino}propoxy)-2-methanesulfonylbenzoate |
| 337 | methyl 4-(3-{[2-(4-fluorophenyl)ethyl]({[3-(trifluoromethyl)phenyl]methyl})amino}propoxy)-2-methanesulfonylbenzoate |
| 338 | methyl 4-(3-{[2-(4-fluorophenyl)propyl]({[3-(trifluoromethyl)phenyl]methyl})amino}propoxy)-2-methanesulfonylbenzoate |
| 339 | methyl 4-[3-({[2-chloro-3-(trifluoromethyl)phenyl]methyl}[2,2-difluoro-2-(4-fluorophenyl)ethyl]amino)propoxy]-2-methanesulfonylbenzoate |
| 340 | methyl 4-(3-{[2,2-difluoro-2-(4-fluorophenyl)ethyl]({[2-fluoro-3-(trifluoromethyl)phenyl]methyl})amino}propoxy)-2-methanesulfonylbenzoate |
| 341 | methyl 4-(3-{[2,2-difluoro-2-(4-fluorophenyl)ethyl]({[3-(trifluoromethyl)phenyl]methyl})amino}propoxy)-2-methanesulfonylbenzoate |
| 342 | methyl 4-[3-({[2-chloro-3-(trifluoromethyl)phenyl]methyl}(2-methyl-2-phenylpropyl)amino)propoxy]-2-methanesulfonylbenzoate |
| 343 | methyl 4-[3-({[2-chloro-3-(trifluoromethyl)phenyl]methyl}(2-phenylethyl)amino)propoxy]-2-methanesulfonylbenzoate |

TABLE 2-continued

LXRβ agonists

| # | Name |
|---|------|
| 344 | methyl 4-[3-({[2-chloro-3-(trifluoromethyl)phenyl]methyl}(2-phenylpropyl)amino)propoxy]-2-methanesulfonylbenzoate |
| 345 | methyl 4-[3-({[2-chloro-3-(trifluoromethyl)phenyl]methyl}(2,2-diphenylethyl)amino)propoxy]-2-methanesulfonylbenzoate |
| 346 | methyl 4-[3-({[2-chloro-3-(trifluoromethyl)phenyl]methyl}[(4-fluorophenyl)methyl]amino)propoxy]-2-methanesulfonylbenzoate |
| 347 | methyl 4-[3-({[2-chloro-3-(trifluoromethyl)phenyl]methyl}[2-(4-fluorophenyl)-2-methylpropyl]amino)propoxy]-2-methanesulfonylbenzoate |
| 348 | methyl 4-[3-({[2-chloro-3-(trifluoromethyl)phenyl]methyl}[2-(4-fluorophenyl)ethyl]amino)propoxy]-2-methanesulfonylbenzoate |
| 349 | methyl 4-[3-({[2-chloro-3-(trifluoromethyl)phenyl]methyl}[2-(4-fluorophenyl)propyl]amino)propoxy]-2-methanesulfonylbenzoate |
| 350 | methyl 4-[3-({[2-fluoro-3-(trifluoromethyl)phenyl]methyl}(2-methyl-2-phenylpropyl)amino)propoxy]-2-methanesulfonylbenzoate |
| 351 | methyl 4-[3-({[2-fluoro-3-(trifluoromethyl)phenyl]methyl}(2-phenylethyl)amino)propoxy]-2-methanesulfonylbenzoate |
| 352 | methyl 4-[3-({[2-fluoro-3-(trifluoromethyl)phenyl]methyl}(2-phenylpropyl)amino)propoxy]-2-methanesulfonylbenzoate |
| 353 | methyl 4-[3-({[2-fluoro-3-(trifluoromethyl)phenyl]methyl}[(4-fluorophenyl)methyl]amino)propoxy]-2-methanesulfonylbenzoate |
| 354 | methyl 4-[3-({[2-fluoro-3-(trifluoromethyl)phenyl]methyl}[2-(4-fluorophenyl)-2-methylpropyl]amino)propoxy]-2-methanesulfonylbenzoate |
| 355 | methyl 4-[3-({[2-fluoro-3-(trifluoromethyl)phenyl]methyl}[2-(4-fluorophenyl)ethyl]amino)propoxy]-2-methanesulfonylbenzoate |
| 356 | methyl 4-[3-({[2-fluoro-3-(trifluoromethyl)phenyl]methyl}[2-(4-fluorophenyl)propyl]amino)propoxy]-2-methanesulfonylbenzoate |
| 357 | 2-(2-fluoro-6-methanesulfonyl-4-{3-[(2-phenylpropyl)({[3-(trifluoromethyl)phenyl]methyl})amino]propoxy}phenyl)ethan-1-ol |
| 358 | 2-(2-fluoro-6-methanesulfonyl-4-{3-[(2-phenylethyl)({[3-(trifluoromethyl)phenyl]methyl})amino]propoxy}phenyl)ethan-1-ol |
| 359 | 2-(2-fluoro-6-methanesulfonyl-4-{3-[(2-methyl-2-phenylpropyl)({[3-(trifluoromethyl)phenyl]methyl})amino]propoxy}phenyl)ethan-1-ol |
| 360 | 2-(4-{3-[(2,2-diphenylethyl)({[2-fluoro-3-(trifluoromethyl)phenyl]methyl})amino]propoxy}-2-fluoro-6-methanesulfonylphenyl)ethan-1-ol |
| 361 | 2-(4-{3-[benzyl({[2-chloro-3-(trifluoromethyl)phenyl]methyl})amino]propoxy}-2-fluoro-6-methanesulfonylphenyl)ethan-1-ol |
| 362 | 2-(4-{3-[benzyl({[3-(trifluoromethyl)phenyl]methyl})amino]propoxy}-2-fluoro-6-methanesulfonylphenyl)ethan-1-ol |
| 363 | 2-(4-{3-[benzyl({[2-fluoro-3-(trifluoromethyl)phenyl]methyl})amino]propoxy}-2-fluoro-6-methanesulfonylphenyl)ethan-1-ol |
| 364 | 2-[2-fluoro-4-(3-{[2-(4-fluorophenyl)ethyl]({[3-(trifluoromethyl)phenyl]methyl})amino}propoxy)-6-methanesulfonylphenyl]ethan-1-ol |
| 365 | 2-[2-fluoro-4-(3-{[2-(4-fluorophenyl)-2-methylpropyl]({[3-(trifluoromethyl)phenyl]methyl})amino}propoxy)-6-methanesulfonylphenyl]ethan-1-ol |
| 366 | 2-[2-fluoro-4-(3-{[2-(4-fluorophenyl)propyl]({[3-(trifluoromethyl)phenyl]methyl})amino}propoxy)-6-methanesulfonylphenyl]ethan-1-ol |
| 367 | 2-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}ethan-1-ol |
| 368 | 2-[2-fluoro-4-(3-{[(4-fluorophenyl)methyl]({[3-(trifluoromethyl)phenyl]methyl})amino}propoxy)-6-methanesulfonylphenyl]ethan-1-ol |
| 369 | 2-[4-(3-{[2,2-difluoro-2-(4-fluorophenyl)ethyl]({[3-(trifluoromethyl)phenyl]methyl})amino}propoxy)-2-fluoro-6-methanesulfonylphenyl]ethan-1-ol |
| 370 | 2-{4-[3-({[2-chloro-3-(trifluoromethyl)phenyl]methyl}(2-methyl-2-phenylpropyl)amino)propoxy]-2-fluoro-6-methanesulfonylphenyl}ethan-1-ol |
| 371 | 2-(4-{3-[(2,2-diphenylethyl)({[3-(trifluoromethyl)phenyl]methyl})amino]propoxy}-2-fluoro-6-methanesulfonylphenyl)ethan-1-ol |
| 372 | 2-{4-[3-({[2-chloro-3-(trifluoromethyl)phenyl]methyl}(2-phenylethyl)amino)propoxy]-2-fluoro-6-methanesulfonylphenyl}ethan-1-ol |
| 373 | 2-{4-[3-({[2-chloro-3-(trifluoromethyl)phenyl]methyl}(2-phenylpropyl)amino)propoxy]-2-fluoro-6-methanesulfonylphenyl}ethan-1-ol |
| 374 | 2-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}ethan-1-ol |
| 375 | 2-{4-[3-({[2-chloro-3-(trifluoromethyl)phenyl]methyl}[(4-fluorophenyl)methyl]amino)propoxy]-2-fluoro-6-methanesulfonylphenyl}ethan-1-ol |
| 376 | 2-{4-[3-({[2-chloro-3-(trifluoromethyl)phenyl]methyl}[2-(4-fluoropheny])ethyl]amino)propoxy]-2-fluoro-6-methanesulfonylphenyl}ethan-1-ol |

TABLE 2-continued

LXRβ agonists

| # | Name |
|---|---|
| 377 | 2-{4-[3-({[2-chloro-3-(trifluoromethyl)phenyl]methyl}[2-(4-fluorophenyl)propyl]amino)propoxy]-2-fluoro-6-methanesulfonylphenyl}ethan-1-ol |
| 378 | 2-{2-fluoro-4-[3-({[2-fluoro-3-(trifluoromethyl)phenyl]methyl}(2-methyl-2-phenylpropyl)amino)propoxy]-6-methanesulfonylphenyl}ethan-1-ol |
| 379 | 2-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]ethan-1-ol |
| 380 | 2-{2-fluoro-4-[3-({[2-fluoro-3-(trifluoromethyl)phenyl]methyl}(2-phenylpropyl)amino)propoxy]-6-methanesulfonylphenyl}ethan-1-ol |
| 381 | 2-{2-fluoro-4-[3-({[2-fluoro-3-(trifluoromethyl)phenyl]methyl}[(4-fluorophenyl)methyl]amino)propoxy]-6-methanesulfonylphenyl}ethan-1-ol |
| 382 | 2-{2-fluoro-4-[3-({[2-fluoro-3-(trifluoromethyl)phenyl]methyl}(2-phenylethyl)amino)propoxy]-6-methanesulfonylphenyl}ethan-1-ol |
| 383 | 2-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}ethan-1-ol |
| 384 | 2-{2-fluoro-4-[3-({[2-fluoro-3-(trifluoromethyl)phenyl]methyl}[2-(4-fluorophenyl)ethyl]amino)propoxy]-6-methanesulfonylphenyl}ethan-1-ol |
| 385 | 2-{2-fluoro-4-[3-({[2-fluoro-3-(trifluoromethyl)phenyl]methyl}[2-(4-fluorophenyl)propyl]amino)propoxy]-6-methanesulfonylphenyl}ethan-1-ol |
| 386 | 2-(2-methanesulfonyl-4-{3-[(2-methyl-2-phenylpropyl)({[3-(trifluoromethyl)phenyl]methyl})amino]propoxy}phenyl)ethan-1-ol |
| 387 | 2-(2-methanesulfonyl-4-{3-[(2-phenylethyl)({[3-(trifluoromethyl)phenyl]methyl})amino]propoxy}phenyl)ethan-1-ol |
| 388 | 2-(2-methanesulfonyl-4-{3-[(2-phenylpropyl)({[3-(trifluoromethyl)phenyl]methyl})amino]propoxy}phenyl)ethan-1-ol |
| 389 | 2-(4-{3-[(2,2-diphenylethyl)({[2-fluoro-3-(trifluoromethyl)phenyl]methyl})amino]propoxy}-2-methanesulfonylphenyl)ethan-1-ol |
| 390 | 2-(4-{3-[(2,2-diphenylethyl)({[3-(trifluoromethyl)phenyl]methyl})amino]propoxy}-2-methanesulfonylphenyl)ethan-1-ol |
| 391 | 2-(4-{3-[benzyl({[2-chloro-3-(trifluoromethyl)phenyl]methyl})amino]propoxy}-2-methanesulfonylphenyl)ethan-1-ol |
| 392 | 2-(4-{3-[benzyl({[2-fluoro-3-(trifluoromethyl)phenyl]methyl})amino]propoxy}-2-methanesulfonylphenyl)ethan-1-ol |
| 393 | 2-(4-{3-[benzyl({[3-(trifluoromethyl)phenyl]methyl})amino]propoxy}-2-methanesulfonylphenyl)ethan-1-ol |
| 394 | 2-[4-(3-{[(4-fluorophenyl)methyl]({[3-(trifluoromethyl)phenyl]methyl})amino}propoxy)-2-methanesulfonylphenyl]ethan-1-ol |
| 395 | 2-[4-(3-{[2-(4-fluorophenyl)-2-methylpropyl]({[3-(trifluoromethyl)phenyl]methyl})amino}propoxy)-2-methanesulfonylphenyl]ethan-1-ol |
| 396 | 2-[4-(3-{[2-(4-fluorophenyl)ethyl]({[3-(trifluoromethyl)phenyl]methyl})amino}propoxy)-2-methanesulfonylphenyl]ethan-1-ol |
| 397 | 2-[4-(3-{[2-(4-fluorophenyl)propyl]({[3-(trifluoromethyl)phenyl]methyl})amino}propoxy)-2-methanesulfonylphenyl]ethan-1-ol |
| 398 | 2-{4-[3-({[2-chloro-3-(trifluoromethyl)phenyl]methyl}[2,2-difluoro-2-(4-fluorophenyl)ethyl]amino)propoxy]-2-methanesulfonylphenyl}ethan-1-ol |
| 399 | 2-[4-(3-{[2,2-difluoro-2-(4-fluorophenyl)ethyl]({[2-fluoro-3-(trifluoromethyl)phenyl(methyl](amino}propoxy)-2-methanesulfonylphenyl]ethan-1-ol |
| 400 | 2-[4-(3-{[2,2-difluoro-2-(4-fluorophenyl)ethyl]({[3-(trifluoromethyl)phenyl]methyl})amino}propoxy)-2-methanesulfonylphenyl]ethan-1-ol |
| 401 | 2-{4-[3-({[2-chloro-3-(trifluoromethyl)phenyl]methyl}(2-methyl-2-phenylpropyl)amino)propoxy]-2-methanesulfonylphenyl}ethan-1-ol |
| 402 | 2-{4-[3-({[2-chloro-3-(trifluoromethyl)phenyl]methyl}(2-phenylethyl)amino)propoxy]-2-methanesulfonylphenyl}ethan-1-ol |
| 403 | 2-{4-[3-({[2-chloro-3-(trifluoromethyl)phenyl]methyl}(2-phenylpropyl)amino)propoxy]-2-methanesulfonylphenyl}ethan-1-ol |
| 404 | 2-{4-[3-({[2-chloro-3-(trifluoromethyl)phenyl]methyl}(2,2-diphenylethyl)amino)propoxy]-2-methanesulfonylphenyl}ethan-1-ol |
| 405 | 2-{4-[3-({[2-chloro-3-(trifluoromethyl)phenyl]methyl}[(4-fluorophenyl)methyl]amino)propoxy]-2-methanesulfonylphenyl}ethan-1-ol |
| 406 | 2-{4-[3-({[2-chloro-3-(trifluoromethyl)phenyl]methyl}[2-(4-fluorophenyl)-2-methylpropyl]amino)propoxy]-2-methanesulfonylphenyl}ethan-1-ol |
| 407 | 2-{4-[3-({[2-chloro-3-(trifluoromethyl(phenyl]methyl}[2-(4-fluorophenyl)ethyl]amino)propoxy]-2-methanesulfonylphenyl}ethan-1-ol |
| 408 | 2-{4-[3-({[2-chloro-3-(trifluoromethyl(phenyl]methyl}[2-(4-fluorophenyl)propyl]amino)propoxy]-2-methanesulfonylphenyl}ethan-1-ol |

TABLE 2-continued

LXRβ agonists

| # | Name |
|---|---|
| 409 | 2-{4-[3-({[2-fluoro-3-(trifluoromethyl)phenyl]methyl}(2-methyl-2-phenylpropyl)amino)propoxy]-2-methanesulfonylphenyl}ethan-1-ol |
| 410 | 2-{4-[3-({[2-fluoro-3-(trifluoromethyl)phenyl]methyl}(2-phenylethyl)amino)propoxy]-2-methanesulfonylphenyl}ethan-1-ol |
| 411 | 2-{4-[3-({[2-fluoro-3-(trifluoromethyl)phenyl]methyl}(2-phenylpropyl)amino)propoxy]-2-methanesulfonylphenyl}ethan-1-ol |
| 412 | 2-{4-[3-({[2-fluoro-3-(trifluoromethyl)phenyl]methyl}[(4-fluorophenyl)methyl]amino)propoxy]-2-methanesulfonylphenyl}ethan-1-ol |
| 413 | 2-{4-[3-({[2-fluoro-3-(trifluoromethyl)phenyl]methyl}[2-(4-fluorophenyl)-2-methylpropyl]amino)propoxy]-2-methanesulfonylphenyl}ethan-1-ol |
| 414 | 2-{4-[3-({[2-fluoro-3-(trifluoromethyl)phenyl]methyl}[2-(4-fluorophenyl)ethyl]amino)propoxy]-2-methanesulfonylphenyl}ethan-1-ol |
| 415 | 2-{4-[3-({[2-fluoro-3-(trifluoromethyl)phenyl]methyl}[2-(4-fluorophenyl)propyl]amino)propoxy]-2-methanesulfonylphenyl}ethan-1-ol |
| 416 | 2-(2-fluoro-6-methanesulfonyl-4-{3-[(2-phenylethyl)({[3-(trifluoromethyl)phenyl]methyl})amino]propoxy}phenyl)acetic acid |
| 417 | 2-(2-fluoro-6-methanesulfonyl-4-{3-[(2-phenylpropyl)({[3-(trifluoromethyl)phenyl]methyl})amino]propoxy}phenyl)acetic acid |
| 418 | 2-(4-{3-[(2,2-diphenylethyl)({[2-fluoro-3-(trifluoromethyl)phenyl]methyl})amino]propoxy}-2-fluoro-6-methanesulfonylphenyl)acetic acid |
| 419 | 2-(4-{3-[benzyl({[2-chloro-3-(trifluoromethyl)phenyl]methyl})amino]propoxy}-2-fluoro-6-methanesulfonylphenyl)acetic acid |
| 420 | 2-(4-{3-[benzyl({[2-fluoro-3-(trifluoromethyl)phenyl]methyl})amino]propoxy}-2-fluoro-6-methanesulfonylphenyl)acetic acid |
| 421 | 2-(4-{3-[benzyl({[3-(trifluoromethyl)phenyl]methyl})amino]propoxy}-2-fluoro-6-methanesulfonylphenyl)acetic acid |
| 422 | 2-[2-fluoro-4-(3-{[(4-fluorophenyl)methyl]({[3-(trifluoromethyl)phenyl]methyl})amino}propoxy)-6-methanesulfonylphenyl]acetic acid |
| 423 | 2-[2-fluoro-4-(3-{[2-(4-fluorophenyl)-2-methylpropyl]({[3-(trifluoromethyl)phenyl]methyl})amino}propoxy)-6-methanesulfonylphenyl]acetic acid |
| 424 | 2-[2-fluoro-4-(3-{[2-(4-fluorophenyl)ethyl]({[3-(trifluoromethyl)phenyl]methyl})amino}propoxy)-6-methanesulfonylphenyl]acetic acid |
| 425 | 2-[2-fluoro-4-(3-{[2-(4-fluorophenyl)propyl]({[3-(trifluoromethyl)phenyl]methyl})amino}propoxy)-6-methanesulfonylphenyl]acetic acid |
| 426 | 2-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}acetic acid |
| 427 | 2-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]acetic acid |
| 428 | 2-[4-(3-{[2,2-difluoro-2-(4-fluorophenyl)ethyl]({[3-(trifluoromethyl)phenyl]methyl})amino}propoxy)-2-fluoro-6-methanesulfonylphenyl]acetic acid |
| 429 | 2-{4-[3-({[2-chloro-3-(trifluoromethyl)phenyl]methyl}(2-methyl-2-phenylpropyl)amino)propoxy]-2-fluoro-6-methanesulfonylphenyl}acetic acid |
| 430 | 2-{4-[3-({[2-chloro-3-(trifluoromethyl)phenyl]methyl}(2-phenylethyl)amino)propoxy]-2-fluoro-6-methanesulfonylphenyl}acetic acid |
| 431 | 2-{4-[3-({[2-chloro-3-(trifluoromethyl)phenyl]methyl}(2-phenylpropyl)amino)propoxy]-2-fluoro-6-methanesulfonylphenyl}acetic acid |
| 432 | 2-{4-[3-({[2-chloro-3-(trifluoromethyl)phenyl]methyl}(2,2-diphenylethyl)amino)propoxy]-2-fluoro-6-methanesulfonylphenyl}acetic acid |
| 433 | 2-{4-[3-({[2-chloro-3-(trifluoromethyl)phenyl]methyl}[(4-fluorophenyl)methyl]amino)propoxy]-2-fluoro-6-methanesulfonylphenyl}acetic acid |
| 434 | 2-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}acetic acid |
| 435 | 2-{4-[3-({[2-chloro-3-(trifluoromethyl)phenyl]methyl}[2-(4-fluorophenyl)ethyl]amino)propoxy]-2-fluoro-6-methanesulfonylphenyl}acetic acid |
| 436 | 2-{4-[3-({[2-chloro-3-(trifluoromethyl)phenyl]methyl}[2-(4-fluorophenyl)propyl]amino)propoxy]-2-fluoro-6-methanesulfonylphenyl}acetic acid |
| 437 | 2-(4-{3-[(2,2-diphenylethyl)({[3-(trifluoromethyl)phenyl]methyl})amino]propoxy}-2-fluoro-6-methanesulfonylphenyl)acetic acid |
| 438 | 2-{2-fluoro-4-[3-({[2-fluoro-3-(trifluoromethyl)phenyl]methyl}(2-methyl-2-phenylpropyl)amino)propoxy]-6-methanesulfonylphenyl}acetic acid |
| 439 | 2-(2-fluoro-6-methanesulfonyl-4-{3-[(2-methyl-2-phenylpropyl)({[3-(trifluoromethyl)phenyl]methyl})amino]propoxy}phenyl)acetic acid |
| 440 | 2-{2-fluoro-4-[3-({[2-fluoro-3-(trifluoromethyl)phenyl]methyl}(2-phenylpropyl)amino)propoxy]-6-methanesulfonylphenyl}acetic acid |

TABLE 2-continued

LXRβ agonists

| # | Name |
|---|---|
| 441 | 2-{2-fluoro-4-[3-({[2-fluoro-3-(trifluoromethyl)phenyl]methyl}[(4-fluorophenyl)methyl]amino)propoxy]-6-methanesulfonylphenyl}acetic acid |
| 442 | 2-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}acetic acid |
| 443 | 2-{2-fluoro-4-[3-({[2-fluoro-3-(trifluoromethyl)phenyl]methyl}[2-(4-fluorophenyl)ethyl]amino)propoxy]-6-methanesulfonylphenyl}acetic acid |
| 444 | 2-{2-fluoro-4-[3-({[2-fluoro-3-(trifluoromethyl)phenyl]methyl}(2-phenylethyl)amino)propoxy]-6-methanesulfonylphenyl}acetic acid |
| 445 | 2-{2-fluoro-4-[3-({[2-fluoro-3-(trifluoromethyl)phenyl]methyl}[2-(4-fluorophenyl)propyl]amino)propoxy]-6-methanesulfonylphenyl}acetic acid |
| 446 | 2-(2-methanesulfonyl-4-{3-[(2-methyl-2-phenylpropyl)({[3-(trifluoromethyl)phenyl]methyl})amino]propoxy}phenyl)acetic acid |
| 447 | 2-(2-methanesulfonyl-4-{3-[(2-phenylethyl)({[3-(trifluoromethyl)phenyl]methyl})amino]propoxy}phenyl)acetic acid |
| 448 | 2-(2-methanesulfonyl-4-{3-[(2-phenylpropyl)({[3-(trifluoromethyl)phenyl]methyl})amino]propoxy}phenyl)acetic acid |
| 449 | 2-(4-{3-[(2,2-diphenylethyl)({[2-fluoro-3-(trifluoromethyl)phenyl]methyl})amino]propoxy}-2-methanesulfonylphenyl)acetic acid |
| 450 | 2-(4-{3-[(2,2-diphenylethyl)({[3-(trifluoromethyl)phenyl]methyl})amino]propoxy}-2-methanesulfonylphenyl)acetic acid |
| 451 | 2-(4-{3-[benzyl({[2-chloro-3-(trifluoromethyl)phenyl]methyl})amino]propoxy}-2-methanesulfonylphenyl)acetic acid |
| 452 | 2-(4-{3-[benzyl({[2-fluoro-3-(trifluoromethyl)phenyl]methyl})amino]propoxy}-2-methanesulfonylphenyl)acetic acid |
| 453 | 2-(4-{3-[benzyl({[3-(trifluoromethyl)phenyl]methyl})amino]propoxy}-2-methanesulfonylphenyl)acetic acid |
| 454 | 2-[4-(3-{[(4-fluorophenyl)methyl]({[3-(trifluoromethyl)phenyl]methyl})amino}propoxy)-2-methanesulfonylphenyl]acetic acid |
| 455 | 2-[4-(3-{[2-(4-fluorophenyl)-2-methylpropyl]({[3-(trifluoromethyl)phenyl]methyl})amino}propoxy)-2-methanesulfonylphenyl]acetic acid |
| 456 | 2-[4-(3-{[2-(4-fluorophenyl)ethyl]({[3-(trifluoromethyl)phenyl]methyl})amino}propoxy)-2-methanesulfonylphenyl]acetic acid |
| 457 | 2-[4-(3-{[2-(4-fluorophenyl)propyl]({[3-(trifluoromethyl)phenyl]methyl})amino}propoxy)-2-methanesulfonylphenyl]acetic acid |
| 458 | 2-{4-[3-({[2-chloro-3-(trifluoromethyl)phenyl]methyl}[2,2-difluoro-2-(4-fluorophenyl)ethyl]amino)propoxy]-2-methanesulfonylphenyl}acetic acid |
| 459 | 2-[4-(3-{[2,2-difluoro-2-(4-fluorophenyl)ethyl]({[2-fluoro-3-(trifluoromethyl)phenyl]methyl})amino}propoxy)-2-methanesulfonylphenyl]acetic acid |
| 460 | 2-[4-(3-([2,2-difluoro-2-(4-fluorophenyl)ethyl]({[3-(trifluoromethyl)phenyl]methyl})amino}propoxy)-2-methanesulfonylphenyl]acetic acid |
| 461 | 2-{4-[3-({[2-chloro-3-(trifluoromethyl)phenyl]methyl}(2-methyl-2-phenylpropyl)amino)propoxy]-2-methanesulfonylphenyl}acetic acid |
| 462 | 2-{4-[3-({[2-chloro-3-(trifluoromethyl(phenyl]methyl}(2-phenylethyl)amino)propoxy]-2-methanesulfonylphenyl}acetic acid |
| 463 | 2-{4-[3-({[2-chloro-3-(trifluoromethyl)phenyl]methyl}(2-phenylpropyl)amino)propoxy]-2-methanesulfonylphenyl}acetic acid |
| 464 | 2-{4-[3-({[2-chloro-3-(trifluoromethyl)phenyl]methyl}(2,2-diphenylethyl)amino)propoxy]-2-methanesulfonylphenyl}acetic acid |
| 465 | 2-{4-[3-({[2-chloro-3-(trifluoromethyl)phenyl]methyl}[(4-fluorophenyl)methyl]amino)propoxy]-2-methanesulfonylphenyl}acetic acid |
| 466 | 2-{4-[3-({[2-chloro-3-(trifluoromethyl)phenyl]methyl}[2-(4-fluorophenyl)-2-methylpropyl]amino)propoxy]-2-methanesulfonylphenyl}acetic acid |
| 467 | 2-{4-[3-({[2-chloro-3-(trifluoromethyl)phenyl]methyl}[2-(4-fluorophenyl)ethyl]amino)propoxy]-2-methanesulfonylphenyl}acetic acid |
| 468 | 2-{4-[3-({[2-chloro-3-(trifluoromethyl)phenyl]methyl}[2-(4-fluorophenyl)propyl]amino)propoxy]-2-methanesulfonylphenyl}acetic acid |
| 469 | 2-{4-[3-({[2-fluoro-3-(trifluoromethyl)phenyl]methyl}(2-methyl-2-phenylpropyl)amino)propoxy]-2-methanesulfonylphenyl}acetic acid |
| 470 | 2-{4-[3-({[2-fluoro-3-(trifluoromethyl)phenyl]methyl}(2-phenylethyl)amino)propoxy]-2-methanesulfonylphenyl}acetic acid |
| 471 | 2-{4-[3-({[2-fluoro-3-(trifluoromethyl)phenyl]methyl}(2-phenylpropyl)amino)propoxy]-2-methanesulfonylphenyl}acetic acid |
| 472 | 2-{4-[3-({[2-fluoro-3-(trifluoromethyl)phenyl]methyl}[(4-fluorophenyl)methyl]amino)propoxy]-2-methanesulfonylphenyl}acetic acid |

TABLE 2-continued

LXRβ agonists

| # | Name |
|---|---|
| 473 | 2-{4-[3-({[2-fluoro-3-(trifluoromethyl)phenyl]methyl}[2-(4-fluorophenyl)-2-methylpropyl]amino)propoxy]-2-methanesulfonylphenyl}acetic acid |
| 474 | 2-{4-[3-({[2-fluoro-3-(trifluoromethyl)phenyl]methyl}[2-(4-fluorophenyl)ethyl]amino)propoxy]-2-methanesulfonylphenyl}acetic acid |
| 475 | 2-{4-[3-({[2-fluoro-3-(trifluoromethyl)phenyl]methyl}[2-(4-fluorophenyl)propyl]amino)propoxy]-2-methanesulfonylphenyl}acetic acid |
| 476 | N-[(2-fluoro-6-methanesulfonyl-4-{3-[(2-phenylethyl)({[3-(trifluoromethyl)phenyl]methyl})amino]propoxy}phenyl)methyl]acetamide |
| 477 | N-[(4-{3-[(2,2-diphenylethyl)({[2-fluoro-3-(trifluoromethyl)phenyl]methyl})amino]propoxy}-2-fluoro-6-methanesulfonylphenyl)methyl]acetamide |
| 478 | N-[(2-fluoro-6-methanesulfonyl-4-{3-[(2-phenylpropyl)({[3-(trifluoromethyl)phenyl]methyl})amino]propoxy}phenyl)methyl]acetamide |
| 479 | N-[(2-fluoro-6-methanesulfonyl-4-{3-[(2-methyl-2-phenylpropyl)({[3-(trifluoromethyl)phenyl]methyl})amino]propoxy}phenyl)methyl]acetamide |
| 480 | N-[(4-{3-[(2,2-diphenylethyl)({[3-(trifluoromethyl)phenyl]methyl})amino]propoxy}-2-fluoro-6-methanesulfonylphenyl)methyl]acetamide |
| 481 | N-[(4-[3-[benzyl({[2-chloro-3-(trifluoromethyl)phenyl]methyl})amino]propoxy}-2-fluoro-6-methanesulfonylphenyl)methyl]acetamide |
| 482 | N-[(4-{3-[benzyl({[3-(trifluoromethyl)phenyl]methyl})amino]propoxy}-2-fluoro-6-methanesulfonylphenyl)methyl]acetamide |
| 483 | N-{[2-fluoro-4-(3-{[(4-fluorophenyl)methyl]({[3-(trifluoromethyl)phenyl]methyl})amino}propoxy)-6-methanesulfonylphenyl]methyl}acetamide |
| 484 | N-{[2-fluoro-4-(3-{[2-(4-fluorophenyl)-2-methylpropyl]({[3-(trifluoromethyl)phenyl]methyl})amino}propoxy)-6-methanesulfonylphenyl]methyl}acetamide |
| 485 | N-{[2-fluoro-4-(3-{[2-(4-fluorophenyl)propyl]({[3-(trifluoromethyl)phenyl]methyl})amino}propoxy)-6-methanesulfonylphenyl]methyl}acetamide |
| 486 | N-{[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]methyl}acetamide |
| 487 | N-({4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}methyl)acetamide |
| 488 | N-{[4-(3-{[2,2-difluoro-2-(4-fluorophenyl)ethyl]({[3-(trifluoromethyl)phenyl]methyl})amino}propoxy)-2-fluoro-6-methanesulfonylphenyl]methyl}acetamide |
| 489 | N-({4-[3-({[2-chloro-3-(trifluoromethyl)phenyl]methyl}(2-methyl-2-phenylpropyl)amino)propoxy]-2-fluoro-6-methanesulfonylphenyl}methyl)acetamide |
| 490 | N-({4-[3-({[2-chloro-3-(trifluoromethyl)phenyl]methyl}(2-phenylethyl)amino)propoxy]-2-fluoro-6-methanesulfonylphenyl}methyl)acetamide |
| 491 | N-({4-[3-({[2-chloro-3-(trifluoromethyl)phenyl]methyl}(2-phenylpropyl)amino)propoxy]-2-fluoro-6-methanesulfonylphenyl}methyl)acetamide |
| 492 | N-({4-[3-({[2-chloro-3-(trifluoromethyl)phenyl]methyl}[(4-fluorophenyl)methyl]amino)propoxy]-2-fluoro-6-methanesulfonylphenyl}methyl)acetamide |
| 493 | N-({4-[3-({[2-chloro-3-(trifluoromethyl)phenyl]methyl}[2-(4-fluorophenyl)-2-methylpropyl]amino)propoxy]-2-fluoro-6-methanesulfonylphenyl}methyl)acetamide |
| 494 | N-({4-[3-({[2-chloro-3-(trifluoromethyl)phenyl]methyl}[2-(4-fluorophenyl)ethyl]amino)propoxy]-2-fluoro-6-methanesulfonylphenyl}methyl)acetamide |
| 495 | N-([4-[3-({[2-chloro-3-(trifluoromethyl)phenyl]methyl}[2-(4-fluorophenyl)propyl]amino)propoxy]-2-fluoro-6-methanesulfonylphenyl}methyl)acetamide |
| 496 | N-({2-fluoro-4-[3-({[2-fluoro-3-(trifluoromethyl)phenyl]methyl}(2-methyl-2-phenylpropyl)amino)propoxy]-6-methanesulfonylphenyl}methyl)acetamide |
| 497 | N-({2-fluoro-4-[3-({[2-fluoro-3-(trifluoromethyl)phenyl]methyl}(2-phenylethyl)amino)propoxy]-6-methanesulfonylphenyl}methyl)acetamide |
| 498 | N-({2-fluoro-4-[3-({[2-fluoro-3-(trifluoromethyl)phenyl]methyl}(2-phenylpropyl)amino)propoxy]-6-methanesulfonylphenyl}methyl)acetamide |
| 499 | N-{[2-fluoro-4-(3-{[2-(4-fluorophenyl)ethyl]({[3-(trifluoromethyl)phenyl]methyl})amino}propoxy)-6-methanesulfonylphenyl]methyl}acetamide |
| 500 | N-[(4-{3-[benzyl({[2-fluoro-3-(trifluoromethyl)phenyl]methyl})amino]propoxy}-2-fluoro-6-methanesulfonylphenyl)methyl]acetamide |

TABLE 2-continued

LXRβ agonists

| # | Name |
|---|------|
| 501 | N-({2-fluoro-4-[3-({[2-fluoro-3-(trifluoromethyl)phenyl]methyl}[(4-fluorophenyl)methyl]amino)propoxy]-6-methanesulfonylphenyl}methyl)acetamide |
| 502 | N-({2-fluoro-4-[3-({[2-fluoro-3-(trifluoromethyl)phenyl]methyl}[2-(4-fluorophenyl)-2-methylpropyl]amino)propoxy]-6-methanesulfonylphenyl}methyl)acetamide |
| 503 | N-({2-fluoro-4-[3-({[2-fluoro-3-(trifluoromethyl)phenyl]methyl}[2-(4-fluorophenyl)ethyl]amino)propoxy]-6-methanesulfonylphenyl}methyl)acetamide |
| 504 | N-({2-fluoro-4-[3-({[2-fluoro-3-(trifluoromethyl)phenyl]methyl}[2-(4-fluorophenyl)propyl]amino)propoxy]-6-methanesulfonylphenyl}methyl)acetamide |
| 505 | N-[(2-methanesulfonyl-4-{3-[(2-methyl-2-phenylpropyl)({[3-(trifluoromethyl)phenyl]methyl})amino]propoxy}phenyl)methyl]acetamide |
| 506 | N-[(2-methanesulfonyl-4-{3-[(2-phenylethyl)({[3-(trifluoromethyl)phenyl]methyl})amino]propoxy}phenyl)methyl]acetamide |
| 507 | N-[(2-methanesulfonyl-4-{3-[(2-phenylpropyl)({[3-(trifluoromethyl)phenyl]methyl})amino]propoxy}phenyl)methyl]acetamide |
| 508 | N-[(4-{3-[(2,2-diphenylethyl)({[2-fluoro-3-(trifluoromethyl)phenyl]methyl})amino]propoxy}-2-methanesulfonylphenyl)methyl]acetamide |
| 509 | N-[(4-{3-[(2,2-diphenylethyl)({[3-(trifluoromethyl)phenyl]methyl})amino]propoxy}-2-methanesulfonylphenyl)methyl]acetamide |
| 510 | N-[(4-{3-[benzyl({[2-chloro-3-(trifluoromethyl)phenyl]methyl})amino]propoxy}-2-methanesulfonylphenyl)methyl]acetamide |
| 511 | N-[(4-{3-[benzyl({[2-fluoro-3-(trifluoromethyl)phenyl]methyl})amino]propoxy}-2-methanesulfonylphenyl)methyl]acetamide |
| 512 | N-[(4-{3-[benzyl({[3-(trifluoromethyl)phenyl]methyl})amino]propoxy}-2-methanesulfonylphenyl)methyl]acetamide |
| 513 | N-{[4-(3-{[(4-fluorophenyl)methyl]({[3-(trifluoromethyl)phenyl]methyl})amino}propoxy)-2-methanesulfonylphenyl]methyl}acetamide |
| 514 | N-{[4-(3-{[2-(4-fluorophenyl)-2-methylpropyl]({[3-(trifluoromethyl)phenyl]methyl})amino}propoxy)-2-methanesulfonylphenyl]methyl}acetamide |
| 515 | N-{[4-(3-{[2-(4-fluorophenyl)ethyl]({[3-(trifluoromethyl)phenyl]methyl})amino}propoxy)-2-methanesulfonylphenyl]methyl}acetamide |
| 516 | N-{[4-(3-{[2-(4-fluorophenyl)propyl]({[3-(trifluoromethyl)phenyl]methyl})amino}propoxy)-2-methanesulfonylphenyl]methyl}acetamide |
| 517 | N-({4-[3-({[2-chloro-3-(trifluoromethyl)phenyl]methyl}[2,2-difluoro-2-(4-fluorophenyl)ethyl]amino)propoxy]-2-methanesulfonylphenyl}methyl)acetamide |
| 518 | N-{[4-(3-{[2,2-difluoro-2-(4-fluorophenyl)ethyl]({[2-fluoro-3-(trifluoromethyl)phenyl]methyl})amino}propoxy)-2-methanesulfonylphenyl]methyl}acetamide |
| 519 | N-{[4-(3-{[2,2-difluoro-2-(4-fluorophenyl)ethyl]({[3-(trifluoromethyl)phenyl]methyl})amino}propoxy)-2-methanesulfonylphenyl]methyl}acetamide |
| 520 | N-({4-[3-({[2-chloro-3-(trifluoromethyl)phenyl]methyl}(2-methyl-2-phenylpropyl)amino)propoxy]-2-methanesulfonylphenyl}methyl)acetamide |
| 521 | N-({4-[3-({[2-chloro-3-(trifluoromethyl)phenyl]methyl}(2-phenylethyl)amino)propoxy]-2-methanesulfonylphenyl}methyl)acetamide |
| 522 | N-({4-[3-({[2-chloro-3-(trifluoromethyl)phenyl]methyl}(2-phenylpropyl)amino)propoxy]-2-methanesulfonylphenyl}methyl)acetamide |
| 523 | N-({4-[3-({[2-chloro-3-(trifluoromethyl)phenyl]methyl}(2,2-diphenylethyl)amino)propoxy]-2-methanesulfonylphenyl}methyl)acetamide |
| 524 | N-({4-[3-({[2-chloro-3-(trifluoromethyl)phenyl]methyl}[(4-fluorophenyl)methyl]amino)propoxy]-2-methanesulfonylphenyl}methyl)acetamide |
| 525 | N-({4-[3-({[2-chloro-3-(trifluoromethyl)phenyl]methyl}[2-(4-fluorophenyl)-2-methylpropyl]amino)propoxy]-2-methanesulfonylphenyl}methyl)acetamide |
| 526 | N-({4-[3-({[2-chloro-3-(trifluoromethyl)phenyl]methyl}[2-(4-fluorophenyl)ethyl]amino)propoxy]-2-methanesulfonylphenyl}methyl)acetamide |
| 527 | N-({4-[3-({[2-chloro-3-(trifluoromethyl)phenyl]methyl}[2-(4-fluorophenyl)propyl]amino)propoxy]-2-methanesulfonylphenyl}methyl)acetamide |
| 528 | N-({4-[3-({[2-fluoro-3-(trifluoromethyl)phenyl]methyl}(2-methyl-2-phenylpropyl)amino)propoxy]-2-methanesulfonylphenyl}methyl)acetamide |
| 529 | N-({4-[3-({[2-fluoro-3-(trifluoromethyl)phenyl]methyl}(2-phenylethyl)amino)propoxy]-2-methanesulfonylphenyl}methyl)acetamide |

TABLE 2-continued

| LXRβ agonists | |
|---|---|
| # | Name |
| 530 | N-({4-[3-({[2-fluoro-3-(trifluoromethyl)phenyl]methyl}(2-phenylpropyl)amino)propoxy]-2-methanesulfonylphenyl}methyl)acetamide |
| 531 | N-({4-[3-({[2-fluoro-3-(trifluoromethyl)phenyl]methyl}[(4-fluorophenyl)methyl]amino)propoxy]-2-methanesulfonylphenyl}methyl)acetamide |
| 532 | N-({4-[3-({[2-fluoro-3-(trifluoromethyl)phenyl]methyl}[2-(4-fluorophenyl)-2-methylpropyl]amino)propoxy]-2-methanesulfonylphenyl}methyl)acetamide |
| 533 | N-({4-[3-({[2-fluoro-3-(trifluoromethyl)phenyl]methyl}[2-(4-fluorophenyl)ethyl]amino)propoxy]-2-methanesulfonylphenyl}methyl)acetamide |
| 534 | N-({4-[3-({[2-fluoro-3-(trifluoromethyl)phenyl]methyl}[2-(4-fluorophenyl)propyl]amino)propoxy]-2-methanesulfonylphenyl}methyl)acetamide |
| 535 | 2-(2-fluoro-6-methanesulfonyl-4-{3-[(2-methyl-2-phenylpropyl)({[3-(trifluoromethyl)phenyl]methyl})amino]propoxy}phenyl)propan-2-ol |
| 536 | 2-(2-fluoro-6-methanesulfonyl-4-{3-[(2-phenylethyl)({[3-(trifluoromethyl)phenyl]methyl})amino]propoxy}phenyl)propan-2-ol |
| 537 | 2-(2-fluoro-6-methanesulfonyl-4-{3-[(2-phenylpropyl)({[3-(trifluoromethyl)phenyl]methyl})amino]propoxy}phenyl)propan-2-ol |
| 538 | 2-(4-{3-[(2,2-diphenylethyl)({[3-(trifluoromethyl)phenyl]methyl})amino]propoxy}-2-fluoro-6-methanesulfonylphenyl)propan-2-ol |
| 539 | 2-(4-{3-[benzyl({[2-chloro-3-(trifluoromethyl)phenyl]methyl})amino]propoxy}-2-fluoro-6-methanesulfonylphenyl)propan-2-ol |
| 540 | 2-(4-{3-[benzyl({[2-fluoro-3-(trifluoromethyl)phenyl]methyl})amino]propoxy}-2-fluoro-6-methanesulfonylphenyl)propan-2-ol |
| 541 | 2-(4-{3-[benzyl({[3-(trifluoromethyl)phenyl]methyl})amino]propoxy}-2-fluoro-6-methanesulfonylphenyl)propan-2-ol |
| 542 | 2-(4-{3-[(2,2-diphenylethyl)({[2-fluoro-3-(trifluoromethyl)phenyl]methyl})amino]propoxy}-2-fluoro-6-methanesulfonylphenyl)propan-2-ol |
| 543 | 2-[2-fluoro-4-(3-{[(4-fluorophenyl)methyl]({[3-(trifluoromethyl)phenyl]methyl})amino}propoxy)-6-methanesulfonylphenyl]propan-2-ol |
| 544 | 2-[2-fluoro-4-(3-{[2-(4-fluorophenyl)ethyl]({[3-(trifluoromethyl)phenyl]methyl})amino}propoxy)-6-methanesulfonylphenyl]propan-2-ol |
| 545 | 2-[2-fluoro-4-(3-{[2-(4-fluorophenyl)-2-methylpropyl]({[3-(trifluoromethyl)phenyl]methyl})amino}propoxy)-6-methanesulfonylphenyl]propan-2-ol |
| 546 | 2-[2-fluoro-4-(3-{[2-(4-fluorophenyl)propyl]({[3-(trifluoromethyl)phenyl]methyl})amino}propoxy)-6-methanesulfonylphenyl]propan-2-ol |
| 547 | 2-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}propan-2-ol |
| 548 | 2-[4-(3-{[2,2-difluoro-2-(4-fluorophenyl)ethyl]({[3-(trifluoromethyl)phenyl]methyl})amino}propoxy)-2-fluoro-6-methanesulfonylphenyl]propan-2-ol |
| 549 | 2-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]propan-2-ol |
| 550 | 2-{4-[3-({[2-chloro-3-(trifluoromethyl)phenyl]methyl}(2-methyl-2-phenylpropyl)amino)propoxy]-2-fluoro-6-methanesulfonylphenyl}propan-2-ol |
| 551 | 2-{4-[3-({[2-chloro-3-(trifluoromethyl)phenyl]methyl}(2-phenylethyl)amino)propoxy]-2-fluoro-6-methanesulfonylphenyl}propan-2-ol |
| 552 | 2-{4-[3-({[2-chloro-3-(trifluoromethyl)phenyl]methyl}[(4-fluorophenyl)methyl]amino)propoxy]-2-fluoro-6-methanesulfonylphenyl}propan-2-ol |
| 553 | 2-{4-[3-({[2-chloro-3-(trifluoromethyl)phenyl]methyl}(2-phenylpropyl)amino)propoxy]-2-fluoro-6-methanesulfonylphenyl}propan-2-ol |
| 554 | 2-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}propan-2-ol |
| 555 | 2-{4-[3-({[2-chloro-3-(trifluoromethyl)phenyl]methyl}[2-(4-fluorophenyl)ethyl]amino)propoxy]-2-fluoro-6-methanesulfonylphenyl}propan-2-ol |
| 556 | 2-{2-fluoro-4-[3-({[2-fluoro-3-(trifluoromethyl)phenyl]methyl}(2-methyl-2-phenylpropyl)amino)propoxy]-6-methanesulfonylphenyl}propan-2-ol |
| 557 | 2-{4-[3-({[2-chloro-3-(trifluoromethyl)phenyl]methyl}[2-(4-fluorophenyl)propyl]amino)propoxy]-2-fluoro-6-methanesulfonylphenyl}propan-2-ol |
| 558 | 2-{2-fluoro-4-[3-({[2-fluoro-3-(trifluoromethyl)phenyl]methyl}(2-phenylethyl)amino)propoxy]-6-methanesulfonylphenyl}propan-2-ol |
| 559 | 2-{2-fluoro-4-[3-({[2-fluoro-3-(trifluoromethyl)phenyl]methyl}(2-phenylpropyl)amino)propoxy]-6-methanesulfonylphenyl}propan-2-ol |

TABLE 2-continued

LXRβ agonists

| # | Name |
|---|---|
| 560 | 2-{2-fluoro-4-[3-({[2-fluoro-3-(trifluoromethyl)phenyl]methyl}[(4-fluorophenyl)methyl]amino)propoxy]-6-methanesulfonylphenyl}propan-2-ol |
| 561 | 2-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}propan-2-ol |
| 562 | 2-{2-fluoro-4-[3-({[2-fluoro-3-(trifluoromethyl)phenyl]methyl}[2-(4-fluorophenyl)ethyl]amino)propoxy]-6-methanesulfonylphenyl}propan-2-ol |
| 563 | 2-{2-fluoro-4-[3-({[2-fluoro-3-(trifluoromethyl)phenyl]methyl}[2-(4-fluorophenyl)propyl]amino)propoxy]-6-methanesulfonylphenyl}propan-2-ol |
| 564 | 2-(2-methanesulfonyl-4-{3-[(2-methyl-2-phenylpropyl)({[3-(trifluoromethyl)phenyl]methyl})amino]propoxy}phenyl)propan-2-ol |
| 565 | 2-(2-methanesulfonyl-4-{3-[(2-phenylethyl)({[3-(trifluoromethyl)phenyl]methyl})amino]propoxy}phenyl)propan-2-ol |
| 566 | 2-(2-methanesulfonyl-4-{3-[(2-phenylpropyl)({[3-(trifluoromethyl)phenyl]methyl})amino]propoxy}phenyl)propan-2-ol |
| 567 | 2-(4-{3-[(2,2-diphenylethyl)({[2-fluoro-3-(trifluoromethyl)phenyl]methyl})amino]propoxy}-2-methanesulfonylphenyl)propan-2-ol |
| 568 | 2-(4-{3-[(2,2-diphenylethyl)({[3-(trifluoromethyl)phenyl]methyl})amino]propoxy}-2-methanesulfonylphenyl)propan-2-ol |
| 569 | 2-(4-{3-[benzyl({[2-chloro-3-(trifluoromethyl)phenyl]methyl})amino]propoxy}-2-methanesulfonylphenyl)propan-2-ol |
| 570 | 2-(4-{3-[benzyl({[2-fluoro-3-(trifluoromethyl)phenyl]methyl})amino]propoxy}-2-methanesulfonylphenyl)propan-2-ol |
| 571 | 2-(4-{3-[benzyl({[3-(trifluoromethyl)phenyl]methyl})amino]propoxy}-2-methanesulfonylphenyl)propan-2-ol |
| 572 | 2-[4-(3-{[(4-fluorophenyl)methyl]({[3-(trifluoromethyl)phenyl]methyl})amino}propoxy)-2-methanesulfonylphenyl]propan-2-ol |
| 573 | 2-[4-(3-{[2-(4-fluorophenyl)-2-methylpropyl]({[3-(trifluoromethyl)phenyl]methyl})amino}propoxy)-2-methanesulfonylphenyl]propan-2-ol |
| 574 | 2-[4-(3-{[2-(4-fluorophenyl)ethyl]({[3-(trifluoromethyl)phenyl]methyl})amino}propoxy)-2-methanesulfonylphenyl]propan-2-ol |
| 575 | 2-[4-(3-{[2-(4-fluorophenyl)propyl]({[3-(trifluoromethyl)phenyl]methyl})amino}propoxy)-2-methanesulfonylphenyl]propan-2-ol |
| 576 | 2-{4-[3-({[2-chloro-3-(trifluoromethyl)phenyl]methyl}[2,2-difluoro-2-(4-fluorophenyl)ethyl]amino)propoxy]-2-methanesulfonylphenyl}propan-2-ol |
| 577 | 2-[4-(3-{[2,2-difluoro-2-(4-fluorophenyl)ethyl]({[2-fluoro-3-(trifluoromethyl)phenyl]methyl})amino}propoxy)-2-methanesulfonylphenyl]propan-2-ol |
| 578 | 2-[4-(3-{[2,2-difluoro-2-(4-fluorophenyl)ethyl]({[3-(trifluoromethyl)phenyl]methyl})amino}propoxy)-2-methanesulfonylphenyl]propan-2-ol |
| 579 | 2-{4-[3-({[2-chloro-3-(trifluoromethyl)phenyl]methyl}(2-methyl-2-phenylpropyl)amino)propoxy]-2-methanesulfonylphenyl}propan-2-ol |
| 580 | 2-{4-[3-({[2-chloro-3-(trifluoromethyl)phenyl]methyl}(2-phenylethyl)amino)propoxy]-2-methanesulfonylphenyl}propan-2-ol |
| 581 | 2-{4-[3-({[2-chloro-3-(trifluoromethyl)phenyl]methyl}(2-phenylpropyl)amino)propoxy]-2-methanesulfonylphenyl}propan-2-ol |
| 582 | 2-{4-[3-({[2-chloro-3-(trifluoromethyl)phenyl]methyl}[(4-fluorophenyl)methyl]amino)propoxy]-2-methanesulfonylphenyl}propan-2-ol |
| 583 | 2-{4-[3-({[2-chloro-3-(trifluoromethyl)phenyl]methyl}[2-(4-fluorophenyl)-2-methylpropyl]amino)propoxy]-2-methanesulfonylphenyl}propan-2-ol |
| 584 | 2-{4-[3-({[2-chloro-3-(trifluoromethyl)phenyl]methyl}[2-(4-fluorophenyl)ethyl]amino)propoxy]-2-methanesulfonylphenyl}propan-2-ol |
| 585 | 2-{4-[3-({[2-chloro-3-(trifluoromethyl)phenyl]methyl}[2-(4-fluorophenyl)propyl]amino)propoxy]-2-methanesulfonylphenyl}propan-2-ol |
| 586 | 2-{4-[3-({[2-fluoro-3-(trifluoromethyl)phenyl]methyl}(2-methyl-2-phenylpropyl)amino)propoxy]-2-methanesulfonylphenyl}propan-2-ol |
| 587 | 2-{4-[3-({[2-fluoro-3-(trifluoromethyl)phenyl]methyl}(2-phenylethyl)amino)propoxy]-2-methanesulfonylphenyl}propan-2-ol |
| 588 | 2-{4-[3-({[2-fluoro-3-(trifluoromethyl)phenyl]methyl}(2-phenylpropyl)amino)propoxy]-2-methanesulfonylphenyl}propan-2-ol |
| 589 | 2-{4-[3-({[2-fluoro-3-(trifluoromethyl)phenyl]methyl}[(4-fluorophenyl)methyl]amino)propoxy]-2-methanesulfonylphenyl}propan-2-ol |
| 590 | 2-{4-[3-({[2-fluoro-3-(trifluoromethyl)phenyl]methyl}[2-(4-fluorophenyl)-2-methylpropyl]amino)propoxy]-2-methanesulfonylphenyl}propan-2-ol |
| 591 | 2-{4-[3-({[2-fluoro-3-(trifluoromethyl)phenyl]methyl}[2-(4-fluorophenyl)ethyl]amino)propoxy]-2-methanesulfonylphenyl}propan-2-ol |
| 592 | 2-{4-[3-({[2-fluoro-3-(trifluoromethyl)phenyl]methyl}[2-(4-fluorophenyl)propyl]amino)propoxy]-2-methanesulfonylphenyl}propan-2-ol |

TABLE 2-continued

LXRβ agonists

| # | Name |
|---|------|
| 593 | 2-{4-[3-({[2-chloro-3-(trifluoromethyl)phenyl]methyl}(2,2-diphenylethyl)amino)propoxy]-2-methanesulfonylphenyl}propan-2-ol |
| 594 | 6-(3-{[(4-fluorophenyl)methyl]({[3-(trifluoromethyl)phenyl]methyl})amino}propoxy)-3,4-dihydro-1H-2-benzopyran-3-one |
| 595 | 6-(3-{[2-(4-fluorophenyl)-2-methylpropyl]({[3-(trifluoromethyl)phenyl]methyl})amino}propoxy)-3,4-dihydro-1H-2-benzopyran-3-one |
| 596 | 6-(3-{[2-(4-fluorophenyl)ethyl]({[3-(trifluoromethyl)phenyl]methyl})amino}propoxy)-3,4-dihydro-1H-2-benzopyran-3-one |
| 597 | 6-(3-{[2-(4-fluorophenyl)propyl]({[3-(trifluoromethyl)phenyl]methyl})amino}propoxy)-3,4-dihydro-1H-2-benzopyran-3-one |
| 598 | 6-[3-({[2-chloro-3-(trifluoromethyl)phenyl]methyl}[2,2-difluoro-2-(4-fluorophenyl)ethyl]amino)propoxy]-3,4-dihydro-1H-2-benzopyran-3-one |
| 599 | 6-(3-{[2,2-difluoro-2-(4-fluorophenyl)ethyl]({[2-fluoro-3-(trifluoromethyl)phenyl]methyl})amino}propoxy)-3,4-dihydro-1H-2-benzopyran-3-one |
| 600 | 6-(3-{[2,2-difluoro-2-(4-fluorophenyl)ethyl]({[3-(trifluoromethyl)phenyl]methyl})amino}propoxy)-3,4-dihydro-1H-2-benzopyran-3-one |
| 601 | 6-[3-({[2-chloro-3-(trifluoromethyl)phenyl]methyl}(2-methyl-2-phenylpropyl)amino)propoxy]-3,4-dihydro-1H-2-benzopyran-3-one |
| 602 | 6-[3-({[2-chloro-3-(trifluoromethyl)phenyl]methyl}(2-phenylethyl)amino)propoxy]-3,4-dihydro-1H-2-benzopyran-3-one |
| 603 | 6-[3-({[2-chloro-3-(trifluoromethyl)phenyl]methyl}(2-phenylpropyl)amino)propoxy]-3,4-dihydro-1H-2-benzopyran-3-one |
| 604 | 6-[3-({[2-chloro-3-(trifluoromethyl)phenyl]methyl}[(4-fluorophenyl)methyl]amino)propoxy]-3,4-dihydro-1H-2-benzopyran-3-one |
| 605 | 6-[3-({[2-chloro-3-(trifluoromethyl)phenyl]methyl}[2-(4-fluorophenyl)-2-methylpropyl]amino)propoxy]-3,4-dihydro-1H-2-benzopyran-3-one |
| 606 | 6-[3-({[2-chloro-3-(trifluoromethyl)phenyl]methyl}[2-(4-fluorophenyl)ethyl]amino)propoxy]-3,4-dihydro-1H-2-benzopyran-3-one |
| 607 | 6-[3-({[2-chloro-3-(trifluoromethyl)phenyl]methyl}[2-(4-fluorophenyl)propyl]amino)propoxy]-3,4-dihydro-1H-2-benzopyran-3-one |
| 608 | 6-[3-({[2-fluoro-3-(trifluoromethyl)phenyl]methyl}(2-methyl-2-phenylpropyl)amino)propoxy]-3,4-dihydro-1H-2-benzopyran-3-one |
| 609 | 6-[3-({[2-fluoro-3-(trifluoromethyl)phenyl]methyl}(2-phenylethyl)amino)propoxy]-3,4-dihydro-1H-2-benzopyran-3-one |
| 610 | 6-[3-({[2-fluoro-3-(trifluoromethyl)phenyl]methyl}(2-phenylpropyl)amino)propoxy]-3,4-dihydro-1H-2-benzopyran-3-one |
| 611 | 6-[3-({[2-fluoro-3-(trifluoromethyl)phenyl]methyl}[(4-fluorophenyl)methyl]amino)propoxy]-3,4-dihydro-1H-2-benzopyran-3-one |
| 612 | 6-[3-({[2-fluoro-3-(trifluoromethyl)phenyl]methyl}[2-(4-fluorophenyl)-2-methylpropyl]amino)propoxy]-3,4-dihydro-1H-2-benzopyran-3-one |
| 613 | 6-[3-({[2-fluoro-3-(trifluoromethyl)phenyl]methyl}[2-(4-fluorophenyl)ethyl]amino)propoxy]-3,4-dihydro-1H-2-benzopyran-3-one |
| 614 | 6-[3-({[2-fluoro-3-(trifluoromethyl)phenyl]methyl}[2-(4-fluorophenyl)propyl]amino)propoxy]-3,4-dihydro-1H-2-benzopyran-3-one |
| 615 | 6-{3-[(2-methyl-2-phenylpropyl)({[3-(trifluoromethyl)phenyl]methyl})amino]propoxy}-3,4-dihydro-1H-2-benzopyran-3-one |
| 616 | 6-{3-[(2-phenylethyl)({[3-(trifluoromethyl)phenyl]methyl})amino]propoxy}-3,4-dihydro-1H-2-benzopyran-3-one |
| 617 | 6-{3-[(2-phenylpropyl)({[3-(trifluoromethyl)phenyl]methyl})amino]propoxy}-3,4-dihydro-1H-2-benzopyran-3-one |
| 618 | 6-{3-[(2,2-diphenylethyl)({[2-fluoro-3-(trifluoromethyl)phenyl]methyl})amino]propoxy}-3,4-dihydro-1H-2-benzopyran-3-one |
| 619 | 6-{3-[(2,2-diphenylethyl)({[3-(trifluoromethyl)phenyl]methyl})amino]propoxy}-3,4-dihydro-1H-2-benzopyran-3-one |
| 620 | 6-{3-[benzyl({[2-chloro-3-(trifluoromethyl)phenyl]methyl})amino]propoxy}-3,4-dihydro-1H-2-benzopyran-3-one |
| 621 | 6-{3-[benzyl({[2-fluoro-3-(trifluoromethyl)phenyl]methyl})amino]propoxy}-3,4-dihydro-1H-2-benzopyran-3-one |
| 622 | 6-{3-[benzyl({[3-(trifluoromethyl)phenyl]methyl})amino]propoxy}-3,4-dihydro-1H-2-benzopyran-3-one |
| 623 | {3-[(1-methanesulfonylpiperidin-3-yl)oxy]propyl}(2-methyl-2-phenylpropyl){[3-(trifluoromethyl)phenyl]methyl}amine |
| 624 | {3-[(1-methanesulfonylpiperidin-3-yl)oxy]propyl}(2-phenylethyl){[3-(trifluoromethyl)phenyl]methyl}amine |

TABLE 2-continued

LXRβ agonists

| # | Name |
|---|------|
| 625 | {3-[(1-methanesulfonylpiperidin-3-yl)oxy]propyl}(2-phenylpropyl){[3-(trifluoromethyl)phenyl]methyl}amine |
| 626 | (2,2-diphenylethyl)({[2-fluoro-3-(trifluoromethyl)phenyl]methyl}){3-[(1-methanesulfonylpiperidin-3-yl)oxy]propyl}amine |
| 627 | (2,2-diphenylethyl)({3-[(1-methanesulfonylpiperidin-3-yl)oxy]propyl}){[3-(trifluoromethyl)phenyl]methyl}amine |
| 628 | benzyl({[2-chloro-3-(trifluoromethyl)phenyl]methyl}){3-[(1-methanesulfonylpiperidin-3-yl)oxy]propyl)amine |
| 629 | benzyl({[2-fluoro-3-(trifluoromethyl)phenyl]methyl}){3-[(1-methanesulfonylpiperidin-3-yl)oxy]propyl}amine |
| 630 | benzyl({3-[(1-methanesulfonylpiperidin-3-yl)oxy]propyl}){[3-(trifluoromethyl)phenyl]methyl}amine |
| 631 | [(4-fluorophenyl)methyl]({3-[(1-methanesulfonylpiperidin-3-yl)oxy]propyl}){[3-(trifluoromethyl)phenyl]methyl}amine |
| 632 | [2-(4-fluorophenyl)-2-methylpropyl]({3-[(1-methanesulfonylpiperidin-3-yl)oxy]propyl}){[3-(trifluoromethyl)phenyl]methyl}amine |
| 633 | [2-(4-fluorophenyl)ethyl]({3-[(1-methanesulfonylpiperidin-3-yl)oxy]propyl}){[3-(trifluoromethyl)phenyl]methyl}amine |
| 634 | [2-(4-fluorophenyl)propyl]({3-[(1-methanesulfonylpiperidin-3-yl)oxy]propyl}){[3-(trifluoromethyl)phenyl]methyl}amine |
| 635 | {[2-chloro-3-(trifluoromethyl)phenyl]methyl}[2,2-difluoro-2-(4-fluorophenyl)ethyl]{3-[(1-methanesulfonylpiperidin-3-yl)oxy]propyl}amine |
| 636 | [2,2-difluoro-2-(4-fluorophenyl)ethyl]({[2-fluoro-3-(trifluoromethyl)phenyl]methyl}){3-[(1-methanesulfonylpiperidin-3-yl)oxy]propyl}amine |
| 637 | [2,2-difluoro-2-(4-fluorophenyl)ethyl]({3-[(1-methanesulfonylpiperidin-3-yl)oxy]propyl}){[3-(trifluoromethyl)phenyl]methyl}amine |
| 638 | {[2-chloro-3-(trifluoromethyl)phenyl]methyl}({3-[(1-methanesulfonylpiperidin-3-yl)oxy]propyl})(2-methyl-2-phenylpropyl)amine |
| 639 | {[2-chloro-3-(trifluoromethyl)phenyl]methyl}({3-[(1-methanesulfonylpiperidin-3-yl)oxy]propyl})(2-phenylethyl)amine |
| 640 | {[2-chloro-3-(trifluoromethyl)phenyl]methyl}({3-[(1-methanesulfonylpiperidin-3-yl)oxy]propyl})(2-phenylpropyl)amine |
| 641 | {[2-chloro-3-(trifluoromethyl)phenyl]methyl}[(4-fluorophenyl)methyl]{3-[(1-methanesulfonylpiperidin-3-yl)oxy]propyl}amine |
| 642 | {[2-chloro-3-(trifluoromethyl)phenyl]methyl}[2-(4-fluorophenyl)-2-methylpropyl]{3-[(1-methanesulfonylpiperidin-3-yl)oxy]propyl}amine |
| 643 | {[2-chloro-3-(trifluoromethyl)phenyl]methyl}[2-(4-fluorophenyl)ethyl]{3-[(1-methanesulfonylpiperidin-3-yl)oxy]propyl}amine |
| 644 | {[2-chloro-3-(trifluoromethyl)phenyl]methyl}[2-(4-fluorophenyl)propyl]{3-[(1-methanesulfonylpiperidin-3-yl)oxy]propyl}amine |
| 645 | {[2-fluoro-3-(trifluoromethyl)phenyl]methyl}({3-[(1-methanesulfonylpiperidin-3-yl)oxy]propyl})(2-methyl-2-phenylpropyl)amine |
| 646 | {[2-fluoro-3-(trifluoromethyl)phenyl]methyl}({3-[(1-methanesulfonylpiperidin-3-yl)oxy]propyl})(2-phenylethyl)amine |
| 647 | {[2-fluoro-3-(trifluoromethyl)phenyl]methyl}({3-[(1-methanesulfonylpiperidin-3-yl)oxy]propyl})(2-phenylpropyl)amine |
| 648 | {[2-fluoro-3-(trifluoromethyl)phenyl]methyl}[(4-fluorophenyl)methyl]{3-[(1-methanesulfonylpiperidin-3-yl)oxy]propyl}amine |
| 649 | {[2-fluoro-3-(trifluoromethyl)phenyl]methyl}[2-(4-fluorophenyl)-2-methylpropyl]{3-[(1-methanesulfonylpiperidin-3-yl)oxy]propyl}amine |
| 650 | {[2-fluoro-3-(trifluoromethyl)phenyl]methyl}[2-(4-fluorophenyl)ethyl]{3-[(1-methanesulfonylpiperidin-3-yl)oxy]propyl}amine |
| 651 | {[2-fluoro-3-(trifluoromethyl)phenyl]methyl}[2-(4-fluorophenyl)propyl]{3-[(1-methanesulfonylpiperidin-3-yl)oxy]propyl}amine |
| 652 | {3-[(1-methanesulfonylazetidin-3-yl)oxy]propyl}(2-methyl-2-phenylpropyl){[3-(trifluoromethyl)phenyl]methyl}amine |
| 653 | {3-[(1-methanesulfonylazetidin-3-yl)oxy]propyl}(2-phenylethyl){[3-(trifluoromethyl)phenyl]methyl}amine |
| 654 | {3-[(1-methanesulfonylazetidin-3-yl)oxy]propyl}(2-phenylpropyl){[3-(trifluoromethyl)phenyl]methyl}amine |
| 655 | (2,2-diphenylethyl)({[2-fluoro-3-(trifluoromethyl)phenyl]methyl}){3-[(1-methanesulfonylazetidin-3-yl)oxy]propyl}amine |
| 656 | (2,2-diphenylethyl)({3-[(1-methanesulfonylazetidin-3-yl)oxy]propyl}){[3-(trifluoromethyl)phenyl]methyl}amine |
| 657 | benzyl({[2-chloro-3-(trifluoromethyl)phenyl]methyl}){3-[(1-methanesulfonylazetidin-3-yl)oxy]propyl}amine |
| 658 | benzyl({[2-fluoro-3-(trifluoromethyl)phenyl]methyl}){3-[(1-methanesulfonylazetidin-3-yl)oxy]propyl}amine |
| 659 | benzyl({3-[(1-methanesulfonylazetidin-3-yl)oxy]propyl}){[3-(trifluoromethyl)phenyl]methyl}amine |
| 660 | [(4-fluorophenyl)methyl]({3-[(1-methanesulfonylazetidin-3-yl)oxy]propyl}){[3-(trifluoromethyl)phenyl]methyl}amine |
| 661 | [2-(4-fluorophenyl)-2-methylpropyl]({3-[(1-methanesulfonylazetidin-3-yl)oxy]propyl}){[3-(trifluoromethyl)phenyl]methyl}amine |

TABLE 2-continued

LXRβ agonists

| # | Name |
|---|------|
| 662 | [2-(4-fluorophenyl)ethyl]({3-[(1-methanesulfonylazetidin-3-yl)oxy]propyl}){[3-(trifluoromethyl)phenyl]methyl}amine |
| 663 | [2-(4-fluorophenyl)propyl]({3-[(1-methanesulfonylazetidin-3-yl)oxy]propyl}){[3-(trifluoromethyl)phenyl]methyl}amine |
| 664 | {[2-chloro-3-(trifluoromethyl)phenyl]methyl}[2,2-difluoro-2-(4-fluorophenyl)ethyl]{3-[(1-methanesulfonylazetidin-3-yl)oxy]propyl}amine |
| 665 | [2,2-difluoro-2-(4-fluorophenyl)ethyl]({[2-fluoro-3-(trifluoromethyl)phenyl]methyl}){3-[(1-methanesulfonylazetidin-3-yl)oxy]propyl}amine |
| 666 | [2,2-difluoro-2-(4-fluorophenyl)ethyl]({3-[(1-methanesulfonylazetidin-3-yl)oxy]propyl}){[3-(trifluoromethyl)phenyl]methyl}amine |
| 667 | {[2-chloro-3-(trifluoromethyl)phenyl]methyl}({3-[(1-methanesulfonylazetidin-3-yl)oxy]propyl})(2-methyl-2-phenylpropyl)amine |
| 668 | {[2-chloro-3-(trifluoromethyl)phenyl]methyl}({3-[(1-methanesulfonylazetidin-3-yl)oxy]propyl})(2-phenylethyl)amine |
| 669 | {[2-chloro-3-(trifluoromethyl)phenyl]methyl}({3-[(1-methanesulfonylazetidin-3-yl)oxy]propyl})(2-phenylpropyl)amine |
| 670 | {[2-chloro-3-(trifluoromethyl)phenyl]methyl}[(4-fluorophenyl)methyl]{3-[(1-methanesulfonylazetidin-3-yl)oxy]propyl}amine |
| 671 | {[2-chloro-3-(trifluoromethyl)phenyl]methyl}[2-(4-fluorophenyl)-2-methylpropyl]{3-[(1-methanesulfonylazetidin-3-yl)oxy]propyl}amine |
| 672 | {[2-chloro-3-(trifluoromethyl)phenyl]methyl}[2-(4-fluorophenyl)ethyl]{3-[(1-methanesulfonylazetidin-3-yl)oxy]propyl}amine |
| 673 | {[2-chloro-3-(trifluoromethyl)phenyl]methyl}[2-(4-fluorophenyl)propyl]{3-[(1-methanesulfonylazetidin-3-yl)oxy]propyl}amine |
| 674 | {[2-fluoro-3-(trifluoromethyl)phenyl]methyl}({3-[(1-methanesulfonylazetidin-3-yl)oxy]propyl})(2-methyl-2-phenylpropyl)amine |
| 675 | {[2-fluoro-3-(trifluoromethyl)phenyl]methyl}({3-[(1-methanesulfonylazetidin-3-yl)oxy]propyl})(2-phenylethyl)amine |
| 676 | {[2-fluoro-3-(trifluoromethyl)phenyl]methyl}({3-[(1-methanesulfonylazetidin-3-yl)oxy]propyl})(2-phenylpropyl)amine |
| 677 | {[2-fluoro-3-(trifluoromethyl)phenyl]methyl}[(4-fluorophenyl)methyl]{3-[(1-methanesulfonylazetidin-3-yl)oxy]propyl}amine |
| 678 | {[2-fluoro-3-(trifluoromethyl)phenyl]methyl}[2-(4-fluorophenyl)-2-methylpropyl]{3-[(1-methanesulfonylazetidin-3-yl)oxy]propyl}amine |
| 679 | {[2-fluoro-3-(trifluoromethyl)phenyl]methyl}[2-(4-fluorophenyl)ethyl]{3-[(1-methanesulfonylazetidin-3-yl)oxy]propyl}amine |
| 680 | {[2-fluoro-3-(trifluoromethyl)phenyl]methyl}[2-(4-fluorophenyl)propyl]{3-[(1-methanesulfonylazetidin-3-yl)oxy]propyl}amine |

Compounds of Formula I can be synthesized as described in International Patent Publication No. WO2015/106164, incorporated herein by reference.

In some embodiments of any of the foregoing methods, the LXRβ agonist has the structure of Formula II:

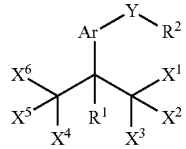

Formula II or a pharmaceutically acceptable salt thereof, wherein

Ar is an aryl group;

$R^1$ is a member selected from the group consisting of
—OH, —CO$_2$H, —O—(C$_1$-C$_7$)alkyl, —OC(O)—(C$_1$-C$_7$)alkyl, —O—(C$_1$-C$_7$)heteroalkyl, —OC(O)—(C$_1$-C$_7$)heteroalkyl, —NH$_2$, —NH(C$_1$-C$_7$) alkyl, —N((C$_1$-C$_7$)alkyl)$_2$ and —NH—S(O)$_2$(C$_1$-C$_5$)alkyl;

$R^2$ is a member selected from the group consisting of (C$_1$-C$_7$)alkyl, (C$_1$-C$_7$)heteroalkyl, aryl and aryl (C$_1$-C$_7$)alkyl;

$X^1$, $X^2$, $X^3$, $X^4$, $X^5$ and $X^6$ are each independently a member selected from the group consisting of H, (C$^1$-C$^5$)alkyl, (C$^1$-C$^5$)heteroalkyl, F and Cl, with the proviso that no more than three of $X^1$ through $X^6$ are H, (C$^1$-C$^5$)alkyl, (C$^1$-C$^5$)heteroalkyl; and Y is a divalent linking group selected from the group consisting of:
—N(R$^{12}$)S(O)$_m$—, —N(R$^{12}$)S(O)$_m$N(R$^{13}$)—, —N(R$^{12}$)C(O)—, —N(R$^{12}$)C(O)N(R$^{13}$)—, —N(R$^{12}$)C(S)— and —N(R$^{12}$)C(O)O—;

wherein $R^{12}$ and $R^{13}$ are each independently selected from the group consisting of:
H, (C$_1$-C$_7$)alkyl, (C$_1$-C$_7$)heteroalkyl, aryl and aryl(C$_1$-C$_7$) alkyl, and optionally when Y is
—N(R$^{12}$)S(O)$_m$— or —N(R$^{12}$)S(O)$_m$N(R$^{13}$)—, $R^{12}$ forms a five- or six-membered ring fused to Ar or to $R^2$ through covalent attachment to Ar or to $R^2$, respectively; and the subscript m is an integer of from 1 to 2;

with the proviso that when $R^1$ is OH, and —Y—$R^2$ is —N(R$^{12}$)S(O)$_m$—$R^2$ or —N(R$^{12}$)C(O)N(R$^{13}$)—$R^2$ and is attached to a position para to the quaternary carbon attached to Ar, and when $R^2$ is phenyl, benzyl, or benzoyl, then i) at least one of $R^{12}$ or $R^{13}$ is other than hydrogen and contains an electron-withdrawing substituent, or ii) $R^2$ is substituted with a moiety other than amino, acetamido, di(C$_1$-C$_7$)alkylamino, (C$_1$-C$_7$)alkylamino, halogen, hydroxy, nitro, or (C$_1$-C$_7$)alkyl, or iii) the benzene ring portion of $R^2$ is substituted with at least three independently selected groups in addition to the Y group or point of attachment to Y.

In some embodiments, Y is —N(R$^{12}$)S(O)$_2$— and $R^1$ is OH.

Accordingly, the compounds of Formula I include but are not limited the compound with the structure shown below:

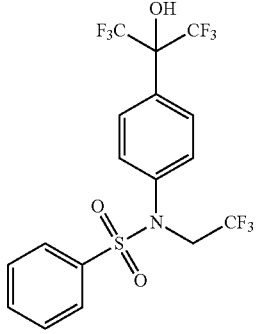

681

Compounds of Formula II can be synthesized as described by U.S. Pat. No. 6,316,503, incorporated herein by reference.

In some embodiments of any of the foregoing methods, the LXRβ agonist has the structure of Formula III:

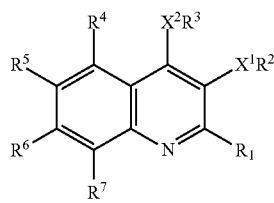

Formula III wherein:
$R^1$ is —H;
$X^1$ is a bond, $C_1$ to $C_5$ alkyl, —C(O)—, —C(=$CR^8R^9$)—, —O—, —S(O)$_t$—, —$NR^8$—, —$CR^8R^9$—, —$CHR^{23}$—, —$CR^8(CR^9)$—, —$C(CR^8)_2$—, —$CR_8(OC(O)R^9)$—, —C=$NOR^9$—, —C(O)$NR^8$—, —$CH_2O$—, —$CH_2S$—, —$CH_2NR^8$—, —$OCH_2$—, —$SCH_2$—, —$NR^8CH_2$—, or

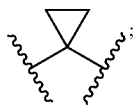 [SMILES: *C1(*)CC1 ; ";"]

$R^2$ is H, $C_1$ to $C_6$alkyl, $C_2$ to $C_6$alkenyl, $C_2$ to $C_6$alkynyl, $C_3$ to $C_6$ cycloalkyl, —$CH_2OH$, C7 to $C_{11}$ arylalkyl, phenyl, naphthyl, $C_1$ to $C_3$ perfluoroalkyl, CN, C(O)$NH_2$, $CO_2R^{12}$ or phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —$NO_2$, —$NR^8R^9$, —CN, —OH, and $C_1$ to $C_3$alkyl substituted with 1 to 5 fluorines, or $R^2$ is a heterocycle selected from the group consisting of pyridine, thiophene, benzisoxazole, benzothiophene, oxadiazole, pyrrole, pyrazole, imidazole, and furan, each of which may be optionally substituted with one to three groups independently selected from $C_1$ to C3alkyl, $C_1$ to $C_3$ alkoxy, $C_1$ to $C_3$ perfluoroalkyl, halogen, —$NO_2$, —$NR^8R^9$, —CN, and $C_1$ to $C_3$alkyl substituted with 1 to 5 fluorines;
$X^2$ is a bond or —$CH_2$—;

$R^3$ is phenyl, naphthyl, or phenyl or naphthyl substituted independently by one to four groups independently selected from $C_1$ to $C_3$ alkyl, hydroxy, phenyl, acyl, halogen, —$NH_2$, —CN, —$NO_2$, $C_1$ to $C_3$ alkoxy, $C_1$ to $C_3$perfluoroalkyl, $C_1$ to $C_3$ alkyl substituted with 1 to 5 fluorines, $NR^{14}R^{15}$, —C(O)$R^{10}$
—C(O)$NR^{10}R^{11}$, —C(O)$NR^{11}$A, —C≡$CR^8$, —CH=$CHR^8$, —WA, —C≡CA, —CH=CHA, —WYA, —WY$NR^{11}$-A, —WY$R^{10}$, —WY(CH2)$_j$A, —WCHR$^{11}$(CH2)$_j$A, —W(CH2)$_j$A, —W(CH2)$_j$R$^{10}$, —CHR$^{11}$W(CH$_2$)$_j$R$^{10}$, —CHR$^{11}$W(CH$_2$)$_j$A, —CHR$^{11}$NR$^{12}$YA, —CHR$^{11}$NR$^{12}$YR$^{10}$, pyrrole, —W(CH$_2$)$_j$A(CH$_2$)$_k$D(CH$_2$)$_p$Z,
—W(CR$^{18}$R$^{19}$)A(CH$_2$)$_k$D(CH$_2$)$_p$Z, —(CH$_2$)$_j$WA(CH$_2$)$_k$D(CH$_2$)$_p$Z, —CH=CHA(CH2)$_k$D(CH2)pZ,
—C≡CA(CH$_2$)$_k$D(CH$_2$)$_p$Z, —W(CH$_2$)$_j$C≡CA(CH$_2$)$_k$D(CH2)$_p$Z, and —W(CH$_2$)$_j$Z, or $R^3$ is a heterocycle selected from pyrimidine, thiophene, furan, benzothiophene, indole, benzofuran, benzimidazole, benzothiazole, benzoxazole, and quinoline, each of which may be optionally substituted with one to three groups independently selected from $C_1$ to $C_3$alkyl, $C_1$ to $C_3$ alkoxy, hydroxy, phenyl, acyl, halogen, —$NH_2$, —CN, —$NO_2$, $C_1$ to $C_3$ perfluoroalkyl, $C_1$ to $C_3$ alkyl substituted with 1 to 5 fluorines, —C(O)$R^{10}$, —C(O)$NR^{10}R^{11}$, —C(O)$NR^{11}$A, —C≡$CR^8$, —CH=$CHR^8$, —WA, —C≡CA, —CH=CHA, —WYA, —WY$R^{10}$, —WY(CH$_2$)$_j$A, —W(CH$_2$)$_j$A, —W(CH$_2$)$_j$R$^{10}$, —CHR$^{11}$W(CH$_2$)$_j$R$^{10}$, —CHR$^{11}$W(CH$_2$)$_j$A, —CHR$^{11}$NR$^{12}$YA, —CHR$^{11}$NR$^{12}$YR$^{10}$,
—WCHR$^1$(CH$_2$)$_j$A, —W(CH$_2$)$_j$A(CH$_2$)kD(CH$_2$)$_p$Z, —W(CR$^{18}$R$^{19}$)A(CH$_2$)$_k$D(CH$_2$)$_p$Z, —(CH$_2$)$_j$WA(CH$_2$)$_k$D(CH$_2$)$_p$Z, —CH=CHA(CH$_2$)$_k$D(CH$_2$)$_p$Z, —C≡CA(CH$_2$)$_k$D(CH$_2$)$_p$Z, —W(CH$_2$)$_j$C≡CA(CH$_2$)$_k$D(CH$_2$)$_p$Z, and —W(CH$_2$)$_j$Z;
W is a bond, —O—, —S—, —S(O)—, —S(O)$_2$—, —NR$^{11}$—, or —N(COR$^{12}$)—;
Y is —CO—, —S(O)$^2$—, —CONR$^{13}$—, —CONR$^{13}$CO—, —CONR$^{13}$SO$_2$—, —C(NCN)—, —CSNR$^{13}$, —C(NH)NR$^{13}$, or —C(O)O—;
j is 0 to 3;
k is 0 to 3;
t is 0 to 2;
D is a bond, —CH=CH—, —C≡C—, —C=, —C(O)—, phenyl, —O—, —NH—, —S—, —CHR$^{14}$—, —CR$^{14}$R$^{15}$—,
—OCHR$^{14}$, —OCR$^{14}$R$^{15}$—, or —CH(OH)CH(OH)—;
p is 0 to 3;
Z is —CO$_2$R$^{11}$, —CONR$^{10}$R$^{11}$, —C(NR$^{10}$)NR$^{11}$R$^{12}$, —CONH$_2$NH$_2$, —CN, —CH$_2$OH, —NR$^{16}$R$^{17}$, phenyl, CONHCH(R$^{20}$)COR$^{12}$, phthalimide, pyrrolidine-2,5dione, thiazolidine-2,4-dione, tetrazolyl, pyrrole, indole, oxazole, 2-thioxo-1,3-thiazolinin-4-one, $C_1$ to $C_7$ amines, $C_3$ to $C_7$ cyclic amines, or $C_1$ to $C_3$ alkyl substituted with one to two OH groups; wherein said pyrrole is optionally substituted with one or two substituents independently selected from the group consisting of —CO$_2$CH$_3$, —CO$_2$H, —COCH$_3$, —CONH$_2$, and —CN;
wherein said $C_1$ to $C_7$amines are optionally substituted with one to two substituents independently
selected from the group consisting of —OH, halogen, —OCH$_3$,and —C≡CH;
wherein said phenyl is optionally substituted with CO$_2$R$^{11}$, and wherein said $C_3$ to $C_7$ cyclic amines are optionally substituted with one or two substituents independently selected from the group consisting of —OH—

CH$_2$OH, C$_1$ to C$_3$ alkyl, —CH$_2$OCH$_3$, —CO$_2$CH$_3$, and —CONH$_2$, and wherein said oxazole is optionally substituted with CH$_2$CO$_2$R$^{11}$;

A is phenyl, naphthyl, tetrahydronaphthyl, indan or biphenyl, each of which may be optionally substituted by one to four groups independently selected from halogen, C$_1$ to C$_3$ alkyl, C$_2$ to C$_4$ alkenyl, C$_2$ to C$_4$ alkynyl, acyl, hydroxy, halogen, —CN, —NO$_2$, —CO$_2$R$^{11}$, —CH$_2$CO$_2$R$^{11}$, phenyl, C$_1$ to C$_3$perfluoroalkoxy, C$_1$ to C$_3$ perfluoroalkyl, —NR$^{10}$R$^{11}$, —CH$_2$NR$^{10}$R$^{11}$, —SR$^{11}$, C$_1$ to C$_6$ alkyl substituted with 1 to 5 fluorines, C$_1$ to C$_3$alkyl substituted with 1 to 2-OH groups, C$_1$ to C$_6$ alkoxy optionally substituted with 1 to 5 fluorines, or phenoxy optionally substituted with 1 to 2 CF$_3$ groups; or A is a heterocycle selected from pyrrole, pyridine, pyridine-N-oxide, pyrimidine, pyrazole, thiophene, furan, quinoline, oxazole, thiazole, imidazole, isoxazole, indole, benzo[1,3]-dioxole, benzo[1,2,5]-oxadiazole, isochromen-1-one, benzothiophene, benzofuran, 2,3-di-5 hydrobenzo[1,4]-dioxine, bitheinyl, quinazolin-2,4-9[3H]dione, and 3-H-isobenzofuran-1-one, each of which may be optionally substituted by one to three groups independently selected from halogen, C$_1$ to C$_3$ alkyl, acyl, hydroxy, —CN, —NO$_2$, C$_1$ to C$_3$perfluoroalkyl, —NR$^{10}$R$^{11}$, —CH$_2$NR$^{10}$R$^{11}$, —SR$^{11}$, C$_1$ to C$_3$ alkyl substituted with 1 to 5 fluorines, and C$_1$ to C$_3$ alkoxy optionally substituted with 1 to 5 fluorines;

R$^4$, R$^5$, and R$^6$ are each, independently, —H or —F;

R$^7$ is C$_1$ to C$_4$ alkyl, C$_1$ to C$_4$ perfluoroalkyl, halogen, —NO$_2$, —CN, phenyl or phenyl substituted with one or two groups independently selected from halogen, C$_1$ to C$_2$alkyl and OH;

provided that if X$_1$R$^2$ forms hydrogen, then R$^3$ is selected from:

(a) phenyl substituted by —W(CH$_2$)$_j$A(CH$_2$)$_k$D(CH$_2$)$_p$Z, —W(CR$^{18}$R$^{19}$)A(CH$_2$)$_k$D(CH$_2$)$_p$Z, —(CH$_2$)$_j$WA(CH$_2$)$_k$D(CH$_2$)$_p$Z, —CH=CHA(CH$_2$)$_k$D(CH$_2$)$_p$Z, —C≡CA(CH$_2$)$_k$D(CH$_2$)$_p$Z, or —W(CH$_2$)$_j$C≡CA(CH$_2$)$_k$D(CH$_2$)$_p$Z, wherein the phenyl moiety is further optionally substituted with one or two groups independently selected from C$_1$ to C$_2$ alkyl, C$_1$ to C$_2$perfluoroalkyl, halogen, and CN; and (b) a heterocycle selected from pyrimidine, thiophene, and furan, each of which is substituted by one of —W(CH$_2$)$_j$A(CH$_2$)$_k$D(CH$_2$)$_p$Z, —W(CR$^{18}$R$^{19}$)A(CH$_2$)$_k$D(CH$_2$)$_p$Z, —(CH$_2$)$_j$WA(CH$_2$)$_k$D(CH$_2$)$_p$Z, —CH=CHA(CH$_2$)$_k$D(CH$_2$)$_p$Z, —C≡CA(CH$_2$)$_k$D(CH$_2$)$_p$Z, or —W(CH$_2$)$_j$C≡CA(CH$_2$)$_k$D(CH$_2$)$_p$Z;

each R$^8$ is independently-H, or C$_1$ to C$_3$alkyl;

each R$^9$ is independently-H, or C$_1$ to C$_3$alkyl;

each R$^{10}$ is independently-H, —CH, C$_1$ to C$_3$alkoxy, C$_1$ to C$_7$ alkyl, C$_3$ to C$_7$ alkenyl, C$_3$ to C$_7$ alkynyl, C$_3$ to C$_7$ cycloalkyl, —CH$_2$CH$_2$OCH$_3$, 2-methyl-tetrahydro-furan, 2-methyl-tetrahydro-pyran, 4-methyl-piperidine, morpholine, pyrrolidine, or phenyl optionally substituted with one or two C$_1$ to C$_3$alkoxy groups, wherein said C$_1$ to C$_7$ alkyl is optionally substituted with 1, 2 or 3 groups independently selected from C$_1$ to C$_3$ alkoxy, C$_1$ to C$_3$thioalkoxy, and CN;

each R$^{11}$ is independently-H, C$_1$ to C$_3$alkyl or R$^{22}$; or R$^{10}$ and R$^{11}$, when attached to the same atom, together with said atom form:

a 5 to 7 membered saturated ring, optionally substituted by 1 to 2 groups independently selected from C$_1$ to C$_3$ alkyl, OH and C$_1$-C$_3$alkoxy; or a 5 to 7 membered ring containing 1 or 2 heteroatoms, optionally substituted by 1 to 2 groups independently selected from C$_1$ to C$_3$alkyl, OH and C1-C$_3$ alkoxy;

each R$^{12}$ is independently-H, or C$_1$ to C$_3$alkyl;

each R$^{13}$ is independently-H, or C$_1$ to C$_3$alkyl;

each R$^{14}$ and R$^{15}$ is, independently, C$_1$ to C$_7$ alkyl, C$_3$ to C$_8$ cycloalkyl, C$_2$ to C$_7$ alkenyl, C$_2$ to C$_7$ alkynyl, —CH, —F, C$_7$ to C$_{14}$arylalkyl, where said arylalkyl is optionally substituted with 1 to 3 groups independently selected from NO$_2$, C$_1$ to C$_6$ alkyl, C$_1$ to C$_3$perhaloalkyl, halogen, CH$_2$CO$_2$R$^{11}$, phenyl and C$_1$ to C$_3$ alkoxy, or R$^{12}$ and R$^{15}$ together with the atom to which they are attached can form a 3 to 7 membered saturated ring;

each R$^{16}$ and R$^{17}$ is, independently, hydrogen, C$_1$ to C$_3$ alkyl, C$_1$ to C3alkenyl, C$_1$ to C$_3$ alkynyl, phenyl, benzyl or C$_3$ to C$_8$ cycloalkyl, wherein said C$_1$ to C$_3$ alkyl is optionally substituted with one OH group, and wherein said benzyl is optionally substituted with 1 to 3 groups selected from C$_1$ to C$_3$alkyl and C$_1$ to C$_3$alkoxy; or R$^{16}$ and R$^{17}$, together with the atom to which they are attached, can form a 3 to 8 membered heterocycle which is optionally substituted with one or two substituents independently selected from the group consisting of C$_1$ to C$_3$alkyl, —OH, CH$_2$OH, —CH$_2$OCH$_3$, —CO$_2$CH$_3$, and —CONH$_2$;

each R$^{18}$ and R$^{19}$ is, independently, C$_1$ to C$_3$alkyl;

each R$^{20}$ is independently H, phenyl, or the side chain of a naturally occurring alpha amino acid;

each R$^{22}$ is independently arylalkyl optionally substituted with CH$_2$COOH; and each R$_{23}$ is phenyl;

or a pharmaceutically acceptable salt thereof.

Compounds of Formula II can be synthesized as described in U.S. Pat. No. 7,576,215, incorporated herein by reference. The compound of formula II can be any of compounds 26-32, or a pharmaceutically acceptable salt thereof.

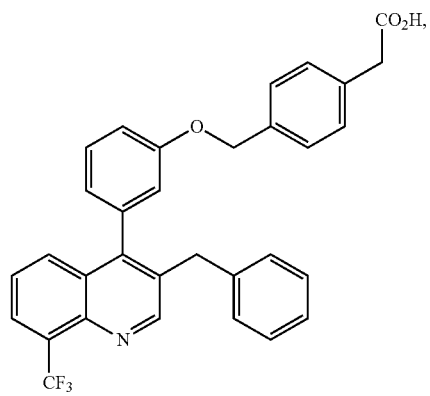

706

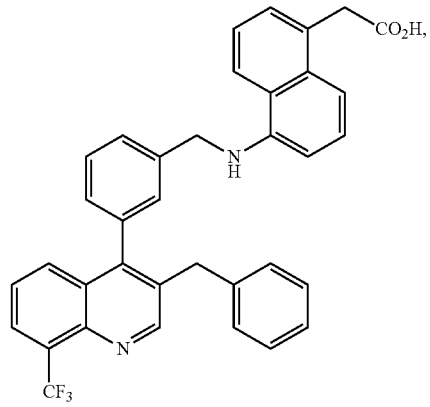

707

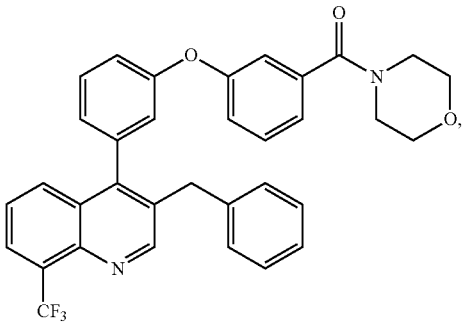

708

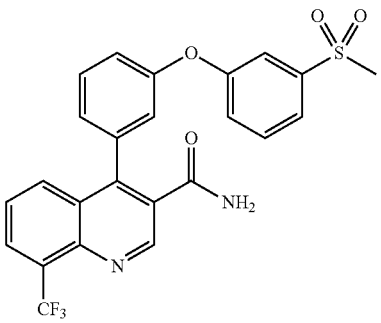

712

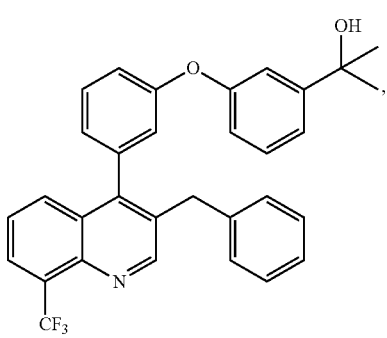

709

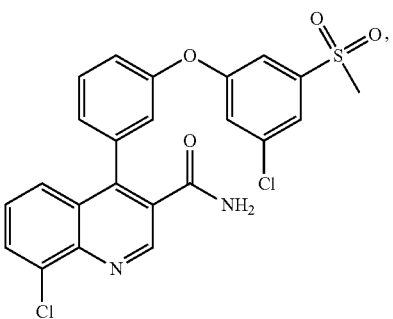

710

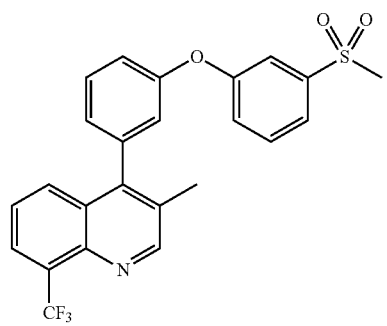

711

In some embodiments, the LXRβ agonist has the structure of Formula IV:

Formula IV wherein:

X is selected from hydrogen, $C_1$-$C_8$ alkyl, halo, —OR$^{10}$, —NR$^{10}$R$^{11}$, nitro, cyano, —COOR$^{10}$, or —COR$^{10}$ Z is CH, CR$^3$ or N, wherein when Z is CH or CR$^3$, k is 0-4 and t is 0 or 1, and when Z is N, k is 0-3 and t is 0;

Y is selected from —O—, —S—, —N(R$^{12}$)—, and —C(R$^4$)(R$^5$)—;

W$^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-CO$_2$R$^{12}$, —$C_0$-$C_6$alkyl-C(O)SR$^{12}$, —$C_0$-$C_6$alkyl-CONR$^{13}$R$^{14}$, —$C_0$-$C_6$ alkyl-COR$^{15}$, —$C_0$-$C_6$ alkyl-NR$^{13}$R$^{14}$, —$C_0$-$C_6$ alkyl-SR$^{12}$, —$C_0$-$C_6$alkyl-OR$^{12}$, —$C_0$-$C_6$alkyl-SO$_3$H, —$C_0$-$C_6$alkyl-SO$_2$NR$^{13}$R$^{14}$, —$C_0$-$C_6$alkyl-SO$_2$R$^{12}$, —$C_0$-$C_6$alkyl-SOR$^{15}$, —$C_0$-$C_6$alkylOCOR$^{15}$, —$C_0$-$C_6$alkyl-OC(O)NR$^{13}$R$^{14}$, —$C_0$-$C_6$alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}$R$^{14}$, and —$C_0$-$C_6$ alkyl-NR$^{13}$COR$^{15}$, where said $C_1$-$C_6$ alkyl, is optionally unsubstituted or substituted by one or more halo substituents;

W$^2$ is selected from H, halo, $C_1$-$C_6$alkyl, $C_2$-$C_6$alkenyl, $C_2$-$C_6$ alkynyl, —$C_0$-$C_6$ alkyl-NR$^{13}$R$^{14}$, —$C_0$-$C_6$alkyl-SR$^{12}$, —$C_0$-$C_6$ alkyl-OR$^{12}$, —$C_0$-$C_6$alkylCO$_2$R$^{12}$, —$C_0$-$C_6$alkyl-C(O)SR$^{12}$, —$C_0$-$C_6$ alkylCONR$^{13}$R$^{14}$, —$C_0$-$C_6$alkyl-COR$^{15}$, —$C_0$-$C_6$ alkylOCOR$^{15}$, —$C_0$-$C_6$alkyl-OCONR$^{13}$R$^{14}$, —$C_0$-$C_6$alkyl-NR$^{13}$CONR$^{13}$R$^{14}$, —$C_0$-$C_6$ alkyl-NR$^{13}$COR$^{15}$, —$C_0$-$C_6$alkyl-Het, —$C_0$-$C_6$alkyl-Ar and —$C_0$-$C_6$alkyl-$C_3$-$C_7$ cycloalkyl, wherein said $C_1$-$C_6$ alkyl is optionally unsubstituted or substituted by one or more halo substituents, and wherein the $C_3$-$C_7$cycloalkyl, Ar and Het moieties of said —$C_0$-$C_6$alkyl-Het, —$C_0$-$C_6$alkyl-Ar and —$C_0$-$C_6$alkyl-$C_3$-$C_7$cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$alkyl-$CO_2R^{12}$, —$C_0$-$C_6$ alkyl-C(O)SR$^{12}$, —$C_0$-$C_6$alkyl-CONR$^{13}$R$^{14}$, —$C_0$-$C_6$alkyl-COR$^{15}$, —$C_0$-$C_6$alkyl-NR$^{13}$R$^{14}$, —$C_0$-$C_6$alkyl-SR$^{12}$, —$C_0$-$C_6$alkyl-OR$^{12}$, —$C_0$-$C_6$ alkyl-SO$_3$H, —$C_0$-$C_6$alkyl-SO$_2$NR$^{13}$R$^{14}$, —$C_0$-$C_6$alkyl-SO$_2$R$^{12}$, —$C_0$-$C_6$alkyl-SOR$^{15}$, —$C_0$-$C_6$alkyl-OCOR$^{15}$, —$C_0$-$C_6$alkylOC(O)NR$^{13}$R$^{14}$, —$C_0$-$C_6$alkyl-OC(O)OR$^5$, —$C_0$-$C_6$alkyl-NR$^{13}$C(O)OR$^{15}$, —$C_0$-$C_6$alkyl-NR$^{13}$C(O)NR$^{13}$R$^{14}$, and —$C_0$-$C_6$alkyl-NR$^{13}$COR$^{15}$, where said $C_1$-$C_6$ alkyl, is optionally unsubstituted or substituted by one or more halo substituents;

W$^3$ is selected from the group consisting of: H, halo, $C_1$-$C_6$ alkyl, —$C_0$-$C_6$ alkyl-NR$^{13}$R$^{14}$, —$C_0$-$C_6$alkyl SR$^{12}$, —$C_0$-$C_6$alkyl-OR$^{12}$, —$C_0$-$C_6$alkyl-CO$_2$R$^{12}$, —$C_0$-$C_6$alkyl-C(O)SR$^{12}$, —$C_0$-$C_6$alkyl-CONR$^{13}$R$^{14}$, —$C_0$-$C_6$alkyl-COR$^{15}$, —$C_0$-$C_6$alkyl-OCOR$^{15}$, —$C_0$-$C_6$ alkyl-OCONR$^{13}$R$^{14}$, —$C_0$-$C_6$alkylNR$^{13}$CONR$^{13}$R$^{14}$, —$C_0$-$C_6$alkyl-NR$^{13}$COR$^{15}$, —$C_0$-$C_6$alkyl-Het, —$C_1$-$C_6$alkyl-Ar and —$C_1$-$C_6$alkyl-$C_3$-$C_7$cycloalkyl, wherein said $C_1$-$C_6$ alkyl is optionally unsubstituted or substituted by one or more halo substituents;

Q is selected from $C_3$-$C_8$cycloalkyl, Ar and Het; wherein said $C_3$-$C_8$cycloalkyl, Ar and Het are optionally unsubstituted or substituted with one or more groups independently selected from halo, cyano, nitro, $C_1$-$C_6$alkyl, $C_3$-$C_6$alkenyl, $C_3$-$C_6$alkynyl, —$C_0$-$C_6$alkylCO$_2$R$^{12}$, —$C_0$-$C_6$ alkyl-C(O)SR$^{12}$, —$C_0$-$C_6$alkylCONR$^{13}$R$^{14}$, —$C_0$-$C_6$ alkyl-COR$^{15}$, —$C_0$-$C_6$alkylNR$^{13}$R$^{14}$, —$C_0$-$C_6$alkyl-SR$^{12}$, —$C_0$-$C_6$alkyl-OR$^{12}$, —CO—$C_6$ alkyl-SO$_3$H, —$C_0$-$C_6$ alkyl-SO$_2$NR$^{13}$R$^{14}$, —$C_0$-$C_6$alkyl-SO$_2$R$^{12}$, —$C_0$-$C_6$alkyl-SOR$^{15}$, —$C_0$-$C_6$alkyl-OCOR$^{15}$, —$C_0$-$C_6$alkyl-OC(O)NR$^{13}$R$^{14}$, —$C_0$-$C_6$alkyl-OC(O)OR$^{15}$, —$C_0$-$C_6$alkylNR$^{13}$C(O)OR$^{15}$, —$C_0$-$C_6$ alkyl-NR$^{13}$C(O)NR$^{13}$R$^{14}$, and —$C_0$-$C_6$alkyl-NR$^{13}$COR$^{15}$, where said $C_1$-$C_6$alkyl is optionally unsubstituted or substituted by one or more halo substituents;

p is 0-8;
n is 2-8;
m is 0 or 1;
q is 0 or 1;
t is 0 or 1;

each R$^1$ and R$^2$ are independently selected from H, halo, $C_1$-$C_6$alkyl, $C_3$-$C_6$alkenyl, $C_3$-$C_6$ alkynyl, —$C_0$-$C_6$alkyl-NR$^{13}$R$^{14}$, —$C_0$-$C_6$alkyl-OR$^{12}$, —$C_0$-$C_6$ alkyl-SR$^{12}$, —C1-$C_6$alkyl-Het, —$C_1$-$C_6$alkyl-Ar and —$C_1$-$C_6$alkyl-$C_3$-$C_7$cycloalkyl, or R$^1$ and R$^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each R$^3$ is the same or different and is independently selected from halo, cyano, nitro, $C_1$-$C_6$ alkyl, $C_3$-$C_6$alkenyl, $C_3$-$C_6$alkynyl, —$C_0$-$C_6$alkyl-Ar, —$C_0$-$C_6$alkyl-Het, —$C_0$-$C_6$alkyl-$C_3$-$C_7$cycloalkyl, —$C_0$-$C_6$alkyl-CO$_2$R$^{12}$, —$C_0$-$C_6$alkyl-C(O)SR$^{12}$, —$C_0$-$C_6$alkyl-CONR$^{13}$R$^{14}$, —$C_0$-$C_6$alkyl-COR$^{15}$, —$C_0$-$C_6$alkyl-NR$^{13}$R$^{14}$, —$C_0$-$C_6$alkyl-SR$^{12}$, —$C_0$-$C_6$alkyl-OR$^{12}$, —$C_0$-$C_6$alkyl-SO$_3$H, —$C_0$-$C_6$alkylSO$_2$NR$^{13}$R$^{14}$, —$C_0$-$C_6$ alkyl-SO$_2$R$^{12}$, —$C_0$-$C_6$alkylSOR$^{15}$, —$C_0$-$C_6$alkyl-OCOR$^{15}$, —$C_0$-$C_6$ alkyl-OC(O)NR$^{13}$R$^{14}$, —$C_0$-$C_6$alkyl-OC(O)OR$^{15}$, —$C_0$-$C_6$alkyl-NR$^{13}$C(O)OR$^{15}$, —$C_0$-$C_6$alkyl-NR$^{13}$C(O)NR$^{13}$R$^{14}$, and —$C_0$-$C_6$alkyl-NR$^{13}$COR$^{15}$, wherein said $C_1$-$C_6$alkyl is optionally unsubstituted or substituted by one or more halo substituents;

each R$^4$ and R$^5$ is independently selected from H, halo, $C_1$-$C_6$alkyl, —$C_0$-$C_6$alkyl-Het, —$C_0$-$C_6$alkyl-Ar and —$C_0$-$C_6$alkyl-$C_3$-$C_7$cycloalkyl;

R$^6$ and R$^7$ are each independently selected from H, halo, $C_1$-$C_6$ alkyl, —$C_0$-$C_6$alkyl-Het, —$C_0$-$C_6$ alkyl-Ar and —$C_0$-$C_6$alkyl-$C_3$-$C_7$cycloalkyl;

R$^8$ and R$^9$ are each independently selected from H, halo, $C_1$-$C_6$ alkyl, —$C_0$-$C_6$alkyl-Het, —$C_0$-$C_6$ alkyl-Ar and —$C_0$-$C_6$alkyl-$C_3$-$C_7$ cycloalkyl;

R$^{10}$ and R$^{11}$ are each independently selected from H, $C_1$-$C_{12}$ alkyl, $C_3$-$C_{12}$alkenyl, $C_3$-$C_{12}$alkynyl, —$C_0$-$C_8$alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$alkyl-O-Het, —$C_0$-$C_8$ alkyl-O—$C_3$-$C_7$cycloalkyl, —$C_0$-$C_8$alkyl-S(O)$_x$—$C_0$-$C_6$alkyl, —$C_0$-$C_8$alkyl-S(O)$_x$—Ar, —$C_0$-$C_8$ alkyl-S(O)$_x$—Het, —$C_0$-$C_8$ alkyl-S(O)x-$C_3$-$C_7$cycloalkyl, —$C_0$-$C_8$alkyl-NH—Ar, —$C_0$-$C_8$alkyl-NH-Het, —$C_0$-$C_8$alkyl-NH—$C_3$-$C_7$cycloalkyl, —$C_0$-$C_8$alkyl-N($C_1$-$C_4$ alkyl)-Ar, —$C_0$-$C_8$alkyl-N($C_1$-$C_4$alkyl)-Het, —$C_0$-$C_8$alkyl-N($C_1$-$C_4$alkyl)-$C_3$-$C_7$cycloalkyl, —$C_0$-$C_8$alkyl-Ar, —$C_0$-$C_8$alkyl-Het and —$C_0$-$C_8$alkyl-$C_3$-$C_7$cycloalkyl, where x is 0, 1, or 2, or R$^{10}$ and R$^{11}$, together with the nitrogen to which they are attached, form a 4-7 membered heterocyclic ring which optionally contains one or more additional heteroatoms selected from N, O, and S, wherein said $C_1$-$C_{12}$alkyl, $C_3$-$C_{12}$ alkenyl, or $C_3$-$C_{12}$alkynyl is optionally substituted by one or more of the substituents independently selected from the group halo, —OH, —SH, —NH$_2$, —NH(unsubstituted $C_1$-$C_6$alkyl), —N(unsubstituted $C_1$-$C_6$ alkyl)(unsubstituted $C_1$-$C_6$alkyl), unsubstituted —O$C_1$-$C_6$ alkyl, —CO$_2$H, —CO$_2$(unsubstituted $C_1$-$C_6$ alkyl), —CONH$_2$, —CONH(unsubstituted $C_1$-$C_6$ alkyl), —CON(unsubstituted $C_1$-$C_6$alkyl)(unsubstituted $C_1$-$C_6$ alkyl), —SO$_3$H, —SO$_2$NH$_2$, —SO$_2$NH(unsubstituted $C_1$-$C_6$alkyl) and —SO$_2$N(unsubstituted $C_1$-$C_6$alkyl)(unsubstituted $C_1$-$C_6$ alkyl);

R$^{12}$ is selected from H, $C_1$-$C_6$ alkyl, $C_3$-$C_6$alkenyl, $C_3$-$C_6$alkynyl, —$C_0$-$C_6$alkyl-Ar, —$C_0$-$C_6$alkyl-Het and —$C_0$-$C_6$alkyl-$C_3$-$C_7$cycloalkyl;

each R$^{13}$ and each R$^{14}$ are independently selected from H, $C_1$-$C_6$alkyl, $C_3$-$C_6$alkenyl, $C_3$-$C_6$alkynyl, —$C_0$-$C_6$alkyl-Ar, —$C_0$-$C_6$alkyl-Het and —$C_0$-$C_6$alkyl-$C_3$-$C_7$cycloalkyl, or R$^{13}$ and R$^{14}$ together with the nitrogen to which they are attached form a 4-7 membered heterocyclic ring which optionally contains one or more additional heteroatoms selected from N, O, and S;

and R$^{15}$ is selected from $C_1$-$C_6$alkyl, $C_3$-$C_6$ alkenyl, $C_3$-$C_6$alkynyl, —$C_0$-$C_6$alkyl-Ar, —$C_0$-$C_6$ alkyl-Het and —$C_0$-$C_6$ alkyl-$C_3$-$C_7$ cycloalkyl;

or a pharmaceutically acceptable salt thereof.

In some embodiments, X is hydrogen, p is 0, t is 0, Z is CH, and Y is —O—.

In further embodiments, X is hydrogen, p is 0, t is 0, Z is CH, and Y is —O—, W$^1$ and W$^2$ are phenyl, W$^3$ is hydrogen, q is 1, and R$^8$ and R$^9$ are hydrogen.

In other embodiments, X is hydrogen, p is 0, t is 0, Z is CH, and Y is —O—, W$^1$ and W$^2$ are phenyl, W$^3$ is hydrogen, q is 1, R$^8$ and R$^9$ are hydrogen, and Q is Ar.

Accordingly, the compounds of Formula IV include but are not limited the compounds with structures shown below GW3965 682 and SB742881 705:

682

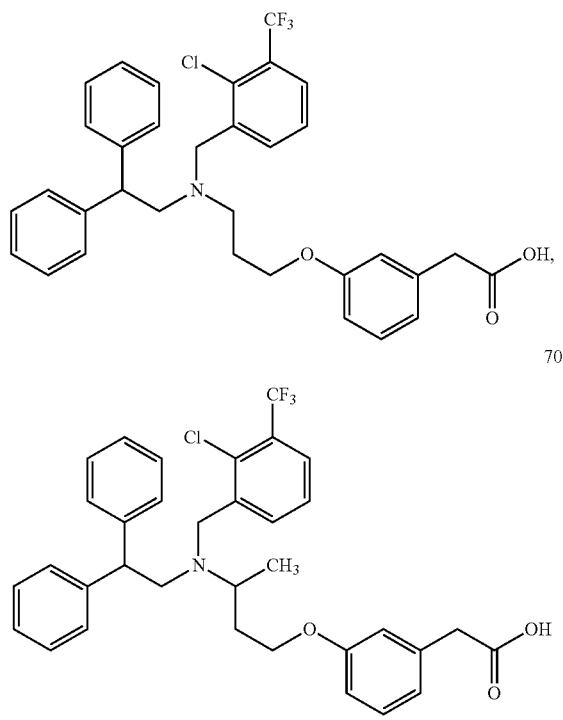

705

Compounds of Formula IV can be synthesized as described in U.S. Pat. Nos. 7,365,085 and 7,560,586 incorporated herein by reference.

In some embodiments of any of the foregoing methods, the LXR agonist has the structure of Formula V:

Formula V

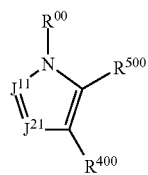

or a pharmaceutically acceptable salt thereof, wherein:
$J^{11}$ is —N= and $J^{21}$ is —$CR^{300}$—, or $J^{11}$ is —$CR^{200}$— and $J21$ is =N—;
$R^{00}$ is $G^1$, $G^{21}$, or $R^N$;
$R^{200}$ is $G^1$, $G^{21}$, or $R^C$;
$R^{300}$ and $R^{400}$ are independently $R^C$ or Q, provided one and only one of $R^{300}$, $R^{400}$, and $R^{500}$ is Q;
Q is $C_{3-6}$ cycloalkyl, heteroaryl or heterocyclyl, each optionally substituted with 1 to $4R^Q$, or Q is —X— Y—Z; wherein each $R^Q$ is independently aryloxy, aralkyloxy, aryloxyalkyl, aryl$C_0$-$C_6$alkylcarboxy, $C(R^{110})$=$C(R^{110})$— COOH, oxo, =S, —Z, —Y'—Z, or —X—Y—Z, wherein each $R^Q$ is optionally substituted with 1 to 4 $R^{80}$;
$R^{500}$ is $G^1$ $G^{21}$, Q, or $R^C$; provided that only one of $R^{00}$, $R^{200}$, and $R^{500}$ is $G^1$ and only one of $R^{00}$, N=, and $R^{500}$ is $G^{21}$;
$G^{21}$ is -$J^o$-$K^o$, wherein $J^o$ and $K^o$ are independently aryl or heteroaryl, each optionally substituted with one to four $R^K$ groups; each $R^K$ is independently hydrogen, halogen, $CR^{110}$=$CR^{110}COOR^{110}$, nitro, —Z, —Y—Z, or —X—Y—Z;
$G^1$ is -$L^{10}$-R, wherein $L^{10}$ is a bond, $L^{50}$, $L^{60}$, -$L^{50}$-$L^{60}$-$L^{50}$-, or -$L^{60}$-$L^{50}$-$L^{50}$-, wherein
each $L^{50}$ is independently —$[C(R^{150})_2]_m$—;
each $L^{60}$ is independently —CS—, —CO—, —$SO_2$—, —O—, —$CON(R^{110})$—, —$CONR^{110}N(R^{110})$—, —$C(=NR^{110})$—, —$C(NOR^{11})$—, —$C(=N-N(R^{110})_2)$—, —$C_3$-$C_8$cycloalkyl-, or -heterocyclyl-, wherein the cycloalkyl or heterocyclyl is optionally substituted with one to 4 $R^{140}$ groups; or each $L^{60}$ is independently $C_2$-$C_6$ alidiyl, wherein the alidiyl chain is optionally interrupted by —$C(R^{100})_2$—, —$C(R^{110})_2C(R^{110})_2$—, —$C(R^{11})C(R^{110})$—, —$C(R^{110})_2O$—, —$C(R^{110})_2NR^{110}$—, —C C—, —O—, —S—, —N(RO)CO—, —$N(R^{100})CO_2$—, —$CON(R^{110})$—, —CO—, —$CO_2$—, —OC(=O)—, —$OC(=O)N(R^{100})$—, —$SO_2$—, —$N(R^{100})SO_2$—, or —$SO_2N(R^{100})$;
R is aryl, heterocyclyl, heteroaryl or —($C_3$-$C_6$)cycloalkyl, wherein R is optionally substituted with 1 to 4 $R^A$, wherein each $R^A$ is independently halogen, nitro, heterocyclyl, $C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_1C_6$ alkenyl-, arylalkyl, aryloxy, aryl$C_{1-6}$ alkoxy, $C_1$-$C_6$ haloalkyl, $SO_2R^{110}$, $OR^{110}$, $SR^{110}$, $N_3$, $SOR^{110}$, $COR^{110}$, $SO_2N(R^{110})_2$, $SO_2NR^{110}COR^{110}$, C≡N, C(O)$OR^{110}$, $CON(R^{110})_2$, —$CON(R^{110})OR^{110}$, $OCON(R^{110})_2$, —$NR^{110}COR^{110}$, $NR^{110}CON(R^{110})_2$, $NR^{110}COOR^{110}$, —$C(=N-OH)R^{11}$, —$C(=S)N(R^{110})_2$, —$S(=O)N(R^{110})_2$, —$S(=O)OR^{110}$, —$N(R^{110})S(=O)_2R^{110}$, —$C(=O)N(R^{110})N(R^{110})_2$, —$OC(=O)$—$R^{110}$, —$OC(=O)$—$OR^{110}$ or $N(R^{11})_2$, wherein each $R^A$ is optionally substituted with 1 to 4 groups which independently are -halogen, —$C_1$-$C_6$ alkyl, aryloxy, $C_{0-6}$ alkyl$SO_2R^{110}$, $C_{0-6}$ alkyl$COOR^{110}$, $C_{1-6}$ alkoxyaryl, $C_1$-$C_6$ haloalkyl, —$SO_2R^{110}$, —$OR^{110}$, —$SR^{110}$, —$N_3$, —$SO_2R^{110}$, —$COR^{110}$, —$SO_2N(R^{110})_2$, —$SO_2NR^{110}COR^{110}$, —C≡N, —C(O)$OR^{110}$, —$CON(R^{110})_2$, —$CON(R^{110})OR^{110}$, —$OCON(R^{110})_2$, —$NR^{110}COR^{110}$, —$NR^{110}CON(R^{110})_2$, —$NR^{110}COOR^{110}$, or —$N(R^{110})_2$;
$R^N$ is -$L^{31}$-$R^{60}$, wherein $L^{31}$ is a bond, —$X^3(CH_2)_n$—$X^3$—, —$(CH_2)_m$—X3-$(CH_2)_n$— or —$(CH_2)_{1+w}$, —$Y^3$—$(CH_2)_w$, wherein each w is independently 0-5: and each $X^3$ is independently a bond, —$C(R^{110})_2$—, —$C(R^{110})_2C(R^{110})_2$—, —$C(R^{110})$=$C(R^{110})$—, —C≡C—, —CO—, —CS—, —$CONR^{100}$—, —$C(=N)(R^{100})$—, —$C(=N-OR^{110})$—, —$C[=N-N(R^{110})_2]$, —$CO_2$—, —$SO_2$—, or —$SO_2N(R^{110})$—; and
$Y^3$ is —O—, —S—, —$NR^{70}$—, —$N(R^{100})CO$—, —$N(R^{110})CO2$-, —OCO—, —$OC(=O)N(R^{100})$—, —$NR^{100}CONR^{100}$—, —$N(R^{110})SO_2$—, or —$NR^{100}CSNR^{100}$—;
or $L^{31}$ is $C_{2-6}$ alidiyl chain wherein the alidiyl chain is optionally interrupted by —$C(R^{110})_2$— —$C(R^{110})_2C(R^{110})_2$—, —$C(R^{110})$=$C(R^{110})$—, —$C(R^{110})_2O$—, —$C(R^{110})_2NR^{110}$—, —C≡C—, —O—, —S—, —$N(R^{100})CO$—, —$N(R^{100})CO_2$—, —$CON(R^{100})$—, —CO—, —$CO_2$—, —OC(=O)—, —$OC(=O)N(R^{110})$—, —$SO_2$—, —$N(R^{100})SO_2$—, or —$SO_2N(R^{100})$; and
$R^{60}$ is $C_1$-$C_6$ alkyl, $C_1$-$C_6$ halo alkyl, aryl, $C_3$-$C_8$ cycloalkyl, heteroaryl, heterocyclyl, —CN, —$C(=O)R^{110}$, —$C(=O)OR^{110}$, —$C(=O)N(R^{110})_2$, —$N(R^{110})_2$, —$SO_2R^{110}$, —$S(=O)_2N(R^{110})_2$, —C(=O)N $(R^{110})N(R^{110})_2$, or —C(=O)N($R^{11}$)(O$R^{110}$), wherein the aryl, heteroaryl, cycloalkyl, or heterocyclyl is optionally substituted with 1 to 4 $R^{60a}$, wherein each $R^{60a}$ is independently —Z, —Y'—Z, or —X—Y—Z;

each $R^C$ is independently -$L^{30}$-$R^{70}$, wherein each $L^{30}$ is independently a bond or —(CH$_2$)$_m$—$V^{10}$—(CH$_2$)$_n$—, wherein $V^{10}$ is —C($R^{110}$)$_2$—, —C($R^{110}$)$_2$C($R^{110}$)$_2$—, —C($R^{110}$)=C($R^{110}$)—, —C($R^{110}$)$_2$O—, —C($R^{110}$)$_2$N$R^{110}$—, —C≡C—, —O—, —S—, —N$R^{10}$—, —N($R^{100}$)CO—, —N($R^{100}$)CO2-, —OCO—, —CO—, —CS—, —CON$R^{100}$—, —C(=N—$R^{110}$)—, —C(=N—O$R^{110}$)—, —C[=N—N($R^{110}$)$_2$], —CO$_2$—, —OC(=O)—, —OC(=O)N($R^{100}$)—, —SO$_2$—, —N($R^{100}$)SO$_2$—, —SO$_2$N($R^{100}$)—, —N$R^{100}$CON$R^{100}$—, —N$R^{100}$CSN$R^{100}$—, C$_3$-C$_6$ cyclo alkyl, or C$_3$-C$_6$ cyclohaloalkyl; or each $L^{30}$ is independently C$_2$-C$_6$ alidiyl, wherein the alidiyl chain is optionally interrupted by —C($R^{110}$)$_2$—, —C($R^{110}$)$_2$C($R^{110}$)$_2$—, —C($R^{110}$)C($R^{110}$)—, —C($R^{110}$)$_2$O—, —C($R^{110}$)$_2$N$R^{110}$—, —C≡C—, —O—, —S—, —N($R^{100}$)CO—, —N($R^{100}$)CO$_2$—, —N$R^{110}$—, —CON($R^{100}$)—, —CO—, —CO$_2$—, —O(C=O)—, —O(C=O)N($R^{100}$)—, —SO$_2$—, —N($R^{100}$)SO$_2$—, Or —SO$_2$N($R^{100}$)—;

each $R^{70}$ is independently hydrogen, halogen, nitro, aryl, heteroaryl, heterocyclyl, —Z, —Y—Z, or —X—YZ, wherein the aryl, heteroaryl, and heterocyclyl, are each optionally substituted with 1 to 4 $R^{70a}$, wherein each $R^{70a}$ is independently aryloxy, aralkyloxy, aryloxyalkyl, arylC$_o$-C$_6$alkylcarboxy, C($R^{110}$)=C($R^{110}$)COOH, oxo, —Z, —Y'—Z, or —X—Y—Z, wherein each $R^{70a}$ is optionally substituted with 1 to 4 $R^{80}$, and wherein each $R^{80}$ is independently halogen, C$_1$-C$_6$ alkyl, C$_1$-C$_6$ alkoxy, C$_1$-C$_8$haloalkyl, C$_1$-C$_8$ haloalkyl(O$R^{110}$), C$_0$-C$_6$ alkylO$R^{110}$, C$_0$-C$_6$ alkylCON($R^{110}$)$_2$, C$_0$-C$_6$ alkylCO$R^{110}$, C$_0$-C$_6$ alkylCOO$R^{110}$, or C$_0$-C$_6$ alkylSO$_2R^{110}$;

each $R^{100}$ is independently —$R^{110}$, —C(=O)$R^{110}$, —CO$_2R^{110}$, or —SO$_2R^{110}$;

each $R^{110}$ is independently -hydrogen, —C$_1$-C$_6$ alkyl, C$_2$-C$_6$ alkenyl, C$_1$-C$_6$ alkynyl, —C$_1$-C$_6$ haloalkyl, or —N($R^{12}$)$_2$, wherein any of $R^{110}$ is optionally substituted with 1 to 4 radicals of $R^{120}$;

each $R^{120}$ is independently halogen, cyano, nitro, oxo, —B(O$R^{130}$), C$_0$-C$_6$ alkylN($R^{13}$)$_2$, C$_1$-C$_6$haloalkyl, C$_1$-C$_6$ alkyl, C$_1$-C$_6$ alkoxy, (C$_0$-C$_6$ alkyl)C=O(O$R^{130}$), C$_0$-C$_6$ alkylO$R^{130}$, C$_0$-C$_6$ alkylCO$R^{130}$, C$_0$-C$_6$alkylSO$_2R^{130}$, C$_0$-C$_6$alkylCON($R^{13}$)$_2$, C$_0$-C$_6$alkylCON$R^{130}$O$R^{130}$, C$_0$-C$_6$alkylSO$_2$N($R^{130}$)$_2$, C$_0$-C$_6$alkylS$R^{130}$, C$_0$-C$_6$ haloalkylO$R^{130}$, C$_0$-C$_6$alkylCN, —C$_0$-C$_6$alkyN($R^{13}$)$_2$, —N$R^{13}$SO$_2R^{13}$, or —OC$_{0-6}$ alkylCOO$R^{130}$;

each $R^{130}$ is independently hydrogen, C$_1$-C$_6$ alkyl, C$_2$-C$_6$ alkenyl, or C$_2$-C$_6$ alkynyl;

each $R^{140}$ is independently C$_1$-C$_6$ alkyl, C$_1$-C$_6$ alkoxy, halogen, C$_1$-C$_6$ haloalkyl, C$_0$-C$_6$ alkylCON($R^{110}$)$_o$, C$_0$-C$_6$ alkylCON$R^{110}R^{10}$, C$_0$-C$_6$ alkylO$R^{110}$, or C$_0$-C$_6$ alkylCOO$R^{110}$; and each $R^{150}$ is independently hydrogen, halogen, O$R^{130}$, (C$_1$-C$_6$)alkyl or (C$_1$-C$_6$)haloalkyl, wherein each alkyl is optionally substituted with at least one group which are each independently halogen, cyano, nitro, azido, O$R^{130}$, C(O)$R^{130}$, C(O)O$R^{13}$C(O)N($R^{130}$)$_2$, N($R^{130}$)$_2$, N($R^{130}$)C(O)$R^{130}$, N($R^{130}$)S(O)$_2R^{13}$, —OC(O)O$R^{130}$, OC(O)N($R^{130}$)$_2$, N($R^{130}$)C(O)O$R^{130}$, N($R^{130}$)C(O)N($R^{130}$), S$R^{130}$, S(O)$R^{130}$, S(O)$_2$R', or S(O)$_2$N($R^{130}$)$_2$; or two $R^{150}$ (bonded to same or different atoms) can be taken together to form a C$_3$-C$_6$ cycloalkyl;

each X is independently —O—, —S—, or —N($R^{100}$)—;

each Y is independently —[C($R^{150}$)$_2$]$_p$—, or —C$_2$-C$_6$ alkenyl, wherein p is 1, 2, 3, 4, 5, or 6;

each Y' is independently —[C($R^{150}$)$_2$]$_p$—, —C$_2$-C$_6$ alkenyl C$_3$-C$_8$ cycloalkyl, or heterocyclyl, wherein the cycloalkyl or heterocyclyl is optionally substituted with 1 to 3 Z groups;

each Z is independently —H, halogen, —O$R^{110}$, —S$R^{110}$, —C(=O)$R^{110}$, —C(=O)O$R^{110}$, —C(=O)N($R^{110}$)$_2$, —N($R^{100}$)$_2$, —N$_3$, —NO$_2$, —C(=N—OH)$R^{110}$, —C(=S)N($R^{110}$)$_2$, —CN, —S(=O)$R^{110}$, —S(=O)N($R^{110}$)$_2$, —S(=O)O$R^{110}$, —S(=O)$_2R^{110}$, S(=O)$_2$N($R^{110}$)$_2$, —N$R^{110}$CO$R^{110}$, —N($R^{110}$)C(=O)N($R^{110}$)$_2$, —N($R^{110}$)COO$R^{110}$, —N($R^{110}$)S(=O)$_2R^{110}$, —C(=O)N($R^{110}$)N($R^{110}$)$_2$, —C(=O)N($R^{110}$)(O$R^{110}$), —OC(=O)—$R^{110}$, —OC(=O)—O$R^{110}$, or —OC(=O)—N($R^{110}$)$_2$; and each m and n is independently 0, 1,2,3,4,5, or 6.

In some embodiments the compound of Formula V has a structure of Formula VI or VII:

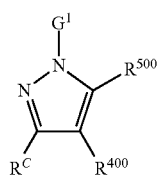

Formula VI

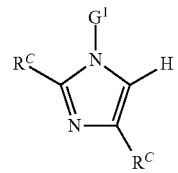

Formula VII

In other embodiments the compound of Formula VII has a structure of Formula VIII:

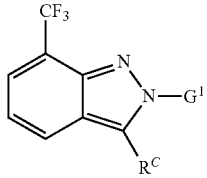

Formula VIII

In yet other embodiments the compound of Formula VI has a structure of Formula IX:

Formula IX
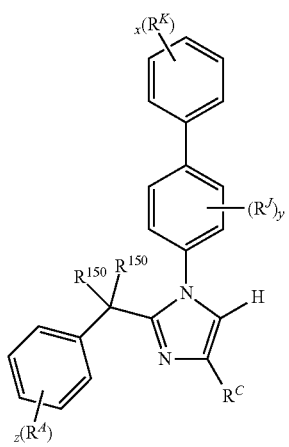
In still further embodiments the compound of Formula VI has a structure of Formula X:
Formula X
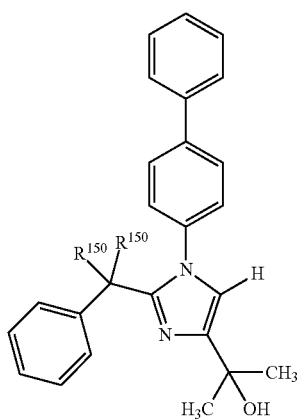
Accordingly, the compounds of Formula V which can be useful in the methods of the invention include, but are not limited to, compounds having the structures are shown below, and pharmaceutically acceptable salts thereof:
683
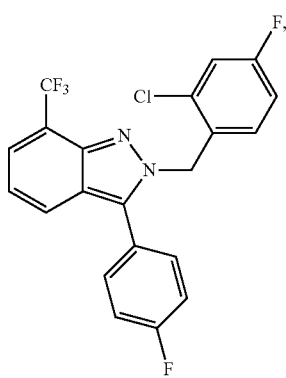
-continued
684
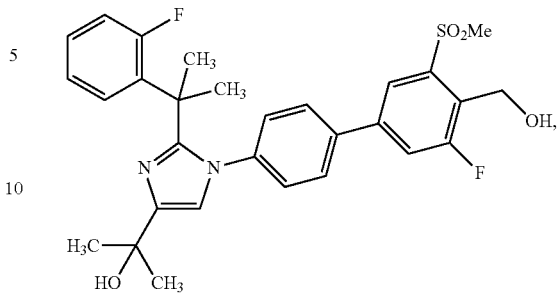
685
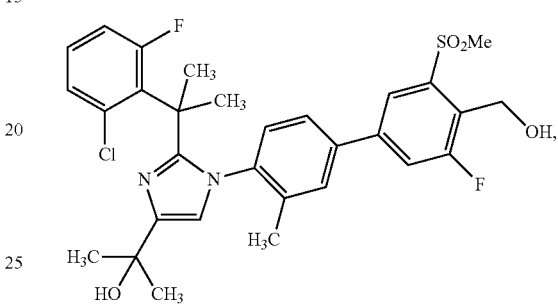
686
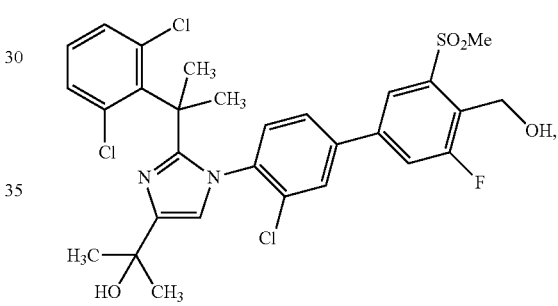
687
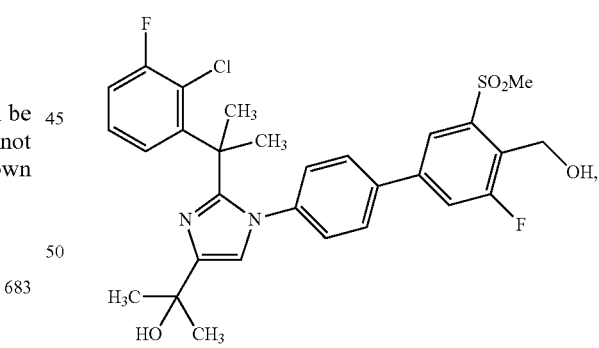
688
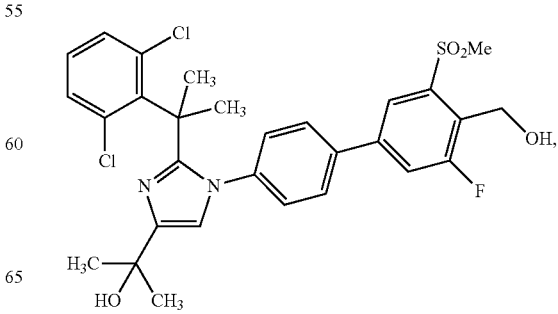

689
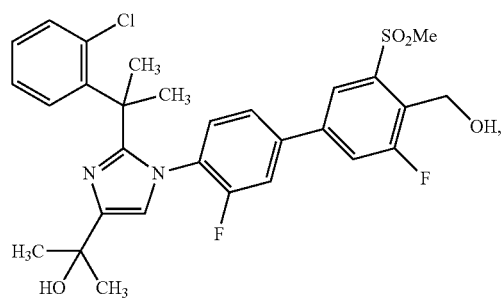
690
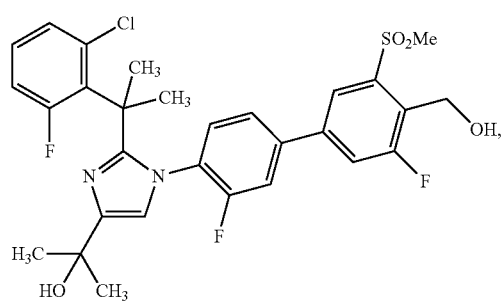
691
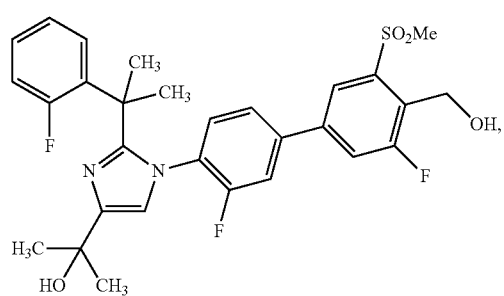
692
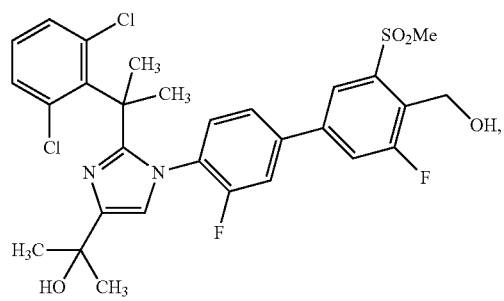
693
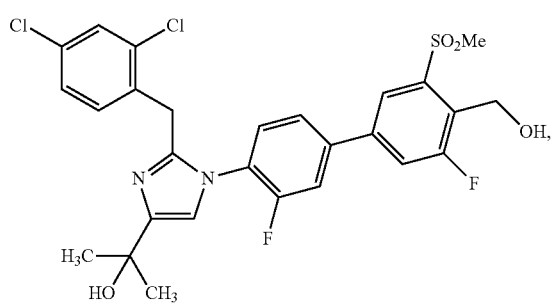
694
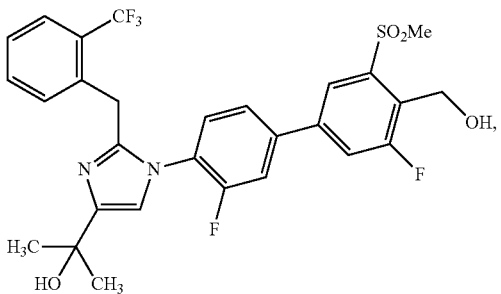
695
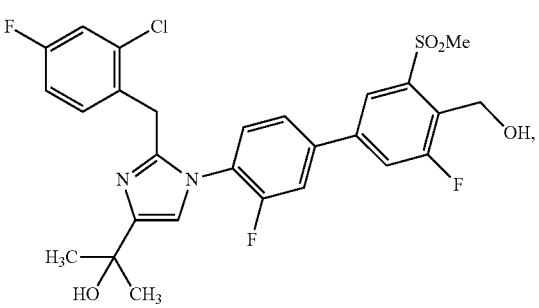
696
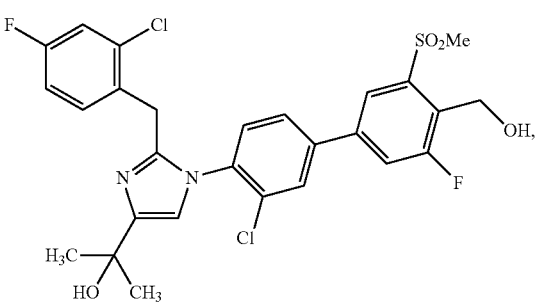
697
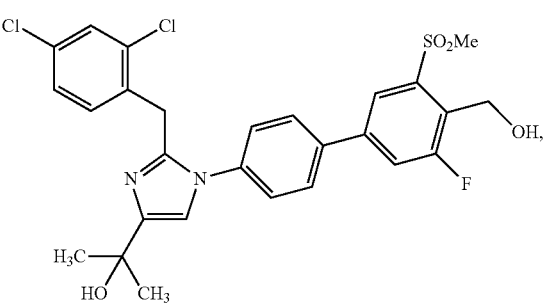
698
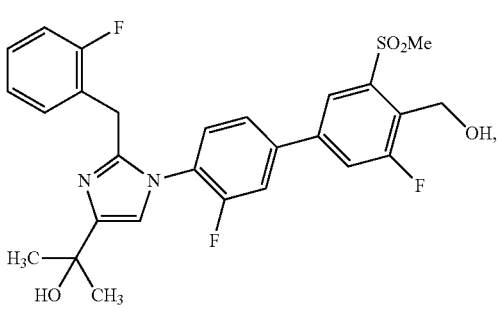

-continued

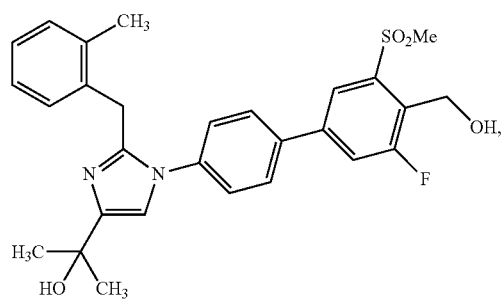
699

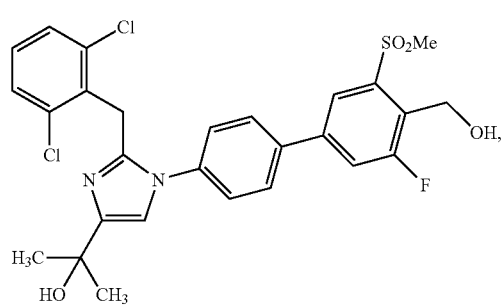
700

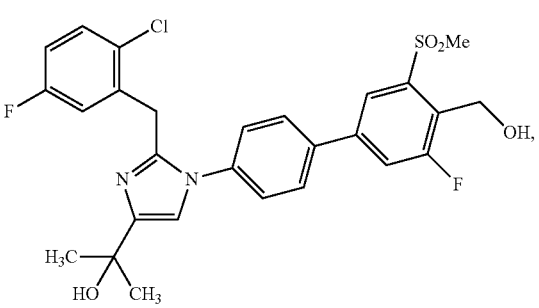
701

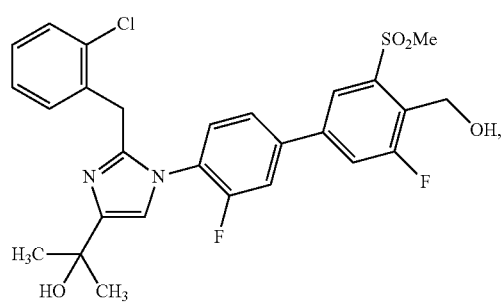
702

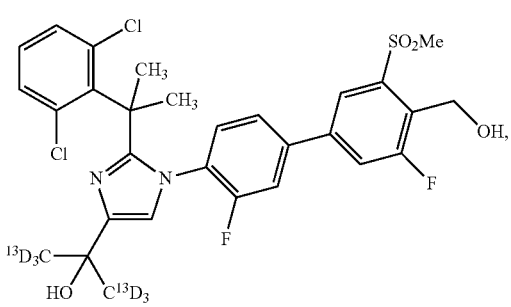
703

-continued

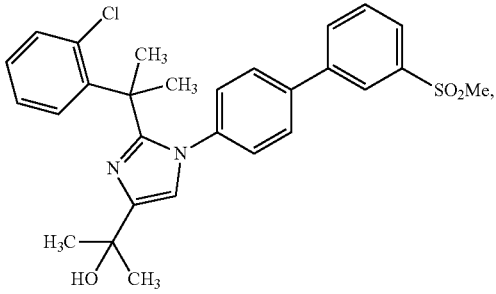
718

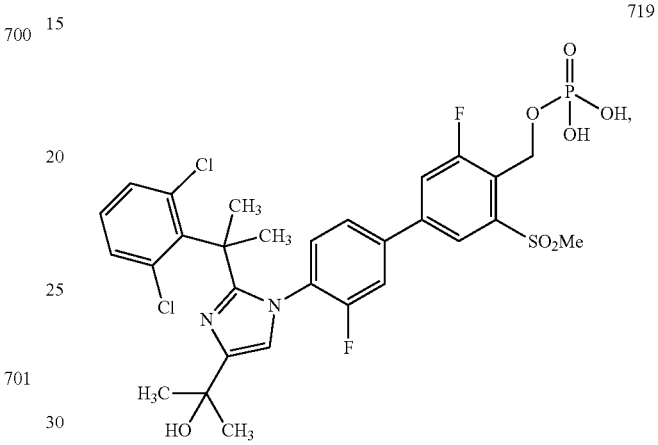
719 and or selected from the list comprising:

713 2-(1-(3 chloro-3'-fluoro-4'-(hydroxymethyl)-5'-(methylsulfonyl)biphenyl-4-yl)-2-(2-(2,6dichlorophenyl)propan-2-yl)-1H-imidazol-4-yl)propan-2-ol; 714 2-(2-(2(2-chloro-3-fluorophenyl)propan-2-yl)-1-(3'-fluoro-4'-(hydroxymethyl)-5'(methylsulfonyl)biphenyl-4-yl)-1H-imidazol-4-yl)propan-2-ol; 715 2-(2-(2(2,6-dichlorophenyl)propan-2-yl)-1-(3'-fluoro-4'-(hydroxymethyl)-5' (methylsulfonyl)biphenyl-4-yl)-1H-imidazol-4-yl)propan-2-ol; 716 2-(2-(2(2,6-dichlorophenyl)propan-2-yl)-1-(3,3'-difluoro-4'-(hydroxymethyl)-5'(methylsulfonyl)biphenyl-4-yl)-1H-imidazol-4-yl)propan-2-ol; and 717 2-(2-[1 (2,6-dichlorophenyl)ethyl]-1-[3,3'-difluoro-4'-(hydroxymethyl)-5'(methylsulfonyl)biphenyl-4-yl]-1H-imidazol-4-yl)propan-2-ol. Compound 692 is also known as WO2010 0138598 Ex. 9. Compound 718 is also known WO2007 002563 Ex. 19. Compound 719 is also known as WO2012 0135082.

Compounds of Formula V can be synthesized as described in PCT publication No. US2010/0069367 and WO2010/138598 incorporated herein by reference.

The LXR agonist that can be used for the treatment and/or prevention of metastasis can be compound 704, or a pharmaceutically acceptable salt thereof.

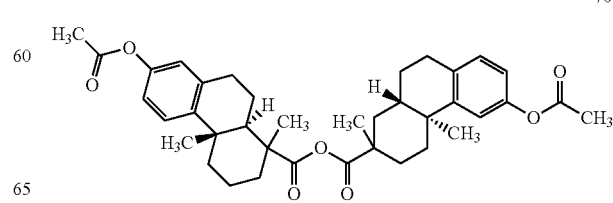
704

In further embodiments compounds that can be used for the treatment and/or prevention of metastasis can be found in the PCT publications in the list consisting of: WO2006/094034, WO2008/049047, WO2009/020683, WO2009/086138, WO2009/086123, WO2009/086130, WO2009/086129, WO2007/002559, WO2007/002563, WO2007/081335, WO2006/017055, WO2006/102067, WO2009/024550, US2006/0074115, US2006/0135601, WO2009/021868, WO2009/040289, WO2007/047991, WO2007/050425, WO2006/073363, WO2006/073364, WO2006/073365, WO2006/073366, WO2006/073367, US2009/0030082, WO2008/065754, JP2008/179562, WO2007/092065, US2010/0069367, U.S. Pat. Nos. 7,998,995, 7,247,748, WO2010/138598, U.S. Pat. Nos. 7,365,085, 75,776, 215, U.S. 63/136,503, US2004/0072868, US2005/0107444, US2005/0113580, US2005/0131014, US2005/0282908, US2009/0286780, incorporated herein by reference.

In some embodiments of any of the foregoing methods, the LXR agonist is a compound of Formula XI:

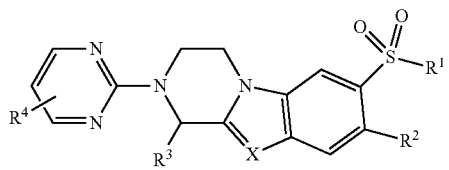

Formula XI or a pharmaceutically acceptable salt thereof;

X is N or $CR^c$;

$R^1$ is alkyl or $-NR^aR^b$b $R^2$ is H; halogen; —CN; —NRC(O)R; —C(O)OR; —C(O)$NR^aR^b$; monocyclic heteroaromatic optionally substituted with one or more groups selected from alkyl, —CN, —NRC(O)R, —C(O)OR, —C(O)$NR^aR^b$ and halogen; monocyclic non-aromatic heterocycle optionally substituted with one or more groups selected from alkyl, halogen, —CN and =O; or alkyl optionally substituted by one or more groups selected from halogen, hydroxyl, alkoxy, —$NR^aR^b$, —NRC(O)R, —NRC(O)O(alkyl), —NRC(O)N(R)$_2$, —C(O)OR, thiol, alkylthiol, nitro, —CN, =O, —OC(O)H, —OC(O)(alkyl), —OC(O)O(alkyl), —OC(O)N(R)$_2$, and —C(O)$NR^aR$;

$R^3$ is alkyl, haloalkyl, hydroxyalkyl, alkoxyalkyl, cycloalkyl, monocyclic nonaromatic heterocycle, monocyclic heteroaromatic or phenyl, wherein the phenyl, monocyclic non-aromatic heterocycle and monocyclic heteroaromatic group represented by $R^3$ are optionally substituted with one or more groups selected from alkyl, halogen, haloalkyl, alkoxy, haloalkoxy, nitro and —CN;

$R^4$ is halogen, —CN, —OR, —SR, —N(R)$_2$, —C(O)R, —C(O)OR, —OC(O)O(alkyl), —C(O)O(haloalkyl)-OC(O)R, —C(O)N(R)$_2$, —OC(O)N(R)$_2$, —NRC(O)R, —NRC(O)O(alkyl), —S(O)R—SO$_2$R, —SO$_2$N(R)$_2$, —NRS(O)R, —NRSO$_2$R, —NRC(O)N(R)$_2$, —NRSO$_2$N(R)$_2$, haloalkyl, haloalkoxy, cycloalkoxy, cycloalkyl, monocyclic non-aromatic heterocycle, monocyclic heteroaromatic or alkyl, wherein the monocyclic non-aromatic heterocycle, monocyclic heteroaromatic and alkyl group represented by $R^4$ are optionally substituted with one or more groups selected from —CN, —OR, —SR, —N(R)$_2$, =O, —C(O)R, —C(O)OR, —C(O)O(haloalkyl), —OC(O)R, —OC(O)O(alkyl), —C(O)N(R)$_2$, —OC(O)N(R)$_2$, —NRC(O)R, —NRC(O)O (alkyl), —S(O)R, —SO$_2$R, —SO$_2$N(R)$_2$, —NRS(O)R, —NRSO$_2$R, —NRC(O)N(R)$_2$ and —NRSO$_2$N(R)$_2$;

each R is, independently, H or alkyl;

$R^a$ and $R^b$ are, independently, H, alkyl or $R^a$ and $R^b$ can be taken together with the nitrogen to which they are attached to form a monocyclic non-aromatic heterocycle; and $R^c$ is H, alkyl, or halogen.

In some embodiments, the compound of Formula XI has the structure of any one of Formulae XII-XVI:

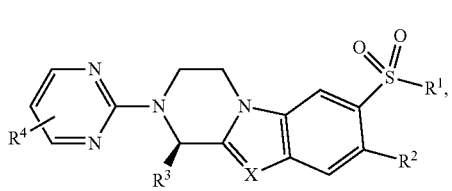

Formula XII

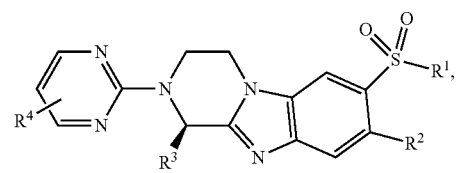

Formula XIII

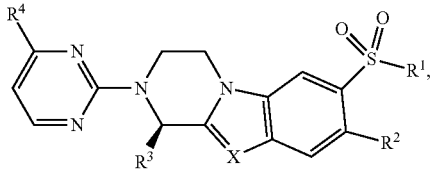

Formula XIV

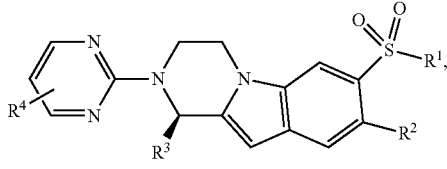

Formula XV

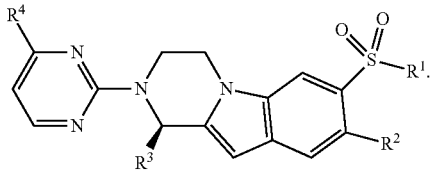

Formula XVI

In some embodiments of the compounds of Formula XI-XVI, $R^3$ is alkyl, haloalkyl, hydroxyalkyl, alkoxyalkyl, cycloalkyl or phenyl, wherein the phenyl represented by $R^3$ is optionally substituted with one or more groups selected from alkyl, halogen, haloalkyl, alkoxy, haloalkoxy, nitro and —CN; and $R^4$ is halogen, —CN, —OR, SR, —N(R)$_2$, —C(O)R, —C(O)OR, —OC(O)O(alkyl), —C(O)O(haloalkyl), —OC(O)R, —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$, —NRSO$_2$N(R)$_2$, haloalkyl, haloalkoxy, cycloalkoxy, cycloalkyl, or alkyl, wherein the alkyl group represented by $R^4$ is optionally substituted with one or more groups selected from —CN, —OR, —SR, —N(R)$_2$, =O, —C(O)R, —C(O)OR, —C(O)O(haloalkyl), —OC(O)R, —OC(O)O(alkyl), —C(O)N(R)₂, —OC(O)N(R)₂, —NRC(O)R, —NRC(O)O(alkyl), S(O)R, —SO₂R, —SO₂N(R)₂, —NRS(O)R, —NRSO₂R, —NRC(O)N(R)₂, and —NRSO₂N(R)₂.

In other embodiments of the compounds of Formula XI-XVI, $R^1$ is methyl or —NH₂; $R^2$ is H or methyl, wherein the methyl group represented by $R^2$ is optionally substituted with one or more groups selected from halogen hydroxyl, alkoxy, —NR$^a$R$^b$, —NRC(O)R, —NRC(O)O(alkyl), —NRC(O)N(R)₂, —C(O)OR, thiol, alkylthiol, nitro, —CN, =O, —OC(O)H, —OC(O)(alkyl), —OC(O)O(alkyl), —C(O)NR$^a$R$^b$, and —OC(O)N(R)₂, preferably, $R^2$ is H or —CH₂OH; $R^3$ is methyl, ethyl, propyl, isopropyl, tert-butyl, sec-butyl, iso-butyl, —CH₂CF₃, —CH(CH₂F)₂, —CH(CHF₂)₂, —CH(CF₃)₂, —CF(CH₃)₂, —CF₃, cyclopropyl, cyclobutyl, cyclopentyl, cyclohexyl, —C(OH)(CH₃)₂, —CH(OH)(CH₃), or phenyl, wherein the phenyl group represented by $R^3$ is optionally substituted with one or more groups selected from alkyl, halogen, haloalkyl, alkoxy, haloalkoxy, nitro, and —CN; and $R^c$, where present, is H.

In certain embodiments of the compounds of Formula XI-XVI, $R^1$ is methyl; $R^2$ is —CH₂OH; and $R^3$ is isopropyl.

In some embodiments of the compounds of Formula XI-XVI, $R^4$ is halogen, hydroxy, alkyl, cycloalkyl, cycloalkoxy, alkoxy, haloalkoxy, haloalkyl, —N(R)₂, —C(O)OH, —C(O)O(alkyl), —C(O)O(haloalkyl), —C(O)(alkyl), —C(O)N(R)₂, —NRC(O)R, —SO₂N(R)₂, —OC(O)N(R)₂, —CN, hydroxyalkyl, or dihydroxyalkyl.

In other embodiments of the compounds of Formula I-VI, $R^4$ is alkyl, haloalkyl, cycloalkyl, alkoxy, or haloalkoxy.

In certain embodiments of the compounds of Formula XI-XVI, $R^4$ is methyl, ethyl, hydroxy, —CF₃, isopropyl, cyclopropyl, —CH₂OH, —CH(OH)(CH₂)(OH), —C(OH)(CH₃)₂, —CH(OH)(CH₃), —CH(OH)(CH₂)(CH₃), —CH(OH)(CH₂)₂(CH₃), —C(O)NH₂, —C(O)N(CH₃)₂, —C(O)OH, —C(O)NH(CH₃), —C(O)CH₃, —C(O)CH₂CH₃, —C(O)O(CH₂)(CH₃), —C(O)O(tert-butyl), —C(O)O(C)(CH₃)₂(CF₃), —NHC(O)CH₃, —OCHF₂, —OCF₃, —OCH₂CH₃, —OCH(CH₃)₂, or —OCH₃, preferably, $R^5$ is —C(CH₃)₂OH.

In some embodiments of the compounds of Formula XI-XVI, $R^4$ is methyl, halogenated methyl, cyclopropyl, —OCHF₂, or —OCH₃, preferably, $R^4$ is CF₃.

In other embodiments of any of the foregoing methods, the LXR agonist is any one of compounds 720-726:

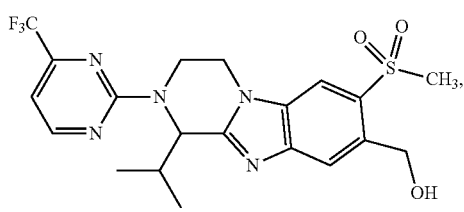
720

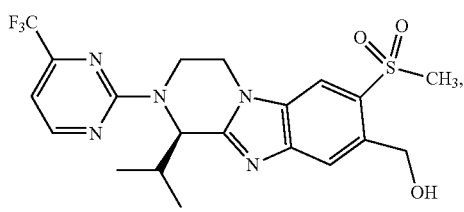
721

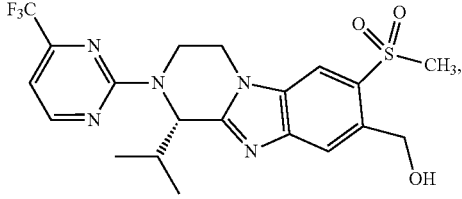
722

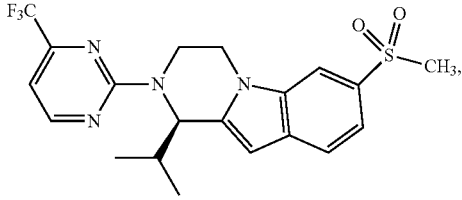
723

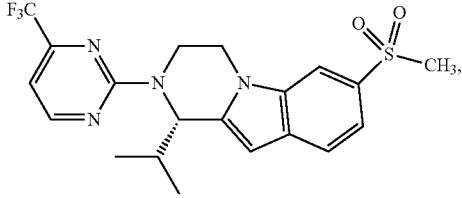
724

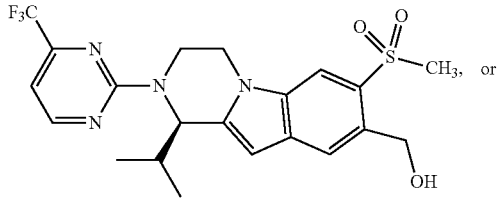
725, or

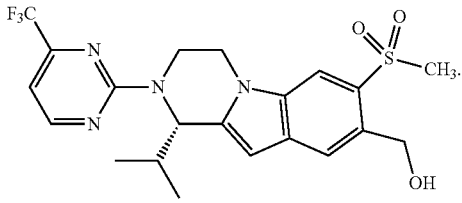
726

Compounds of Formula XI-XVI may be synthesized by methods known in the art, e.g., those described in International Patent Publication No. WO2013/138565. In some embodiments, the LXR agonist is a compound disclosed in U.S. Publication No. 2015/0246924, U.S. Publication No. 2015/0051214, U.S. Publication No. 2015/0065515, U.S. Publication No. 2015/0080406, or U.S. Publication No. 2015/033693, the compounds of which are herein incorporated by reference.

In some embodiments of any of the foregoing methods, the LXR agonist is a compound of Formula XVII:

Formula XVII

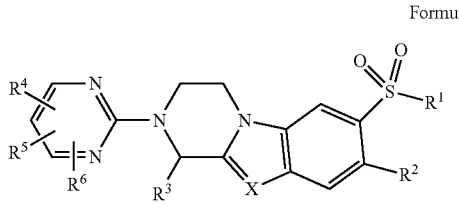

or a pharmaceutically acceptable salt thereof;

X is N or CRC;

$R^1$ is alkyl or —$NR^aR^b$ $R^2$ is H; halogen; —CN; —NRC(O)R; —C(O)OR; —C(O)$NR^aR^b$; monocyclic heteroaromatic optionally substituted with one or more groups selected from alkyl, —CN, —NRC(O)R, —C(O)OR, —C(O)$NR^aR^b$, and halogen; monocyclic non-aromatic heterocycle optionally substituted with one or more groups selected from alkyl, halogen, —CN, and =O; or alkyl optionally substituted by one or more groups selected from halogen, hydroxy, alkoxy, —$NR^aR^b$, —NRC(O)R, —NRC(O)O(alkyl), —NRC(O)N$(R)_2$, —C(O)OR, thiol, alkylthiol, nitro, CN, =O, —OC(O)H, —OC(O)(alkyl), —OC(O)O(alkyl), —OC(O)N$(R)_2$, and —C(O)$NR^aR^b$;

$R^3$ is alkyl, haloalkyl, hydroxyalkyl, alkoxyalkyl, cycloalkyl, monocyclic nonaromatic heterocycle, monocyclic heteroaromatic, or phenyl, wherein the phenyl, monocyclic non-aromatic heterocycle and monocyclic heteroaromatic group represented by $R^3$ are optionally substituted with one or more groups selected from alkyl, halogen, haloalkyl, alkoxy, haloalkoxy, nitro, and —CN;

$R^4$ and $R^5$ are, independently, is halogen, —CN, —OR, —SR, —N$(R)_2$, —C(O)R, —C(O)OR, —OC(O)O(alkyl), —C(O)O(haloalkyl), —OC(O)R, —C(O)N$(R)_2$, —OC(O)N$(R)_2$, —NRC(O)R, —NRC(O)O(alkyl), —S(O)R, —SO$_2$R, —SO$_2$N$(R)_2$, —NRS(O)R, —NRSO$_2$R, —NRC(O)N$(R)_2$, —NRSO$_2$N$(R)_2$, haloalkyl, haloalkoxy, cycloalkoxy, cycloalkyl, monocyclic non-aromatic heterocycle, monocyclic heteroaromatic, or alkyl, wherein the alkyl, monocyclic non-aromatic heterocycle, and monocyclic heteroaromatic group represented by $R^4$ or $R^5$ are optionally substituted with one or more groups selected from —CN, —OR, —SR, —N$(R)_2$, =O, —C(O)R, —C(O)OR, —C(O)O(haloalkyl), —OC(O)R, —OC(O)O(alkyl), —C(O)N$(R)_2$, —OC(O)N$(R)_2$, —NRC(O)R, —NRC(O)O(alkyl), —S(O)R, —SO$_2$R, —SO$_2$N$(R)_2$, —NRS(O)R, —NRSO$_2$R, —NRC(O)N$(R)_2$, and —NRSO$_2$N$(R)_2$;

$R^6$ is H, halogen, —CN, —OR, —SR, —N$(R)_2$, —C(O)R, —C(O)OR, —OC(O)O(alkyl), —C(O)O(haloalkyl), —OC(O)R, —C(O)N$(R)_2$, —OC(O)N$(R)_2$, —NRC(O)R, —NRC(O)O(alkyl), —S(O)R, —SO$_2$R, —SO$_2$N$(R)_2$, —NRS(O)R, —NRSO$_2$R, —NRC(O)N$(R)_2$, —NRSO$_2$N$(R)_2$, haloalkyl, haloalkoxy, cycloalkoxy, cycloalkyl, or alkyl, wherein the alkyl group represented by $R^6$ is optionally substituted with one or more groups selected from —CN, —OR, —SR, —N$(R)_2$, =O, —C(O)R, —C(O)OR, —C(O)O(haloalkyl), —OC(O)R, —OC(O)O(alkyl), —C(O)N$(R)_2$, —OC(O)N$(R)_2$, —NRC(O)R, —NRC(O)O(alkyl), —S(O)R, —SO$_2$R, —SO$_2$N$(R)_2$, —NRS(O)R, —NRSO$_2$R, —NRC(O)N$(R)_2$, and —NRSO$_2$N$(R)_2$; or $R^5$ and $R^6$, taken together with the carbon atoms to which they are bonded, form a moncyclic non-aromatic heterocycle optionally substituted with one or more groups selected from alkyl, halogen, hydroxyalkyl, alkoxyalkyl, haloalkyl, and =O;

each R is, independently, H or alkyl;

$R^a$ and $R^b$ are, independently, H, alkyl, or $R^a$ and $R^b$ can be taken together with the nitrogen to which they are attached to form a monocyclic non-aromatic heterocycle; and $R^c$ is H, alkyl, or halogen.

In some embodiments, the compound of Formula XVII has the structure of Formula XVIII-XXIII:

Formula XVIII

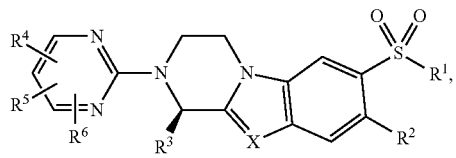

Formula XIX

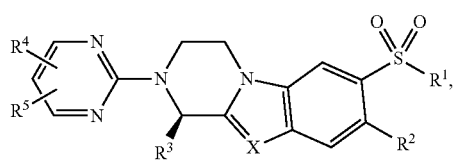

Formula XX

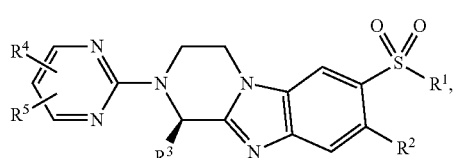

Formula XXI

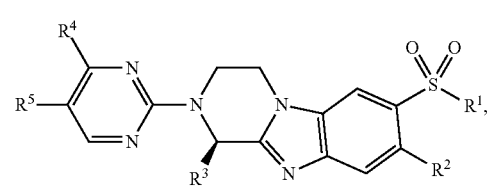

Formula XXII

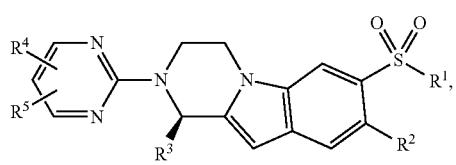

Formula XXIII

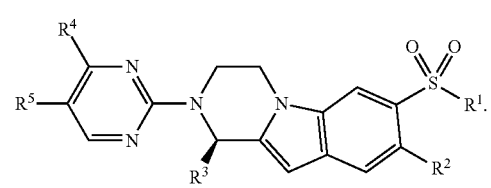

In some embodiments of the compounds of Formula XVII-XXIII, $R^3$ is alkyl, haloalkyl, hydroxyalkyl, alkoxyalkyl, cycloalkyl, or phenyl, wherein the phenyl group represented by $R^3$ is optionally substituted with one or more groups selected from alkyl, halogen, halo alkyl, alkoxy, haloalkoxy, nitro, and —CN; $R^4$ and $R^5$ independently are halogen, —CN, —OR, —SR, —N$(R)_2$, —C(O)R, —C(O)

OR, —OC(O)O(alkyl), —C(O)O(haloalkyl), —OC(O)R, —C(O)N(R)₂, —OC(O)N(R)₂, —NRC(O)R, —NRC(O)O(alkyl), —S(O)R, —SO₂R, —SO₂N(R)₂, —NRS(O)R, —NRSO₂R, —NRC(O)N(R)₂, —NRSO₂N(R)₂, haloalkyl, haloalkoxy, cycloalkoxy, cycloalkyl, or alkyl, wherein the alkyl represented by R⁴ or R⁵ is optionally substituted with one or more groups selected from —CN, —OR, —SR, —N(R)₂, =O, —C(O)R, —C(O)OR, —C(O)O(haloalkyl), —OC(O)R, —OC(O)O(alkyl), —C(O)N(R)₂, —OC(O)N(R)₂, —NRC(O)R, —NRC(O)O(alkyl), —S(O)R, —SO₂R, —SO₂N(R)₂, —NRS(O)R, —NRSO₂R, —NRC(O)N(R)₂, and —NRSO₂N(R)₂; R⁶ is H, halogen, —CN, —OR, —SR, —N(R)₂, —C(O)R, —C(O)OR, —OC(O)O(alkyl), —C(O)O(haloalkyl), —OC(O)R, —C(O)N(R)₂, —OC(O)N(R)₂, —NRC(O)R, —NRC(O)O(alkyl), —S(O)R, —SO₂R, —SO₂N(R)₂, —NRS(O)R, —NRSO₂R, —NRC(O)N(R)₂, —NRSO₂N(R)₂, haloalkyl, haloalkoxy, cycloalkoxy, cycloalkyl, or alkyl, wherein the alkyl group represented by R⁶ is optionally substituted with one or more groups selected from —CN, —OR, —SR, —N(R)₂, =O, —C(O)R, —C(O)OR, —C(O)O(haloalkyl), —OC(O)R, —OC(O)O(alkyl), —C(O)N(R)₂, —OC(O)N(R)₂, —NRC(O)R, —NRC(O)O(alkyl), —S(O)R, —SO₂R, —SO₂N(R)₂, —NRS(O)R, —NRSO₂R, —NRC(O)N(R)₂, and —NRSO₂N(R)₂.

In other embodiments of the compounds of Formula XVII-XXIII, R¹ is methyl or —NH₂; R² is H or methyl, wherein the methyl group represented by R² is optionally substituted with one or more groups selected from halogen, hydroxy, alkoxy, —NR$^a$R$^b$, —NRC(O)R, —NRC(O)O(alkyl), —NRC(O)N(R)₂, —C(O)OR, thiol, alkylthiol, nitro, —CN, =O, —OC(O)H, —OC(O)(alkyl), —OC(O)O(alkyl), —C(O)NR$^a$R$^b$, and —OC(O)N(R)₂, preferably, R² is H or —CH₂OH; R³ is methyl, ethyl, propyl, isopropyl, tert-butyl, sec-butyl, iso-butyl, —CH₂CF₃, —CH(CH₂F)₂, —CH(CHF₂)₂, —CH(CF3)₂, —CF(CH3)₂, —CF₃, cyclopropyl, cyclobutyl, cyclopentyl, cyclohexyl, —C(OH)(CH3)₂, —CH(OH)(CH₃), or phenyl, wherein the phenyl group represented by R³ is optionally substituted with one or more groups selected from alkyl, halogen, haloalkyl, alkoxy, haloalkoxy, nitro, and —CN; and R$^c$, where present, is H.

In certain embodiments of the compounds of Formula XVII-XXIII, R¹ is methyl; R₂ is —CH₂OH; and R3 is isopropyl.

In some embodiments of the compounds of Formula XVII-XXIII, R⁴ and R⁵ independently are halogen, hydroxy, alkyl, cycloalkyl, cycloalkoxy, alkoxy, haloalkoxy, haloalkyl, —N(R)₂, —C(O)OH, —C(O)O(alkyl), —C(O)O(haloalkyl), —C(O)(alkyl), —C(O)N(R)₂, —NRC(O)R, —SO₂N(R)₂, —OC(O)N(R)₂, —CN, hydroxyalkyl, or dihydroxyalkyl.

In other embodiments of the compounds of Formula XVII-XXIII, R⁴ is alkyl, halo alkyl, cycloalkyl, alkoxy, or haloalkoxy.

In certain embodiments of the compounds of Formula XVII-XXIII, R⁴ and R⁵ independently are methyl, ethyl, hydroxy, —CF3, isopropyl, cyclopropyl, —CH₂OH, —CH(OH)(CH₂)(OH), —C(OH)(CH₃)₂, —CH(OH)(CH₃), —CH(OH)(CH₂)(CH₃), —CH(OH)(CH₂)₂(CH₃), —C(O)NH₂, —C(O)N(CH₃)₂, —C(O)OH, —C(O)NH(CH₃), —C(O)CH₃, —C(O)CH₂CH₃, —C(O)O(CH₂)(CH₃), —C(O)O(tert-butyl), —C(O)O(C)(CH₃)₂(CF₃), —NHC(O)CH₃, —OCHF₂, —OCF₃, —OCH₂CH₃, —OCH(CH₃)₂, or —OCH₃, preferably, R⁴ is as just described and R⁵ is —C(OH)(CH₃)₂.

In some embodiments of the compounds of Formula XVII-XXIII, R⁴ is methyl, halogenated methyl, cyclopropyl, —OCHF₂, or —OCH₃, preferably, R⁴ is CF₃.

In other embodiments of any of the foregoing methods, the LXR agonist is any one of compounds 727-773:

727
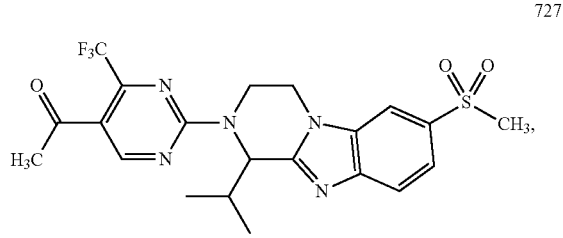

728
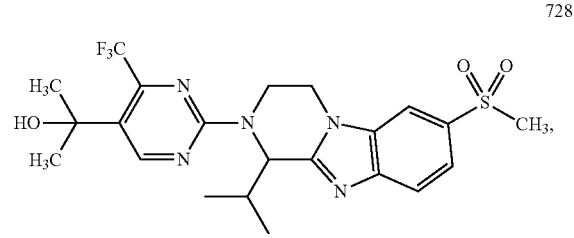

729
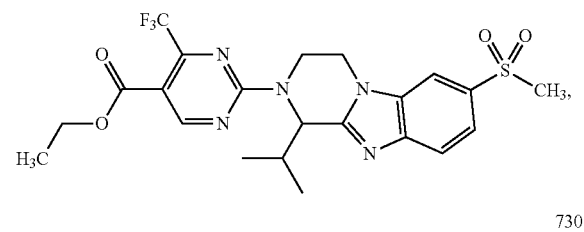

730
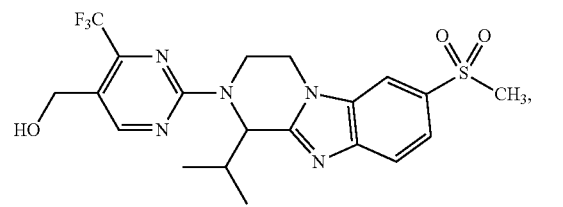

731
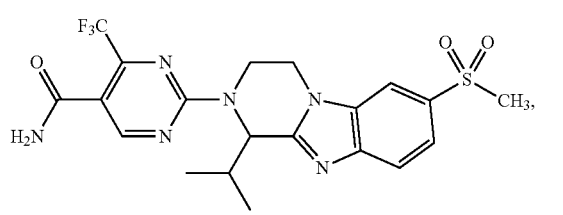

732
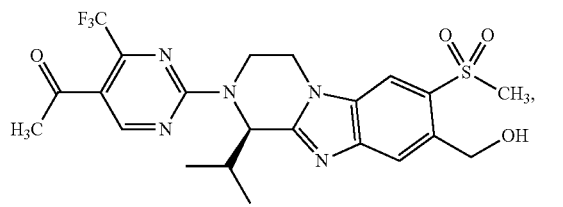

733
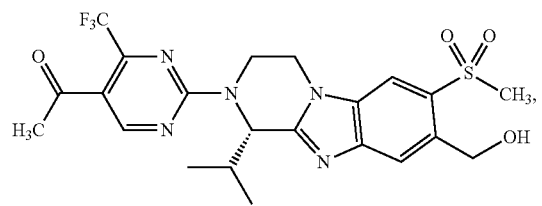
734
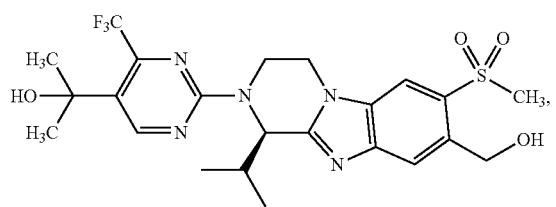
735
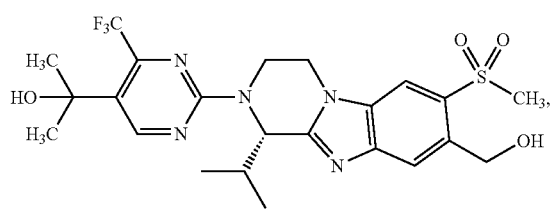
736
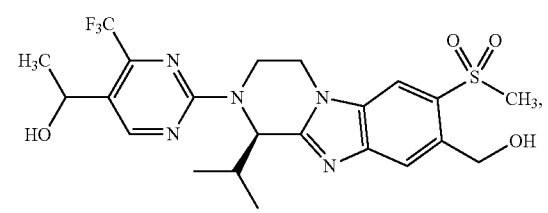
737
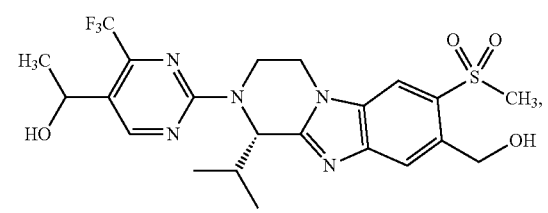
738
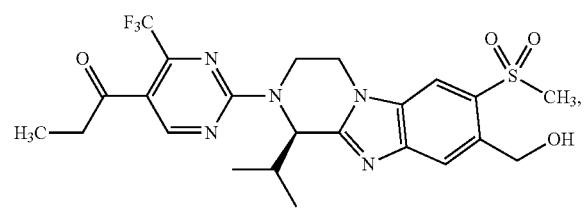
739
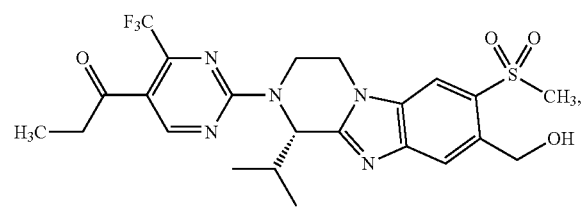
740
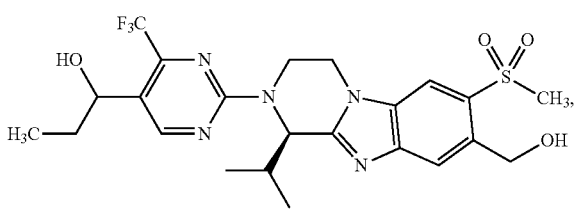
741
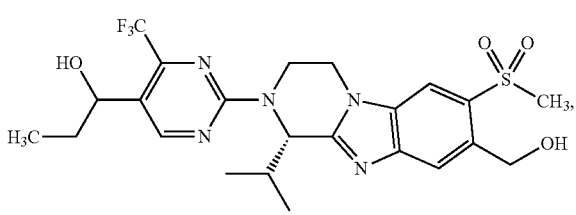
742
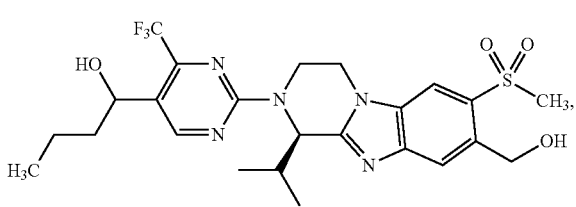
743
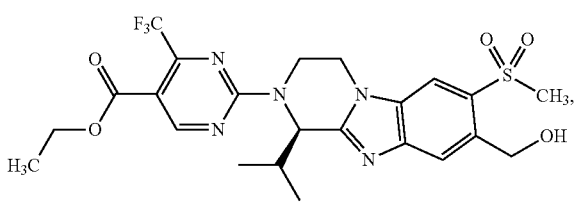
744
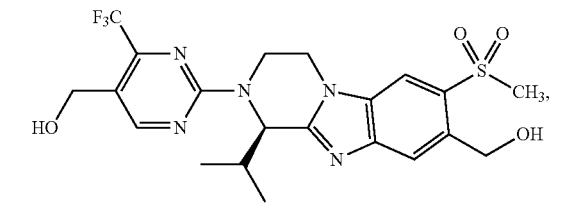
745
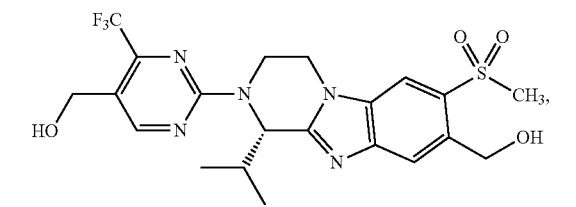
746
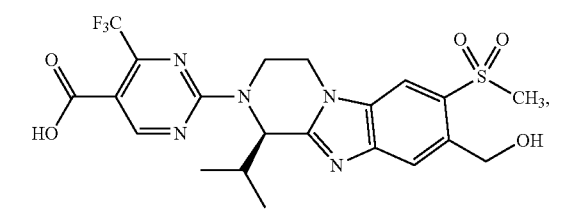

163
-continued
747
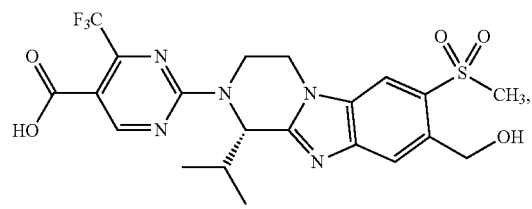
748
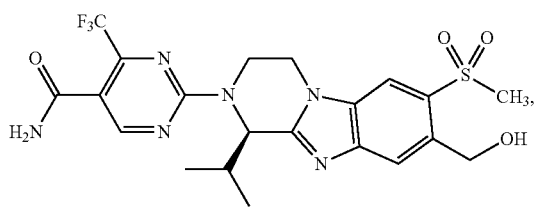
749
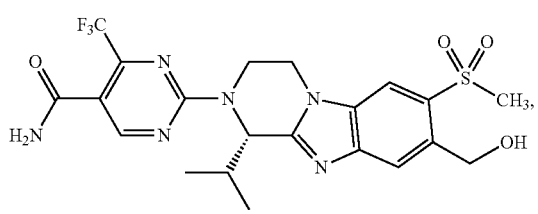
750
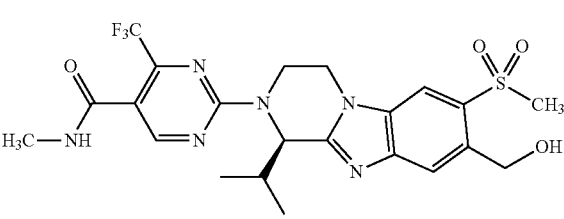
751
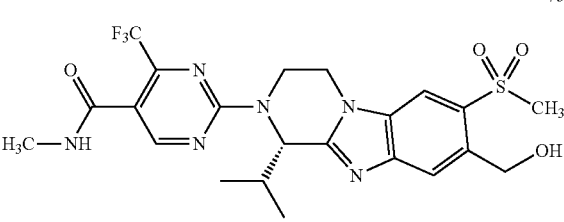
752
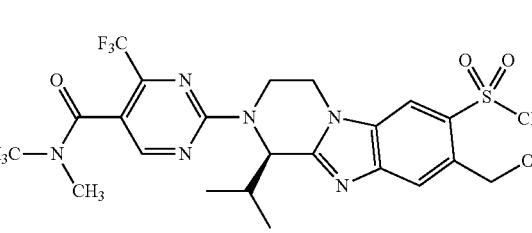
753
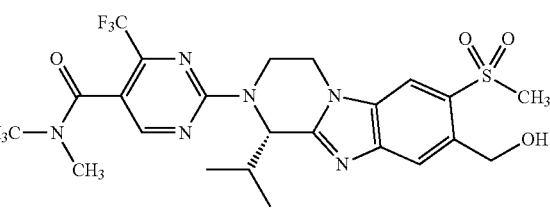
164
-continued
754
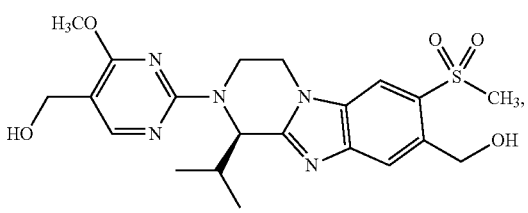
755
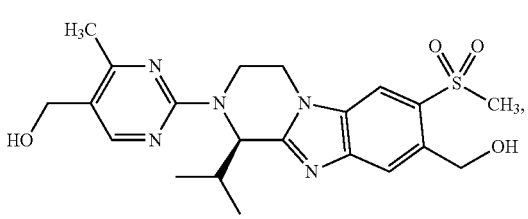
756
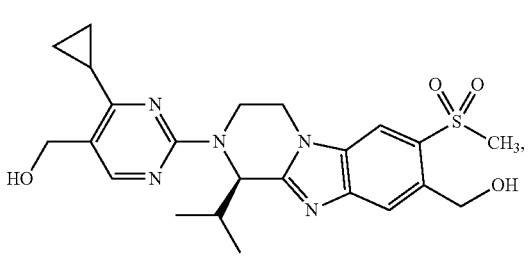
757
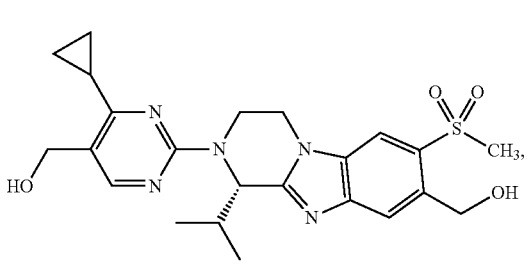
758
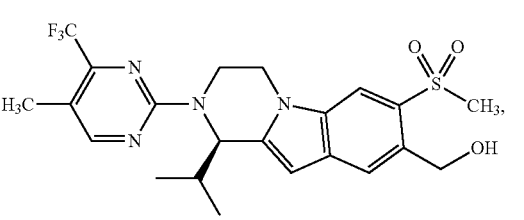
759
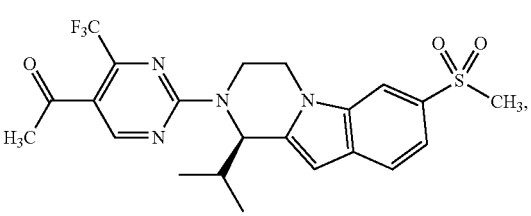

Compounds of Formula VII may be synthesized by methods known in the art, e.g., methods described in International Patent Publication No. WO2013/138568.

In certain embodiments of any of the foregoing methods, the LXR agonist is a compound of Formula XXIV:

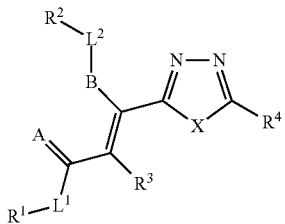

Formula XXIV or a pharmaceutically acceptable salt thereof;

wherein X is —O— or —S—;

A and B are each nitrogen, wherein A and B are bonded together to form a five-membered heteroaryl ring;

$L^1$ and $L^2$ are each independently a bond, $C_1$-$C_6$ alkyl, or $C_1$-$C_6$ heteroalkyl;

$R^1$ is hydrogen, halogen, —$CF_3$, —$OR^8$, —$N(R^8)_2$, —C(=O)$R^8$, —C(=O)O$R^8$, —C(=O)N$(R^8)_2$, —C(=NOH)$R^8$, —C(=S)N$(R^8)_2$, or —C(=O)OCH$_2$SCH$_3$;

$R^2$ is —$OR^9$, —$N(R^9)_2$, —C(=O)$R^9$, —C(=O)O$R^9$, —C(=O)N$(R^9)_2$, —$NR^{10}$C(=O)$R^9$, —C(=N—OH)$R^9$, C(=S)N$(R^9)_2$, —C(=O)OCH$_2$SCH$_3$, $C_1$-$C_6$ alkyl, $C_3$-$C_8$ cycloalkyl, $C_1$-$C_6$ haloalkyl, $C_1$-$C_6$ heteroalkyl, optionally substituted heterocycloalkyl, optionally substituted aryl, or optionally substituted heteroaryl;

$R^3$ is hydrogen, halogen, $C_1$-$C_6$ alkyl, or $C_1$-$C_6$ haloalkyl;

$R^4$ is aryl or heteroaryl; wherein aryl or heteroaryl is substituted with at least one $R^{11}$;

each $R^8$, each $R^9$, and each $R^{10}$ are each, independently, hydrogen, $C_1$-$C_6$ alkyl, $C_1$-$C_6$ heteroalkyl, $C_1$-$C_6$ alkyl-aryl, aryl, or heteroaryl; and $R^{11}$ is, independently, halogen, nitro, —$OR^{10}$, —$N(R^{10})_2$, —CN, —C(=O)$R^{10}$, —C(=O)O$R^{10}$, C(=O)N$(R^{10})_2$, —$NR^{10}$C(=O)$R^{10}$, $NR^{10}SO_2R^{10}$, —$SOR^{10}$, —$SO_2R^{10}$, —$SO_2N(R^{10})_2$, —C(=O)OCH$_2$SCH$_3$, $C_1$-$C_6$ alkyl, $C_1$-$C_6$ cycloalkyl, $C_1$-$C_6$ haloalkyl, $C_1$-$C_6$ heteroalkyl, $C_1$-$C_6$ alkyl-aryl, optionally substituted aryl, or optionally substituted heteroaryl.

In some embodiments of any of the foregoing methods, the LXR agonist is a compound of Formula XXV:

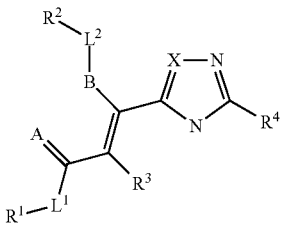

Formula XXV or a pharmaceutically acceptable salt thereof;

wherein X is —O— or —S—;

A and B are each nitrogen, wherein A and B are bonded together to form a five-membered heteroaryl ring;

$L^1$ and $L^2$ are each independently a bond, $C_1$-$C_6$ alkyl, or $C_1$-$C_6$ heteroalkyl;

$R^1$ is hydrogen, halogen, —$CF_3$, —$OR^8$, —$N(R^8)_2$, —C(=O)$R^8$, —C(=O)O$R^8$, —C(=O)N$(R^8)_2$, —C(=NOH)$R^8$, —C(=S)N$(R)_2$, or —C(=O)OCH$_2$SCH$_3$;

$R^2$ is —$OR^9$, —$N(R^9)_2$, —C(=O)$R^9$, —C(=O)O$R^9$, —C(=O)N$(R^9)_2$, —$NR^{10}$C(=O)$R^9$, C(=N—OH)$R^9$, C(=S)N$(R^9)_2$, —C(=O)OCH$_2$SCH$_3$, $C_1$-$C_6$ alkyl, $C_3$-$C_8$ cycloalkyl, $C_1$-$C_6$ haloalkyl, $C_1$-$C_6$ heteroalkyl, optionally substituted heterocycloalkyl, optionally substituted aryl, or optionally substituted heteroaryl;

$R^3$ is hydrogen, halogen, $C_1$-$C_6$ alkyl, or $C_1$-$C_6$ haloalkyl;

$R^4$ is aryl or heteroaryl; wherein aryl or heteroaryl is substituted with at least one $R^{11}$;

each $R^8$, each $R^9$, and each $R^{10}$ are each, independently, hydrogen, $C_1$-$C_6$ alkyl, C1-$C_6$ heteroalkyl, $C_1$-$C_6$ alkyl-aryl, aryl, or heteroaryl; and $R^{11}$ is, independently, halogen, nitro, —$OR^{10}$, —$N(R^{10})_2$, —CN, —C(=O)$R^{10}$, —C(=O)O$R^{10}$, C(=O)N$(R^{10})_2$, —$NR^{10}$C(=O)$R^{10}$, $NR^{10}SO_2R^{10}$, —$SOR^{10}$, —$SO_2R^{10}$, —$SO_2N(R^{10})_2$, —C(=O)OCH$_2$SCH$_3$, $C_1$-$C_6$ alkyl, $C_3$-$C_8$ cycloalkyl, $C_1$-$C_6$ haloalkyl, $C_1$-$C_6$ heteroalkyl, $C_1$-$C_6$ alkyl-aryl, optionally substituted aryl, or optionally substituted heteroaryl.

In other embodiments of any of the foregoing methods, the LXR agonist is a compound of Formula XXVI:

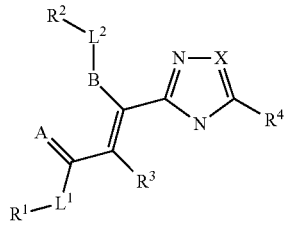

Formula XXVI or a pharmaceutically acceptable salt thereof;

wherein X is —O— or —S—;

A and B are each nitrogen, wherein A and B are bonded together to form a five-membered heteroaryl ring;

$L^1$ and $L^2$ are each independently a bond, $C_1$-$C_6$ alkyl, or $C_1$-$C_6$ heteroalkyl;

$R^1$ is hydrogen, halogen, —$CF_3$, —$OR^8$, —$N(R^8)_2$, —C(=O)$R^8$, —C(=O)O$R^8$, —C(=O)N$(R^8)_2$, —C(=NOH)$R^8$, —C(=S)N$(R^8)_2$, or —C(=O)OCH$_2$SCH$_3$;

$R^2$ is —$OR^9$, —$N(R^9)_2$, —C(=O)$R^9$, —C(=O)O$R^9$, —C(=O)N$(R^9)_2$, —$NR^{10}$C(=O)$R^9$, —C(=N—OH)$R^9$, C(=S)N$(R^9)_2$, —C(=O)OCH$_2$SCH$_3$, $C_1$-$C_6$ alkyl, $C_3$-$C_8$ cycloalkyl, $C_1$-$C_6$ haloalkyl, $C_1$-$C_6$ heteroalkyl, optionally substituted heterocycloalkyl, optionally substituted aryl, or optionally substituted heteroaryl;

$R^3$ is hydrogen, halogen, $C_1$-$C_6$ alkyl, or $C_1$-$C_6$ haloalkyl;

$R^4$ is aryl or heteroaryl; wherein aryl or heteroaryl is substituted with at least one $R^{11}$;

each $R^8$, each $R^9$, and each $R^{10}$ are each, independently, hydrogen, $C_1$-$C_6$ alkyl, $C_1$-$C_6$ heteroalkyl, $C_1$-$C_6$ alkyl-aryl, aryl, or heteroaryl; and $R^{11}$ is, independently, halogen, nitro, —$OR^{10}$, —$N(R^{10})_2$, —CN, —C(=O)$R^{10}$, —C(=O)O$R^{10}$, C(=O)N$(R^{10})_2$, —NR¹⁰C(=O)R¹⁰, NR¹⁰SO₂R¹⁰, —SOR¹⁰, —SO₂R¹⁰, —SO₂N(R¹⁰)₂, —C(=O)OCH₂SCH₃, $C_1$-$C_6$ alkyl, $C_3$-$C_8$ cycloalkyl, $C_1$-$C_6$ haloalkyl, $C_1$-$C_6$ heteroalkyl, $C_1$-$C_6$ alkyl-aryl, optionally substituted aryl, or optionally substituted heteroaryl.

In certain embodiments of any of the foregoing methods, the LXR agonist is a compound of Formula XXVII:

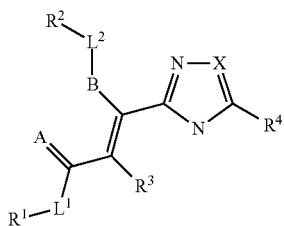

Formula XXVII or a pharmaceutically acceptable salt thereof;

wherein X is —N(R¹²)—, or —O—;

A and B are each nitrogen, wherein A and B are bonded together to form a five-membered heteroaryl ring;

L¹ is a bond, $C_1$-$C_6$ alkyl, or $C_1$-$C_6$ heteroalkyl;

L² is $C_1$-$C_6$ alkyl or C1-$C_6$ heteroalkyl;

R¹ is hydrogen, halogen, —CF₃, —OR⁸, —N(R⁸)₂, —C(=O)R⁸, —C(=O)OR⁸, —C(=O)N(R⁸)₂, —C(=NOH)R⁸, —C(=S)N(R⁸)₂, —C(=CH₂)CH₃, or —C(=O)OCH₂SCH₃;

R² is —C(=O)OR⁹, —C(=O)N(R⁹)₂, —NR¹⁰C(=O)R⁹, —C(=N—OH)R⁹, —C(=S)N(R⁹)₂, or —C(=O)OCH₂SCH₃;

R³ is hydrogen, halogen, $C_1$-$C_6$ alkyl, or $C_1$-$C_6$ haloalkyl;

R⁴ is aryl or heteroaryl; wherein aryl or heteroaryl is substituted with at least one R¹¹;

each R⁸, each R⁹, and each R¹⁰ are each, independently, hydrogen, $C_1$-$C_6$ alkyl, $C_1$-$C_6$ heteroalkyl, —$C_1$-$C_6$ alkyl-aryl, aryl, or heteroaryl;

R¹¹ is, independently, halogen, nitro, —OR¹⁰, —N(R¹⁰)₂, —CN, —C(=O)R¹⁰, —C(=O)OR¹⁰, C(=O)N(R¹⁰)₂, —NR¹⁰C(=O)R¹⁰, NR¹⁰SO₂R¹⁰, —SOR¹⁰, —SO₂R¹⁰, —SO₂N(R¹⁰)₂, —C(=O)OCH₂SCH₃, $C_1$-$C_6$ alkyl, $C_{3-8}$ cycloalkyl, $C_1$-$C_6$ haloalkyl, $C_1$-$C_6$ heteroalkyl, —$C_1$-$C_{6b}$alkyl-aryl, optionally substituted aryl, or optionally substituted heteroaryl; and R¹² is hydrogen or $C_1$-$C_6$ alkyl.

In some embodiments of any of the foregoing methods, the LXR agonist is a compound of Formula XXVIII:

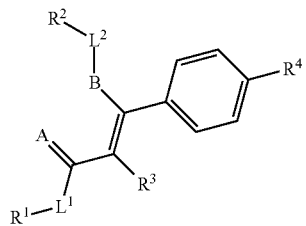

Formula XXVII or a pharmaceutically acceptable salt thereof;

wherein A and B are each nitrogen, wherein A and B are bonded together to form a five-membered heteroaryl ring;

L¹ and L² are each independently a bond, $C_1$-$C_6$ alkyl, or $C_1$-$C_6$ heteroalkyl;

R¹ is hydrogen, halogen, —CF₃, —OR⁸, —N(R⁸)₂, —C(=O)R⁸, —C(=O)OR⁸, —C(=O)N(R⁸)₂, —C(=NOH)R⁸, —C(=S)N(R⁸)₂, or —C(=O)OCH₂SCH₃;

R² is —OR⁹, —N(R⁹)₂, —C(=O)R⁹, —C(=O)OR⁹, —C(=O)N(R⁹)₂, —NR¹⁰C(=O)R⁹, —C(=N—OH)R⁹, C(=S)N(R⁹)₂, —C(=O)OCH₂SCH₃, $C_1$-$C_6$ alkyl, $C_3$-$C_8$ cycloalkyl, $C_1$-$C_6$ haloalkyl, $C_1$-$C_6$ heteroalkyl, optionally substituted heterocycloalkyl, optionally substituted aryl, or optionally substituted heteroaryl;

R³ is hydrogen, halogen, $C_1$-$C_6$ alkyl, or $C_1$-$C_6$ haloalkyl;

R⁴ is aryl or heteroaryl; wherein aryl or heteroaryl is substituted with at least one R¹¹;

each R⁸, each R⁹, and each R¹⁰ are each, independently, hydrogen, $C_1$-$C_6$ alkyl, $C_1$-$C_6$ heteroalkyl, $C_1$-$C_6$ alkyl-aryl, aryl, or heteroaryl; and R¹¹ is, independently, halogen, nitro, —OR¹⁰, —N(R¹⁰)₂, —CN, —C(=O)R¹⁰, —C(=O)OR¹⁰, C(=O)N(R¹⁰)₂, —NR¹⁰C(=O)R¹⁰, NR¹⁰SO₂R¹⁰, —SOR¹⁰, —SO₂R¹⁰, —SO₂N(R)₂, —C(=O)OCH₂SCH₃, $C_1$-$C_6$ alkyl, $C_3$-$C_8$ cycloalkyl, $C_1$-$C_6$ haloalkyl, $C_1$-$C_6$ heteroalkyl, $C_1$-$C_6$ alkyl-aryl, optionally substituted aryl, or optionally substituted heteroaryl.

In other embodiments of any of the foregoing methods, the LXR agonist is a compound of Formula XXVII:

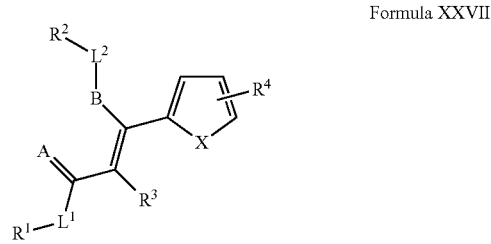

Formula XXVII or a pharmaceutically acceptable salt thereof;

wherein X is —S—;

A and B are each nitrogen, wherein A and B are bonded together to form a five-membered heteroaryl ring;

L¹ is a bond, $C_1$-$C_6$ alkyl, or $C_1$-$C_6$ heteroalkyl;

L² is $C_1$-$C_6$ alkyl or $C_1$-$C_6$ heteroalkyl;

R¹ is hydrogen, halogen, $C_1$-$C_6$ alkyl, $C_2$-$C_6$ alkenyl, $C_2$-$C_6$ alkynyl, —CF₃, —OR⁸, —N(R⁸)₂, C(=O)R⁸, —C(=O)OR⁸, —C(=O)N(R⁸)₂, —C(=N—OH)R⁸, —C(=S)N(R⁸)₂, —C(=CH₂)CH₃, or C(=O)OCH₂SCH₃;

R² is —C(=O)OR¹³, —NR¹⁰C(=O)R⁹, —C(=N—OH) R⁹, —C(=S)N(R⁹)₂, or —C(=O)OCH₂SR¹⁵;

R³ is hydrogen, halogen, $C_1$-$C_6$ alkyl, or $C_1$-$C_6$ haloalkyl;

R⁴ is aryl or heteroaryl; wherein aryl or heteroaryl is substituted with at least one R¹¹;

each R⁸, each R⁹, and each R¹⁰ are each, independently, hydrogen, $C_1$-$C_6$ alkyl, $C_1$-$C_6$ heteroalkyl, —$C_1$-$C_6$ alkyl-aryl, aryl, or heteroaryl;

R¹¹ is, independently, halogen, nitro, —OR¹⁰, —N(R¹⁰)₂, —CN, —C(=O)R¹⁰, —C(=O)OR¹⁰, C(=O)N(R¹⁰)₂, —NR¹⁰C(=O)R¹, —NR¹⁰SO₂R¹⁰, —SOR¹⁰, —SO₂R¹⁴, —SO₂N(R¹⁰)₂, —C(=O)OCH₂SCH₃, optionally substituted $C_1$-$C_6$ alkyl, optionally substituted $C_3$-$C_8$ cycloalkyl, $C_1$-$C_6$ haloalkyl, optionally substituted $C_1$-$C_6$ heteroalkyl, optionally substituted —$C_1$-$C_6$ alkyl-aryl, optionally substituted aryl, or optionally substituted heteroaryl;

$R^{13}$ is hydrogen, $C_1$-$C_6$ alkyl, $C_1$-$C_6$ heteroalkyl, —$C_1$-$C_6$ alkyl-aryl, aryl, or heteroaryl;

$R^{14}$ is $C_1$-$C_6$ alkyl, $C_1$-$C_6$ heteroalkyl, —$C_1$-$C_6$ alkyl-aryl, aryl, or heteroaryl; and $R^{15}$ is $C_1$-$C_6$ alkyl.

In certain embodiments of any of the foregoing methods, the LXR agonist is any one of compounds 774-780:

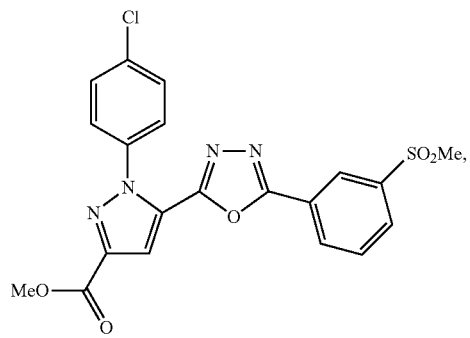

774

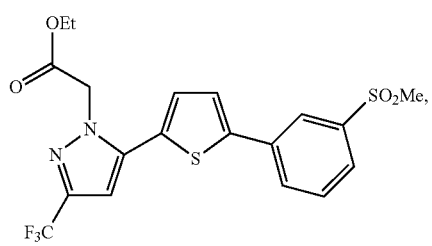

775

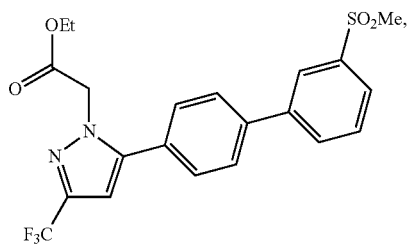

776

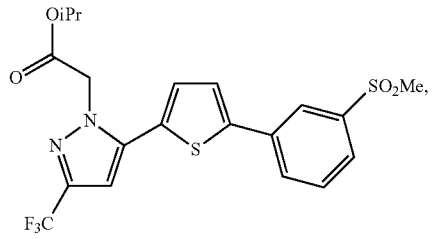

777

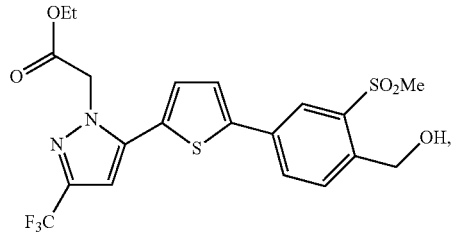

778

-continued

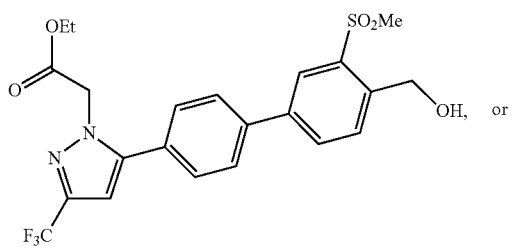

779

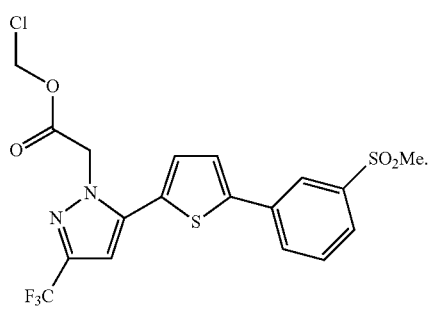

780

Compounds of Formula XXVII may be synthesized by methods known in the art, e.g., methods described in International Patent Publication No. WO2013/130892.

In some embodiments, the LXR agonist is a compound disclosed in U.S. Publication No. 2015/0152094 or U.S. Publication No. 2015/0045399, the compounds of which are herein incorporated by reference.

In some embodiments of any of the foregoing methods, the LXR agonist is a compound of Formula XXVIII:

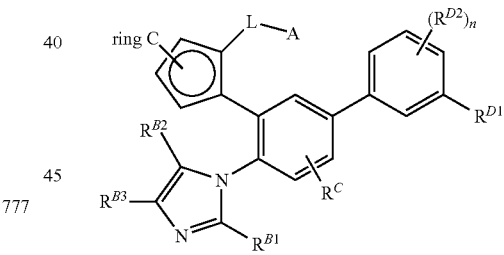

Formula XXVIII or a pharmaceutically acceptable salt thereof;

L is a bond, —[C($R^1$)$_2$]$_m$—, -cyclopropyl-, or —CO—;

m is 1 or 2;

n is 0, 1, 2, 3, or 4;

$R^1$ is independently selected from H, $C_{1-3}$ alkyl, —OH, or halo;

A is phenyl, cyclohexyl, a 5 or 6 membered heterocyclyl, or a 5 or 6 membered heteroaryl, wherein the phenyl is optionally fused to a 5 or 6 membered heterocyclyl or 5 or 6 membered heteroaryl, wherein A is optionally substituted with 1, 2, or 3 $R^A$ groups, wherein each $R^A$ is independently $R^{A1}$, —$C_1$-$C_6$ alkyl-$R^{A1}$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, or heterocyclyl, wherein the cycloalkyl or heterocyclyl are each optionally substituted with 1, 2, 3, or 4 groups that are independently $R^{A1}$, $C_1$-$C_6$ alkyl, or —$C_1$-$C_6$ alkyl-$R^{A1}$, wherein each $R^{A1}$ is independently halogen, cyano, nitro, —OR, —NR$_2$, —SR, —C(O)R, or —C(O)OR; alternatively, 2 $R^A$ on adjacent carbons can join to form a —O—CH$_2$—O—, —O—CH$_2$—CH$_2$—, —O—CH$_2$—CH$_2$—O—, —O—CF$_2$—O—, or —CH$_2$—CH$_2$—CH$_2$—;

ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with C$_1$-C$_4$ alkyl, C$_2$-C$_3$ alkenyl, C$_1$-C$_3$ haloalkyl, C$_3$-C$_6$ cycloalkyl, CF$_3$, C$_1$-C$_4$ alkyl-OH, C$_1$-C$_4$ alkyl-O—C$_1$-C$_3$ alkyl, C$_1$-C$_3$ alkyl-NR$_2$; C$_1$-C$_3$ alkyl-CO$_2$H, C$_1$-C$_3$ alkyl-NHSO$_2$—C$_1$-C$_3$ alkyl, —NH—C$_1$-C$_3$alkyl-OR, C$_1$-C$_3$ alkyl-pyrrolidinyl;

$R^{B1}$ is hydrogen, C$_1$-C$_3$ alkyl, halo, or C$_1$-C$_3$haloalkyl;

$R^{B2}$ is hydrogen, C$_1$-C$_3$ alkyl, halo, or C$_1$-C$_3$ haloalkyl;

$R^{B3}$ is hydrogen, C$_1$-C$_4$ alkyl, halo, CN, C$_1$-C$_4$ haloalkyl, —C(O)—C$_1$-C$_3$ alkyl, —CO—NH$_2$, —CO—NR$_2$, or —C$_1$-C$_3$ alkyl-OH;

each $R^{D1}$ and $R^{D2}$ are independently $R^{D3}$, C$_1$-C$_6$ alkyl, —C$_1$-C$_6$ alkyl-R$^{D3}$, C$_1$-C$_6$ haloalkyl, C$_2$-C$_6$ alkenyl, C$_2$-C$_6$ alkynyl, C$_3$-C$_8$ cycloalkyl, or heterocyclyl, wherein the cycloalkyl and heterocyclyl are each optionally substituted with 1, 2, 3, or 4 groups that are independently $R^{D3}$, C$_1$-C$_6$ alkyl, C$_3$-C$_8$ cycloalkyl, or —C$_1$-C$_6$ alkyl-R$^{D3}$, wherein each $R^{D3}$ is independently halogen, cyano, —OR, —NR$_2$, —SR, —C(O)R, —C(O)OR, —C(O)NR$_2$, —S(O)R, —S(O)$_2$R, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)$_2$R, —N(R)S(O)$_2$OR, —N(R)S(O)$_2$NR$_2$, or —S(O)$_2$N(R)C(O)NR$_2$; and $R^C$ is hydrogen, halogen, cyano, or C$_1$-C$_6$ alkyl;

each R group is independently hydrogen, C$_1$-C$_6$ alkyl, —C$_1$-C$_6$ alkyl-R$^2$, C$_1$-C$_6$ haloalkyl, —C$_1$-C$_6$ haloalkyl-R$^2$, C$_2$-C$_6$ alkenyl, C$_2$-C$_6$ alkynyl, or C$_3$-C$_8$ cycloalkyl, wherein each $R^2$ is independently cyano, —OR$^3$, —N(R$^3$)$_2$, —N(R$^3$)S(O)$_2$R$^3$, —N(R$^3$)S(O)$_2$OR$^3$, or —N(R$^3$)S(O)$_2$N(R$^3$)$_2$, wherein each $R^3$ is independently hydrogen, C$_1$-C$_6$ alkyl, or C$_1$-C$_6$ haloalkyl.

In other embodiments of any of the foregoing methods, the LXR agonist is a compound of Formula XXIX:

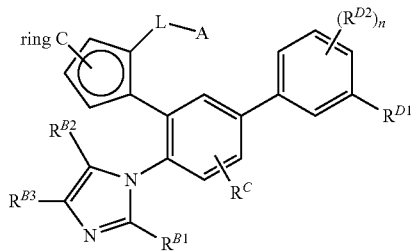

Formula XXIX or a pharmaceutically acceptable salt thereof;

L is a bond, —[C(R$^1$)$_2$]$_m$—, -cyclopropyl-, or —CO—;

m is 1 or 2;

$R^1$ is independently selected from H, C$_1$-C$_3$ alkyl, —OH, or halo;

A is phenyl, cyclohexyl, benzofuranyl, 2,3-dihydro-1H-indenyl, pyridyl, pyrazinyl, pyrimidinyl, dihydrobenzofuranyl, pyridin-2(1H)-one, imidazo[1,2-a]pyridinyl, or piperidinyl, wherein A is optionally substituted with 1, 2, or 3 $R^A$ groups, wherein each $R^A$ is independently halo, CN, C$_1$-C$_6$ alkyl, C$_1$-C$_6$ haloalkyl, —O—R, NR$_2$, —O—C$_1$-C$_6$ alkyl, —O—C$_1$-C$_6$ alkyl-C$_3$-C$_6$ cycloalkyl, —S—R, —CO—R, —C(O)OR, —C$_1$-C$_6$ alkyl-CO—NR$_2$, pyrrolidinone, or pyrrolidinyl, alternatively, 2 $R^A$ on adjacent carbons can join to form a —O—CH$_2$—O—, —O—CH$_2$CH$_2$—, —O—CH$_2$—CH$_2$—O—, or —O—CF$_2$—O—;

ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with C$_1$-C$_4$ alkyl, C$_2$-C$_3$ alkenyl, C$_1$-C$_3$ haloalkyl, C$_3$-C$_6$ cycloalkyl, —CF$_3$, —C$_1$-C$_4$ alkyl-OH, —C$_1$-C$_4$ alkyl-O—C$_1$-C$_3$ alkyl, —C$_1$-C$_3$ alkyl-NR$_2$, —C1-C$_3$ alkyl-CO$_2$H, —C$_1$-C$_3$ alkyl-NHSO$_2$-C1-C$_3$ alkyl, —NH—C$_1$-C$_3$ alkyl-OR, or —C$_1$-C$_3$ alkyl-pyrrolidinyl;

$R^{B1}$ is hydrogen, C$_1$-C$_3$ alkyl, halo, or C$_1$-C$_3$ haloalkyl;

$R^{B2}$ is hydrogen, methyl or halo;

$R^{B3}$ is hydrogen, C$_1$-C$_4$ alkyl, halo, CN, C$_1$-C$_4$ haloalkyl, cyclopropyl, —CO—NH$_2$, —CONR$_2$, or —C$_1$-C$_3$ alkyl-OH, $R^C$ is hydrogen, halogen, or cyano;

n is 0, 1, 2, 3, or 4;

$R^{D1}$ is —SO$_2$—C$_1$-C$_6$ alkyl, —SO$_2$—C$_1$-C$_6$ haloalkyl, —SO$_2$—C$_3$-C$_6$ cycloalkyl, —SO$_2$—C$_1$-C$_6$ alkyl-OH, —SO$_2$—C$_1$-C$_6$ alkyl-O—C$_1$-C$_6$ alkyl, —C(Me)$_2$-COOH, C(Me)$_2$-CONR$_2$, cyclopropyl-CONR$_2$, —SO$_2$NR$_2$, —SO$_2$NR—C$_1$-C$_6$ alkyl-OH, —SO$_2$-pyrrolidinyl, or CONR$_2$;

$R^{D2}$ is independently C$_1$-C$_6$ haloalkyl, —C$_1$-C$_6$ alkyl-OH, halo, —C$_1$-C$_6$ alkyl-O—C$_1$-C$_6$ alkyl, —C$_1$-C$_6$ alkyl-NHSO$_2$—C$_1$-C$_6$ alkyl, C$_1$-C$_6$ haloalkyl, or —O—C$_1$-C$_6$ alkyl-O—C$_1$-C$_6$ haloalkyl, each R group is independently hydrogen, C$_1$-C$_6$ alkyl, —C$_1$-C$_6$ alkyl-R$^2$, C$_1$-C$_6$ haloalkyl, —C$_1$-C$_6$ haloalkyl-R$^2$, C$_2$-C$_6$ alkenyl, C$_2$-C$_6$ alkynyl, C$_1$-C$_6$ cycloalkyl;

each $R^2$ is independently —OR$^3$, wherein each $R^3$ is independently hydrogen; and C$_1$-C$_6$ alkyl, or C$_1$-C$_6$ haloalkyl.

In certain embodiments of any of the foregoing methods, the LXR agonist is a compound of Formula XXX:

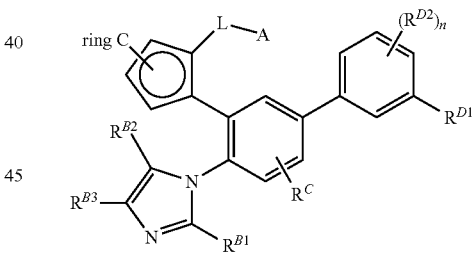

Formula XXX or a pharmaceutically acceptable salt thereof;

L is a bond, —[C(R$^1$)$_2$]$_m$—, -cyclopropyl-, or —CO—;

m is 1 or 2;

n is 0, 1, 2, 3, or 4;

$R^1$ is independently selected from H, C$_1$-C$_3$ alkyl, C$_1$-C$_3$ haloalkyl, —OH, and halo;

A is phenyl, cyclohexyl, a 5 or 6 membered heterocycle, or a 5 or 6 membered heteroaryl, wherein the phenyl is optionally fused to a 5 or 6 membered heterocycle or 5 or 6 membered heteroaryl, wherein A is optionally substituted with 1, 2, or 3 $R^A$ groups, wherein each $R^A$ is independently $R^{A1}$, —C$_1$-C$_6$ alkyl-R$^{A1}$, C$_1$-C$_6$ alkyl, C$_1$-C$_6$ haloalkyl, C$_2$-C$_6$ alkenyl, C$_2$-C$_6$ alkynyl, C$_3$-C$_8$ cycloalkyl, or heterocyclyl, wherein the cycloalkyl or heterocyclyl are each optionally substituted with 1, 2, 3, or 4 groups that are independently $R^{A1}$, C$_1$-C$_6$ alkyl, or —C$_1$-C$_6$ alkyl-R$^{A1}$, wherein each $R^{A1}$ is independently halogen, cyano, nitro, —OR, —NR$_2$, —SR, —C(O)R, or —C(O)OR, alternatively, 2 $R^A$ on adjacent carbons can join to form a —O—$CH_2$—O—, —O—$CH_2$—$CH_2$—, —O—$CH_2$—$CH_2$—O—, —$CH_2$—$CH_2$—$CH_2$—, or —O—$CF_2$—O—;

ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with $C_1$-$C_4$ alkyl, $C_2$-$C_3$ alkenyl, $C_1$-$C_3$ haloalkyl, $C_3$-$C_6$ cycloalkyl, —$CF_3$, —$C_1$-$C_4$ alkyl-OH, —$C_1$-$C_4$ alkyl-O—$C_1$-$C_3$ alkyl, —$C_1$-$C_3$ alkyl-$NR_2$, —$C_1$-$C_3$ alkyl-$CO_2$H, —$C_1$-$C_3$ alkyl-$NHSO_2$—$C_1$-$C_3$alkyl, —NH—$C_1$-$C_3$ alkyl-OR, or —$C_1$-$C_3$ alkyl-pyrrolidinyl;

$R^{B1}$ is hydrogen, $C_1$-$C_3$ alkyl, halo, or $C_1$-$C_3$ haloalkyl;

$R^{B2}$ is hydrogen or halo;

$R^{B3}$ is hydrogen, $C_1$-$C_3$ alkyl, halo, CN, $C_1$-$C_3$ haloalkyl, —C(O)—$C_1$-$C_3$ alkyl, —CO—$NH_2$, —CO—$N(R)_2$, or —$C_1$-$C_3$ alkyl-OH;

$R^{D1}$ and $R^{D2}$ are each independently $R^{D3}$, $C_1$-$C_6$ alkyl, —$C_1$-$C_6$ alkyl-$R^{D3}$, $C_1$-$C_6$ haloalkyl, $C_2$-$C_6$ alkenyl, $C_2$-$C_6$ alkynyl, or $C_3$-$C_8$ cycloalkyl, or heterocyclyl, wherein the cycloalkyl or heterocyclyl are each optionally substituted with 1, 2, 3, or 4 groups that are independently $R^{D3}$, $C_1$-$C_6$ alkyl, $C_3$-$C_6$ cycloalkyl, or —$C_1$-$C_6$ alkyl-$R^{D3}$, wherein each $R^{D3}$ is independently halogen, cyano, —OR, —$NR_2$, —SR, —C(O)R, —C(O)OR, —C(O)$NR_2$, —S(O)R, —S(O)$_2$R, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)$_2$R, —N(R)S(O)$_2$OR, —N(R)S(O)$_2NR_2$, or —S(O)$_2$N(R)C(O)$NR_2$;

$R^C$ is hydrogen, halogen, $C_1$-$C_6$ alkyl, cyano, or nitro; and each R group is independently hydrogen, $C_1$-$C_6$ alkyl, —$C_1$-$C_6$ alkyl-$R^2$, $C_1$-$C_6$ haloalkyl, —$C_1$-$C_6$ haloalkyl-$R^2$, $C_2$-$C_6$ alkenyl, $C_2$-$C_6$ alkynyl, $C_3$-$C_8$ cycloalkyl, or —$C_1$-$C_6$ alkyl-$C3$-$C_8$ cycloalkyl, wherein each $R^2$ is independently cyano, —$OR^3$, —$N(R^3)_2$, —$N(R^3)S(O)_2R^3$, —$N(R^3)S(O)_2OR^3$, or —$N(R^3)S(O)_2N(R^3)_2$, wherein each $R^3$ is independently hydrogen, $C_1$-$C_6$ alkyl, or $C_1$-$C_6$ haloalkyl.

In some embodiments of any of the foregoing methods, the LXR agonist is a compound of Formula XXXI:

—O—$CH_2$—O—, —O—$CH_2$—$CH_2$—, —O—$CH_2$—$CH_2$—O—, or —O—$CF_2$—O—;

ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with $C_1$-$C_4$ alkyl, $C_2$-$C_3$ alkenyl, $C_{1-3}$ haloalkyl, $C_3$-$C_6$ cycloalkyl, —$CF_3$, —$C_1$-$C_4$ alkyl-OH, —$C_1$-$C_4$ alkyl-O—$C_1$-$C_3$ alkyl, —$C_1$-$C_3$ alkyl-$NR_2$; —$C_1$-$C_3$ alkyl-$CO_2$H, —$C_1$-$C_3$ alkyl-$NHSO_2$—$C_1$-$C_3$ alkyl, —NH—$C_1$-$C_3$ alkyl-OR, or —$C_1$-$C_3$ alkyl-pyrrolidinyl;

$R^{B1}$ is hydrogen, $C_1$-$C_3$ alkyl, halo, or $C_1$-$C_3$ haloalkyl;

$R^{B2}$ is hydrogen or halo;

$R^{B3}$ is hydrogen, $C_1$-$C_3$ alkyl, halo, CN, $C_1$-$C_4$ haloalkyl, cyclopropyl, —CO—$NH_2$, —$CONR_2$, or —$C_1$-$C_3$ alkyl-OH;

$R^C$ is hydrogen, halogen, or cyano;

n is 0, 1, 2, 3, or 4;

$R^{D1}$ is —$SO_2$—$C_1$-$C_6$ alkyl, —$SO_2$—$C_1$-$C_6$ haloalkyl, —$SO_2$—$C_3$-$C_6$ cycloalkyl, —$SO_2$—$C_1$-$C_6$ alkylOH, —$SO_2$—$C_1$-$C_6$ alkyl-O—$C_1$-$C_6$ alkyl, —C(Me)$_2$-COOH, —C(Me)$_2$-$CONR_2$, -cyclopropyl-$CONR_2$—, —$SO_2NR_2$, —$SO_2$NR—$C_1$-$C_6$ alkyl-OH, —$SO_2$-pyrrolidinyl, or —$CONR_2$;

$R^{D2}$ is independently —$C_1$-$C_6$ haloalkyl-$C_1$-$C_6$ alkyl-OH, halo, —$C_1$-$C_6$ alkyl-O—$C_1$-$C_6$ alkyl, —$C_1$-$C_6$alkyl-$NHSO_2$—$C_1$-$C_6$ alkyl, $C_1$-$C_6$ haloalkyl, or —O—$C_1$-$C_6$ alkyl-O—$C_1$-$C_6$ haloalkyl, each R group is independently hydrogen, $C_1$-$C_6$ alkyl, —$C_1$-$C_6$ alkyl-$R^2$, $C_1$-$C_6$ haloalkyl, —$C_1$-$C_6$ haloalkyl-$R^2$, $C_2$-$C_6$ alkenyl, $C_2$-$C_6$ alkynyl, or $C_3$-$C_8$ cycloalkyl; and each $R^2$ is independently —$OR^3$, wherein each $R^3$ is independently hydrogen, $C_1$-$C_6$ alkyl, or $C_1$-$C_6$ haloalkyl.

Compounds of Formula XXVIII-XXXI may be synthesized by methods known in the art, e.g., methods described in International Patent Publication No. WO2014/144037.

In other embodiments of any of the foregoing methods, the LXR agonist is a compound of Formula XXXII:

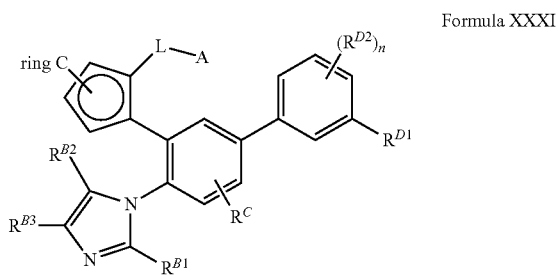

Formula XXXI

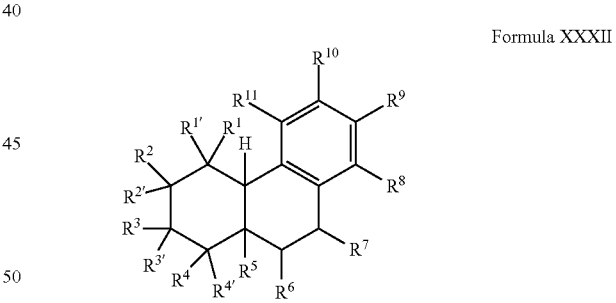

Formula XXXII or a pharmaceutically acceptable salt thereof;

L is a bond, —[C($R^1$)$_2$]$_m$—, -cyclopropyl-, or —CO—;

m is 1 or 2;

$R^1$ is independently selected from H, $C_1$-$C_3$ alkyl, $C_1$-$C_3$ haloalkyl, —OH, and halo;

A is phenyl, cyclohexyl, naphthalenyl, benzofuranyl, 2,3-dihydro-1H-indenyl, 1H-indolyl, pyridyl, pyrazinyl, pyrimidinyl, dihydrobenzofuranyl, pyridin-2(1H)-one, imidazo[1,2-a]pyridinyl, or piperidinyl, wherein A is optionally substituted with 1, 2, or 3 $R^A$ groups; wherein each $R^A$ is independently halo, CN, $C_1$-$C_6$ alkyl, $C_1$-$C_6$ haloalkyl, —O—R, —$NR_2$, —O—$C_1$-$C_6$ alkyl, —O—$C_1$-$C_6$ alkyl-$C_3$-$C_6$ cycloalkyl, —S—R, —CO—R, —C(O)O—R, —$C_1$-$C_6$ alkyl-CO—$NR_2$, pyrrolidinone, or pyrrolidinyl, alternatively, 2 $R^A$ on adjacent carbons can join to form a or a pharmaceutically acceptable salt thereof;

wherein $R^1$ and $R^{1'}$ are independently selected from —H, OR, or —$OR^a$, wherein $R^a$ is a hydroxyl protecting group or $COR^b$, or $R^1$ and $R^{1'}$ taken together form a keto function;

$R^2$ and $R^{2'}$ are independently selected from the group consisting of —H, —$C_1$-$C_6$ alkyl, phenyl, or substituted phenyl, —OH, —$OR^a$, or $R^2$ and $R^{2'}$ taken together to form a keto function;

$R^3$ and $R^{3'}$ are independently selected from the group consisting of —H, —$C_1$-$C_6$ alkyl, phenyl, or substituted phenyl, —OH, —$OR^a$; or $R^3$ and $R^{3'}$ taken together form a keto function;

$R^b$ is selected from the group consisting of —$C_1$-$C_6$ alkyl, —$C_3$-$C_7$ cycloalkyl, phenyl, aryl, alkylaryl, and alkylheterocyclic;

$R^4$ is selected from the group consisting of —H, —OH, —OR$^a$, —$C_1$-$C_6$ alkyl, phenyl, or substituted phenyl; $R^{4'}$ is —H;

$R^5$ is a group selected from hydrogen, —$C_1$-$C_6$ alkyl, phenyl, or substituted phenyl;

$R^6$ and $R^7$ are each independently selected from the group consisting of —H, —$C_1$-$C_6$ alkyl, —$C_2$-$C_8$ alkenyl, phenyl, or substituted phenyl;

$R^8$ and $R^9$ are each independently selected from —H, —$C_1$-$C_6$ alkyl, phenyl, or substituted phenyl, halo, —$NO_2$, —$NR^{12}R^{13}$, —$CONR^{14}R^{15}$, and —$COOR^{16}$;

$R^{10}$ is —H, OH, OR$^a$, COR$^a$, —$C_1$-$C_6$ alkyl, —$C_2$-$C_6$ alkenyl, —$C_2$-$C_6$ alkynyl, phenyl, or substituted phenyl, $CH_2OR^a$, —CHO, —$CONR^{14}R^{15}$, or —$COOR^{16}$;

$R^{11}$ is —H, —$C_1$-$C_6$ alkyl, —$C_2$-$C_8$ alkenyl, phenyl or substituted phenyl, aryl, alkylaryl, or alkylheterocycle;

$R^{12}$ and $R^{13}$ are independently selected from —H, —$C_1$-$C_6$ alkyl, —$C_3$-$C_7$ cycloalkyl, phenyl, aryl, alkylaryl, or $R^{12}$ taken together with $R^{13}$ forms a 4, 5, 6, or 7-membered heterocyclic ring containing a nitrogen atom;

$R^{14}$ and $R^{15}$ are each independently selected from H, —$C_1$-$C_6$ alkyl, —$C_3$-$C_7$ cycloalkyl, phenyl, aryl, alkylaryl, or taken together form a 4, 5, 6, or 7-membered heterocyclic ring containing a nitrogen atom; and $R^{16}$ is —H, —$C_1$-$C_6$ alkyl, phenyl, substituted phenyl, or benzyl;

In some embodiments of the compounds of Formula XXII, when $R^9$ is pyrolidine, $R^5$ is methyl, and $R^{10}$ is carboxyethyl ester group, and $R^1$ is in a trans relationship to R' then $R^1$ is not —OH; and if $R^1$ and $R^{1'}$ are —OH and H respectively, or taken together to form a ketone, then $R^9$ is not pyrolidinyl and $R^{10}$ is not methyl, or hydroxylmethyl.

In certain embodiments of any of the foregoing methods, the LXR agonist is: trans-8-Hydroxy-9-hydro-1,2-[a,b] [(1-carboxyethyl-2-Npyrolidinyl)benzo-4,5-yl]-cis-10-methyl-decalin; 8-keto-1,2-[a,b] [(1-carboxyethyl-1-N-pyrolidinyl)benzo-4,5-yl]-10-methyldecalin; 8-hydroxy-1,2-[a,b] [(1-hydroxymethyl-1-N-pyrolidinyl)benzo-4,5-yl]-10-methyldecalin; or 8-hydroxy-1,2-[a,b] [(1-methyl-1-N-pyrolidinyl)benzo-4,5-yl]-10-methyldecalin.

Compounds of Formula XXXII may be synthesized by methods known in the art, e.g., methods described in International Patent Publication No. WO03/031408.

In some embodiments of any of the foregoing methods, the LXR agonist is a compound of Formula XXXIII:

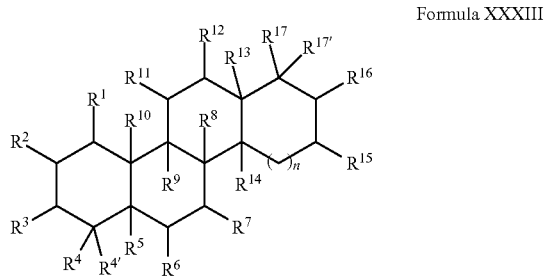

Formula XXXIII wherein $R^3$ is hydrogen, amino, carboxyl, oxo, halo, sulfonic acid, —O-sulfonic acid, or.

alkyl that is optionally inserted with —NH—, —N(alkyl)-, —O—, —S—, —SO—, —$SO_2$—, —$OSO_2$—, —$SO_2$—O—, —O—$SO_3$—, —$SO_3$—O—, —CO—, —CO—O—, —O—CO—, —CO—NH—, —CON(alkyl)-, —NH—CO—, or —N(alkyl)-CO—, and further optionally substituted with hydroxy, halo, amino, carboxyl, sulfonic acid, or —O-sulfonic acid. Each of $R^1$, $R^2$, $R^4$, $R^{4'}$, $R^6$, $R^7$, $R^{11}$, $R^{12}$, $R^{15}$, $R^{16}$, and $R^{17'}$ is, independently, hydrogen, hydroxy, amino, carboxyl, oxo, halo, sulfonic acid, —O-sulfonic acid, or alkyl that is optionally inserted with —NH—, —N(alkyl)-, —O—, —S—, —SO—, —$SO_2$—, —O—$SO_2$—, —$SO_2O$—, —O—$SO_3$—, —$SO_3$—O—, —CO—, —CO—O—, —O—CO—, —CO—NH—, —CO—N(alkyl)-, —NH—CO—, or —N(alkyl)-CO—, and further optionally substituted with hydroxy, halo, amino, carboxyl, sulfonic acid, or —O-sulfonic acid. Each of $R^5$, $R^8$, $R^9$, $R^{10}$, $R^{13}$, and $R^{14}$, independently, is hydrogen, alkyl, haloalkyl, hydroxyalkyl, alkoxy, hydroxy, or amino. $R^{17}$ is —X—Y—Z. X is a bond, or alkyl or alkenyl, optionally inserted with —NH—, —N(alkyl)-, —O—, or —S—, and further optionally forming a cyclic moiety with $R^{16}$ and the 2 ring carbon atoms to which $R^{16}$ and $R^{17}$ are bonded. Y is —CO—, —SO—, —$SO_2$—, —O—$SO_2$—, —$SO_2$—O—, —O—$SO_3$—, —$SO_3$—O—, —CO—O—, —O—CO—, —CONH—, —CO—N(alkyl)-, —NH—CO—, —N(alkyl)-CO—, or a bond. Z is alkyl, alkenyl, alkynyl, cycloalkyl, heterocycloalkyl, cycloalkenyl, heterocycloalkenyl, aryl, heteroaryl, aralkyl, or heteroaralkyl, and is optionally substituted with hydroxy, alkoxy, amino, halo, sulfonic acid, —O-sulfonic acid, carboxyl, oxo, alkyloxycarbonyl, alkylcarbonyloxy, alkylaminocarbonyl, alkylcarbonylamino, alkylcarbonyl, alkylsulfinyl, alkylsulfonyl, or alkylthio; or is —CH(A)-B. A being a side chain of an amino acid, and B is hydrogen, —NR$^a$R$^b$, or —COOR$^c$ wherein each of R$^a$, R$^b$, and R$^c$, independently, is hydrogen or alkyl. n is 0, 1, or 2. Note that when Z is substituted with carboxyl or alkyloxycarbonyl, Y is a bond and either X or Z contains at least one double bond, and that when Y is a bond, either X is —NH-alkyl-, —NH-alkenyl-, —N(alkyl)-alkyl-, —N(alkyl)-alkenyl-, —O-alkyl-, —O-alkenyl-, —S-alkyl-, or —S— alkenyl-; or Z is substituted with halo, sulfonic acid, —O-sulfonic acid, alkylsulfinyl, or alkylsulfonyl, or is alkenyl, or a pharmaceutically acceptable salt thereof.

In other embodiments of any of the foregoing methods, the LXR agonist is any one of compounds 781-806:

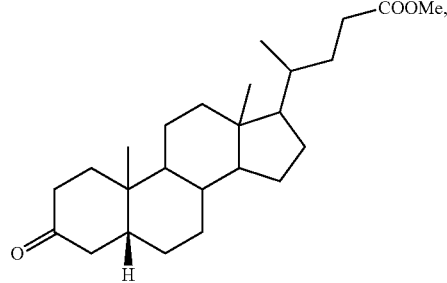

781

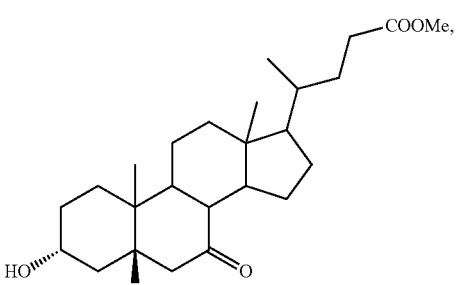

782

783 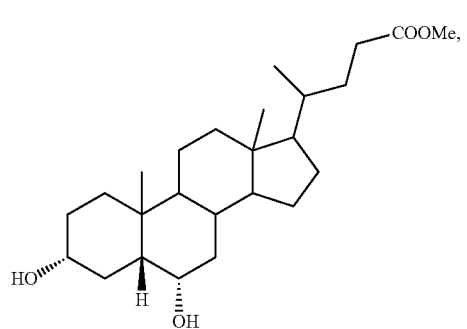
784 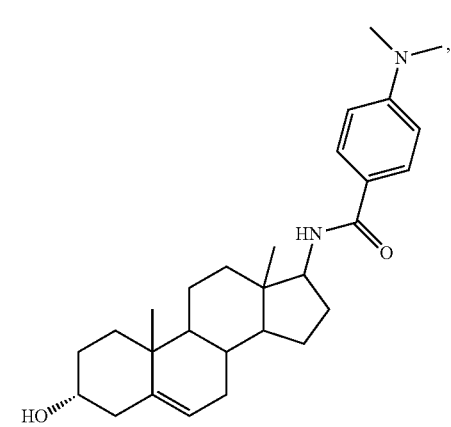
785 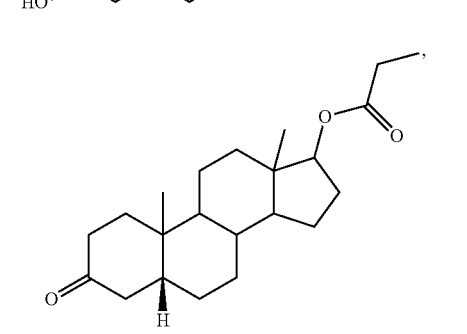
786 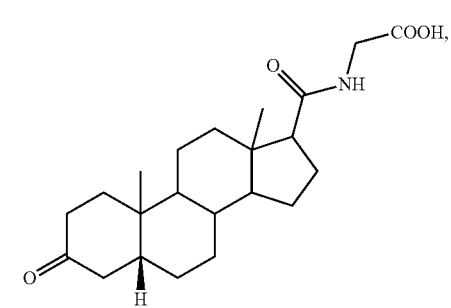
787 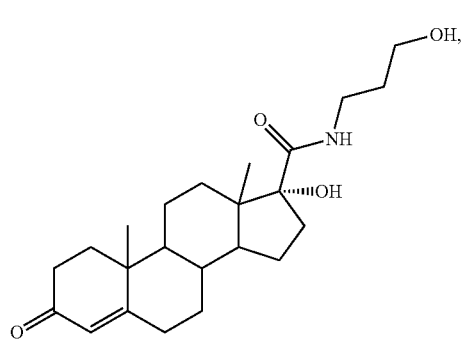
788 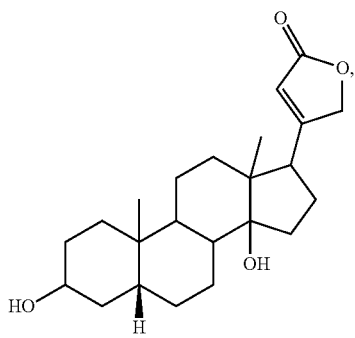
789 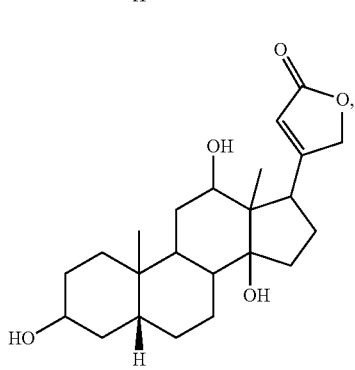
790 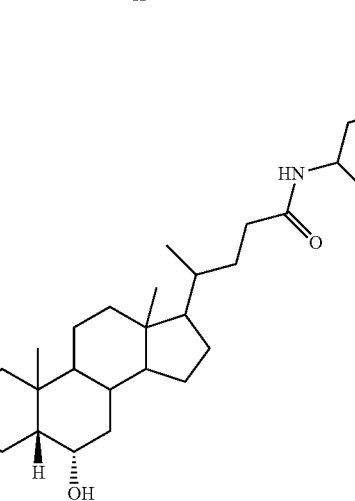
791 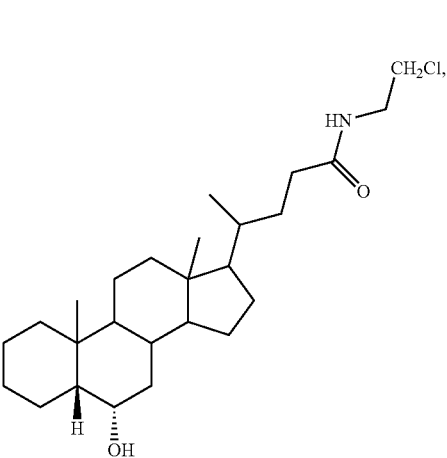

-continued
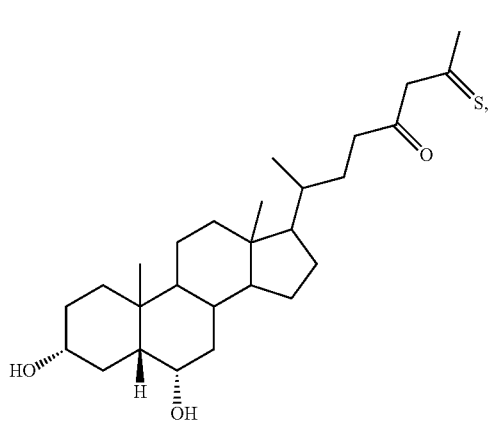
792
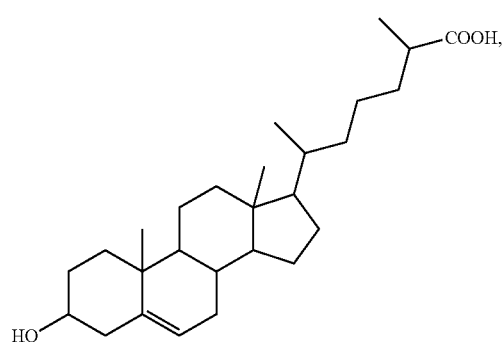
793
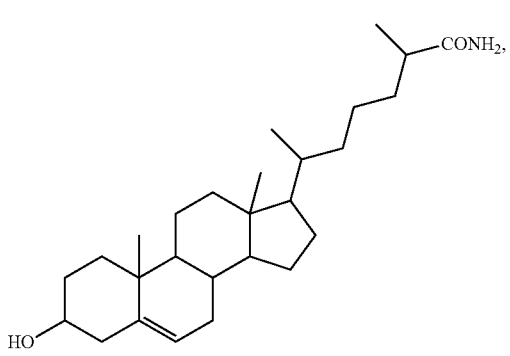
794
795
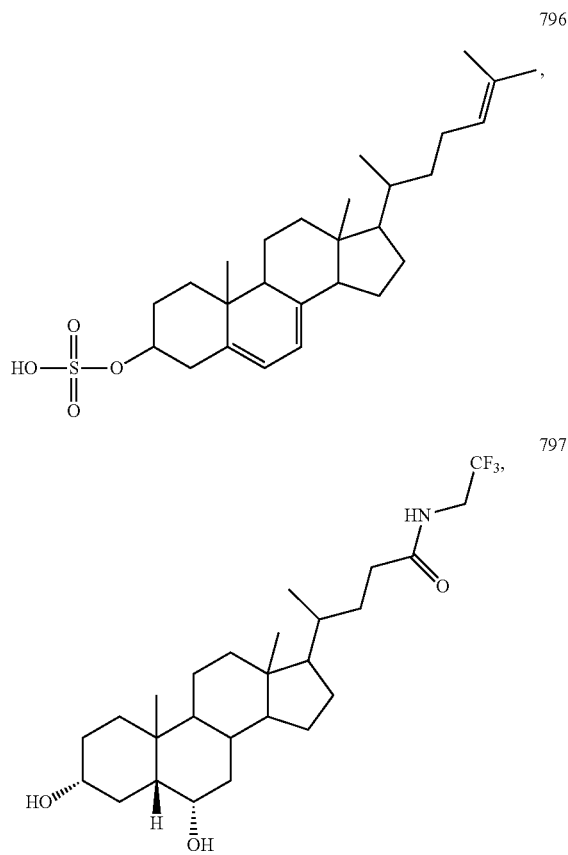
796
797
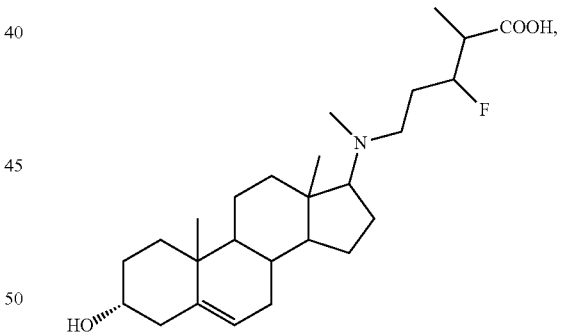
798
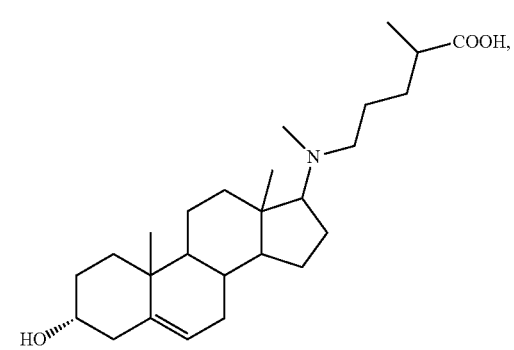
799

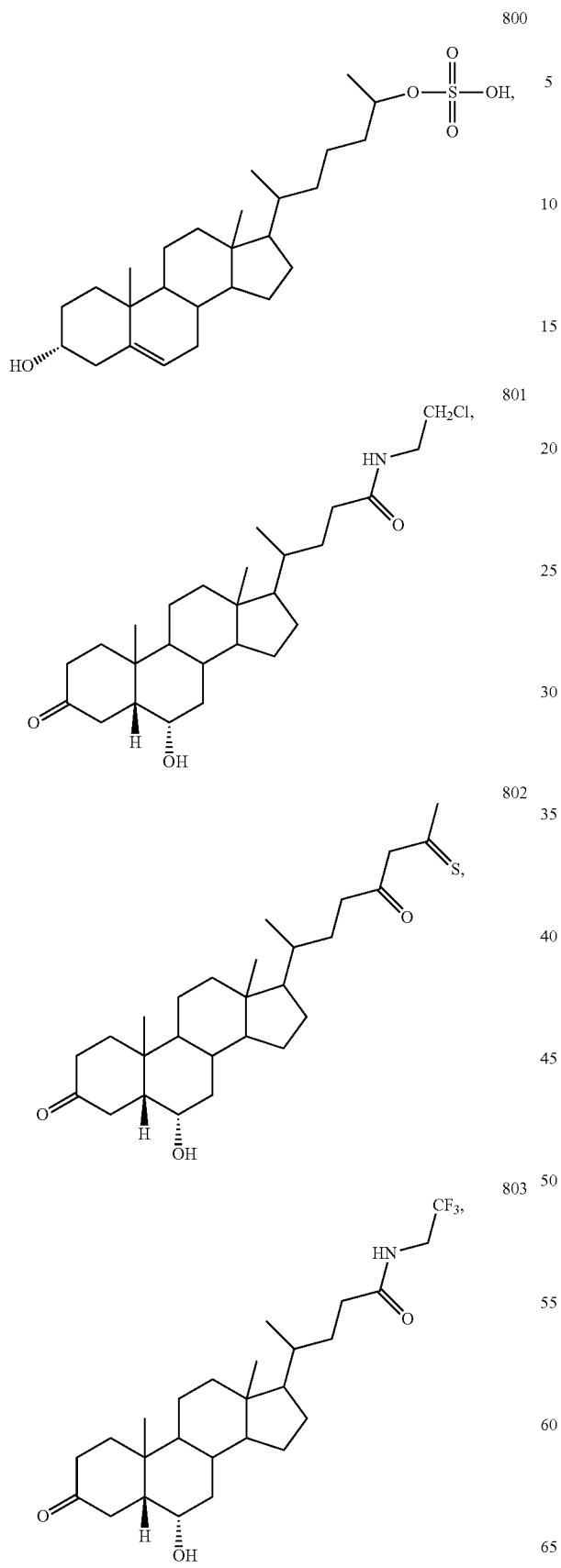
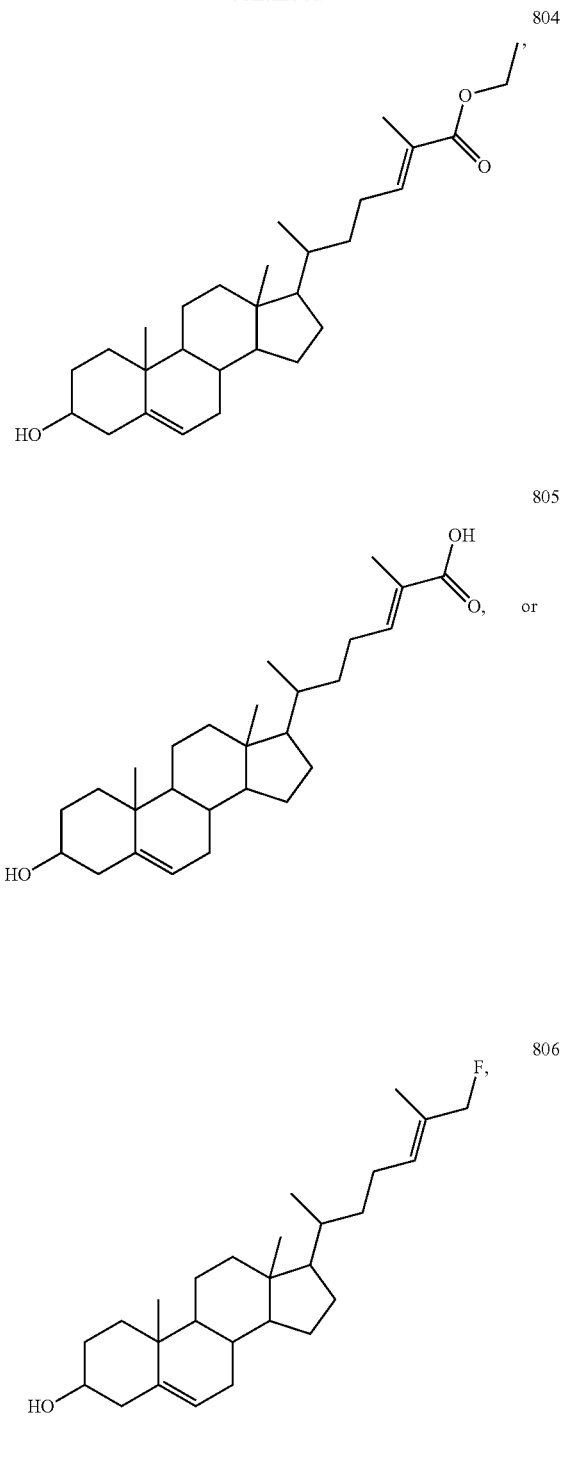
or pharmaceutically acceptable salts thereof.
Compounds of Formula XXXIII may be synthesized by methods known in the art, e.g., methods described in International Patent Publication No. WO00/66611.
In some embodiments of any of the foregoing methods, the LXR agonist is a compound of Formula XXXIV:

Formula XXXIV

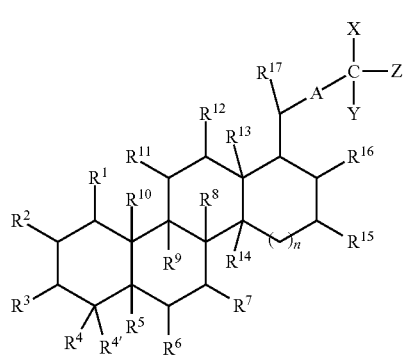

wherein each of $R^1$, $R^2$, $R^3$, $R^4$, $R^{4'}$, $R^5$, $R^6$, $R^7$, $R^{11}$, $R^{12}$, $R^{15}$, $R^{16}$, and $R^{17}$, independently, is hydrogen, halo, alkyl, halo alkyl, hydroxy, amino, carboxyl, oxo, sulfonic acid, or alkyl that is optionally inserted with —NH—, —N(alkyl)-, —O—, —S—, SO—, —SO$_2$—, —O—SO$_2$—, —SO$_2$—O—, —SO$_3$—O—, —CO—, —CO—O—, —O—CO—, —CO—NR'—, —NR'—CO—; or $R^3$ and $R^4$, together, $R^{4'}$, and $R^5$, together, $R^5$, and $R^6$ together, or $R^6$ and $R^7$ together are eliminated so that a C═C bond is formed between the carbons to which they are attached;

each of $R^8$, $R^9$, $R^{10}$, $R^{13}$, and $R^{14}$, independently, is hydrogen, halo, alkyl, haloalkyl, hydroxyalkyl, alkoxy, hydroxy, or amino;

n is 0, 1, or 2;

A is alkylene, alkenylene, or alkynylene; and each of X, Y, and Z, independently, is alkyl, haloalkyl, —OR', —SR', —NR'R", —N(OR')R", or —N(SR')R"; or X and Y together are ═O, ═S, or ═NR';

wherein each of R' and R", independently, is hydrogen, alkyl, or halo alkyl, or a pharmaceutically acceptable salt thereof.

In other embodiments of any of the foregoing methods, the LXR agonist is any one of compounds 807-812:

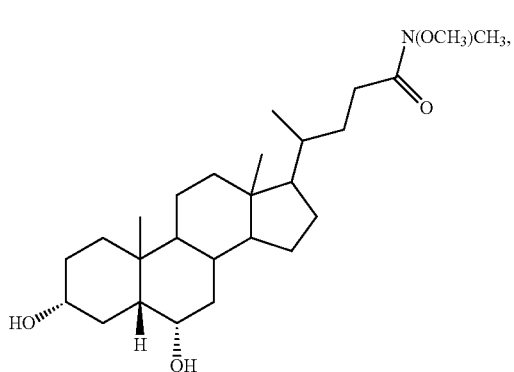
807

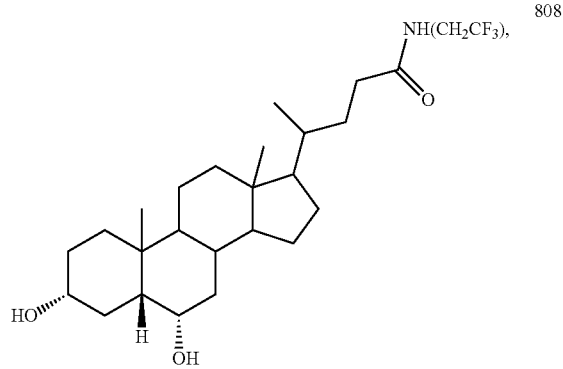
808

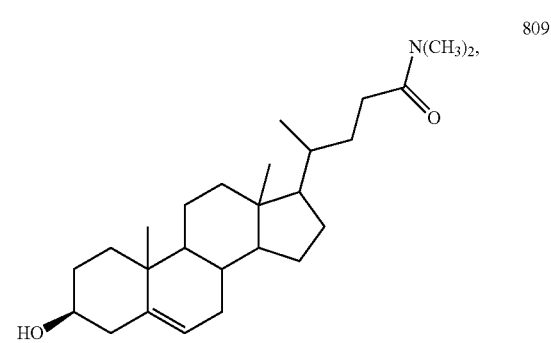
809

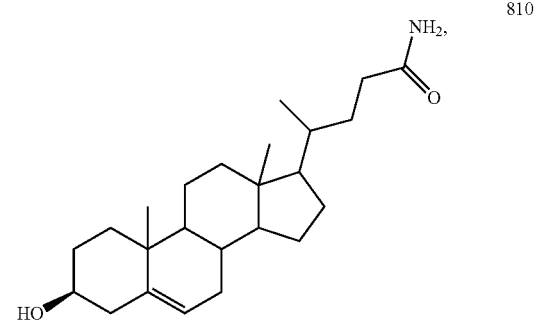
810

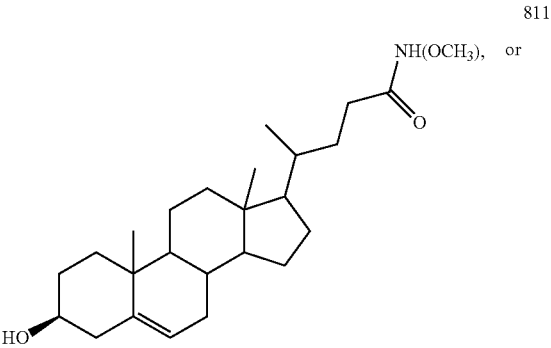
811 or

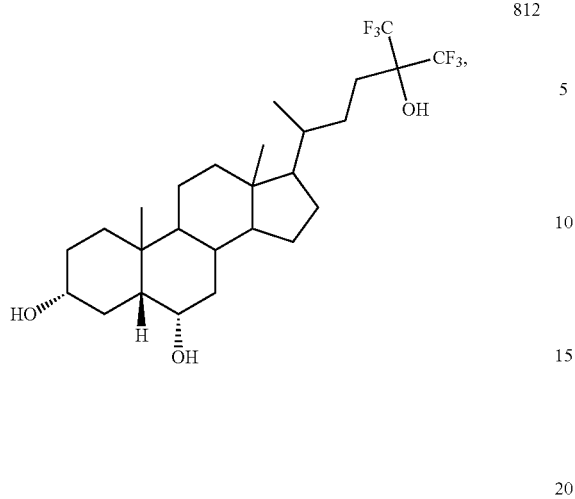

812 or pharmaceutically acceptable salts thereof.

Compounds of Formula XXXIV may be synthesized by methods known in the art, e.g., methods described in International Patent Publication No. WO02/13594.

In certain embodiments of any of the foregoing methods, the LXR agonist is a compound of Formula XXXV:

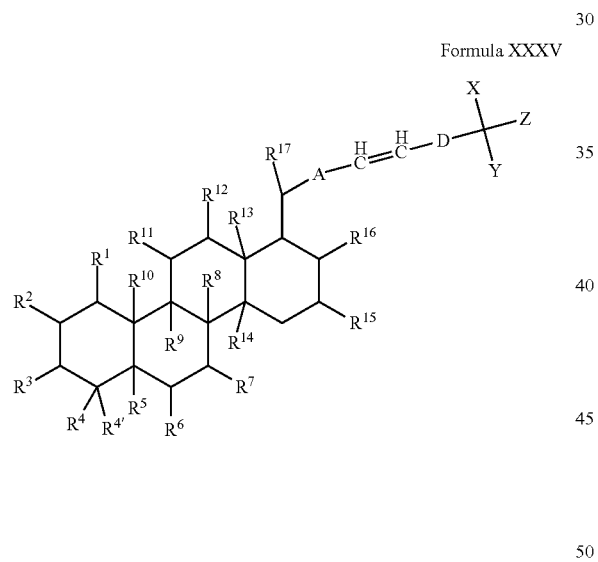

Formula XXXV wherein in which each of $R^1$, $R^2$, $R^4$, $R^5$, $R^{11}$, $R^{12}$, $R^{15}$, $R^{16}$, and $R^{17}$, independently, is hydrogen, halo, alkyl, hydroxyl, amino, carboxyl, or sulfonic acid; each of $R^3$, $R^{3'}$, $R^6$, and $R^{6'}$, independently, is hydrogen, halo, alkyl, hydroxyl, amino, carboxyl, or sulfonic acid, or $R^3$ and $R^{3'}$, together or $R^6$ and $R^{6'}$, together are =O; each of $R^8$, $R^9$, $R^{10}$, $R^{13}$, and $R^{14}$ independently, is hydrogen, halo, alkyl, hydroxyalkyl, alkoxy, hydroxyl, or amino;

each of A and D, independently, is deleted or alkylene; X and Y, independently, is alkyl;

and Z is hydroxyl or alkoxy, or a pharmaceutically acceptable salt thereof.

In some embodiments of any of the foregoing methods, the LXR agonist is any one of compounds 813-816:

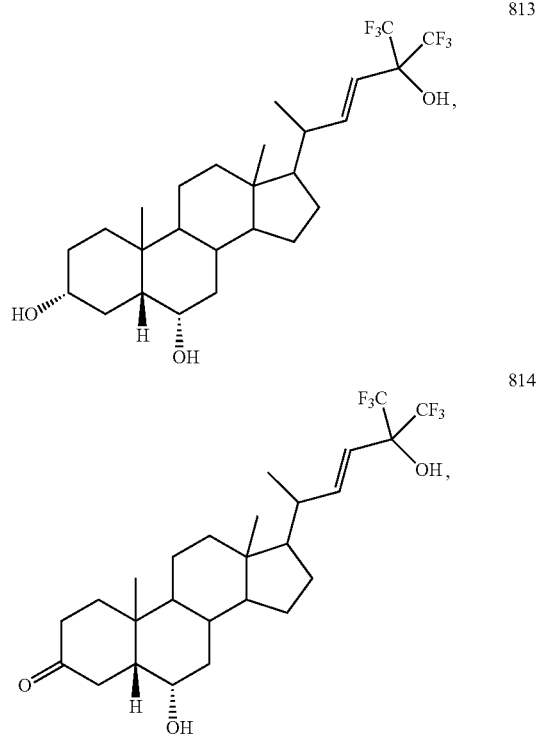

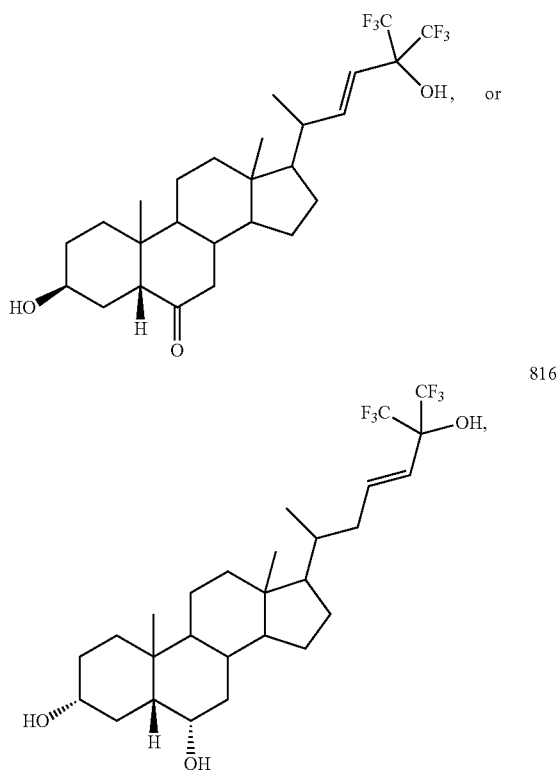

or pharmaceutically acceptable salts thereof.

Compounds of Formula XXXV may be synthesized by methods known in the art, e.g., methods described in International Patent Publication No. WO2011/014661.

In other embodiments of any of the foregoing methods, the LXR agonist is a compound of Formula XXXVI:

Formula XXXVI

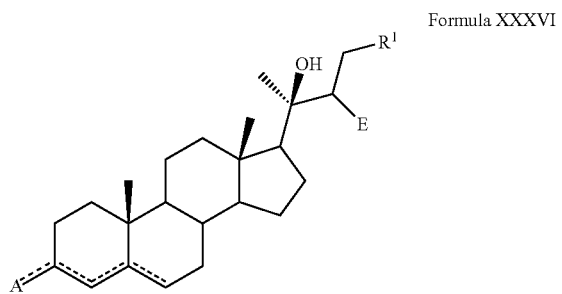

wherein A is selected from the group consisting of hydrogen, hydroxy, or oxygen, wherein the dashed lines are optional double bonds, wherein there are no consecutive double bonds, wherein E is hydrogen or hydroxy, wherein R1 is selected from the group consisting of:

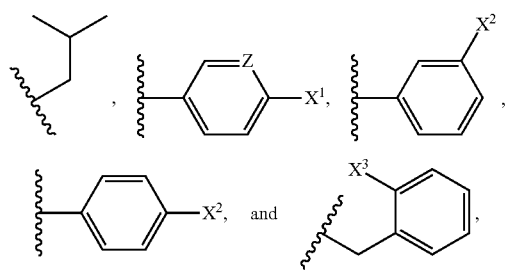

wherein Z is nitrogen that can be anywhere in the ring, wherein $X^1$ can be bonded to any position on the ring and is selected from the group consisting of hydrogen, fluorine, chlorine, bromine, and iodine, and wherein $X^2$ is selected from the group consisting of fluorine, chlorine, bromine, and iodine, wherein $X^3$ can be bonded to any position on the ring and is selected from the group consisting of hydrogen, fluorine, chlorine, bromine, and iodine, or a pharmaceutically acceptable salt thereof.

In certain embodiments of any of the foregoing methods, the LXR agonist is any one of compounds 817-826:

817

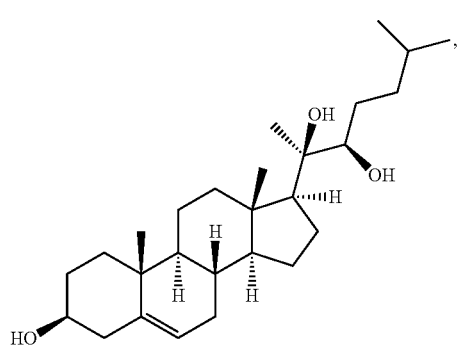

818

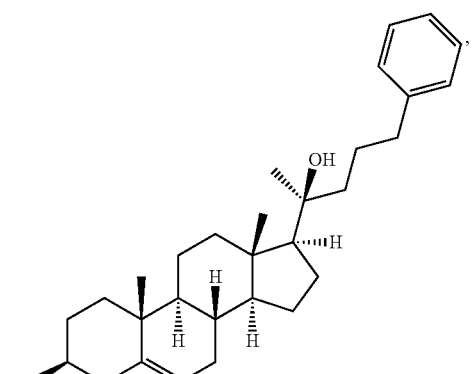

819

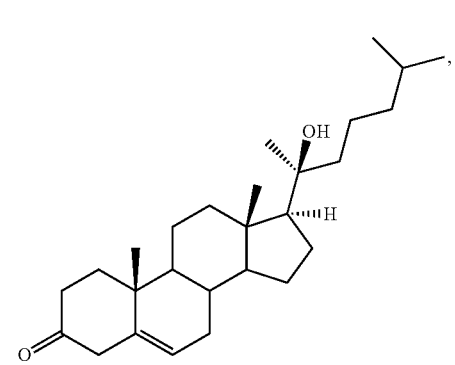

820

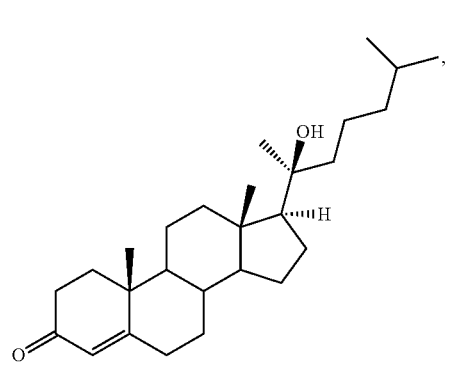

821

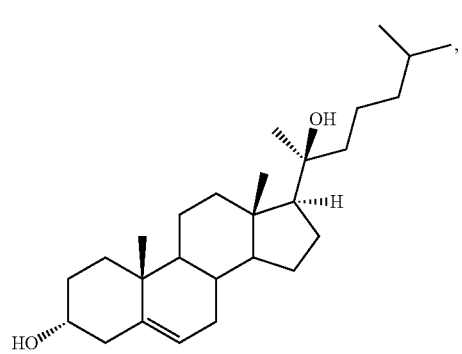

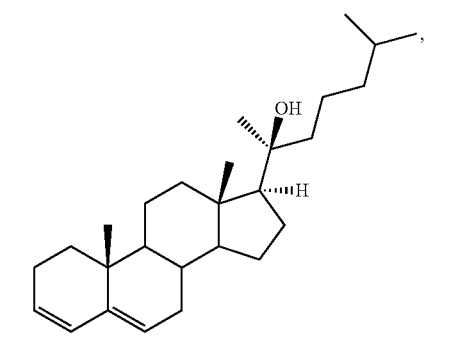

822

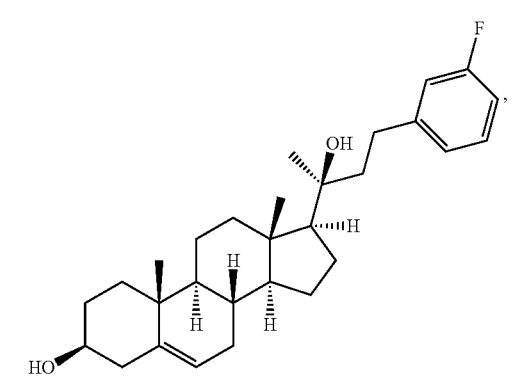

823

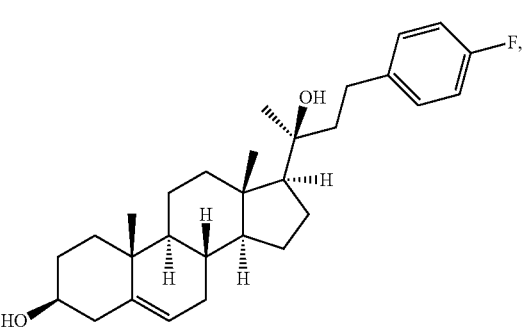

824,

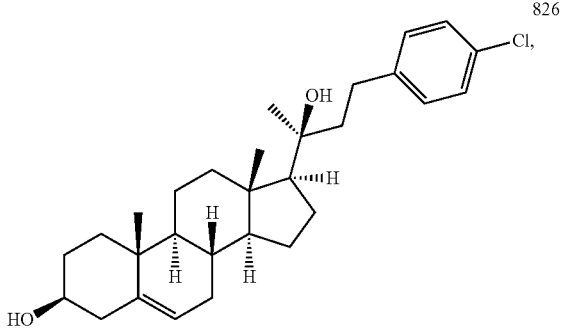

826

825

F, or or pharmaceutically acceptable salts thereof.

Compounds of Formula XXXVI may be synthesized by methods known in the art, e.g., methods described in International Patent Publication No. WO2011/103175.

In further embodiments of any of the foregoing methods, the LXR agonist is hyodeoxycholic acid (also known as 4-[(5R,8S,10R,13R,17R)-3,6-dihydroxy-10,13-dimethyl-2,3,4,5,6,7,8,9,11,12,14,15,16,17-tetradecahydro-1H-cyclopenta[a]phenanthren-17-yl]pentanoic acid) or a pharmaceutically acceptable salt thereof.

In further embodiments of any of the foregoing methods, the LXR agonist is a compound described in International Patent Publication No. WO2006/046593, e.g., any one of (4'-{[2-(tert-butoxycarbonyl)-3-hydroxy-4-(trifluoromethyl)benzyl]oxy}-1,1'-biphenyl-4-yl)acetic acid; 2-(4'-{[2-(tert-butoxycarbonyl)-3-hydroxy-4-(trifluoromethyl)benzyl]oxy}-1,1'-biphenyl-4-yl)propanoic acid; 1-(4'-{[2-(tert-butoxycarbonyl)-3-hydroxy-4-(trifluoromethyl)benzyl]oxy}-1,1'-biphenyl-4-yl)cyclopropanecarboxylic acid; 2-(4'-{[2-(tert-butoxycarbonyl)-3-hydroxy-4-(trifluoromethyl)benzyl]oxy}-1,1'-biphenyl-4-yl)-3-hydroxypropanoic acid; 2-[4'-{[2-(tert-butoxycarbonyl)-3-hydroxy-4-(trifluoromethyl)benzyl]oxy}-1,1'-biphenyl-4-yl]butanoic acid; (4'-{[2-(tert-butoxycarbonyl)-3-hydroxy-4-(trifluoromethyl)benzyl]oxy}-2-methyl-1,1'-biphenyl-3-yl)acetic acid; (4'-{[2-(tert-butoxycarbonyl)-3-hydroxy-4-(trifluoromethyl)benzyl]oxy}-2-methyl-1,1'-biphenyl-4-yl)acetic acid; (4'-{[2-(tert-butoxycarbonyl)-3-hydroxy-4-(trifluoromethyl)benzyl]oxy}-2-chloro-1,1'-biphenyl-4-yl)acetic acid; (4'-{[2-(tert-butoxycarbonyl)-3-hydroxy-4-(trifluoromethyl)benzyl]oxy}-3-fluoro-1,1'-biphenyl-4-yl)acetic acid; (4'-{[2-(tert-butoxycarbonyl)-3-hydroxy-4-(trifluoromethyl)benzyl]oxy}-3-chloro-1,1'-biphenyl-4-yl)acetic acid; 2-(4'-{[2-(tert-butoxycarbonyl)-3-hydroxy-4-(trifluoromethyl)benzyl]oxy}-2-methoxy-1,1'-biphenyl-3-yl)propanoic acid; 2-(4'-{[2-(tert-butoxycarbonyl)-3-hydroxy-4-(trifluoromethyl)benzyl]oxy}-3-fluoro-1,1'-biphenyl-4-yl)propanoic acid; 1-(4'-{[2-(tert-butoxycarbonyl)-3-hydroxy-4-(trifluoromethyl)benzyl]oxy}-3-fluoro-1,1'-biphenyl-4-yl)cyclopropanecarboxylic acid; (4'-{[2-(tert-butoxycarbonyl)-3-hydroxy-4-(trifluoromethyl)benzyl]oxy}-3-methoxy-1,1'-biphenyl-4-yl)acetic acid; (4'-{[2-(tert-butoxycarbonyl)-3-hydroxy-4-(trifluoromethyl)benzyl]oxy}-2-trifluoromethyl-1,1'-biphenyl-4-yl)acetic acid; (4'-{[2-(tert-butoxycarbonyl)-3-hydroxy-4-(trifluoromethyl)benzyl]oxy}-2-ethyl-1,1'-biphenyl-4-yl)acetic acid; tert-butyl 6-[({2'-ethyl-4'-[(methoxycarbonyl)methyl]-1,1'-biphenyl-4-yl}oxy)methyl]-2-hydroxy-3-(trifluoromethyl)benzoate; (4'-{[2-(tert-butoxycarbonyl)-3-hydroxy-4-(trifluoromethyl)benzyl]oxy}-2-nitro-1,1'-biphenyl-4-yl)acetic acid; (2-amino-4'-{[2-(tert-butoxycarbonyl)-3-hydroxy-4-(trifluoromethyl)benzyl-]oxy})-1,1'-biphenyl-4-yl)acetic acid; (4'-{[2-(tert-butoxycarbonyl)-3-hydroxy-4-(trifluoromethyl)benzyl]oxy}-2-isopropyl-1,1'-biphenyl-4-yl)acetic acid; (4'-{[2-(tert-butoxycarbonyl)-3-hydroxy-4-(trifluoromethyl)benzyl]oxy}-2-formyl-1,1'-biphenyl-4-yl)acetic acid; (4'-{[2-(tert-butoxycarbonyl)-3-hydroxy-4-(trifluoromethyl)benzyl]oxy}-2-(hydroxymethyl)-1,1'-biphenyl-4-yl)acetic acid; (4'-{[2-(tert-butoxycarbonyl)-3-hydroxy-4-(trifluoromethyl)benzyl]oxy}-2-cyano-1,1'-biphenyl-4-yl)acetic acid; (4'-{[2-(tert-butoxycarbonyl)-3-hydroxy-4-(trifluoromethyl)benzyl]oxy}-2-cyclopropyl-1,1'-biphenyl-4-yl)acetic acid; (4'-{[2-(tert-butoxycarbonyl)-3-hydroxy-4-(trifluoromethyl)benzyl]oxy}-3-ethyl-1,1'-biphenyl-4-yl)acetic acid; (4'-{[2-(tert-butoxycarbonyl)-3-hydroxy-4-(trifluoromethyl)benzyl]oxy}-2-ethyl-1,1'-biphenyl-4-yl)acetic acid; (4'-{[2-(tert-butoxycarbonyl)-3-hydroxy-4-(trifluoromethyl)benzyl]oxy}-2-ethyl-1,1'-biphenyl-3-yl)acetic acid; 2-(4'-{[2-(tert-butoxycarbonyl)-3-hydroxy-4-(trifluoromethyl)benzyl]oxy}-3-fluoro-1,1'-biphenyl-4-yl)-3-(dimethylamino)propanoic acid; 2-(4'-{[2-(tert-butoxycarbonyl)-3-hydroxy-4-(trifluoromethyl)benzyl]oxy}-2-ethyl-1,1'-biphenyl-4-yl)propanoic acid; 2-(4'-{[2-(tert-butoxycarbonyl)-3-hydroxy-4-(trifluoromethyl)benzyl]oxy}-2-nitro-1,1'-biphenyl-4-yl)propanoic acid; 2-(4'-{[2-(tert-butoxycarbonyl)-3-hydroxy-4-(trifluoromethyl)benzyl]oxy}-2-isopropyl-1,1'-biphenyl-4-yl)propanoic acid; 2-(4'-{[2-(tert-butoxycarbonyl)-3-hydroxy-4-(trifluoromethyl)benzyl]oxy}-2,3-dimethyl-1,1'-biphenyl-4-yl)propanoic acid; or 2-(4'-{[2-(tert-butoxycarbonyl)-3-hydroxy-4-(trifluoromethyl)benzyl]oxy}-2-cyclopropyl-1,1'-biphenyl-4-yl)propanoic acid; or pharmaceutically acceptable salts thereof.

In other embodiments of any of the foregoing methods, the LXR agonist is a compound described in International Patent Publication No. WO2006/073366, e.g., any one of: 2-tert-butyl-4-({3-[3-(hydroxymethyl)phenoxy]propyl}amino)-5-phenylisothiazol-3(2H)-one 1,1-dioxide; 2-tert-butyl-5-phenyl-4-[(4-phenylbutyl)amino]isothiazol-3(2H)-one 1,1-dioxide; 2-tert-butyl-4-{[3-(2-methoxyphenoxy)propyl]amino}-5-phenylisothiazol-3(2H)-one 1,1-dioxide; 2-tert-butyl-4-({3-[4-(hydroxymethyl)phenoxy]propyl}amino)-5-phenylisothiazol-3 (2H)-one 1,1-dioxide; N-(3-{3-[(2-tert-butyl-1,1-dioxido-3-oxo-5-phenyl-2,3-dihydroisothiazol-4-yl)amino]propoxy}phenyl)acetamide; 2-tert-butyl-4-{[3-(2-fluorophenoxy)propyl]amino)}-5-phenylisothiazol-3 (2H)-one 1,1-dioxide; 2-isopropyl-5-phenyl-4-[(4-phenylbutyl)amino]isothiazol-3(2H)-one 1,1-dioxide; 2-(4-{3-[(2-tert-butyl-1,1-dioxido-3-oxo-5-phenyl-2,3-dihydroisothiazol-4-yl)amino]propoxy}phenyl)-N,N-dimethylacetamide; 2-tert-butyl-4-{[3-(2-chlorophenoxy)propyl]amino}-5-phenylisothiazol-3 (2H)-one 1,1-dioxide; 2-tert-butyl-4-{[3-(3-methoxyphenoxy)propyl]amino}-5-phenylisothiazol-3(2H)-one 1,1-dioxide; (3-{3-[(2-tert-butyl-1,1-dioxido-3-oxo-5-phenyl-2,3-dihydroisothiazol-4-yl)amino]propoxy}phenyl)acetic acid; 2-tert-butyl-5-phenyl-4-{[3-(pyridin-3-yloxy)propyl]amino}isothiazol-3 (2H)-one 1,1-dioxide; methyl (3-{3-[(2-tert-butyl-1,1-dioxido-3-oxo-5-phenyl-2,3-dihydroisothiazol-4-yl)amino]propoxy}phenyl)acetate; 2-tert-butyl-5-phenyl-4-{[3-(pyridin-4-yloxy)propyl]amino}isothiazol-3(2H)-one 1,1-dioxide; 4-(benzylamino)-2-tert-butyl-5-phenylisothiazol-3 (2H)-one 1,1-dioxide; 4-({1-[3-chloro-5-(trifluoromethyl)pyridin-2-yl]piperidin-4-yl}amino)-2-isopropyl-5-phenylisothiazol-3(2H)-one 1,1-dioxide; 2-tert-butyl-5-phenyl-4-[(2-phenylethyl)amino]isothiazol-3(2H)-one 1,1-dioxide; 2-cyclopentyl-5-phenyl-4-[(4-phenylbutyl)amino]isothiazol-3(2H)-one 1,1-dioxide; 2-tert-butyl-5-phenyl-4-{[3-(phenylthio)propyl]amino}isothiazol-3(2H)-one 1,1-dioxide 2-tert-butyl-4-[(3-phenoxypropyl)amino]-5-phenylisothiazol-3(2H)-one 1,1-dioxide; 2-tert-butyl-4-{[3-(3-chlorophenoxy)propyl]amino}-5-phenylisothiazol-3 (2H)-one 1,1-dioxide; methyl 3-{3-[(2-tert-butyl-1,1-dioxido-3-oxo-5-phenyl-2,3-dihydroisothiazol-4-yl)amino]propoxy}benzoate; 2-benzyl-5-phenyl-4-[(4-phenylbutyl)amino]isothiazol-3(2H)-one 1,1-dioxide; (4-{3-[(2-tert-butyl-1,1-dioxido-3-oxo-5-phenyl-2,3-dihydroisothiazol-4-yl)amino]propoxy}phenyl)acetic acid; 2-tert-butyl-4-{[3-(3-fluorophenoxy)propyl]amino}-5-phenylisothiazol-3 (2H)-one 1,1-dioxide; methyl (4-{3-[(2-tert-butyl-1,1-dioxido-3-oxo-5-phenyl-2,3-dihydroisothiazol-4-yl)amino]propoxy}phenyl)acetate; 2-tert-butyl-4-{[3-(4-fluorophenoxy)propyl]amino}-5-phenylisothiazol-3(2H)-one 1,1-dioxide; 2-isopropyl-5-phenyl-4-({1-[4-(trifluoromethyl)pyrimidin-2-yl]piperidin-4-yl}) amino) isothiazol-3 (2H)-one 1,1-dioxide; N-(3-{3-[(2-butyl-1,1-dioxido-3-oxo-5-phenyl-2,3-dihydroisothiazol-4-yl)amino]propoxy}phenyl)acetamide; 3-[(2-tert-butyl-1,1-dioxido-3-oxo-5-phenyl-2,3-dihydroisothiazol-4-yl)amino]propyl 4-hydroxybenzoate; 4-(benzylamino)-2-isopropyl-5-phenylisothiazol-3(2H)-one 1,1-dioxide; 2-[2-(3-fluorophenyl)ethyl]-5-phenyl-4-[(4-phenylbutyl)amino]isothiazol-3(2H)-one 1,1-dioxide; 4-[(cis-4-hydroxycyclohexyl)amino]-2-isopropyl-5-phenylisothiazol-3(2H)-one 1,1-dioxide; 2-tert-butyl-4-[(4-phenoxybutyl)amino]-5-phenylisothiazol-3 (2H)-one 1,1-dioxide; 2-tert-butyl-4-({3-[(1-oxidopyridin-3-yl)oxy]propyl}amino)-5-phenylisothiazol-3 (2H)-one 1,1-dioxide; 2-tert-butyl-4-[(2-phenoxyethyl)amino]-5-phenylisothiazol-3(2H)-one 1,1-dioxide; 4-(benzylamino)-2-cyclopentyl-5-phenylisothiazol-3(2H)-one 1,1-dioxide; 2-tert-butyl-4-{[3-(4-methoxyphenoxy)propyl]amino}-5-phenylisothiazol-3 (2H)-one 1,1-dioxide; 4-[(4,4-difluorocyclohexyl)amino]-2-isopropyl-5-phenylisothiazol-3 (2H)-one 1,1-dioxide; 2-isopropyl-4-[(2-phenoxyethyl)amino]-5-phenylisothiazol-3(2H)-one 1,1-dioxide; 5-phenyl-4-[(4-phenylbutyl)amino]-2-(tetrahydrofuran-2-ylmethyl)isothiazol-3(2H)-one 1,1-dioxide; 4-(benzylamino)-2-butyl-5-phenylisothiazol-3(2H)-one 1,1-dioxide; 2-butyl-4-(hexylamino)-5-phenylisothiazol-3(2H)-one 1,1-dioxide; 2-butyl-5-phenyl-4-[(2-phenylethyl)amino]isothiazol-3(2H)-one 1,1-dioxide; 2-butyl-4-{[4-(difluoromethoxy)benzyl]amino}-5-phenylisothiazol-3(2H)-one 1,1-dioxide; 4-[(trans-4-hydroxycyclohexyl)amino]-2-isopropyl-5-phenylisothiazol-3(2H)-one 1,1-dioxide; 2-tert-butyl-4-[(3-hydroxypropyl)amino]-5-phenylisothiazol-3(2H)-one 1,1-dioxide; 5-phenyl-4-[(4-phenylbutyl)amino]-2-(pyridin-3-ylmethyl)isothiazol-3(2H)-one 1,1-dioxide; 2-tert-butyl-4-[(2,3-dihydro-1,4-benzodioxin-2-ylmethyl)amino]-5-phenylisothiazol-3 (2H)-one 1,1-dioxide; 2-butyl-4-[(4-hydroxycyclohexyl)amino]-5-phenylisothiazol-3(2H)-one 1,1-dioxide; 4-{3-[(2-tert-butyl-1,1-dioxido-3-oxo-5-phenyl-2,3-dihydroisothiazol-4-yl)amino]propoxy}benzoic acid; 3-{4-[(2-isopropyl-1,1-dioxido-3-oxo-5-phenyl-2,3-dihydroisothiazol-4-yl)amino]piperidin-1-yl}propanenitrile; 2-tert-butyl-4-{[3-(4-chlorophenoxy)propyl]amino}-5-phenylisothiazol-3 (2H)-one 1,1-dioxide; 5-phenyl-4-[(4-phenylbutyl)amino]-2-(pyridin-4-ylmethyl)isothiazol-3(2H)-one 1,1-dioxide; 4-[(1,3-benzodioxol-5-ylmethyl)amino]-2-butyl-5-phenylisothiazol-3(2H)-one 1,1-dioxide; 4-(2,3-dihydro-1H-inden-2-ylamino)-2-(2-methoxyethyl)-5-phenylisothiazol-3(2H)-one 1,1-dioxide; 2-butyl-4-[(2-morpholin-4-ylethyl)amino]-5-phenylisothiazol-3(2H)-one 1,1-dioxide; 2-tert-butyl-4-{[3-(4-isopropylphenoxy)propyl]amino}-5-phenylisothiazol-3(2H)-one 1,1-dioxide; 4-({3-[benzyl(butyl)amino]propyl}amino)-2-tert-butyl-5-phenylisothiazol-3(2H)-one 1,1-dioxide; 2-tert-butyl-4-{[3-(3,5-dipropoxyphenoxy)propyl]amino}-5-phenylisothiazol-3(2H)-one 1,1-dioxide; 2-tert-butyl-4-[(2,2-diphenylethyl)amino]-5-phenylisothiazol-3(2H)-one 1,1-dioxide; 2-ethyl-4-{[2-(1H-imidazol-4-yl)ethyl]amino}-5-phenylisothiazol-3(2H)-one 1,1-dioxide; 2-butyl-4-[(4-morpholin-4-ylbenzyl)amino]-5-phenylisothiazol-3(2H)-one 1,1-dioxide; 2-butyl-4-{[3-(2-methoxyethoxy)propyl]amino}-5-phenylisothiazol-3(2H)-one 1,1-dioxide; 2-butyl-4-[(3-morpholin-4-ylpropyl)amino]-5-phenylisothiazol-3 (2H)-one 1,1-dioxide; 2-butyl-4-[(2-methoxyethyl)amino]-5-phenylisothiazol-3(2H)-one 1,1-dioxide; 2-(2-methoxyethyl)-5-phenyl-4-(tetrahydro-2H-pyran-4-ylamino)isothiazol-3(2H)-one 1,1-dioxide; 4-(hexylamino)-2-(2-methoxyethyl)-5-phenylisothiazol-3(2H)-one 1,1-dioxide; 4-[(4-hydroxycyclohexyl)amino]-2-(2-methoxyethyl)-5-phenylisothiazol-3(2H)-one 1,1-dioxide; 4-[(1,3-benzodioxol-5-ylmethyl)amino]-2-(2-methoxyethyl)-5-phenylisothiazol-3(2H)-one 1,1-dioxide; 2-butyl-4-[(4-methoxybenzyl)amino]-5-phenylisothiazol-3(2H)-one 1,1-dioxide; 5-phenyl-4-[(4-phenylbutyl)amino]-2-(pyridin-2-ylmethyl)isothiazol-3(2H)-one 1,1-dioxide; 2-tert-butyl-4-{[3-(3-hydroxyphenoxy)propyl]amino}-5-phenylisothiazol-3(2H)-one 1,1-dioxide; 3-{3-[(2-tert-butyl-1,1-dioxido-3-oxo-5-phenyl-2,3-dihydroisothiazol-4-yl)amino]propoxy}benzoic acid; 4-{2-[(2-tert-butyl-1,1-dioxido-3-oxo-5-phenyl-2,3-dihydroisothiazol-4-yl)amino]ethyl}phenyl methanesulfonate; 4-{2-[(2-tert-butyl-1,1-dioxido-3-oxo-5-phenyl-2,3-dihydroisothiazol-4-yl)amino]ethyl}benzenesulfonamide; 2-tert-butyl-4-({1-[3-chloro-5-(trifluoromethyl)pyridin-2-yl]piperidin-4-yl}amino)-5-phenylisothiazol-3-(2H)-one 1,1-dioxide; tert-butyl 3-{2-[(2-tert-butyl-1,1-dioxido-3-oxo-5-phenyl-2,3-dihydroisothiazol-4-yl)amino]ethyl}azetidine-1-carboxylate; 2-{2-[(2-tert-butyl-1,1-dioxido-3-oxo-5-phenyl-2,3-dihydroisothiazol-4-yl)amino]ethoxy}phenyl methanesulfonate; 4-{2-[(2-tert-butyl-1,1-dioxido-3-oxo-5-phenyl-2,3-dihydroisothiazol-4-yl)amino]ethyl}benzonitrile; 4-({4-[(2-tert-butyl-1,1-dioxido-3-oxo-5-phenyl-2,3-dihydroisothiazol-4-yl)amino]piperidin-1-yl}methyl)benzonitrile; 2-tert-butyl-4-(isopropylamino)-5-phenylisothiazol-3 (2H)-one 1,1-dioxide; 4-{2-[(2-isopropyl-1,1-dioxido-3-oxo-5-phenyl-2,3-dihydroisothiazol-4-yl)amino]ethyl}phenyl methanesulfonate; tert-butyl 3-({2-[(2-tert-butyl-1,1-dioxido-3-oxo-5-phenyl-2,3-dihydroisothiazol-4-yl)amino]ethyl}thio)pyrrolidine-1-carboxylate; 2-tert-butyl-5-phenyl-4-{[3-(pyridin-2-yloxy)propyl]amino}isothiazol-3 (2H)-one 1,1-dioxide; 2-tert-butyl-4-[(2-{[3-chloro-5-(trifluoromethyl)pyridin-2-yl]amino}ethyl)amino]-5-phenylisothiazol-3(2H)-one 1,1-dioxide; 2-tert-butyl-5-phenyl-4-({1-[2-(trifluoromethyl)benzoyl]piperidin-4-yl}amino)isothiazol-3 (2H)-one 1,1-dioxide; 2-tert-butyl-4-{[1-(5-methylpyridin-2-yl)piperidin-4-yl]amino}-5-phenylisothiazol-3 (2H)-one 1,1-dioxide; 2-tert-butyl-4-{[1-(6-chloropyridazin-3-yl)piperidin-4-yl]amino}-5-phenylisothiazol-3-(2H)-one 1,1-dioxide; tert-butyl-4-[(2-tert-butyl-1,1-dioxido-3-oxo-5-phenyl-2,3-dihydroisothiazol-4-yl)amino]piperidine-1-carboxylate; methyl 2-{2-[(2-tert-butyl-1,1-dioxido-3-oxo-5-phenyl-2,3-dihydroisothiazol-4-yl)amino]ethoxy}benzoate; methyl 3-({4-[(2-tert-butyl-1,1-dioxido-3-oxo-5-phenyl-2,3-dihydroisothiazol-4-yl)amino]piperidin-1-yl}methyl)benzoate; 2-tert-butyl-4-{[1-(6-methoxypyridazin-3-yl)piperidin-4-yl]amino}-5-phenylisothiazol-3(2H)-one 1,1-dioxide; 2-tert-butyl-4-({1-[(2-chloropyridm-3-yl)carbonyl]piperidin-4-yl}amino)-5-phenylisothiazol-3 (2H)-one 1,1-dioxide; 2-{2-[(2-isopropyl-1,1-dioxido-3-oxo-5-phenyl-2,3-dihydroisothiazol-4-yl)amino]ethoxy}phenyl methanesulfonate; 2-tert-butyl-4-{[1-(6-chloropyridin-3-yl)piperidin-4-yl]amino}-5-phenylisothiazol-3 (2H)-one 1,1-dioxide; 4-[(1-benzylpiperidin-4-yl)amino]-2-tert-butyl-5-phenylisothiazol-3(2H)-one 1,1-dioxide; 4-{2-[(2-isopropyl-1,1-dioxido-3-oxo-5-phenyl-2,3-dmydroisothiazol-4-yl)amino]ethyl}benzenesulfonamide; 4-{2-[(2-isopropyl-1,1-dioxido-3-oxo-5-phenyl-2,3-dihydroisothiazol-4-yl)amino]ethyl}benzonitrile; 2-tert-butyl-4-(ethyl amino)-5-phenylisothiazol-3(2H)-one 1,1-dioxide; 2-tert-butyl-4-({1-[(5-methylisoxazol-3-yl)methyl]piperidin-4-yl}amino)-5-phenylisothiazol-3(2H)-one 1,1-dioxide; 4-[(1-benzoylpiperidin-4-yl)amino]-2-tert-butyl-5-phenylisothiazol-3(2H)-one 1,1-dioxide; 2-tert-butyl-5-phenyl-4-{[1-(phenylacetyl)piperidin-4-yl]amino}isothiazol-3 (2H)-one 1,1-dioxide; 2-tert-butyl-5-phenyl-4-[(1-pyridin-2-ylpiperidin-4-yl)amino]isothiazol-3 (2H)-one 1,1-dioxide; 2-tert-butyl-5-phenyl-4-[(1-pyridazin-3-ylpiperidin-4-yl)amino]isothiazol-3(2H)-one 1,1-dioxide; 2-tert-butyl-5-phenyl-4-{[2-(pyridin-3-yloxy)ethyl]amino}isothiazol-3(2H)-one 1,1-dioxide; 2-tert-butyl-4-{[1-(5-fluoropyridin-2-yl)piperidin-4-yl]amino}-5-phenylisothiazol-3(2H)-one 1,1-dioxide; 2-tert-butyl-4-{[3-(3,5-dimethyl-1H-pyrazol-1-yl)propyl]amino}-5-phenylisothiazol-3(2H)-one 1,1-dioxide; 2-tert-butyl-4-{[1-(2-chloro-6-methylisonicotinoyl)piperidin-4-yl]amino}-5-phenylisothiazol-3(2H)-one 1,1-dioxide; 2-tert-butyl-4-{[1-(5-chloropyridin-2-10 yl)piperidin-4-yl]amino}-5-phenylisothiazol-3(2H)-one 1,1-dioxide; 2-tert-butyl-5-phenyl-4-({1-[4-(trifluoromethyl)pyridin-2-yl]piperidin-4-yl}amino)isothiazol-3(2H)-one 1,1-dioxide; 4-({4-[(2-tert-butyl-1,1-dioxido-3-oxo-5-phenyl-2,3-dihydroisothiazol-4-yl)amino]piperidin-1-yl}carbonyl)benzonitrile; 2-tert-butyl-4-{[1-(3,4-difluorobenzoyl)piperidin-4-yl]amino}-5-phenylisothiazol-3 (2H)-one 1,1-dioxide; 4-[(1-acetylpiperidin-4-yl)amino]-2-tert-butyl-5-phenylisothiazol-3(2H)-one 1,1-dioxide; 3-{2-[(2-isopropyl-1,1-dioxido-3-oxo-5-phenyl-2,3-dihydroisothiazol-4-yl)amino]ethyl}benzonitrile; 2-tert-butyl-5-phenyl-4-({2-[2-(trifluoromethoxy)phenyl]ethyl}amino)isothiazol-3(2H)-one 1,1-dioxide; 4-{2-[(2-tert-butyl-1,1-dioxido-3-oxo-5-phenyl-2,3-dihydroisothiazol-4-yl)amino]ethoxy}phenyl methanesulfonate; 4-[(1-benzylpyrrolidin-3-yl)amino]-2-tert-butyl-5-phenylisothiazol-3(2H)-one 1,1-dioxide; 4-({1-[3-chloro-5-(trifluoromethyl)pyridin-2-yl]azetidin-3-yl}amino)-2-isopropyl-5-phenylisothiazol-3 (2H)-one 1,1-dioxide; N-benzyl-N-(2-tert-butyl-1,1-dioxido-3-oxo-5-phenyl-2,3-dihydroisothiazol-4-yl-glycinamide; 2-tert-butyl-4-[(1-isobutyrylpiperidin-4-yl)amino]-5-phenylisothiazol-3(2H)-one 1,1-dioxide; 2-tert-butyl-5-phenyl-4-[(2-pyridin-2-ylethyl)amino]isothiazol-3(2H)-one 1,1-dioxide; 2-tert-butyl-4-{[2-(2-chlorophenyl)ethyl]amino}-5-phenylisothiazol-3(2H)-one 1,1-dioxide; 2-tert-butyl-5-phenyl-4-{[1-(2-phenylethyl)piperidin-4-yl]amino}isothiazol-3(2H)-one 1,1-dioxide; 2-tert-butyl-5-phenyl-4-({2-[3-(trifluoromethyl)phenyl]ethyl}amino)isothiazol-3(2H)-one 1,1-dioxide; 2-tert-butyl-5-phenyl-4-[(4-{[4-(trifluoromethyl)phenyl]thio}cyclohexyl)amino]isothiazol-3(2H)-one 1,1-dioxide; 2-tert-butyl-5-phenyl-4-[(2-{[3-(trifluoromethoxy)phenyl]thio}ethyl)amino]isothiazol-3 (2H)-one 1,1-dioxide; 2-tert-butyl-4-{[2-(4-chlorophenoxy)ethyl]amino}-5-phenylisothiazol-3(2H)-one 1,1-dioxide; 2-tert-butyl-5-phenyl-4-({1-[5-(trifluoromethyl)pyridin-2-yl]piperidin-4-yl}amino)isothiazol-3(2H)-one 1,1-dioxide; 2-tert-butyl-5-phenyl-4-({2-[3-(trifluoromethoxy)phenoxy]ethyl}amino)isothiazol-3(2H)-one 1,1-dioxide; tert-butyl 3-{2-[(2-tert-butyl-1,1-dioxido-3-oxo-5-phenyl-2,3-dihydroisothiazol-4-yl)amino]ethoxy}azetidine- 1-carboxylate; 2-tert-butyl-4-[(2,2-dimethylpropyl)amino]-5-phenylisothiazol-3(2H)-one 1,1-dioxide; 2-tert-butyl-4-(tert-butylamino)-5-phenylisothiazol-3(2H)-one 1,1-dioxide; methyl ({[(2-tert-butyl-1,1-dioxido-3-oxo-5-phenyl-2,3-dihydroisothiazol-4-yl)amino]acetyl}amino) acetate; 2-tert-butyl-5-phenyl-4-(piperidin-4-ylamino) isothiazol-3 (2H)-one 1,1-dioxide; 2-tert-butyl-4-[(1-methylpiperidin-4-yl)amino]-5-phenylisothiazol-3 (2H)-one 1,1-dioxide; 2-tert-butyl-4-[(2-hydroxyethyl)amino]-5-phenylisothiazol-3(2H)-one 1,1-dioxide; 4-{[2-(biphenyl-2-yl-thio)ethyl]amino}-2-tert-butyl-5-phenylisothiazol-3(2H)-one 1,1-dioxide; 2-tert-butyl-5-phenyl-4-{[2-(pyrrolidin-3-ylthio)ethyl]amino}isothiazol-3(2H)-one 1,1-dioxide; 2-tert-butyl-4-{[(5-methyl-3-phenylisoxazol-4-yl)methyl]amino}-5-phenylisothiazol-3 (2H)-one 1,1-dioxide; 2-tert-butyl-5-phenyl-4-{[(1,3,5-trimethyl-1H-pyrazol-4-yl) methyl]amino}isothiazol-3(2H)-one 1,1-dioxide; 2-tert-butyl-5-phenyl-4-[(2-{[5-(trifluoromethyl)pyridin-2-yl]oxy)}ethyl)amino]isothiazol-3(2H)-one 1,1-dioxide; 2-tert-butyl-5-phenyl-4-({2-[4-(trifluoromethoxy)phenyl] ethyl}amino)isothiazol-3(2H)-one 1,1-dioxide; 2-tert-butyl-5-phenyl-4-[(2,2,2-trifluoroethyl)amino]isothiazol-3(2H)-one 1,1-dioxide; 2-tert-butyl-4-[(2,3-dihydroxypropyl)amino]-5-phenylisothiazol-3(2H)-one 1,1-dioxide; 3-[(2-tert-butyl-1,1-dioxido-3-oxo-5-phenyl-2,3-dihydroisothiazol-4-yl)amino]propanenitrile; 4-{[2-(3,4-dimethoxyphenyl)ethyl]amino}-2-isopropyl-5-phenylisothiazol-3(2H)-one 1,1-dioxide; 4-{[2-(3-chloro-4-methoxyphenyl)ethyl]amino}-2-isopropyl-5-phenylisothiazol-3(2H)-one 1,1-dioxide; 4-{2-[(2-isobutyl-1,1-dioxido-3-oxo-5-phenyl-2,3-dihydroisothiazol-4-yl) amino]ethyl}phenyl methanesulfonate; 2-isopropyl-5-phenyl-4-[(1-pyridin-2-ylpiperidin-4-yl)amino]isothiazol-3 (2H)-one 1,1-dioxide; 4-(2-{[2-(4-fluorobenzyl)-1,1-dioxido-3-oxo-5-phenyl-2,3-dihydroisothiazol-4-yl] amino}ethyl)phenyl methanesulfonate; 2-isopropyl-4-(isopropylamino)-5-phenylisothiazol-3(2H)-one 1,1-dioxide; 2-isopropyl-5-phenyl-4-[(1-pyridin-2-yl-azetidin-3-yl) amino]isothiazol-3(2H)-one 1,1-dioxide; 2-tert-butyl-4-{[(5-methylisoxazol-3-yl)methyl]amino}-5-phenylisothiazol-3(2H)-one 1,1-dioxide; 4-{[2-(4-hydroxy-3,5-dimethoxyphenyl)ethyl]amino}2-isopropyl-5-phenylisothiazol-3 (2H)-one 1,1-dioxide; 4-{[2-(2-aminopyridin-4-yl)ethyl] amino}-2-isopropyl-5-phenylisothiazol-3(2H)-one 1,1-dioxide; 2-isopropyl-5-phenyl-4-[(2-pyridin-4-ylethyl) amino]isothiazol-3(2H)-one 1,1-dioxide; 2-isopropyl-5-phenyl-4-[(2-pyridin-3-ylethyl)amino]isothiazol-3(2H)-one 1,1-dioxide; 4-{[2-(3,5-dimethylisoxazol-4-yl)ethyl] amino}-2-isopropyl-5-phenylisothiazol-3(2H)-one 1,1-dioxide; 4-[2-({2-[(5-methylisoxazol-3-yl)methyl]-1,1-dioxido-3-oxo-5-phenyl-2,3-dihydroisothiazol-4-yl}amino) ethyl]phenyl methanesulfonate; 4-{[2-(3,5-dimethyl-1H-pyrazol-4-yl)ethyl]amino}-2-isopropyl-5-phenylisothiazol-3(2H)-one 1,1-dioxide; 4-[2-({2-[(methylthio)methyl]-1,1-dioxido-3-oxo-5-phenyl-2,3-dihydroisothiazol-4-yl}amino) ethyl]phenyl methanesulfonate; 2,6-dimethylphenyl 4-[(2-tert-butyl-1,1-dioxido-3-oxo-5-phenyl-2,3-dihydroisothiazol-4-yl)amino]butanoate; 2-mesitylethyl N-(2-tert-butyl-1,1-dioxido-3-oxo-5-phenyl-2,3-dihydroisothiazol-4-yl)glycinate; 2-[(2-tert-butyl-1,1-dioxido-3-oxo-5-phenyl-2,3-dihydroisothiazol-4-yl)amino]ethyl (2,6-dimethylphenyl)acetate; phenyl N-(2-tert-butyl-1,1-dioxido-3-oxo-5-phenyl-2,3-dihydroisothiazol-4-yl)-beta-alaninate; 4-(trifluoromethoxy)phenyl N-(2-tert-butyl-1,1-dioxido-3-oxo-5-phenyl-2,3-dihydroisothiazol-4-yl)-beta-alaninate; 1-methylpiperidin-4-yl N-(2-tert-butyl-1,1-dioxido-3-oxo-5-phenyl-2,3-dihydroisothiazol-4-yl)-beta-alaninate; 2-mesityl-1-methyl ethyl[(2-tert-butyl-1,1-dioxido-3-oxo-5-phenyl-2,3-dihydroisothiazol-4-yl)amino]acetate; 4-methoxybenzyl N-(2-tert-butyl-1,1-dioxido-3-oxo-5-phenyl-2,3-dihydroisothiazol-4-yl)glycinate; or 4-methoxyphenyl N-(2-tert-butyl-1,1-dioxido-3-oxo-5-phenyl-2,3-dihydroisothiazol-4-yl)glycinate; or pharmaceutically acceptable salts thereof.

In other embodiments of any of the foregoing methods, the LXR agonist is a compound described in U.S. Patent Publication No. US2009/0247587, e.g., any one of: 5-(2H-1,3-benzodioxol-5-yl)-5-methyl-3-(4-{[7-propyl-3,3-bis(trifluoromethyl)-2,3-dihydro-1-benzofuran-6-yl]oxy}butyl) imidazolidine-2,4-dione; 5-(3-methoxyphenyl)-5-methyl-3-(4-{[7-propyl-3,3-bis(trifluoromethyl)-2,3-dihydro-1l-benzofuran-6-yl]oxy}butyl)imidazolidine-2,4-dione; 5-(3-bromo-4-fluorophenyl)-5-methyl-3-(4-{[7-propyl-3,3-bis(trifluoromethyl)-2,3-dihydro-1-benzofuran-6-yl]oxy}butyl)imidazolidine-2,4-dione; 5,5-dimethyl-3-(5-{[7-propyl-3,3-bis(trifluoromethyl)-2,3-dihydro-1-benzofuran-6-yl]oxy}pentyl)imidazolidine-2,4-dione; 5,5-dimethyl-3-(7-{[7-propyl-3,3-bis(trifluoromethyl)-2,3-dihydro-1-benzofuran-6-yl]oxy}heptyl)imidazolidine-2,4-dione; 3-(4-{[5,7-dipropyl-3,3-bis(trifluoromethyl)-2,3-dihydro-1-benzofuran-6-yl]oxy}butyl)-5-methyl-5-phenylimidazolidine-2,4-dione; 3-(4-{[5,7-dipropyl-3,3-bis(trifluoromethyl)-2,3-dihydro-1-benzofuran-6-yl]oxy}butyl)-5-(4-ethoxyphenyl)-5-methylimidazolidine-2,4-dione; 3-(4-{[5,7-dipropyl-3,3-bis(trifluoromethyl)-2,3-dihydro-1-benzofuran-6-yl]oxy}butyl)-5-methyl-5-(4-propoxyphenyl)imidazolidine-2,4-dione; or 3-(4-{[5,7-dipropyl-3,3-bis(trifluoromethyl)-2,3-dihydro-1-benzofuran-6-yl]oxy}butyl)-5-methyl-5-[4-(propan-2-yloxy)phenyl]imidazolidine-2,4-dione; or pharmaceutically acceptable salts thereof.

In further embodiments of any of the foregoing methods, the LXR agonist is a compound described in International Patent Publication No. WO2009/133692, e.g., any one of: 5-(2H-1,3-benzodioxol-5-yl)-3-(6-{[3-benzyl-8-(trifluoromethyl)quinolin-4-yl]oxy}hexyl)-5-methylimidazolidine-2,4-dione; 3-(6-{[3-benzyl-8-(trifluoromethyl)quinolin-4-yl]oxy}hexyl)-5-methyl-5-(quinoxalin-6-yl)imidazolidine-2,4-dione; 5-(2H-1,3-benzodioxol-5-yl)-3-(3-{3-[3-benzyl-8-(trifluoromethyl)quinolin-4-yl]phenoxy}propyl)-5-methylimidazolidine-2,4-dione; 3-(3-{3-[3-benzyl-8-(trifluoromethyl)quinolin-4-yl]phenoxy}propyl)-5-methyl-5-[4-(propan-2-yloxy)phenyl]imidazolidine-2,4-dione; 5-(2H-1,3-benzodioxol-5-yl)-3-(4-{3-[3-benzyl-8-(trifluoromethyl)quinolin-4-yl]phenoxy}butyl)-5-methylimidazolidine-2,4-dione; 3-(4-{3-[3-benzyl-8-(trifluoromethyl)quinolin-4-yl]phenoxy}butyl)-5-methyl-5-[4-(propan-2-yloxy) phenyl]imidazolidine-2,4-dione; or 5-methyl-5-[3-(propan-2-yloxy)phenyl]-3-(6-{[3-propyl-8-(trifluoromethyl) quinolin-4-yl]oxy}hexyl)imidazolidine-2,4-dione; or pharmaceutically acceptable salts thereof.

In some embodiments of any of the foregoing methods, the LXR agonist is a compound described in International Patent Publication No. WO2010/125811, e.g., any one of: 3-(2-{4-[4-(1,1,1,3,3,3-hexafluoro-2-hydroxypropan-2-yl)-2-propylphenyl]piperazin-1-yl}-2-oxoethyl)-5-methyl-5-[5-(propan-2-yloxy)pyridin-2-yl]imidazolidine-2,4-dione; 3-(2-{4-[4-(1,1,1,3,3,3-hexafluoro-2-hydroxypropan-2-yl)-2-propylphenyl]piperazin-1-yl}-2-oxoethyl)-5-methyl-5-[4-(propan-2-yloxy)phenyl]imidazolidine-2,4-dione; 5-(2H-1,3-benzodioxol-5-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione; 3-{2-[(3R)-4-[4-(1,1,1,3,3,3-hexafluoro-2-hydroxypropan-2-yl)-2- propylphenyl]-3-methylpiperazin-1-yl]-2-oxoethyl}-5-methyl-5-[4-(propan-2-yloxy)phenyl]imidazolidine-2,4-dione; 3-{2-[(3 S)-4-[4-(1,1,1,3,3,3-hexafluoro-2-hydroxypropan-2-yl)-2-propylphenyl]-3-methylpiperazin-1-yl]-2-oxoethyl}-5-methyl-5-[4-(propan-2-yloxy)phenyl]imidazolidine-2,4-dione; 3-{2-[(2R,5S)-4-[4-(1,1,1,3,3,3-hexafluoro-2-hydroxypropan-2-yl)-2-[(1Z)-prop-1-en-1-yl]phenyl]-2,5-dimethylpiperazin-1-yl]-2-oxoethyl)}-5-methyl-5-[4-(propan-2-yloxy)phenyl]imidazolidine-2,4-dione; 3-{2-[(2R,5S)-4-[4-(1,1,1,3,3,3-hexafluoro-2-hydroxypropan-2-yl)-2-propylphenyl]-2,5-dimethylpiperazin-1-yl]-2-oxoethyl}-5-methyl-5-[4-(propan-2-yloxy)phenyl]imidazolidine-2,4-dione; 5-(2,3-dihydro-1-benzofuran-5-yl)-3-{2-[(2R,5S)-4-[4-(1,1,1,3,3,3-hexafluoro-2-hydroxypropan-2-yl)-2-[(1Z)-prop-1-en-1-yl]phenyl]-2,5-dimethylpiperazin-1-yl]-2-oxoethyl}-5-methylimidazolidine-2,4-dione; 5-(2,3-dihydro-1-benzofuran-5-yl)-3-{2-[(2R,5S)-4-[4-(1,1,1,3,3,3-hexafluoro-2-hydroxypropan-2-yl)-2-propylphenyl]-2,5-dimethylpiperazin-1-yl]-2-oxoethyl}-5-methylimidazolidine-2,4-dione; 5-(2,2-dimethyl-2,3-dihydro-1-benzofuran-5-yl)-3-{2-[(3 S)-4-[4-(1,1,1,3,3,3-hexafluoro-2-hydroxypropan-2-yl)-2-propylphenyl]-3-methylpiperazin-1-yl]-2-oxoethyl}-5-methylimidazolidine-2,4-dione; 3-{2-[(2R,5S)-4-[4-(1,1,1,3,3,3-hexafluoro-2-hydroxypropan-2-yl)-2-[(1Z)-prop-1-en-1-yl]phenyl]-2,5-dimethylpiperazin-1-yl]-2-oxoethyl)}-5-methyl-5-[5-(propan-2-yloxy)pyridin-2-yl]imidazolidine-2,4-dione; 3-{2-[(2R,5S)-4-[4-(1,1,1,3,3,3-hexafluoro-2-hydroxypropan-2-yl)-2-propylphenyl]-2,5-dimethylpiperazin-1-yl]-2-oxoethyl}-5-methyl-5-[5-(propan-2-yloxy)pyridin-2-yl]imidazolidine-2,4-dione; 5-[4-(cyclopropylsulfanyl)phenyl]-3-{2-[(2R,5S)-4-[4-(1,1,1,3,3,3-hexafluoro-2-hydroxypropan-2-yl)-2-[(1Z)-prop-1-en-1-yl]phenyl]-2,5-dimethylpiperazin-1-yl]-2-oxoethyl}-5-methylimidazolidine-2,4-dione; 5-(2,3-dihydro-1-benzofuran-5-yl)-3-(2-{4-[4-(1,1,1,3,3,3-hexafluoro-2-hydroxypropan-2-yl)-2-propylphenyl]-1,4-diazepan-1-yl}-2-oxoethyl)-5-methylimidazolidine-2,4-dione; 5-{2H,3H-[1,4]dioxino[2,3-b]pyridin-7-yl}-3-{2-[(3 S)-4-[4-(1,1,1,3,3,3-hexafluoro-2-hydroxypropan-2-yl)-2-propylphenyl]-3-methylpiperazin-1-yl]-2-oxoethyl}-5-methylimidazolidine-2,4-dione; 5-(1-benzofuran-6-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione; or 5-(1-benzofuran-5-yl)-3-{2-[(3 S)-4-[4-(1,1,1,3,3,3-hexafluoro-2-hydroxypropan-2-yl)-2-propylphenyl]-3-methylpiperazin-1-yl]-2-oxoethyl}-5-methylimidazolidine-2,4-dione; or pharmaceutically acceptable salts thereof.

In other embodiments of any one of the foregoing methods, the LXR agonist is a compound described in International Patent Publication No. WO2009/138438, e.g., any one of: 1-(cyclopropylmethyl)-3-(4-(4-(4-(1,1,3,3,3-hexafluoro-2-hydroxypropan-2-yl)-benzyl)piperazine-1-carbonyl)phenyl)urea; 1-butyl-3-(4-(4-(4-(1,1,1,3,3,3-hexafluoro-2-hydroxypropan-2-yl)benzyl)piperazine-1-carbonyl)phenyl)urea; 1-(4-(4-(4-(1,1,1,3,3,3-hexafluoro-2-hydroxypropan-2-yl)benzyl)piperazine-1-carbonyl)phenyl)-3-isobutylurea; 1-cyclobutyl-3-(4-(4-(4-(1,1,1,3,3,3-hexafluoro-2-hydroxypropan-2-yl)benzyl)-piperazine-1-carbonyl)phenyl)urea; 1-(2-fluoro-4-(4-(4-(1,1,1,3,3,3-hexafluoro-2-hydroxypropan-2-yl)benzyl)piperazine-1-carbonyl)phenyl)-3-(2-hydroxy-2-methylpropyl)urea; 1-(2-fluoro-4-(4-(4-(1,1,1,3,3,3-hexafluoro-2-hydroxypropan-2-yl)benzyl)piperazine-1-carbonyl)phenyl)-3-(3-hydroxy-3-methylbutyl)urea; 1-(cyclopropylmethyl)-3-(2-fluoro-4-(4-(4-(1,1,1,3,3,3-hexafluoro-2-hydroxypropan-2-yl)benzyl) piperazine-1-carbonyl)phenyl)urea; (S)-1-(2-fluoro-4-(4-(4-(1,1,1,3,3,3-hexafluoro-2-hydroxypropan-2-yl)benzyl)-piperazine-1-carbonyl)phenyl)-3-(2-hydroxypropyl)urea; (R)-1-(2-fluoro-4-(4-(4-(1,1,1,3,3,3-hexafluoro-2-hydroxy-propan-2-yl)benzyl)-piperazine-1-carbonyl)phenyl)-3-(2-hydroxypropyl)urea; 1-(2-fluoro-4-(4-(4-(1,1,1,3,3,3-hexafluoro-2-hydroxypropan-2-yl)benzyl)piperazine-1-carbonyl)phenyl)-3-((1-hydroxycyclopropyl)methyl)urea; (S)-1-(2-fluoro-4-(4-(4-(1,1,1,3,3,3-hexafluoro-2-hydroxy-propan-2-yl)benzyl)-piperazine-1-carbonyl)phenyl)-3-(1-hydroxy-3-methylbutan-2-yl)urea; trans-1-(2-fluoro-4-(4-(4-(1,1,1,3,3,3-hexafluoro-2-hydroxypropan-2-yl)benzyl)piperazine-1-carbonyl)phenyl)-3-(4-hydroxycyclohexyl)urea; (S)-1-(2-fluoro-4-(4-(4-(1,1,1,3,3,3-hexafluoro-2-hydroxypropan-2-yl)benzyl)-piperazine-1-carbonyl)phenyl)-3-(1-hydroxypentan-2-yl)urea; 1-(2-chloro-4-(4-(4-(1,1,1,3,3,3-hexafluoro-2-hydroxypropan-2-yl)benzyl)piperazine-1-carbonyl)phenyl)-3-(2-hydroxy-2-methylpropyl)urea; (S)-1-(2-chloro-4-(4-(4-(1,1,1,3,3,3-hexafluoro-2-hydroxypropan-2-yl)benzyl)-piperazine-1-carbonyl)phenyl)-3-(2-hydroxypropyl)urea; (R)-1-(2-chloro-4-(4-(4-(1,1,1,3,3,3-hexafluoro-2-hydroxypropan-2-yl)benzyl)-piperazine-1-carbonyl)phenyl)-3-(2-hydroxypropyl)urea; 1-(2-chloro-4-(4-(4-(1,1,1,3,3,3-hexafluoro-2-hydroxypropan-2-yl)benzyl)piperazine-1-carbonyl)phenyl)-3-(3-hydroxy-3-methylbutyl)urea; 1-(2-chloro-4-(4-(4-(1,1,1,3,3,3-hexafluoro-2-hydroxypropan-2-yl)benzyl)piperazine-1-carbonyl)phenyl)-3-((1-hydroxycyclopropyl)methyl)urea; trans-1-(2-chloro-4-(4-(4-(1,1,1,3,3,3-hexafluoro-2-hydroxypropan-2-yl)benzyl) piperazine-1-carbonyl)phenyl)-3-(4-hydroxycyclohexyl)urea; 1-(2-amino-2-methylpropyl)-3-(2-fluoro-4-(4-(4-(1,1,1,3,3,3-hexafluoro-2-hydroxypropan-2-yl)benzyl)piperazine-1-carbonyl)phenyl)urea; 1-(2-fluoro-4-(4-(4-(1,1,1,3,3,3-hexafluoro-2-hydroxypropan-2-yl)benzyl)piperazine-1-carbonyl)phenyl)-3-((1S,2R)-2-hydroxycyclopentyl)urea; 1-(2-fluoro-4-(4-(4-(1,1,1,3,3,3-hexafluoro-2-hydroxypropan-2-yl)benzyl)piperazine-1-carbonyl)phenyl)-3-(3-hydroxycyclobutyl)urea; 1-(2-fluoro-4-(4-(4-(1,1,1,3,3,3-hexafluoro-2-hydroxypropan-2-yl)benzyl)piperazine-1-carbonyl)phenyl)-3-((1-hydroxycyclobutyl)methyl)urea; 1-(2-(dimethylamino)-2-methylpropyl)-3-(2-fluoro-4-(4-(4-(1,1,1,3,3,3-hexafluoro-2-hydroxypropan-2-yl)benzyl)piperazine-1-carbonyl) phenyl)urea; 1-(2-fluoro-4-(4-(4-(1,1,1,3,3,3-hexafluoro-2-hydroxypropan-2-yl)benzyl)piperazine-1-carbonyl)phenyl)-3-(3,3,3-trifluoro-2-hydroxypropyl)urea; 1-(2-fluoro-4-(4-(1,1,1,3,3,3-hexafluoro-2-hydroxypropan-2-yl)benzyl) piperazine-1-carbonyl)phenyl)-3-(tetrahydro-2H-pyran-4-yl)urea; (R)-1-(2-fluoro-4-(4-(4-(1,1,1,3,3,3-hexafluoro-2-hydroxypropan-2-yl)benzyl)piperazine-1-carbonyl)phenyl)-3-(2-hydroxy-2-phenylethyl)urea; (S)-1-(2-fluoro-4-(4-(4-(1,1,1,3,3,3-hexafluoro-2-hydroxypropan-2-yl)benzyl) piperazine-1-carbonyl)phenyl)-3-(2-hydroxy-2-phenylethyl)urea; (S)-1-(2-fluoro-4-(4-(4-(1,1,1,3,3,3-hexafluoro-2-hydroxypropan-2-yl)benzyl)-piperazine-1-carbonyl)phenyl)-3-(6-oxopiperidin-3-yl)urea; cis-1-(2-fluoro-4-{4-[4-(2,2,2-trifluoro-1-hydroxy-1-trifluoromethyl-ethyl)-benzyl]-piperazine-1-carbonyl}-phenyl)-3-(4-hydroxy-1,1-dioxo-tetrahydro-1$\lambda$6-thiophen-3-yl)-urea; 1-(1,1-dioxo-tetrahydro-1$\lambda$6-thiophen-3-yl)-3-(2-fluoro-4-{4-[4-(2,2,2-trifluoro-1-hydroxy-1-trifluoromethyl-ethyl)benzyl]piperazine-1-carbonyl}phenyl)urea; (R)-1-(2-fluoro-4-(4-(4-(1,1,1,3,3,3-hexafluoro-2-hydroxypropan-2-yl)benzyl)-piperazine-1-carbonyl)phenyl)-3-(tetrahydrofuran-3-yl)urea; 1-(1,1-dioxo-hexahydro-1$\lambda$6-thiopyran-4-yl)-3-(2-fluoro-4-{4-[4-

(2,2,2-trifluoro-1-hydroxy-1-trifluoromethyl-ethyl)benzyl]piperazine-1-carbonyl}phenyl)urea; 1-(2-fluoro-4-(4-(4-(1,1,1,3,3,3-hexafluoro-2-hydroxypropan-2-yl)benzyl)piperazine-1-carbonyl)phenyl)-3-((4-hydroxytetrahydro-2H-pyran-4-yl)methyl)urea; (S)-1-(2-fluoro-4-(4-(4-(1,1,1,3,3,3-hexafluoro-2-hydroxypropan-2-yl)benzyl)-piperazine-1-carbonyl)phenyl)-3-(tetrahydrofuran-3-yl)urea; cis-1-(2-fluoro-4-(4-(4-(1,1,1,3,3,3-hexafluoro-2-hydroxypropan-2-yl)benzyl)piperazine-1-carbonyl)phenyl)-3-(4-hydroxytetrahydrofuran-3-yl)urea; 1-(2-fluoro-4-(4-(4-(1,1,1,3,3,3-hexafluoro-2-hydroxypropan-2-yl)benzyl)piperazine-1-carbonyl)phenyl)-3-((1 S,2R)-2-hydroxycyclohexyl)urea; 1-(2-fluoro-4-(4-(4-(1,1,1,3,3,3-hexafluoro-2-hydroxypropan-2-yl)benzyl)piperazine-1-carbonyl)phenyl)-3-(2-hydroxybutyl)urea; cis-1-(2-chloro-4-{4-[4-(2,2,2-trifluoro-1-hydroxy-1-trifluoromethyl-ethyl)-benzyl]-piperazine-1-carbonyl}-phenyl)-3-(4-hydroxy-1,1-dioxo-tetrahydro-1λ6-thiophen-3-yl)urea; 1-(5-tert-butylisoxazol-3-yl)-3-(2-fluoro-4-(4-(4-(1,1,1,3,3,3-hexafluoro-2-hydroxy-propan-2-yl)benzyl)piperazine-1-carbonyl)phenyl)urea; 1-(2-fluoro-4-(4-(4-(1,1,1,3,3,3-hexafluoro-2-hydroxypropan-2-yl)benzyl)piperazine-1-carbonyl)phenyl)-3-(2-methylpyridin-4-yl)urea; 1-(2-fluoro-4-(4-(4-(1,1,1,3,3,3-hexafluoro-2-hydroxypropan-2-yl)benzyl)piperazine-1-carbonyl)phenyl)-3-(2-(trifluoromethyl)pyridin-4-yl)urea; 1-(2-fluoro-4-(4-(4-(1,1,1,3,3,3-hexafluoro-2-hydroxypropan-2-yl)benzyl)piperazine-1-carbonyl)phenyl)-3-(5-methylisoxazol-3-yl)urea; 1-(2-fluoro-4-(4-(4-(1,1,1,3,3,3-hexafluoro-2-hydroxypropan-2-yl)benzyl)piperazine-1-carbonyl)phenyl)-3-(3-fluoropyridin-4-yl)urea; 1-(2-fluoro-4-(4-(4-(1,1,1,3,3,3-hexafluoro-2-hydroxypropan-2-yl)benzyl)piperazine-1-carbonyl)phenyl)-3-(1,3,4-thiadiazol-2-yl)urea; 1-(2-fluoro-4-(4-(4-(1,1,1,3,3,3-hexafluoro-2-hydroxypropan-2-yl)benzyl)piperazine-1-carbonyl)phenyl)-3-(pyridin-4-yl)urea; 1-(2-fluoro-4-(4-(4-(1,1,1,3,3,3-hexafluoro-2-hydroxypropan-2-yl)benzyl)piperazine-1-carbonyl)phenyl)-3-(isoxazol-3-yl)urea; 1-(5-cyanothiazol-2-yl)-3-(2-fluoro-4-(4-(4-(1,1,1,3,3,3-hexafluoro-2-hydroxypropan-2-yl)benzyl)piperazine-1-carbonyl)phenyl)urea; 1-(2-fluoro-4-(4-(4-(1,1,1,3,3,3-hexafluoro-2-hydroxypropan-2-yl)benzyl)piperazine-1-carbonyl)phenyl)-3-(isoxazol-4-yl)urea; 1-(2-fluoro-4-(4-(4-(1,1,1,3,3,3-hexafluoro-2-hydroxypropan-2-yl)benzyl)piperazine-1-carbonyl)phenyl)-3-(pyridin-2-yl)urea; 1-(2-fluoro-4-(4-(4-(1,1,1,3,3,3-hexafluoro-2-hydroxypropan-2-yl)benzyl)piperazine-1-carbonyl)phenyl)-3-(3-methylisoxazol-5-yl)urea; 1-(2-fluoro-4-(4-(4-(1,1,1,3,3,3-hexafluoro-2-hydroxypropan-2-yl)benzyl)piperazine-1-carbonyl)phenyl)-3-(3-methyl-1,2,4-oxadiazol-5-yl)urea; 1-(2-fluoro-4-(4-(4-(1,1,1,3,3,3-hexafluoro-2-hydroxypropan-2-yl)benzyl)piperazine-1-carbonyl)phenyl)-3-(pyridin-3-yl)urea; 1-(2-fluoro-4-(4-(4-(1,1,1,3,3,3-hexafluoro-2-hydroxypropan-2-yl)benzyl)piperazine-1-carbonyl)phenyl)-3-(pyrimidin-4-yl)urea; 1-(2-fluoro-4-(4-(4-(1,1,1,3,3,3-hexafluoro-2-hydroxypropan-2-yl)benzyl)piperazine-1-carbonyl)phenyl)-3-(pyrazin-2-yl)urea; 1-(2-fluoro-4-{4-[4-(2,2,2-trifluoro-1-hydroxy-1-trifluoromethyl-ethyl)-benzyl]-piperazine-1-carbonyl}-phenyl)-3-(1-oxo-tetrahydro-thiopyran-4-yl)-urea; or 1-(2-fluoro-4-{4-[4-(2,2,2-trifluoro-1-hydroxy-1-trifluoromethyl-ethyl)-benzyl]-piperazine-1-carbonyl}-phenyl)-3-(1-oxo-tetrahydro-thiophen-3-yl)-urea; or pharmaceutically acceptable salts thereof.

In further embodiments of any of the foregoing methods, the LXR agonist is a compound described in International Patent Publication No. WO2010/025179, e.g., any one of: N-tert-butyl-5-((4-(4-(3-cyclobutylureido)-3-fluorobenzoyl)piperazin-1-yl)methyl)furan-2-carboxamide; N-tert-butyl-5-((4-(3-fluoro-4-(3-isobutylureido)benzoyl)piperazin-1-yl)methyl)furan-2-carboxamide; N-tert-butyl-5-((4-(4-(3-(cyclopropylmethyl)ureido)-3-fluorobenzoyl)piperazin-1-yl)methyl)furan-2-carboxamide; N-tert-butyl-5-((4-(3-fluoro-4-(3-neopentylureido)benzoyl)piperazin-1-yl)methyl)furan-2-carboxamide; N-tert-butyl-5-((4-(3-fluoro-4-(3-isopentylureido)benzoyl)piperazin-1-yl)methyl)furan-2-carboxamide; N-tert-butyl-5-((4-(4-(3-butylureido)-3-fluorobenzoyl)piperazin-1-yl)methyl)furan-2-carboxamide hydrochloride; N-tert-butyl-5-((4-(3-chloro-4-(3-neopentylureido)benzoyl)piperazin-1-yl)methyl)furan-2-carboxamide; N-tert-butyl-5-((4-(3-chloro-4-(3-isobutylureido)benzoyl)piperazin-1-yl)methyl)furan-2-carboxamide; N-tert-butyl-5-((4-(3-chloro-4-(3-(cyclopropylmethyl)ureido)benzoyl)piperazin-1-yl)methyl)furan-2-carboxamide; N-tert-butyl-5-((4-(3-chloro-4-(3-cyclobutylureido)benzoyl)piperazin-1-yl)methyl)furan-2-carboxamide; N-tert-butyl-5-((4-(3-chloro-4-(3-isopentylureido)benzoyl)piperazin-1-yl)methyl)furan-2-carboxamide; N-tert-butyl-5-((4-(4-(3-butylureido)-3-chlorobenzoyl)piperazin-1-yl)methyl)furan-2-carboxamide; N-tert-butyl-5-((4-(4-(3-(cyclopropylmethyl)ureido)-2,3-difluorobenzoyl)piperazin-1-yl)methyl)furan-2-carboxamide; N-tert-butyl-5-((4-(2,3-difluoro-4-(3-neopentylureido)benzoyl)piperazin-1-yl)methyl)furan-2-carboxamide; N-tert-butyl-5-((4-(2,3-difluoro-4-(3-isobutylureido)benzoyl)piperazin-1-yl)methyl)furan-2-carboxamide; N-tert-butyl-5-((4-(4-(3-cyclobutylureido)-2,3-difluorobenzoyl)piperazin-1-yl)methyl)furan-2-carboxamide; N-tert-butyl-5-((4-(4-(3-butylureido)-2,3-difluorobenzoyl)piperazin-1-yl)methyl)furan-2-carboxamide; N-tert-butyl-5-((4-(2,3-difluoro-4-(3-isopentylureido)benzoyl)piperazin-1-yl)methyl)furan-2-carboxamide; N-tert-butyl-6-((4-(4-(3-cyclobutylureido)-3-fluorobenzoyl)piperazin-1-yl)methyl)picolinamide; N-tert-butyl-6-((4-(3-fluoro-4-(3-neopentylureido)benzoyl)piperazin-1-yl)methyl)picolinamide; N-tert-butyl-6-((4-(3-fluoro-4-(3-isopentylureido)benzoyl)piperazin-1-yl)methyl)picolinamide; or N-tert-butyl-6-((4-(4-(3-(cyclopropylmethyl)ureido)-3-fluorobenzoyl)piperazin-1-yl)methyl)picolinamide; or pharmaceutically acceptable salts thereof.

In further embodiments of any of the foregoing methods, the LXR agonist is a compound described in International Patent Publication No. WO2009/144961, e.g., any one of: 5-(2H-1,3-benzodioxol-5-yl)-3-({3-[4-(1,1,1,3,3,3-hexafluoro-2-hydroxypropan-2-yl)-2-propylphenoxy]phenyl}methyl)-5-methylimidazolidine-2,4-dione; 5-(2,3-dihydro-1-benzofuran-5-yl)-3-({3-[4-(1,1,1,3,3,3-hexafluoro-2-hydroxypropan-2-yl)-2-propylphenoxy]phenyl}methyl)-5-methylimidazolidine-2,4-dione; 5-(2,3-dihydro-1-benzofuran-5-yl)-3-(1-{3-[4-(1,1,1,3,3,3-hexafluoro-2-hydroxypropan-2-yl)-2-propylphenoxy]phenyl}ethyl)-5-methylimidazolidine-2,4-dione; 5-(2H-1,3-benzodioxol-5-yl)-3-({4-[4-(1,1,1,3,3,3-hexafluoro-2-hydroxypropan-2-yl)-2-propylphenoxy]pyridin-2-yl}methyl)-5-methylimidazolidine-2,4-dione; 3-({4-[4-(1,1,1,3,3,3-hexafluoro-2-hydroxypropan-2-yl)-2-propylphenoxy]pyridin-2-yl}methyl)-5-methyl-5-[4-(propan-2-yloxy)phenyl]imidazolidine-2,4-dione; 3-({5-[4-(1,1,1,3,3,3-hexafluoro-2-hydroxypropan-2-yl)-2-propylphenoxy]pyridin-3-yl}methyl)-5-methyl-5-[4-(propan-2-yloxy)phenyl]imidazolidine-2,4-dione; 5-(2,3-dihydro-1-benzofuran-5-yl)-3-({2-[4-(1,1,1,3,3,3-hexafluoro-2-hydroxypropan-2-yl)-2-propylphenoxy]pyridin-4-yl}methyl)-5-methylimidazolidine-2,4-dione; 3-({2-[4-(1,1,1,3,3,3-hexafluoro-2-hydroxypropan-2-yl)-2- propylphenoxy]pyridin-4-yl}methyl)-5-methyl-5-[4-(propan-2-yloxy)phenyl]imidazolidine-2,4-dione; 3-({6-[4-(1,1,1,3,3,3-hexafluoro-2-hydroxypropan-2-yl)-2-propylphenoxy]pyridin-2-yl}methyl)-5-methyl-5-[4-(propan-2-yloxy)phenyl]imidazolidine-2,4-dione; 5-(2H-1,3-benzodioxol-5-yl)-3-(2-{3-[4-(1,1,1,3,3,3-hexafluoro-2-hydroxypropan-2-yl)-2-propylphenyl]phenyl}ethyl)-5-methylimidazolidine-2,4-dione; 3-({2-chloro-5-[4-(1,1,1,3,3,3-hexafluoro-2-hydroxypropan-2-yl)-2-propylphenoxy]phenyl}methyl)-5-methyl-5-[4-(propan-2-yloxy)phenyl]imidazolidine-2,4-dione; 3-({3-[4-(1,1,1,3,3,3-hexafluoro-2-hydroxypropan-2-yl)-2,6-dipropylphenoxy]phenyl}methyl)-5-methyl-5-[4-(propan-2-yloxy)phenyl]imidazolidine-2,4-dione; 3-(2-{4-[4-(1,1,1,3,3,3-hexafluoro-2-hydroxypropan-2-yl)-2-propylphenoxy]phenyl)}ethyl)-5-methyl-5-[5-(propan-2-yloxy)pyridin-2-yl]imidazolidine-2,4-dione; 3-(2-{4-[4-(1,1,1,3,3,3-hexafluoro-2-hydroxypropan-2-yl)-2-propylphenoxy]-2-methylphenyl)}ethyl)-5-methyl-5-[4-(propan-2-yloxy)phenyl]imidazolidine-2,4-dione; 3-(2-{4-[4-(1,1,1,3,3,3-hexafluoro-2-hydroxypropan-2-yl)-2-propylphenoxy]-2-methoxyphenyl}ethyl)-5-methyl-5-[4-(propan-2-yloxy)phenyl]imidazolidine-2,4-dione; 3-(2-{4-[4-(1,1,1,3,3,3-hexafluoro-2-hydroxypropan-2-yl)-2-propylphenoxy]-2-hydroxyphenyl}ethyl)-5-methyl-5-[4-(propan-2-yloxy)phenyl]imidazolidine-2,4-dione; 3-(2-{4-[4-(1,1,1,3,3,3-hexafluoro-2-hydroxypropan-2-yl)-2-propylphenoxy]-2-(methoxymethyl)phenyl}ethyl)-5-methyl-5-[4-(propan-2-yloxy)phenyl]imidazolidine-2,4-dione; 5-[4-(1,1,1,3,3,3-hexafluoro-2-hydroxypropan-2-yl)-2-propylphenoxy]-2-(2-{4-methyl-2,5-dioxo-4-[4-(propan-2-yloxy)phenyl]imidazolidin-1-yl})ethyl)benzonitrile; 3-({4-[4-(1,1,1,3,3,3-hexafluoro-2-hydroxypropan-2-yl)-2-propylphenoxy]pyridin-2-yl}methyl)-5-methyl-5-[5-(propan-2-yloxy)pyridin-2-yl]imidazolidine-2,4-dione; 5-(1-benzofuran-5-yl)-3-({4-[4-(1,1,1,3,3,3-hexafluoro-2-hydroxypropan-2-yl)-2-propylphenoxy]pyridin-2-yl}methyl)-5-methylimidazolidine-2,4-dione; 3-({4-[4-(1,1,1,3,3,3-hexafluoro-2-hydroxypropan-2-yl)-2,6-dipropylphenoxy]pyridin-2-yl}methyl)-5-methyl-5-[4-(propan-2-yloxy)phenyl]imidazolidine-2,4-dione; 3-[(4-{[6-(1,1,1,3,3,3-hexafluoro-2-hydroxypropan-2-yl)-2-propylpyridin-3-yl]oxy}pyridin-2-yl)methyl]-5-methyl-5-[4-(propan-2-yloxy)phenyl]imidazolidine-2,4-dione; 3-({2-[4-(1,1,1,3,3,3-hexafluoro-2-hydroxypropan-2-yl)-2-propylphenoxy]-5-iodopyridin-4-yl}methyl)-5-methyl-5-[4-(propan-2-yl)phenyl]imidazolidine-2,4-dione; 3-({2-[4-(1,1,1,3,3,3-hexafluoro-2-hydroxypropan-2-yl)-2-propylphenoxy]-5-iodopyridin-4-yl}methyl)-5-methyl-5-[4-(propan-2-yloxy)phenyl]imidazolidine-2,4-dione; 3-(2-{5-[4-(1,1,1,3,3,3-hexafluoro-2-hydroxypropan-2-yl)-2-propylphenoxy]pyridin-2-yl}ethyl)-5-methyl-5-[4-(propan-2-yloxy)phenyl]imidazolidine-2,4-dione; 5-[3-fluoro-4-(propan-2-yloxy)phenyl]-3-(2-{5-[4-(1,1,1,3,3,3-hexafluoro-2-hydroxypropan-2-yl)-2-propylphenoxy]pyridin-2-yl}ethyl)-5-methylimidazolidine-2,4-dione; 3-(2-{5-[4-(1,1,1,3,3,3-hexafluoro-2-hydroxypropan-2-yl)-2-propylphenoxy]pyridin-2-yl}ethyl)-5-methyl-5-[5-(propan-2-yloxy)pyridin-2-yl]imidazolidine-2,4-dione; 3-(2-{6-[4-(1,1,1,3,3,3-hexafluoro-2-hydroxypropan-2-yl)-2-propylphenoxy]pyridin-3-yl}ethyl)-5-methyl-5-[4-(propan-2-yloxy)phenyl]imidazolidine-2,4-dione; 3-[2-(4-{[6-(1,1,1,3,3,3-hexafluoro-2-hydroxypropan-2-yl)-2-propylpyridin-3-yl]oxy}phenyl)ethyl]-5-(6-methoxypyridin-3-yl)-5-methylimidazolidine-2,4-dione; 3-[2-(5-{[6-(1,1,1,3,3,3-hexafluoro-2-hydroxypropan-2-yl)-2-propylpyridin-3-yl]oxy}pyridin-2-yl)ethyl]-5-methyl-5-[6-(propan-2-yloxy)pyridin-3-yl]imidazolidine-2,4-dione; 3-(2-{4-[4-(1,1,1,3,3,3-hexafluoro-2-hydroxypropan-2-yl)-2-propylphenoxy]phenyl}-2-oxoethyl)-5-methyl-5-[4-(propan-2-yloxy)phenyl]imidazolidine-2,4-dione; 5-(2,3-dihydro-1-benzofuran-5-yl)-3-(2-{4-[4-(1,1,1,3,3,3-hexafluoro-2-hydroxypropan-2-yl)-2-propylphenoxy]-2-methoxyphenyl)}-2-oxoethyl)-5-methylimidazolidine-2,4-dione; 3-(2-{4-[4-(1,1,1,3,3,3-hexafluoro-2-hydroxypropan-2-yl)-2-propylphenoxy]-2-methylphenyl}-2-oxoethyl)-5-methyl-5-[4-(propan-2-yloxy)phenyl]imidazolidine-2,4-dione; 3-(2-{4-[4-(1,1,1,3,3,3-hexafluoro-2-hydroxypropan-2-yl)-2-propylphenoxy]-2-methylphenyl}-2-oxoethyl)-5-methyl-5-[5-(propan-2-yloxy)pyridin-2-yl]imidazolidine-2,4-dione; 3-(2-{4-[4-(1,1,1,3,3,3-hexafluoro-2-hydroxypropan-2-yl)-2,6-dipropylphenoxy]-2-methylphenyl}-2-oxoethyl)-5-methyl-5-[5-(propan-2-yloxy)pyridin-2-yl]imidazolidine-2,4-dione; 3-(2-{4-[4-(1,1,1,3,3,3-hexafluoro-2-hydroxypropan-2-yl)-2-propylphenoxy]-2-hydroxyphenyl}-2-oxoethyl)-5-methyl-5-[4-(propan-2-yloxy)phenyl]imidazolidine-2,4-dione; 3-(2-{4-[4-(1,1,1,3,3,3-hexafluoro-2-hydroxypropan-2-yl)-2-propylphenoxy]-2-hydroxyphenyl}-2-oxoethyl)-5-methyl-5-[5-(propan-2-yloxy)pyridin-2-yl]imidazolidine-2,4-dione; 3-(2-{5-[4-(1,1,1,3,3,3-hexafluoro-2-hydroxypropan-2-yl)-2-propylphenoxy]pyridin-2-yl}-2-oxoethyl)-5-methyl-5-[4-(propan-2-yloxy)phenyl]imidazolidine-2,4-dione; or 3-(1-{5-[4-(1,1,1,3,3,3-hexafluoro-2-hydroxypropan-2-yl)-2-propylphenoxy]pyridin-2-yl}-1-oxopropan-2-yl)-5-methyl-5-[4-(propan-2-yloxy)phenyl]imidazolidine-2,4-dione; or pharmaceutically acceptable salts thereof.

In further embodiments of any of the foregoing methods, the LXR agonist is a compound described in International Patent Publication No. WO2013/076257, e.g., any one of: 5α-hydroxy-6β-[2-(1H-imidazol-4-yl)ethylamino]cholestan-3β-ol (Dendrogenin A), 5α-hydroxy-6β-[2-(1H-imidazol-4-yl)ethylamino]campestan-3β-ol, 5α-hydroxy-6β-[2-(1H-imidazol-4-yl)ethylamino]sitostan-3β-ol, 3β-acetoxy-5α-hydroxy-6β-[2-(1H-imidazol-4-yl)ethylamino]cholestane, 3β-acetoxy-5α-hydroxy-6β-[2-(1H-imidazol-4-yl)ethylamino]campestane, 3β-acetoxy-5α-hydroxy-6β-[2-(1H-imidazol-4-yl)ethylamino]sitostane, 5α-hydroxy-6β-[2-(1H-indol-3-yl)ethylamino]cholestan-3β-ol, 5α-hydroxy-6β-[2-(1H-indol-3-yl)ethylamino]campestan-3β-ol, 5α-hydroxy-6β-[2-(1H-indol-3-yl)ethylamino]sitostan-3β-ol, 5α-hydroxy-6β-[2-(1H-indol-3-yl)ethylamino]cholest-7-en-3β-ol, 3β-acetoxy-5α-hydroxy-6β-[2-(1H-indol-3-yl)ethylamino]cholestane, 3β-acetoxy-5α-hydroxy-6β-[2-(1H-indol-3-yl)ethylamino]campestane, 3β-acetoxy-5α-hydroxy-6β-[2-1H-indol-3-yl)ethylamino]sitostane, 3β-acetoxy-5α-hydroxy-6β-[2-(1H-indol-3-yl)ethylamino]cholest-7-ene, 5α-hydroxy-6β-[2-(1H-indol-3-yl-5-ol)ethylamino]cholestan-3β-ol, 5α-hydroxy-6β-[2-(1H-indol-3-yl-5-ol)ethyl amino]cholest-7-en-3β-ol, 5α-hydroxy-6β-[2-(1H-indol-3-yl-5-ol)ethylamino]campestan-3β-ol, 5α-hydroxy-6β-[2-(2-(1H-indol-3-yl-5-ol)ethylamino]sitostan-3β-ol, 3β-acetoxy-5α-hydroxy-6β-[2-(2-(1H-indol-3-yl-5-ol)ethylamino]cholestane, 3β-acetoxy-5α-hydroxy-6β-[2-(1H-indol-3-yl -5-ol)ethylamino]cholest-7-ene, 3β-acetoxy-5α-hydroxy-6β-[2-(2-(1H-indol-3-yl-5-ol)ethylamino]campestane, 3β-acetoxy-5α-hydroxy-6β-[2-(1H-indol-3-yl-5-ol)ethylamino]sitostane, 5α-hydroxy-6β-[3-(4-aminobutylamino)propylamino]cholest-7-en-3β-ol (Dendrogenin B), 5α-hydroxy-6β-[4-(3-aminopropylamino)butylamino]cholest-7-en-3β-ol, 5α-hydroxy-6β-[3-(4-aminobutylamino)propylamino]-cholestan-3β-ol, 5α-hydroxy-6β-[4-(3-aminopropylamino)butylamino]-cholestan-3β-ol, 5α-hydroxy-6β-[3-(4-aminobutylamino)propylamino]- campestan-3β-ol, 5α-hydroxy-6β-[4-(3-aminopropylamino)butylamino]-campestan-3β-ol, 5α-hydroxy-6β-[3-(4-aminobutylamino)propylamino]sitostan-3β-ol, 5α-hydroxy-6β-[4-(3-aminopropylamino)butylamino]sitostan-3β-ol, 5α-hydroxy-6β-[(4-aminobutyl)(3-aminopropyl)amino]cholest-7-en-3β-ol, 5α-hydroxy-6β-[(4-aminobutyl)(3-aminopropyl)amino]cholestan-3β-ol, 5α-hydroxy-6β-[(4-aminobutyl)(3-aminopropyl)amino]campestan-3β-ol, 5α-hydroxy-6β-[(4-aminobutyl)(3-aminopropyl)amino]-sitostan-3β-ol, 5αo-hydroxy-6β-{3-[4-(3-aminopropylamino)butylamino]propyl amino}cholest-7-en-3β-ol, 5α-hydroxy-6β-{3-[4-(3-aminopropylamino)butylamino]propyl amino}cholestan-3β-ol, 5α-hydroxy-6β-{3-[4-(3-aminopropylamino)butylamino]propyl amino}campestan-3β-ol, 5αo-hydroxy-6β-{3-[4-(3-aminopropylamino)-butylamino]propyl amino}sitostan-3β-ol, 5αo-hydroxy-6f3-(4-aminobutylamino)cholest-7-en-3β-ol, 5αo-hydroxy-6β-(4-aminobutylamino) cholestan-3β-ol, 5α-hydroxy-6β-(4-aminobutyl amino)campestan-3β-ol, 5α-hydroxy-6β-(4-aminobutylamino)sitostan-3β-ol, 5α-hydroxy-6β-(3-aminopropyl amino)cholest-7-en-3β-ol, 5α-hydroxy-6β-(3-aminopropylamino)cholestan-3β-ol, 5α-hydroxy-6β-(3-aminopropylamino)campestan-3β-ol, 5αo-hydroxy-6β-(3-aminopropylamino) sitostan-3β-ol, 3β-acetoxy-5α-hydroxy-6β-[3-(4-aminobutyl amino)-propylamino]cholest-7-ene, 3β-acetoxy-5α-hydroxy-6β-[4-(3-aminopropylamino)butylamino]cholest-7-ene, 3β-acetoxy-5α-hydroxy-6β-[3-(4-aminobutylamino)propylamino]cholestane, 3β-acetoxy-5α-hydroxy-6β-[4-(3-aminopropylamino)butyl amino]cholestane, 3β-acetoxy-5α-hydroxy-6β-[3-(4-aminobutylamino)-propylamino]campestane, 3β-acetoxy-5α-hydroxy-6β-[4-(3-aminopropylamino)butylamino]campestane, 3β-acetoxy-5α-hydroxy-6β-[3-(4-aminobutylamino)propylamino]sitostane, 3β-acetoxy-5α-hydroxy-6β-[4-(3-aminopropylamino)butylamino]sitostane, 3β-acetoxy-5α-hydroxy-6β-[(4-aminobutyl)(3-aminopropyl)-amino]cholest-7-ene, 3β-acetoxy-5α-hydroxy-6β-[(4-aminobutyl)(3-aminopropyl)amino]cholestane, 3β-acetoxy-5-hydroxy-6β-[(4-aminobutyl)(3-aminopropyl)amino]campestane, 3β-acetoxy-5α-hydroxy-6β-[(4-aminobutyl)(3-aminopropyl)amino]sitostane, 3β-acetoxy-5α-hydroxy-6β-{3-[4-(3-aminopropylamino)-butylamino]propylamino}cholest-7-ene, 3 3-acetoxy-5α-hydroxy-6-{3-[4-(3-aminopropylamino)-butylamino]propylamino}cholestane, 3β-acetoxy-5α-hydroxy-6β-{3-[4-(3-aminopropylamino)-butylamino]propylamino}campestane, 3β-acetoxy-5α-hydroxy-6β-{3-[4-(3aminopropylamino) butylamino]-propylamino}sitostane, 3β-acetoxy-5α-hydroxy-6β-(4-aminobutylamino)cholest-7-ene, 3β-acetoxy-5α-hydroxy-6β-(4-aminobutylamino)cholestane, 3β-acetoxy-5α-hydroxy-6β-(4-aminobutylamino)-campestane, 3β-acetoxy-5α-hydroxy-6β-(4-aminobutylamino)sitostane, 3β-acetoxy-5α-hydroxy-6β-(3-aminopropylamino)-cholest-7-ene, 3β-acetoxy-5α-hydroxy-6β-(3-aminopropylamino)cholestane, 3β-acetoxy-5α-hydroxy-6β-(3-aminopropylamino) campestane, or 3β-acetoxy-5α-hydroxy-6β-(3-aminopropylamino)sitostane. or pharmaceutically acceptable salts thereof.

In further embodiments of any of the foregoing methods, the LXR agonist is a compound described in International Patent Publication No. WO2013/057148, e.g., acid addition salt of 5α-hydroxy-6β-[2-(1H-imidazol-4yl)ethylamino]cholestan-3β-ol such as acid addition salts formed with benzenesulfonic acid, benzoic acid, 4methylbenzenesulfonic acid, 4,4'methylenebis-3-hydroxy-2-naphtoic acid, mesylic acid, L-tartaric acid, D-tartaric acid, L-malic acid, citric acid, 2-(S)-hydroxypropanoic acid, succinic acid, glutaric acid, malonic acid, fumaric acid, acetic acid, hydrochloride acid, or sulfuric acid.

In further embodiments of any of the foregoing methods, the LXR agonist is an LXR agonist described in International Patent Publication Nos: WO2006/046593; WO2006/073366; WO2010/125811; WO2009/144961; WO2009/133692; WO2010/025169; WO2010/125811; WO2011/051282; WO2010/023317; WO2012/135082; WO2009/150109; WO2013/130892; WO2010/059627; WO2012/004748; WO2013/138565; WO2013/138568; WO2011/014661; WO2002/090375; WO00/066611; WO2006/109633; WO2006/003923; WO2005/113499; WO2006/073365; WO2006/073364; WO2006/073363; WO2006/073367; WO2009/021868; WO2006000323; WO2010/125811; WO2009/144961; WO2009/133692; WO2010/025179; WO2009/138438; WO2003/043998, WO2003/045382, WO2003/059874, WO2003/059884, WO2003/060078, WO2003/090732, WO2003/090746, WO2003/090869, WO2003/099769, WO2003/099775, WO2003/106435, WO2004/009091, WO2004/011448, WO2004/026816, WO2004/058717, WO2004/072041, WO2004/072042, WO2004/072046, WO2005/005416, WO2005/005417, WO2005/016277, WO2005/023782, WO2005/077122, WO2005/077124, WO2006/094034, WO2007/024954, WO2007/047991, WO2007/092065, WO2008/049047, WO2009/086123, WO2009/086129, WO2009/086130, WO2009/086138, and WO2011/055391; U.S. Pat. Nos. 6,906,069 and 7,790,745, and U.S. Patent Publication Nos: US2005/0080111, US2006/0135601; US2006/0074115; US2005/0245515; US2005/0215577; US2009/0247587; US2002/0107233, US2003/0125357, US2003/0153541, US2005/0080111, US2005/0113419, US2005/0131014, US2005/0261319, US2006/0030612, US2006/0178398, US2007/0093524, US2009/0030082, and US2015/0299136, the compounds of which are herein incorporated by reference. In other embodiments of any of the foregoing methods, the LXR agonist is an LXR agonist described in Li et al, Expert Opin. Ther. Patents (2010) 20(4):535-562 and Tice et al., J. Med. Chem. (2014) 57:7182-7205, the compounds of which are herein incorporated by reference.

LXR Agonists

LXR agonists include any compound described herein such as a compound of any one of Formula I-XXXVI and/or any one of compounds 1-826, or pharmaceutically acceptable salts thereof.

LXRα and LXRβ, initially discovered by multiple groups at roughly the same time (Apfel et al., 1994; Willy et al., 1995; Song et al., 1994; Shinar et al., 1994; Teboul et al., 1995), belong to a family of nuclear hormone receptors that are endogenously activated by cholesterol and its oxidized derivatives to mediate transcription of genes involved in maintaining glucose, cholesterol, and fatty acid metabolism (Janowski et al., 1996; Calkin and Tontonoz, 2012). Given the intricate link between lipid metabolism and cancer cell growth (Cairns et al., 2011), the ubiquitous expression of LXRβ in melanoma is unlikely to be coincidental, allowing melanoma cells to synthesize lipids and lipoprotein particles to sustain their growth. At the same time, however, such stable basal expression levels make LXRβ an ideal therapeutic target, as exemplified by the broad-ranging responsiveness of melanoma cells to LXRβ activation therapy.

Compounds have been shown to have selectivity for LXRβ or LXRα. This selectivity may allow for increased activity and/or decreased off target effects. Examples of compounds with selectivity towards LXRβ or LXRα are shown in Table 3.

TABLE 3
| Compound | Structure | EC$_{50}$-LXRα (nM) | EC$_{50}$-LXRβ (nM) |
|---|---|---|---|
| GW3965 682 | 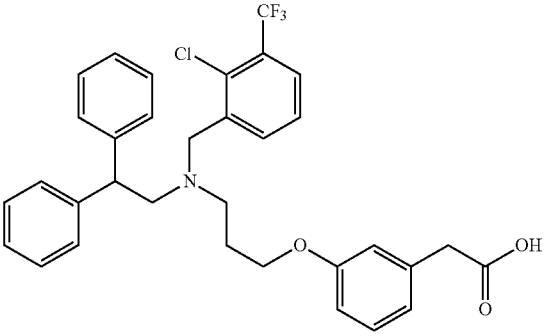 [SMILES: O=C(O)Cc1cccc(OCCCN(Cc2cccc(C(F)(F)F)c2Cl)CC(c2ccccc2)c2ccccc2)c1] | 200 | 40 |
| SB742881 705 | 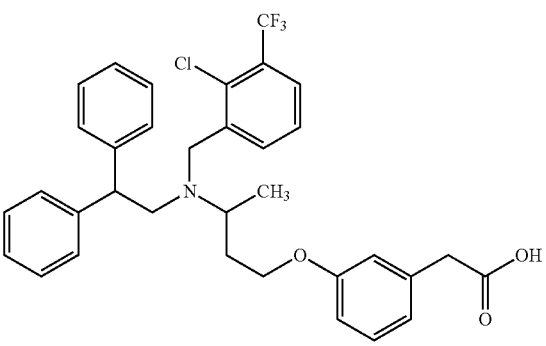 [SMILES: CC(CCOc1cccc(CC(=O)O)c1)N(Cc1cccc(C(F)(F)F)c1Cl)CC(c1ccccc1)c1ccccc1] | 74 | 25 |
| TO901317 681 | 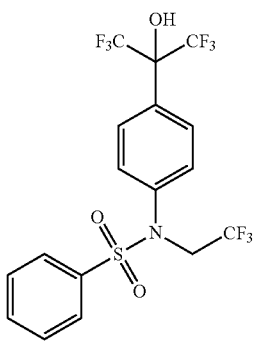 [SMILES: O=S(=O)(c1ccccc1)N(CC(F)(F)F)c1ccc(C(O)(C(F)(F)F)C(F)(F)F)cc1] | 20 | 50 |
| LXR-623 683 | 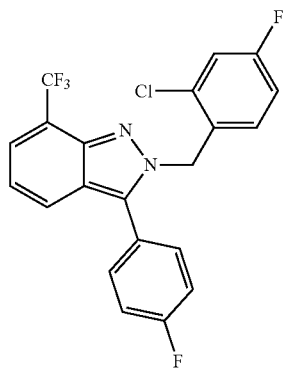 [SMILES: Fc1ccc(-c2c3cccc(C(F)(F)F)c3nn2Cc2ccc(F)cc2Cl)cc1] | 179 | 24 |

TABLE 3-continued

EC$_{50}$ values for selected compounds against LXRα and LXRβ

| Compound | Structure | EC$_{50}$-LXRα (nM) | EC$_{50}$-LXRβ (nM) |
|---|---|---|---|
| 692 | 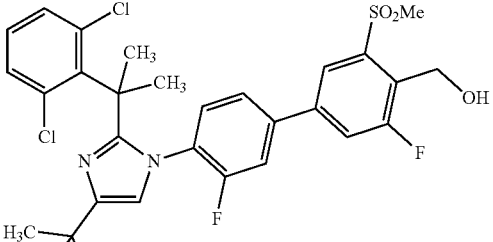 | <100 | 11 |
| 718 | 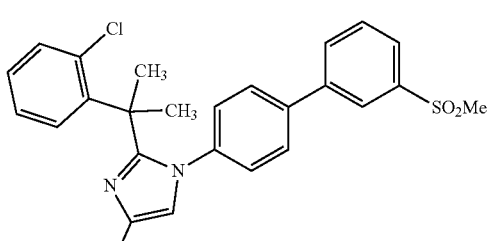 | 101-1000 | 630 |

As used herein, reference to the activity of an LXR agonist at LXRα and LXRβ refer to the activity as measured using the ligand sensing assay (LiSA) described in Spencer et al. Journal of Medicinal Chemistry 2001, 44, 886-897, incorporated herein by reference. In some embodiments, the LXR agonist has an EC50 of less than 1 μM in the ligand sensing assay (e.g., 0.5 nm to 500 nM, 10 nM to 100 nM). For example, the methods of the invention can be performed using an LXRβ agonist having activity for LXRβ that is at least 3-fold greater than the activity of the agonist for LXRα, or having activity for LXRβ that is at least 10-fold greater than the activity of the agonist for LXRα, or having activity for LXRβ that is at least 100-fold greater than the activity of said agonist for LXRα, or having activity for LXRβ that is at least within 3-fold of the activity of the agonist for LXRα. The term "greater activity" in the LiSA assay assay refers to a lower EC$_{50}$. For example, GW3965 682 has approximately 6-fold greater activity for LXRβ(EC$_{50}$=30) compared to LXRα (EC$_{50}$=190).

As used herein, the term "increases the level of ApoE expression in vitro" refers to certain LXR agonists capable of increasing the level of ApoE expression 2.5-fold in a qPCR assay at a concentration of less than 5 μM (e.g., at a concentration of 100 nM to 2 μM, at a concentration of less than or equal to 1 μM). The LXR agonists exhibiting this in vitro effect can be highly efficacious for use in the methods of the invention.

Methods of Treatment

The methods described here can be used to treat cancer.

Treating cancer can result in a reduction in size or volume of a tumor. For example, after treatment, tumor size is reduced by 5% or greater (e.g., 10%, 20%, 30%, 40%, 50%, 60%, 70%, 80%, 90% or greater) relative to its size prior to treatment. Size of a tumor may be measured by any reproducible means of measurement. The size of a tumor may be measured as a diameter of the tumor or by any reproducible means of measurement.

Treating cancer may further result in a decrease in number of tumors. For example, after treatment, tumor number is reduced by 5% or greater (e.g., 10%, 20%, 30%, 40%, 50%, 60%, 70%, 80%, 90% or greater) relative to number prior to treatment. Number of tumors may be measured by any reproducible means of measurement. The number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic noduless may be measured by any reproducible means of measurement. The number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with the compound of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with the compound of the invention. A decrease in the mortality rate of a population may also be measured, for example, by calculating for a population the average number of disease-related deaths per unit time following completion of a first round of treatment with the compound of the invention.

Treating cancer can also result in an increased average progression-free survival time of a population of treated subjects in comparison to an untreated population. For example the average progression-free survival time is increased by more than 30 days (more than 60 days, 90 days, or 120 days). An increase in average progression-free survival time of a population may be measured by any reproducible means. An increase in average progression-free survival time of a population may be measured, for example, by calculating for a population the average length of progression-free survival following initiation of treatment with the compound of the invention. An increase in average progression-free survival time of a population may also be measured, for example, by calculating for a population the average length of progression-free survival following completion of a first round of treatment with the compound of the invention.

In some embodiments, the methods described herein may be useful for the treatment of infections such as bacterial infections, parasitic infections, or fungal infections. Compounds of the present invention may be administered by any appropriate route for treatment or prophylactic treatment of a disease or condition associated with an infection. These may be administered to humans, domestic pets, livestock, or other animals with a pharmaceutically acceptable diluent, carrier, or excipient. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Compositions

Within the scope of this invention is a composition that contains a suitable carrier and one or more of the therapeutic agents described above. The composition can be a pharmaceutical composition that contains a pharmaceutically acceptable carrier, a dietary composition that contains a dietarily acceptable suitable carrier, or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, sodium lauryl sulfate, and D&C Yellow #10.

As used herein, the term "pharmaceutically acceptable salt" refers to those salts which are, within the scope of sound medical judgment, suitable for use in contact with the tissues of humans and lower animals without undue toxicity, irritation, or allergic response, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts, include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Representative alkali or alkaline earth metal salts include sodium, lithium, potassium, calcium, and magnesium. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutical compositions of the present invention additionally include a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, and lubricants, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine. Commercial grades of lecithin which are preferred include those which are available under the trade name Phosal® or Phospholipon® and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The above-described composition, in any of the forms described above, can be used for treating melanoma, or any other disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution.

In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally include one or more excipients or diluents. In some preferred embodiments, the topical formulations include a material that would enhance absorption or penetration of the active agent(s) through the skin or other affected areas.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, or allergic response. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition.

Combination Therapies

In some embodiments of the methods described herein, the pharmaceutical composition may further include an additional compound having antiproliferative activity. The additional compound having antiproliferative activity can be selected from a group of antiproliferative agents including those shown in Table 4.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

By "antiproliferative agent" is meant any antiproliferative agent, including those antiproliferative agents listed in Table 4, any of which can be used in combination with a LXR agonist to treat the medical conditions recited herein. Antiproliferative agents also include organo-platine derivatives, naphtoquinone and benzoquinone derivatives, chrysophanic acid and anthroquinone derivatives thereof.

TABLE 4

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | lomustine | streptozocin |
| | cyclophosphamide | temozolomide |
| | | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | |
| | ZD-0473 (AnorMED) | SM-11355 (Sumitomo) |
| | oxaliplatin | AP-5280 (Access) |
| | carboplatin | cisplatin |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | | elsamitrucin (Spectrum) |
| | dexrazoxanet (TopoTarget) | J-107088 (Merck & Co) |
| | pixantrone (Novuspharma) | BNP-1350 (BioNumerik) |
| | rebeccamycin analogue (Exelixis) | CKD-602 (Chong Kun Dang) |
| | | KW-2170 (Kyowa Hakko) |
| | BBR-3576 (Novuspharma) | hydroxycamptothecin (SN-38) |
| | rubitecan (SuperGen) | |
| | irinotecan (CPT-11) | |
| | topotecan | |
| Antitumor antibiotics | valrubicin | azonafide |
| | therarubicin | anthrapyrazole |
| | idarubicin | oxantrazole |
| | rubidazone | losoxantrone |
| | plicamycin | MEN-10755 (Menarini) |
| | porfiromycin | GPX-100 (Gem Pharmaceuticals) |
| | mitoxantrone (novantrone) | |
| | amonafide | Epirubicin |
| | | mitoxantrone |
| | | doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | |
| | T 138067 (Tularik) | ZD 6126 (AstraZeneca) |
| | cryptophycin 52 (Eli Lilly) | AZ10992 (Asahi) |
| | vinflunine (Fabre) | IDN-5109 (Indena) |
| | auristatin PE (Teikoku Hormone) | AVLB (Prescient NeuroPharma) |
| | BMS 247550 (BMS) | azaepothilone B (BMS) |
| | BMS 184476 (BMS) | BNP-7787 (BioNumerik) |
| | BMS 188797 (BMS) | CA-4 prodrug (OXiGENE) |
| | taxoprexin (Protarga) | dolastatin-10 (NIH) |
| | SB 408075 (GlaxoSmithKline) | CA-4 (OXiGENE) |
| | Vinorelbine | docetaxel |
| | Trichostatin A | vincristine |

TABLE 4-continued

| | | |
|---|---|---|
| Aromatase inhibitors | aminoglutethimide<br>atamestane (BioMedicines)<br>letrozole<br>anastrazole | paclitaxel<br>YM-511 (Yamanouchi)<br>formestane<br>exemestane |
| Thymidylate synthase inhibitors | pemetrexed (Eli Lilly)<br>ZD-9331 (BTG) | nolatrexed (Eximias)<br>CoFactor™ (BioKeys) |
| DNA antagonists | trabectedin (PharmaMar)<br>glufosfamide (Baxter International)<br>albumin + 32P (Isotope Solutions)<br>thymectacin (NewBiotics) | edotreotide (Novartis)<br>mafosfamide (Baxter International)<br>apaziquone (Spectrum Pharmaceuticals)<br>O6 benzyl guanine (Paligent) |
| Farnesyltransferase inhibitors | arglabin (NuOncology Labs)<br>lonafarnib (Schering-Plough)<br>BAY-43-9006 (Bayer) | tipifarnib (Johnson & Johnson)<br>perillyl alcohol (DOR BioPharma) |
| Pump inhibitors | CBT-1 (CBA Pharma)<br>tariquidar (Xenova)<br>MS-209 (Schering AG) | zosuquidar trihydrochloride (Eli Lilly)<br>biricodar dicitrate (Vertex) |
| Histone acetyltransferase inhibitors | tacedinaline (Pfizer)<br>SAHA (Aton Pharma)<br>MS-275 (Schering AG) | pivaloyloxymethyl butyrate (Titan)<br>depsipeptide (Fujisawa) |
| Metalloproteinase inhibitors | Neovastat (Aeterna Laboratories)<br>marimastat (British Biotech) | CMT-3 (CollaGenex)<br>BMS-275291 (Celltech) |
| Ribonucleoside reductase inhibitors | gallium maltolate (Titan)<br>triapine (Vion) | tezacitabine (Aventis)<br>didox (Molecules for Health) |
| TNF alpha agonists/antagonists | virulizin (Lorus Therapeutics)<br>CDC-394 (Celgene) | revimid (Celgene) |
| Endothelin A receptor antagonist | atrasentan (Abbott)<br>ZD-4054 (AstraZeneca) | YM-598 (Yamanouchi) |
| Retinoic acid receptor agonists | fenretinide (Johnson & Johnson)<br>LGD-1550 (Ligand) | alitretinoin (Ligand) |
| Immuno-modulators | interferon<br>oncophage (Antigenics)<br>GMK (Progenics)<br>adenocarcinoma vaccine (Biomira)<br>CTP-37 (AVI BioPharma)<br>IRX-2 (Immuno-Rx)<br>PEP-005 (Peplin Biotech)<br>synchrovax vaccines (CTL Immuno)<br>melanoma vaccine (CTL Immuno)<br>p21 RAS vaccine (Gem Vax)<br>MAGE-A3 (GSK)<br>nivolumab (BMS)<br>abatacept (BMS)<br>pembrolizumab (Merck) | dexosome therapy (Anosys)<br>pentrix (Australian Cancer Technology)<br>ISF-154 (Tragen)<br>cancer vaccine (Intercell)<br>norelin (Biostar)<br>BLP-25 (Biomira)<br>MGV (Progenics)<br>β-alethine (Dovetail)<br>CLL therapy (Vasogen)<br>Ipilimumab (BMS),<br>CM-10 (cCam Biotherapeutics)<br>MPDL3280A (Genentech) |
| Hormonal and antihormonal agents | estrogens<br>conjugated estrogens<br>ethinyl estradiol<br>chlortrianisen<br>idenestrol<br>hydroxyprogesterone caproate<br>medroxyprogesterone<br>testosterone<br>testosterone propionate;<br>fluoxymesterone<br>methyltestosterone<br>diethylstilbestrol<br>megestrol<br>bicalutamide<br>flutamide<br>nilutamide | dexamethasone<br>prednisone<br>methylprednisolone<br>prednisolone<br>aminoglutethimide<br>leuprolide<br>octreotide<br>mitotane<br>P-04 (Novogen)<br>2-methoxyestradiol (EntreMed)<br>arzoxifene (Eli Lilly)<br>tamoxifen<br>toremofine<br>goserelin<br>Leuporelin<br>bicalutamide |
| Photodynamic agents | talaporfin (Light Sciences)<br>Theralux (Theratechnologies)<br>motexafin gadolinium (Pharmacyclics) | Pd-bacteriopheophorbide (Yeda)<br>lutetium texaphyrin (Pharmacyclics)<br>hypericin |
| Kinase Inhibitors | imatinib (Novartis)<br>leflunomide (Sugen/Pharmacia)<br>ZD1839 (AstraZeneca)<br>erlotinib (Oncogene Science)<br>canertinib (Pfizer)<br>squalamine (Genaera)<br>SU5416 (Pharmacia)<br>SU6668 (Pharmacia) | EKB-569 (Wyeth)<br>kahalide F (PharmaMar)<br>CEP-701 (Cephalon)<br>CEP-751 (Cephalon)<br>MLN518 (Millenium)<br>PKC412 (Novartis)<br>Phenoxodiol (Novogen)<br>C225 (ImClone) |

TABLE 4-continued

| | |
|---|---|
| ZD4190 (AstraZeneca) | rhu-Mab (Genentech) |
| ZD6474 (AstraZeneca) | MDX-H210 (Medarex) |
| vatalanib (Novartis) | 2C4 (Genentech) |
| PKI166 (Novartis) | MDX-447 (Medarex) |
| GW2016 (GlaxoSmithKline) | ABX-EGF (Abgenix) |
| EKB-509 (Wyeth) | IMC-1C11 (ImClone) |
| trastuzumab (Genentech) | Tyrphostins |
| OSI-774 (Tarceva ™) | Gefitinib (Iressa) |
| CI-1033 (Pfizer) | PTK787 (Novartis) |
| SU11248 (Pharmacia) | EMD 72000 (Merck) |
| RH3 (York Medical) | Emodin |
| Genistein | Radicinol |
| Radicinol | Vemurafenib (B-Raf enzyme inhibitor, Daiichi Sankyo) |
| Met-MAb (Roche) | |
| SR-27897 (CCK A inhibitor, Sanofi-Synthelabo) | ceflatonin (apoptosis promotor, ChemGenex) |
| tocladesine (cyclic AMP agonist, Ribapharm) | BCX-1777 (PNP inhibitor, BioCryst) |
| alvocidib (CDK inhibitor, Aventis) | ranpirnase (ribonuclease stimulant, Alfacell) |
| CV-247 (COX-2 inhibitor, Ivy Medical) | |
| P54 (COX-2 inhibitor, Phytopharm) | galarubicin (RNA synthesis inhibitor, Dong-A) |
| CapCell ™ (CYP450 stimulant, Bavarian Nordic) | tirapazamine (reducing agent, SRI International) |
| GCS-100 (gal3 antagonist, GlycoGenesys) | |
| G17DT immunogen (gastrin inhibitor, Aphton) | N-acetylcysteine (reducing agent, Zambon) |
| efaproxiral (oxygenator, Alios Therapeutics) | R-flurbiprofen (NF-kappaB inhibitor, Encore) |
| PI-88 (heparanase inhibitor, Progen) | |
| tesmilifene (histamine antagonist, YM BioSciences) | 3CPA (NF-kappaB inhibitor, Active Biotech) |
| histamine (histamine H2 receptor agonist, Maxim) | seocalcitol (vitamin D receptor agonist, Leo) |
| tiazofurin (IMPDH inhibitor, Ribapharm) | 131-I-TM-601 (DNA antagonist, TransMolecular) |
| cilengitide (integrin antagonist, Merck KGaA) | eflornithine (ODC inhibitor, ILEX Oncology) |
| SR-31747 (IL-1 antagonist, Sanofi-Synthelabo) | minodronic acid (osteoclast inhibitor, Yamanouchi) |
| CCI-779 (mTOR kinase inhibitor, Wyeth) | |
| exisulind (PDE V inhibitor, Cell Pathways) | indisulam (p53 stimulant, Eisai) |
| CP-461 (PDE V inhibitor, Cell Pathways) | aplidine (PPT inhibitor, PharmaMar) |
| AG-2037 (GART inhibitor, Pfizer) | gemtuzumab (CD33 antibody, Wyeth Ayerst) |
| WX-UK1 (plasminogen activator inhibitor, Wilex) | |
| PBI-1402 (PMN stimulant, ProMetic LifeSciences) | PG2 (hematopoiesis enhancer, Pharmagenesis) |
| | Immunol ™ (triclosan oral rinse, Endo) |
| bortezomib (proteasome inhibitor, Millennium) | triacetyluridine (uridine prodrug, Wellstat) |
| SRL-172 (T cell stimulant, SR Pharma) | SN-4071 (sarcoma agent, Signature BioScience) |
| TLK-286 (glutathione S transferase inhibitor, Telik) | |
| PT-100 (growth factor agonist, Point Therapeutics) | TransMID-107 ™ (immunotoxin, KS Biomedix) |
| midostaurin (PKC inhibitor, Novartis) | PCK-3145 (apoptosis promotor, Procyon) |
| bryostatin-1 (PKC stimulant, GPC Biotech) | doranidazole (apoptosis promotor, Pola) |
| CDA-II (apoptosis promotor, Everlife) | CHS-828 (cytotoxic agent, Leo) |
| SDX-101 (apoptosis promotor, Salmedix) | trans-retinoic acid (differentiator, NIH) |
| rituximab (CD20 antibody, Genentech) | MX6 (apoptosis promotor, MAXIA) |
| carmustine | apomine (apoptosis promotor, ILEX Oncology) |
| Mitoxantrone | |
| Bleomycin | urocidin (apoptosis promotor, Bioniche) |
| Absinthin | Ro-31-7453 (apoptosis promotor, La Roche) |
| Chrysophanic acid | |
| Cesium oxides | brostallicin (apoptosis promotor, Pharmacia) |
| BRAF inhibitors, | |
| PDL1 inhibitors | β-lapachone |
| MEK inhibitors | gelonin |
| bevacizumab | cafestol |
| angiogenesis inhibitors | kahweol |
| dabrafenib | caffeic acid |
| ramucirumab | Tyrphostin AG |
| glembatumumab | PD-1 inhibitors |
| ANG1005 | CTLA-4 inhibitors |
| | sorafenib |
| | BRAF inhibitors |
| | rindopepimut |
| | vedotin |
| | ANG4043 |

EXAMPLES

General Methods

Animal Experiments

All mouse studies were conducted according to a protocol approved by the Institutional Animal Care and Use Committee at the Rockefeller University. C57BL/6 mice were obtained from the Jackson Laboratory. For experiments testing the effect of LXR agonists on tumor growth, mice were assigned to a control chow or a chow supplemented with compound 682 (Sigma-Aldrich) or compound 705 (Rgenix, Inc.) at 50, or 100 mg/kg/day, as indicated. For combination drug regimens, mice were fed a compound 705-supplemented diet and co-treated with anti-PD-1 antibody (clone RMP1-14 BioXcell), 10 mg/kg by i.p. injection every 3 days for 3 total doses starting on the day of tumor injection. All drug-formulated diets were prepared by Research Diets.

Tumor Growth Assays

All mouse studies were conducted according to a protocol approved by the Institutional Animal Care and Use Committee at the Rockefeller University. C57BL/6 (WT); and Pmel (B6.Cg-Thy1$^a$/Cy Tg(TcraTcrb)8Rest/J mice were obtained from the Jackson Laboratory. To determine the effect of LXR agonists on in vivo primary tumor growth, mice were injected with $5\times10^4$ B16F10 melanoma cells. For all tumor growth experiments, cells (suspension in 50 ml of PBS) were mixed 1:1 with matrigel (356231, BD Biosciences, Bedford, Mass.) and subcutaneously injected into the lower flank of 6-8 week-old sex-matched mice. Following formation of tumors, mice were assigned to the following treatment groups as described below. All drug-formulated diets were prepared by Research Diets. After the indicated number of days, either peripheral blood or tumors were isolated to obtain tumor-infiltrating lymphocytes for flow-cytometry analysis as described below.

Isolation of Tumor-Infiltrating Lymphocytes for Flow Cytometry Analysis

At the indicated day, tumors were isolated from euthanized mice and minced into small (~1 mm²) pieces with a scalpel and then enzymatically dissociated. Enzymatic dissociation was achieved by incubation of minced tumor fragments in HBSS supplemented with 2% FBS, Collagenase 8, Dnasel, Hepes, and NaPyruvate for 30-45 minutes at 37° C. while shaken at 80 RPM. Following enzymatic dissociation, lymphocytes were purified using a 30/70% Percoll gradient (GE Healthcare Life Sciences), followed by filtration through a 40 uM filter (Corning Inc) to obtain a single cell suspension of lymphocytes. Cells were incubated for 10 minutes with anti-CD16/32 antibody (FC block). Cells were then stained with the indicated antibodies: anti-CD45 (clone 104), anti-Gr1 (clone R86-8C5), anti-CD11b (clone M1/70), anti-Ly6G (clone 1A8), anti-Ly6C (clone AL21), anti-TCRβ (clone H57-597), anti-CD8 (clone 53-6.7), anti-CD4 (clone RM4-5), anti-IFNγ (clone XMG1.2), anti-Granzyme-B (clone 16G6). After staining, cells were subsequently analyzed by flow cytometry using an LSRII flow cytometer (BD Biosciences). Data was analyzed using FlowJo software. For assessment of intracellular T-cell activation markers (e.g. IFNγ and Granzyme-B), the intracellular fixation & permeabilization staining kit (BD bioscience) was used to process isolated lymphocytes that had been re-stimulated ex vivo for 2.5 hours with PMA (Sigma), Ionomycin (Sigma), and Brefeldin A (Sigma) during the staining procedure.

Isolation of Lymphocytes from Spleen for Flow Cytometry Analysis

At the indicated day, spleens were isolated from euthanized mice and mechanically dissociated and treated with RBC Lysis Buffer (Sigma) followed by filtration through a 40 uM filter (Corning Inc) to obtain a single cell suspension of lymphocytes. Cells were then stained with the indicated antibodies: anti-CD45 (clone 104), anti-Gr1 (clone R86-8C5), anti-CD11b (clone M1/70), anti-Ly6G (clone 1A8), anti-Ly6C (clone AL21). After staining, cells were subsequently analyzed by flow cytometry using an LSRII flow cytometer (BD Biosciences). Data was analyzed using FlowJo software.

Isolation of Lymphocytes from Circulating Blood for Flow Cytometry Analysis At the indicated day, blood was drawn from mice and treated with RBC Lysis Buffer (Sigma) followed by filtration through a 40 uM filter (Corning Inc) to obtain a single cell suspension of lymphocytes. Cells were then stained with the indicated antibodies: anti-CD45 (clone 104), anti-Gr1 (clone R86-8C5), anti-CD11b (clone M1/70), anti-Ly6G (clone 1A8), anti-Ly6C (clone AL21). After staining, cells were subsequently analyzed by flow cytometry using an LSRII flow cytometer (BD Biosciences). Data was analyzed using FlowJo software.

Immunohistochemistry

For MDSC quantification studies, frozen tumor sections (no fixation) were stained with an antibody against Gr1 (1:1000; BioXcell). Alexa Fluor dye-conjugated secondary antibodies were used to detect Gr1 primary antibody. Sections were counterstained with DAPI and mounted with ProLong Gold antifade reagent (P36930, Invitrogen). Images were then obtained using a confocal microscope (TCS SP5, Leica Microsystems). Gr1+ cell quantification was then performed using ImageJ software.

T-Cell Suppression Assay

CD8+ cells were purified from single cell suspensions from spleens of mice using the MACS CD8+ T-cell isolation kit (Miltenyi Biotech) according to manufacturer's protocol. Cells were then labeled with cell tracker reagent (BV). The labeled CD8+ T cells were plated on 96-well plates coated with 1 mg/ml anti-CD3 and anti-CD28 beads (Dynabeads® Mouse T-Activator CD3/CD28 for T-Cell Expansion and Activation; Gibco). Recombinant IL-2 (Gibco) was then added to the wells according to manufacturer's protocol. MDSC were then isolated using the MACS Myeloid-Derived Suppressor Cell Isolation Kit (Miltenyi Biotech) according to manufacturer's protocol and subsequently added in the indicated MDSC:T-cell ratios. Cells were incubated at 37° C. for 24-36 hours. T-cell activation was measured by flow cytometry by assessing the percent of T-cells positive for IFNγ staining with diluted BV dye.

MDSC Staining

Blood is collected and cryopreserved using BD Vacutainer CPT tubes (BD pharmingen) from patients with melanoma or healthy donors for retrospective analysis. Samples are collected from patients and healthy donors in Cyto-Chex (Streck), Vacutainer CPT, or standard heparin vacutainer tubes for comparative analysis. Peripheral blood mononuclear cells (PBMC; $5\times10^5$) from patients with melanoma or healthy donors are washed with 2 mL FACS buffer (PBS containing 2% bovine serum albumin and 0.05 mmol/L EDTA). The following antibodies are then added for 30 minutes at 4° C.: Lineage (CD3/CD16/CD19/CD20/CD56) cocktail FITC (BD Pharmingen), CD14-PerCP Cy5.5, CD11b-APC Cy7, CD33-PECy7 (BD Pharmingen), and HLA-DR-ECD (Beckman Coulter). Isotype controls are included the appropriate fluorochrome-conjugated mouse IgG1, IgG 1k, IgG2a, or IgG2b k (BD Pharmingen; Beckman Coulter; R&D Systems). Whole blood samples are lysed for 10 minutes in BD Phosflow Lyse/Fix after staining (BD Pharmingen). Stained cells are detected using a LSR Fortessa with FACS Diva software (BD Biosciences). Analysis is carried out using FlowJo (TreeStar). m-MDSCs are quantified as described. Briefly, scale values for HLA-DR within a singlet, live, lineage-negative (Lin⁻; CD3, CD16, CD19, CD20, and CD56) cell population that expressed $CD14^+$ $CD11b^+$ are exported from FlowJo and analyzed using code written in R software to derive the CV, a ratio of standard deviation (SD; σ) and geometric mean fluorescence intensity (GMFI). A % m-MDSC frequency defined as the % HLA-$DR^{low/-}$ among $CD14^+CD11b^+$ cells is derived using a nomogram based on the $99^{th}$ percentile CVHLA-DR among $CD14^+$ $CD1$ $1b^+$ cells from healthy donors. Absolute number of m-MDSC (/mL) in peripheral blood
is estimated using the formula: (% m-MDSC)×(number of monocytes (/μL) from a complete blood count on the same day.

MDSC Abundance Assay

MDSCs were isolated from the spleens of tumor-bearing wild-type or ApoE−/− mice, as indicated, using the MACS Myeloid-Derived Suppressor Cell Isolation Kit (Miltenyi Biotech) according to manufacturer's protocol. MDSCs were then incubated in RPMI (Sigma) supplemented with 10% FBS and either COMPOUND 705 (dissolved in 2% DMSO at the indicated concentration) or control (2% DMSO) and subsequently incubated at 37° C. for the indicated time. Abundance was assessed by quantifying the percent of live cells using propidium Iodide staining.

Example 1. Treatment of Tumors with Compound 682

After tumor cell injection, animals were palpated every two days for tumor formation. Upon detection of tumors measuring 5-10 mm3 in volume, mice were randomly assigned to a control diet treatment or a GW3 965-supplemented diet (100 mg/kg/day; Sigma-Aldrich). Tumor dimensions were measured using digital calipers, and tumor volume was calculated as (small diameter)²×(large diameter)/2. Tumors were isolated on day 12-14 for flow-cytometry analysis of tumor-infiltrating lymphocytes.

As shown in FIGS. 1A-1E, treatment with the LXR agonist compound 682 reduces the number of tumor-infiltrating myeloid-derived suppressor cells (MDSCs) in B16F10 melanoma. Further, as shown in FIGS. 2A-2C, treatment with the LXR agonist compound 682 increases the number of tumor-infiltrating activated CD8+ T-cells in B16F10 melanoma.

Example 2. Treatment of Tumors with Compound 705

After tumor cell injection, animals were palpated every two days for tumor formation. Upon detection of tumors measuring 5-10 mm3 in volume, mice were randomly assigned to receive a 100 uL daily I.P. injection of either vehicle control (5% ethanol/95% corn oil) or COMPOUND 705 (2 mg dissolved in vehicle control; Rgenix). Tumor dimensions were measured using digital calipers, and tumor volume was calculated as (small diameter)²×(large diameter)/2. Tumors were isolated on day 12-14 for flow-cytometry analysis of tumor-infiltrating lymphocytes.

Figure 3B:
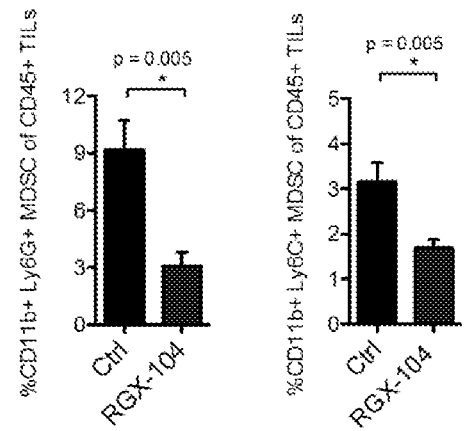
FIG. 3B is a graph illustrating quantification of G-MDSCs (Ly6-G+) and M-MDSCs (Ly6-C+) in control treated B16F10 tumor-bearing mice compared to B16F10 tumor-bearing mice treated with compound 705 as a percentage of total tumor-infiltrating CD45+ TILs.
Figure 3C:
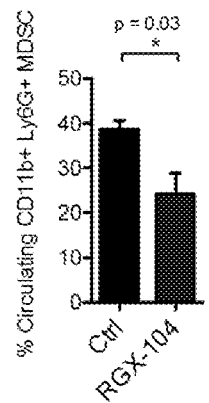
FIG. 3C is a graph illustrating quantification of circulating MDSCs (CD11b+Ly6G+ cells) in control treated or compound 705 treated B16F10 tumor-bearing mice as a total percentage of circulating CD45+ lymphocytes.
Figure 4A:
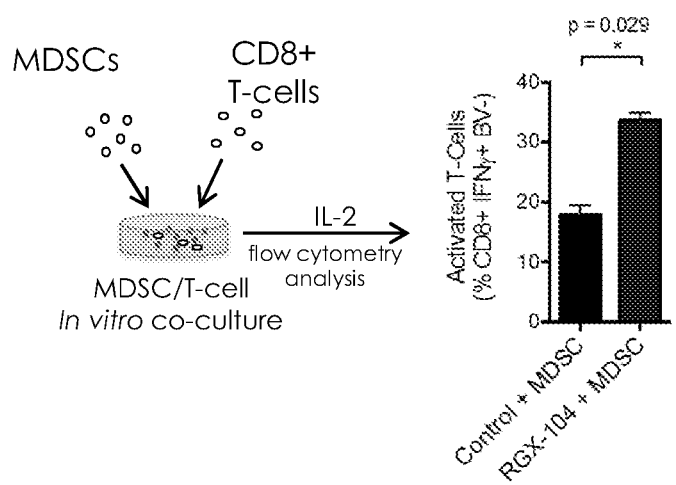
FIG. 4A is an image illustrating quantification of MDSC abundance in vitro after 3 hours of treatment with 1 µM compound 705 or control (DMSO).
Figure 4B:
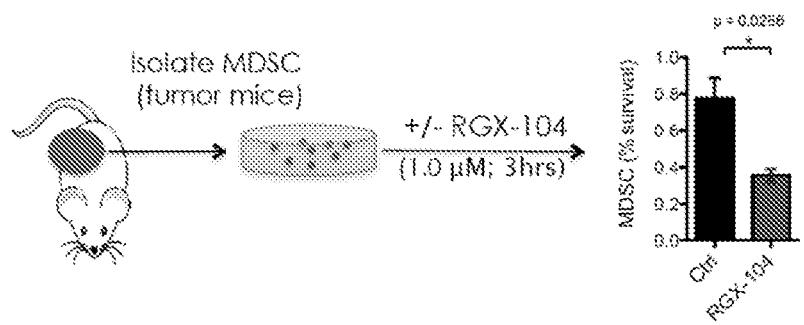
FIG. 4B is an image illustrating quantification of CD8+ cell activation (percentage of CD8+ IFNγ+BV− cells of the total CD8+ population) after 24 hours of co-culture with MDSCs isolated from control-treated or compound 705 treated tumor-bearing mice.

As shown in FIGS. 3A-3C, treatment with the LXR agonist compound 705 reduces the number of both granulocytic MDSCs (G-MDSC) and monocytic MDSCs (M-MDSC) in B16F10 melanoma. Further, as shown in FIGS. 4A and 4B, treatment with compound 705 reduces abundance of MDSCs in vitro and reverses MDSC-mediated suppression of CD8+ T-cells.

Example 3. Treatment of Tumors with Compound 705+Anti-PD1 Antibody

After tumor cell injection, animals were treated with anti-PD-1 antibody at a dose of 10 mg/kg (clone RMP1-14; BioXcell), by intraperitoneal (I.P.) injection every 3 days for 3 total doses starting on the day of tumor injection. Upon detection of tumors measuring 5-10 mm3 in volume, mice were randomly assigned to receive a control diet treatment or an COMPOUND 705-supplemented diet (50 mg/kg/day; Rgenix). Tumor dimensions were measured using digital calipers, and tumor volume was calculated as (small diameter)²×(large diameter)/2. Tumors were isolated on day 12-14 for flow-cytometry analysis of tumor-infiltrating lymphocytes.

Figure 5A:
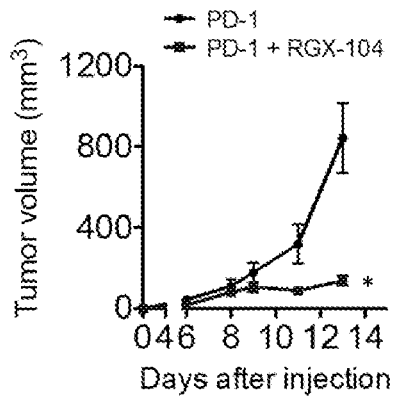
FIG. 5A is a graph illustrating tumor growth by B16F10 cells subcutaneously injected into pmel mice. Following tumor cell injection, animals were injected once every 3 days with 250 µg of anti-PD1 antibody I.P. and either fed a control chow or a chow supplemented with compound 705 (50 mg/kg) once tumor growth reached 5-10 mm$^3$ in volume.
Figure 5B:
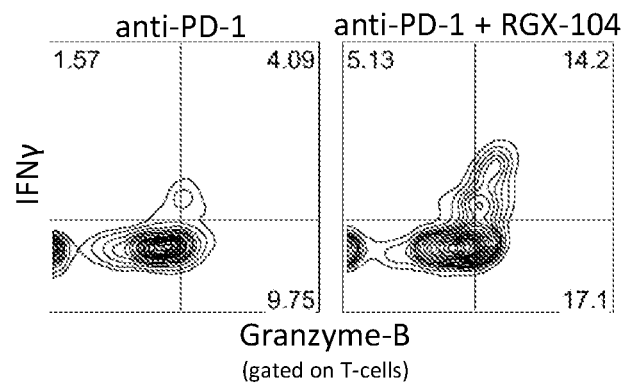
FIG. 5B is an image of flow-cytometry plots showing the population of activated CD8+ cells (CD8+ IFNγ+ Granzyme-B+ cells) in mice treated with either anti-PD-1 antibody alone or anti-PD-1 antibody in combination with compound 705.
Figure 5C:
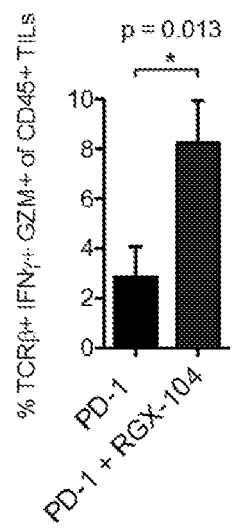
FIG. 5C is graph illustrating quantification of activated CD8+ cells (CD8+ IFNγ+ Granzyme-B+ cells) in mice treated with either anti-PD-1 antibody alone or anti-PD-1 antibody in combination with compound 705.

As shown in FIGS. 5A and 5B, treatment with compound 705 enhances the anti-tumor T-cell response induced with anti-PD-1 antibody therapy.

Example 4. Compound 705+ T-Cell Adoptive Transfer

After tumor cell injection, tumor volumes were measured every two days. Upon tumors measuring 90-100 mm³ in volume (day 6-7), mice were randomly assigned to a control diet treatment or a COMPOUND 705-supplemented diet (50 mg/kg/day; Rgenix).

The following day, 2×10⁶ CD8+ T-cells from Pmel mice were adoptively transferred via retro-orbital injection into both control and COMPOUND 705 treated mice. To isolate CD8+ T-cells, spleens and lymph nodes were obtained from 6-8 week old Pmel mice. A single cell suspension was obtained by mechanical dissociation followed by filtration through a 70 uM filter (Corning Inc). CD8+ T-cells were then purified from the suspension using the MACS CD8+ T-cell isolation kit (Miltenyi Biotec) according to manufacturer's protocol. CD8+ T-cells were re-suspended in 100 uL of PBS in preparation for adoptive transfer. For survival analyses, mice were euthanized when total tumor burden exceeded 1,500 mm³ in volume.

Figure 6:
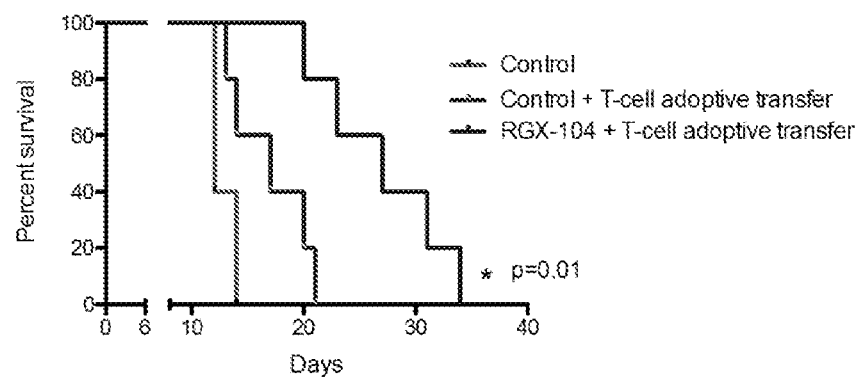
FIG. 6 is a Kaplan-Meier survival curve showing the survival of mice injected subcutaneously with B 16F10 and treated with either control chow, control chow plus intravenous adoptive transfer of 2×10^6 CD8+ T-cells from pmel mice, or chow supplemented with compound 705 (50 mg/kg) plus intravenous adoptive transfer of 2×10^6 CD8+ T-cells from pmel mice.

As shown in FIG. 6, treatment with compound 705 enhances the anti-tumor activity of adoptively transferred melanoma-targeting CD8+ T-cells.

Example 5. Treatment of Tumors with Compound 682 in ApoE Deficient Mice

B16F10 cells depleted of ApoE by shRNA were subcutaneously injected into ApoE deficient mice. Following tumor growth to 5-10 mm3 in volume, mice were fed a control chow or a chow supplemented with GW3965 (100 mg/kg) n=8.

Figure 7A:
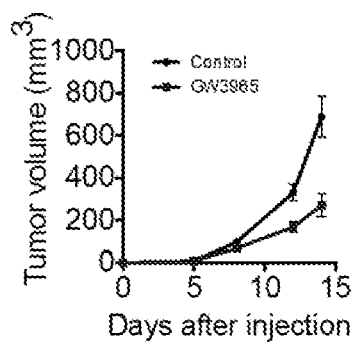
FIG. 7A is a graph illustrating tumor growth by B 16F10 cells subcutaneously injected into C57BL/6 mice. Following tumor growth to 5-10 mm$^3$ in volume, mice were fed a control chow or a chow supplemented with compound 682 (100 mg/kg).
Figure 7A:
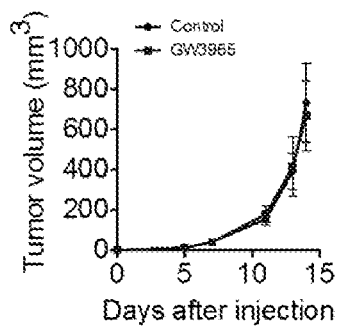
Figure 7A:
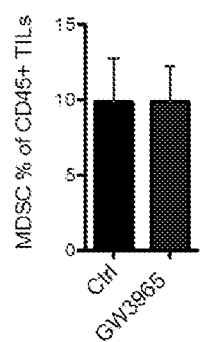
Figures 8A, 8B:
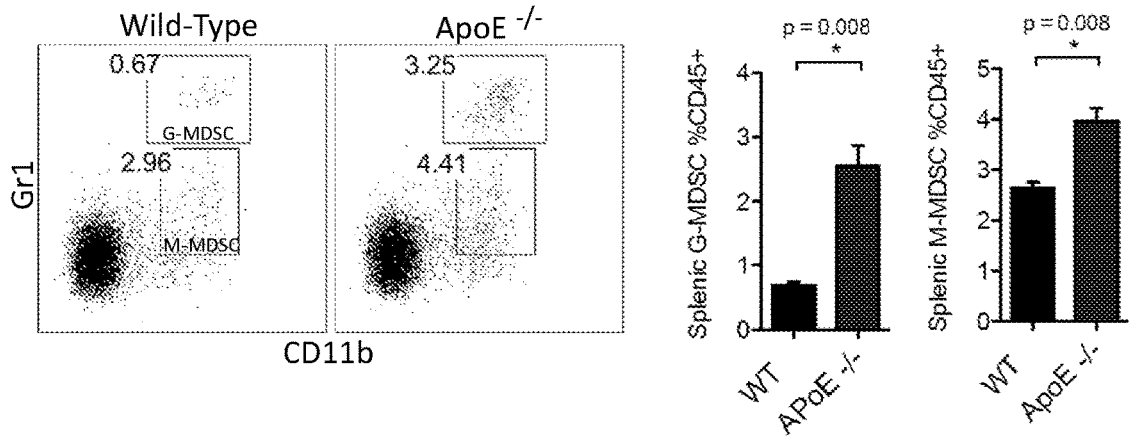
FIG. 8A is an image of flow-cytometry plots showing the populations of splenic G-MDSCs (Gr1 high) and M-MDSCs (Gr1 int) in wild type and ApoE deficient mice.
FIG. 8B is a graph illustrating quantification of splenic G-MDSCs and M-MDSCs in wild type and ApoE deficient mice.
Figures 8C, 8D:
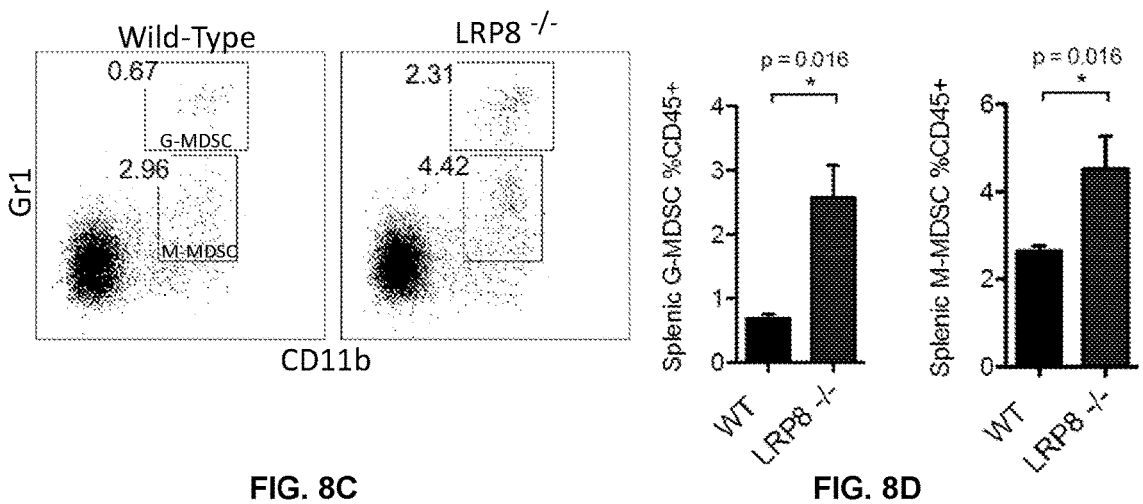
FIG. 8C is an image of flow-cytometry plots showing the populations of splenic G-MDSCs (Gr1 high) and M-MDSCs (Gr1 int) in wild type and LRP8 deficient mice.
FIG. 8D is a graph illustrating quantification of splenic G-MDSCs and M-MDSCs in wild type and LRP8 deficient mice.
Figures 8E, 8F:
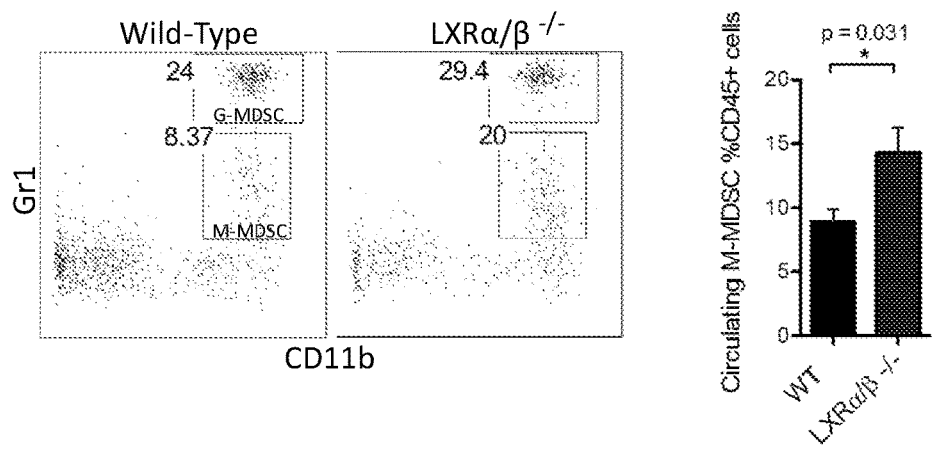
FIG. 8E is an image of flow-cytometry plots showing the populations of splenic G-MDSCs (Gr1 high) and M-MDSCs (Gr1 int) in wild type and LRP8 deficient mice.
FIG. 8F is a graph illustrating quantification of splenic M-MDSCs in wild type and LXRα/β deficient mice.

As shown in FIGS. 7A-C, the effect of LXR agonists on tumor-infiltrating MDSCs requires ApoE.

Example 6. Determination of Baseline Levels of MDSCs in Mice that are Deficient in ApoE, LRP8, or LXRα/β

The levels of MDSCs in mice deficient in ApoE, LRP8, or LXRα/β were determined using flow cytometry as described above.

As shown in FIGS. 8A-8F, Mice that are deficient in ApoE, LRP8, or LXRα/β, have higher baseline numbers of systemic MDSCs.

Example 7. Determination of the Effect of ApoE Deficient MDSCs on CD+8 T-Cell Activation CD8+ T-cell activation (percentage of CD8+ IFNγ+BV− cells of the total CD8+ population) was determined as described above after 24 hours of co-culture in vitro with MDSCs isolated from ApoE deficient mice, in either 1:3 or 1:1 ratio of MDSC to CD8+ T-cells. n=4

Figure 9:
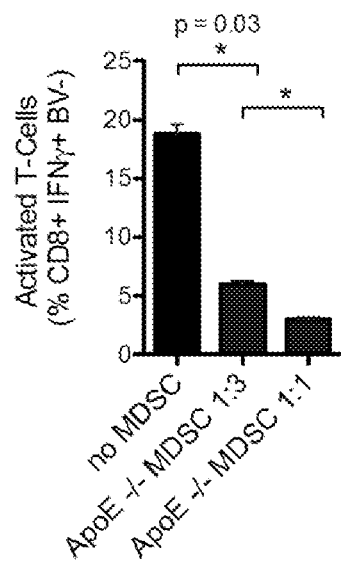
FIG. 9 is a graph illustrating quantification of CD8+ T-cell activation (percentage of CD8+ IFNγ+BV− cells of the total CD8+ population) after 24 hours of co-culture in vitro with MDSCs isolated from ApoE deficient mice, in either 1:3 or 1:1 ratio of MDSC to CD8+ T-cells.

As shown in FIG. 9, ApoE deficient MDSCs suppress CD8+ T-cell activation in vitro.

Example 8. Treatment of ApoE Deficient MDSCs with LXR Agonists

Abundance of wild-type and ApoE deficient MDSCs 4 hours after treatment with compound 705 or control (DMSO) was measured as described above. n=4

Figure 10A:
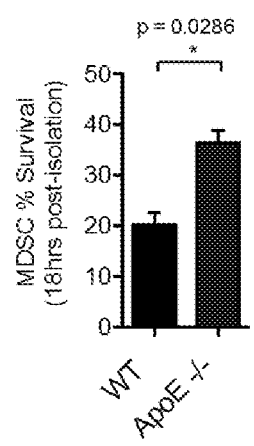
FIG. 10A is a graph illustrating quantification of MDSC abundance in vitro 18 hours after isolation from either wild-type mice or ApoE deficient mice.
Figure 10B:
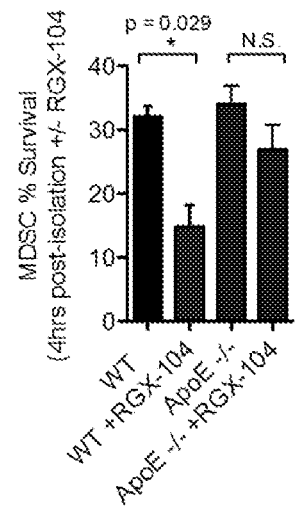
FIG. 10B is a graph illustrating quantification of abundance of wild-type and ApoE deficient MDSCs 4 hours after treatment with compound 705 or control (DMSO).

As shown in FIGS. 10A and 10B, ApoE deficient MDSCs exhibit enhanced abundance in vitro and are resistant to LXR agonist-mediated cell-death.

Example 9. Determining the Effect of ApoE Deficiency on Tumor Growth and MDSC Levels in Mice B16F10 cells were subcutaneously injected into C57BL/6 mice or B16F10 cells depleted of ApoE with shRNA injected in ApoE deficient mice. n=5 Tumor growth and MDSC levels were measured as described above.

As shown in FIGS. 11A-11C, ApoE deficiency results in accelerated tumor growth and increased circulating MDSCs in B16F10 tumor-bearing mice.

Example 10. Correlation Between LRP1 Expression and Response to LXR Agonists

Gene expression was determined in the following cell lines: MeWo, A375, HT-144, SK-Mel2, SK-Mel 334_2, SK-Mel 239. For ApoE analysis, the following cell lines were used: MeWo, A375, HT-144, SK-Mel2, SK-Mel 334 2. RNA was extracted from whole cell lysates using the Total RNA Purification Kit (17200, Norgen, Thorold, Canada). 600 ng of total RNA was reverse transcribed into cDNA using the verso cDNA Synthesis Kit (AB 1453B, Invitrogen), and 6 ng of the resulting cDNA was then mixed with SYBR green PCR Master Mix (4385617, Life Technology) and the appropriate primers. Each reaction was performed in quadruplicate, and mRNA expression was quantified by performing real-time PCR amplification using an ABI Step One Plus PCR System (Applied Biosystems). GAPDH was used as an endogenous control for normalization and relative expression levels analyzed by normalization to MeWo cells.

The following qRT-PCR primers were used:

```
LRP1 Forward:
5'-TTTAACAGCACCGAGTACCAG-3'

LRP1 Reverse:
5'-CAGGCAGATGTCAGAGCAG-3'
```

For correlation analysis, tumor growth inhibition data at the end point of the experiment were obtained from Pencheva et al, Cell 2014 correlated with gene the gene expression analysis performed as described.

Figure 12:
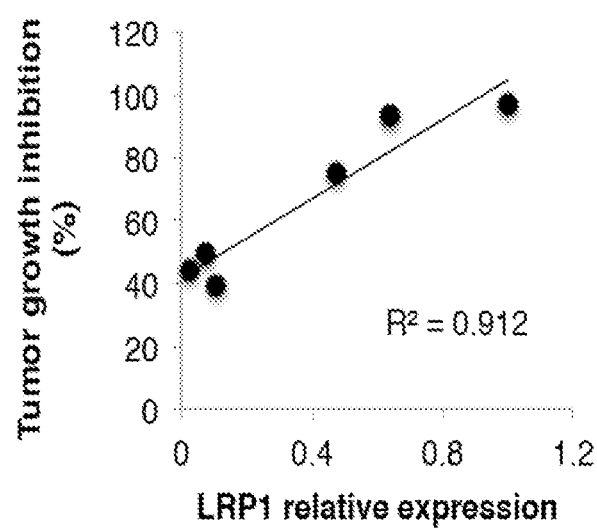
FIG. 12 is a graph illustrating correlation analysis of tumor growth inhibition in vivo after administration of LXR agonist compound 682 (Y-axis) versus baseline gene-expression of LRP1 in tumor cells (X-axis) measured by real-time quantitative PCR.

As shown in FIG. 12, LRP1 gene expression in tumors correlates with response to LXR agonists.

Other Embodiments

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While the methods have been described in conjunction with various embodiments and examples, it is not intended that the methods be limited to such embodiments or examples. On the contrary, the present disclosure encompasses various alternatives, modifications, and equivalents, as will be appreciated by those of skill in the art.

While the methods have been particularly shown and described with reference to specific illustrative embodiments, it should be understood that various changes in form and detail may be made without departing from the spirit and scope of the present disclosure. Therefore, all embodiments that come within the scope and spirit of the present disclosure, and equivalents thereto, are intended to be claimed. The claims, descriptions and diagrams of the methods, systems, and assays of the present disclosure should not be read as limited to the described order of elements unless stated to that effect.

The invention claimed is:

1. A method of treating lung cancer in a subject, the method comprising:
   (a) selecting a predetermined effective amount of an LXRβ agonist, wherein the predetermined amount is effective to decrease the level of myeloid derived suppressor cells in the subject by more than 20%;
   (b) administering the effective amount of the LXRβ agonist to the subject; and
   (c) administering an effective amount of an immunotherapy to the subject, wherein the LXRβ agonist is compound 705, or a pharmaceutically acceptable salt thereof, wherein the subjection is human, wherein the immunotherapy is a CTLA-4 inhibitor, a PD1 inhibitor, a PDL1 inhibitor, or adoptive T-cell transfer therapy.

2. The method of claim 1, wherein the lung cancer has failed to respond to a previously administered an immunotherapy.

3. The method of claim 1, wherein the lung cancer is resistant to an immunotherapy.

4. The method of claim 1, wherein the method further comprises administering to the subject an additional anticancer therapy.

5. The method of claim 4, wherein the additional anticancer therapy is a second immunotherapy.

6. The method of claim 1, wherein the myeloid derived suppressor cells are monocytic myeloid derived suppressor cells and/or granulocytic myeloid derived suppressor cells.

7. The method of claim 1, wherein the myeloid derived suppressor cells are circulating myeloid derived suppressor cells.

8. The method of claim 1, wherein the myeloid derived suppressor cells express CD11b(+), Lin(−), HLA-DR (low/−), and/or CD14(+) on the cell surface.

9. The method of claim 8, wherein the myeloid derived suppressor cells express CD11b(+), Lin(−), HLA-DR (low/−), and CD14(+) on the cell surface.

10. The method of claim 1, wherein the myeloid derived suppressor cells express CD11b(+), Lin(−), HLA-DR (low/−), and/or CD15(+) on the cell surface.

11. The method of claim 10, wherein the myeloid derived suppressor cells express CD11b(+), Lin(−), HLA-DR (low/−), and CD15(+) on the cell surface.

12. The method of claim 5, wherein the second immunotherapy is a CTLA-4 inhibitor, a PD1 inhibitor, a PDL1 inhibitor, or adoptive T-cell transfer therapy.

13. The method of claim 1, wherein the predetermined effective amount is effective to decrease the level of myeloid derived suppressor cells in the subject by more than 50%.

14. The method of claim 1, further comprising determining the subject as having an elevated level of myeloid derived suppressor cells in the tumor microenvironment.

15. The method of claim 1, wherein the immunotherapy is pembrolizumab, nivolumab, or ipilimumab.

16. The method of claim 1, wherein the predetermined effective amount is effective to increase the level of activated T-cells in the subject by more than 50%.

* * * * *